United States Patent
Jo

(10) Patent No.: US 10,323,063 B2
(45) Date of Patent: Jun. 18, 2019

(54) ADVANCED MACROMOLECULE TRANSDUCTION DOMAIN (AMTD) SEQUENCES FOR IMPROVEMENT OF CELL-PERMEABILITY, POLYNUCLEOTIDES ENCODING THE SAME, METHOD TO IDENTIFY THE UNIQUE FEATURES OF AMTDS COMPRISING THE SAME, METHOD TO DEVELOP THE AMTD SEQUENCES COMPRISING THE SAME

(71) Applicant: CELLIVERY THERAPEUTICS, INC., Seoul (KR)

(72) Inventor: Daewoong Jo, Brentwood, TN (US)

(73) Assignee: CELLIVERY THERAPEUTICS, INC., Seoul (KR)

( * ) Notice: Subject to any disclaimer, the term of this patent is extended or adjusted under 35 U.S.C. 154(b) by 0 days.

(21) Appl. No.: 15/503,117

(22) PCT Filed: Aug. 17, 2015

(86) PCT No.: PCT/KR2015/008544
§ 371 (c)(1),
(2) Date: Feb. 10, 2017

(87) PCT Pub. No.: WO2016/028036
PCT Pub. Date: Feb. 25, 2016

(65) Prior Publication Data
US 2017/0240598 A1  Aug. 24, 2017

Related U.S. Application Data

(60) Provisional application No. 62/038,346, filed on Aug. 17, 2014.

(51) Int. Cl.
*C07K 7/08* (2006.01)
*C07K 7/06* (2006.01)
*G01N 33/50* (2006.01)

(52) U.S. Cl.
CPC .......... *C07K 7/08* (2013.01); *C07K 7/06* (2013.01); *G01N 33/5035* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 2003/0104622 A1 | 6/2003 | Robbins et al. | |
| 2010/0209447 A1 | 8/2010 | Kumar-Singh et al. | |
| 2014/0141452 A1 | 5/2014 | Watt et al. | |
| 2014/0186379 A1 † | 7/2014 | Jo | |

FOREIGN PATENT DOCUMENTS

| | | | |
|---|---|---|---|
| EP | 1 362 917 | 11/2003 | |
| JP | 2010-516758 A | 5/2010 | |
| KR | 10-1258279 † | 4/2013 | |
| WO | 01/27154 | 4/2001 | |
| WO | 03/097671 | 11/2003 | |
| WO | 2008/093982 | 8/2008 | |
| WO | 2009/139599 A2 | 11/2009 | |
| WO | 2012/050402 A2 | 4/2012 | |
| WO | WO-2012072088 A1 * | 6/2012 | ............. A61K 39/12 |

OTHER PUBLICATIONS

ChemPages. Hydrophobic Amino Acids. Datasheet [online]. ChemPages Netorials. [retrieved on Jun. 15, 2018]. Retrieved from the internet: <URL: https://www.chem.wisc.edu/deptfiles/genchem/neotorial/modules/biomolecules/modules/protein1/prot13.htm>.*
Medical Physiology/Basic Biochemistry/Amino Acids. Classification of Amino Acids. [retrieved on Jun. 15, 2018]. Retrieved from the internet: <URL: https://en.wikibooks.org/w/index.php?title=Medical_Physiology/Basic_Biochemistry/Amino_Acids_and_Proteins & oldid=3436225.Last edited on Jun. 15, 2018.p. 3.*
ExPASy. ProtParam.Gasteiger, E et al. Protein idenrtification and analysis tools on the ExPASy server. In: The Proteomics Protocols Handbook; Ed.: John M. Walker.Copyright 2005 Humana Press, [retrieved on Jun. 15, 2018].Retrieved from the internet <https://web.expasy.org/cgi-bin/protparam/protparam, p. 1.*
International Searching Authority, International Search Report for PCT/KR2015/008544 dated Nov. 16, 2015.
Japanese Patent Office; Communication dated Feb. 20, 2018 in counterpart Japanese application No. 2017-510405.
European Patent Office; Communication dated Feb. 9, 2018 in counterpart European application No. 15833496.1.
Australian Patent Office, communication dated Oct. 13, 2017 by the Australian Patent Office in counterpart Application No. 2015304194.
European Patent Office, communication dated Nov. 27, 2017 by the European Patent Office in counterpart Application No. 15 833 496.1.

* cited by examiner
† cited by third party

*Primary Examiner* — Renee Claytor
*Assistant Examiner* — Sharon M. Papciak
(74) *Attorney, Agent, or Firm* — Sughrue Mion, PLLC

(57) ABSTRACT

The present invention is to execute macromolecule intracellular transduction technology (MITT) for delivering biologically active macromolecules into the cells; specifically, by exploiting well-enhanced hydrophobic cell penetrating peptide (CPP)—advanced macromolecule transduction domain (aMTD)—to effectively transduce biologically active molecules into the plasma membrane, polynucleotides encoding the same, methods of identifying the same, systems of genetically engineering a biologically active molecule with much enhanced cell-permeability by using the same, methods of importing a biologically active molecule into a cell by using the same, and uses thereof.

5 Claims, 61 Drawing Sheets
Specification includes a Sequence Listing.

[Fig. 1]
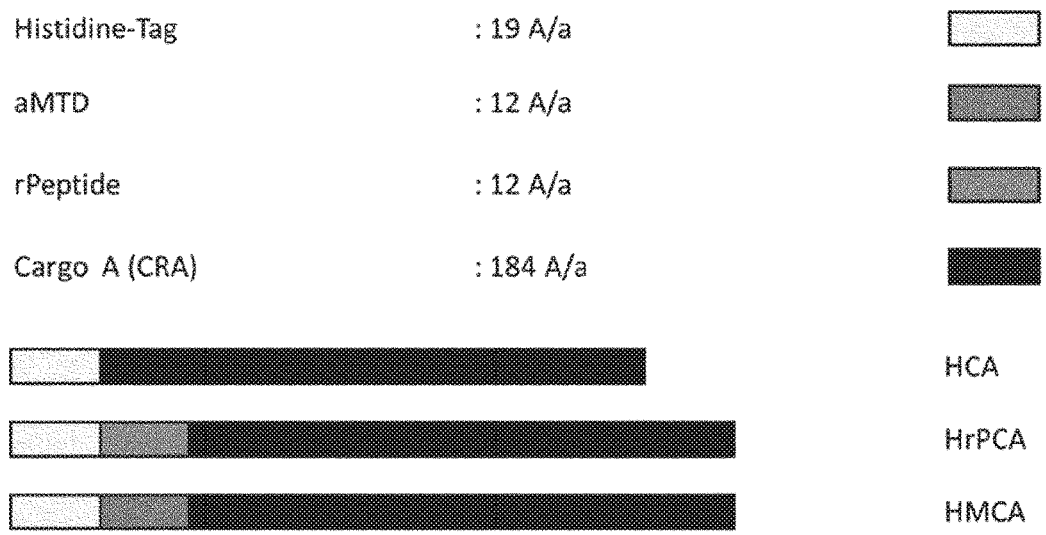
[Fig. 2a]
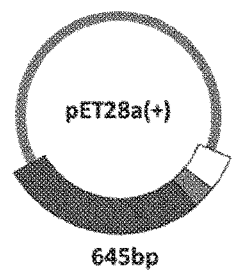

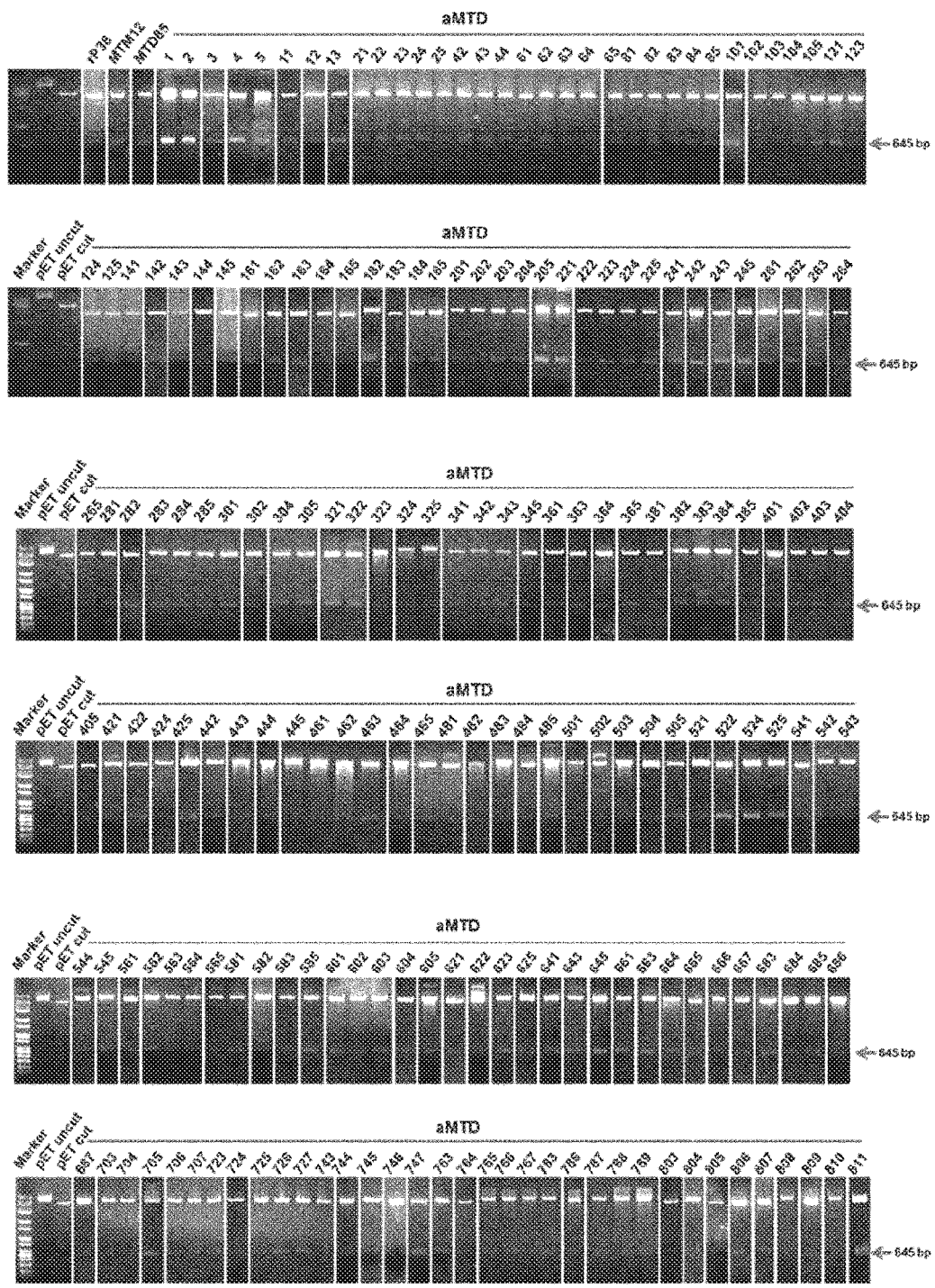
[Fig. 2b]

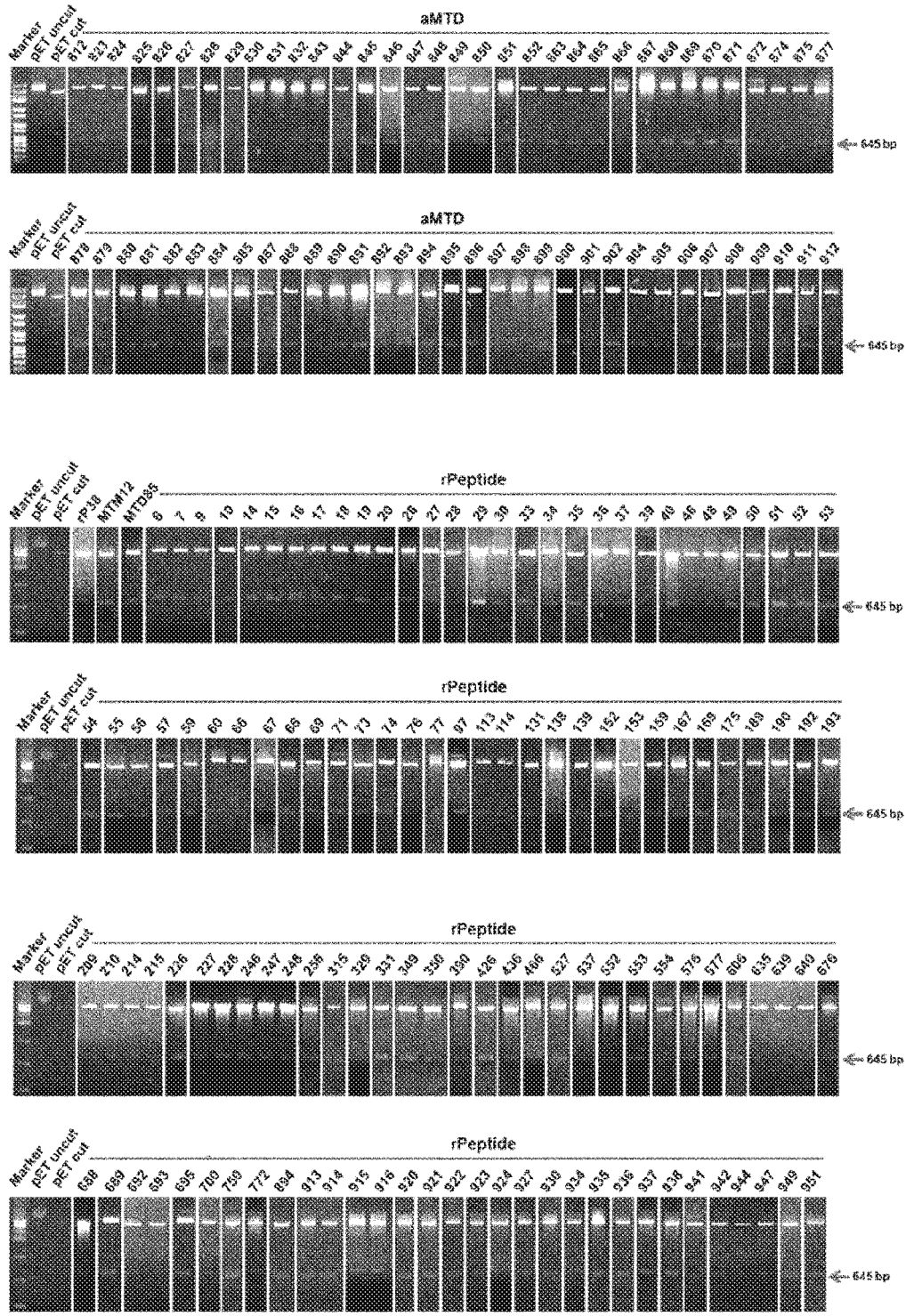
[Fig. 2c]

[Fig. 3a]
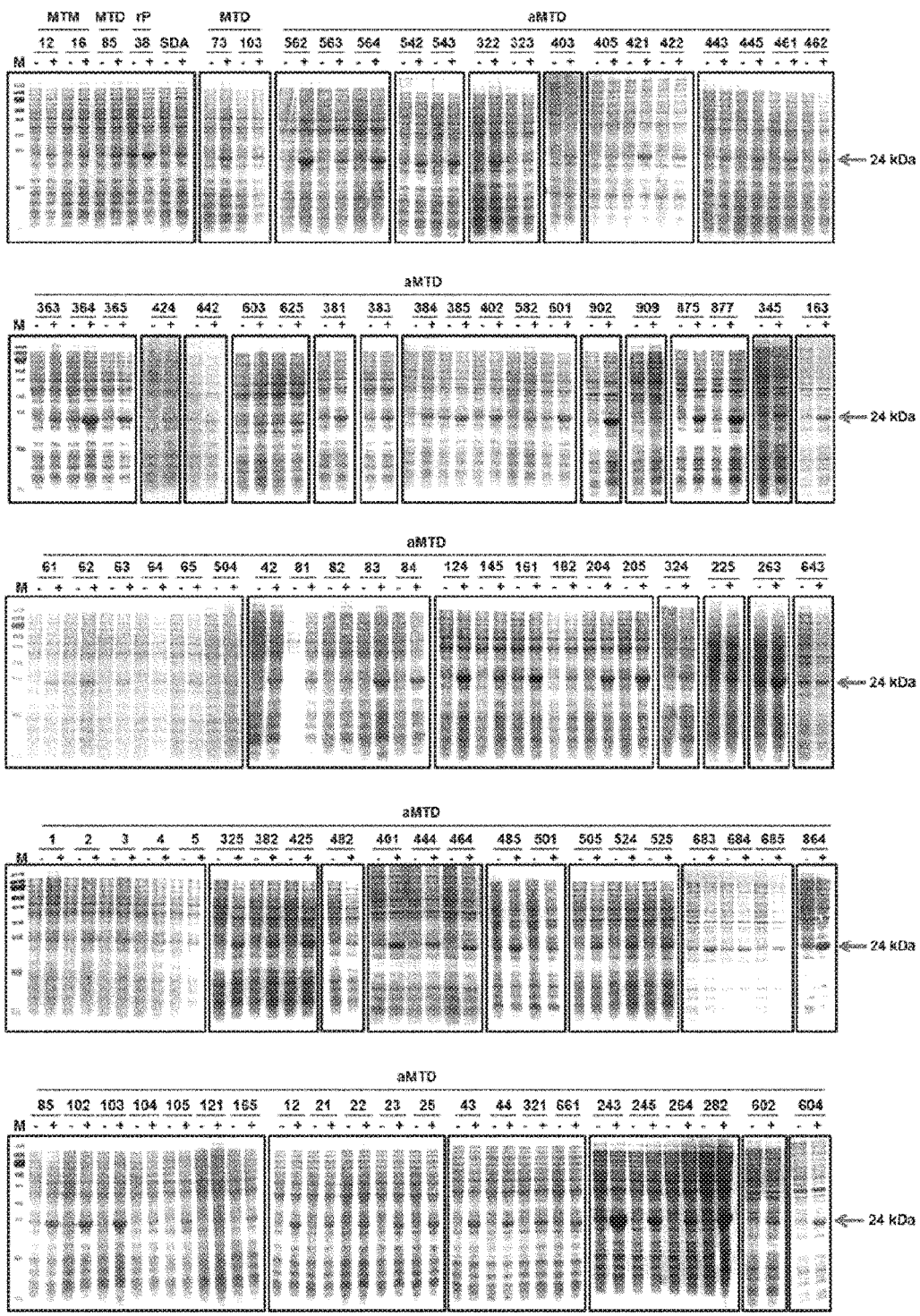

[Fig. 3b]
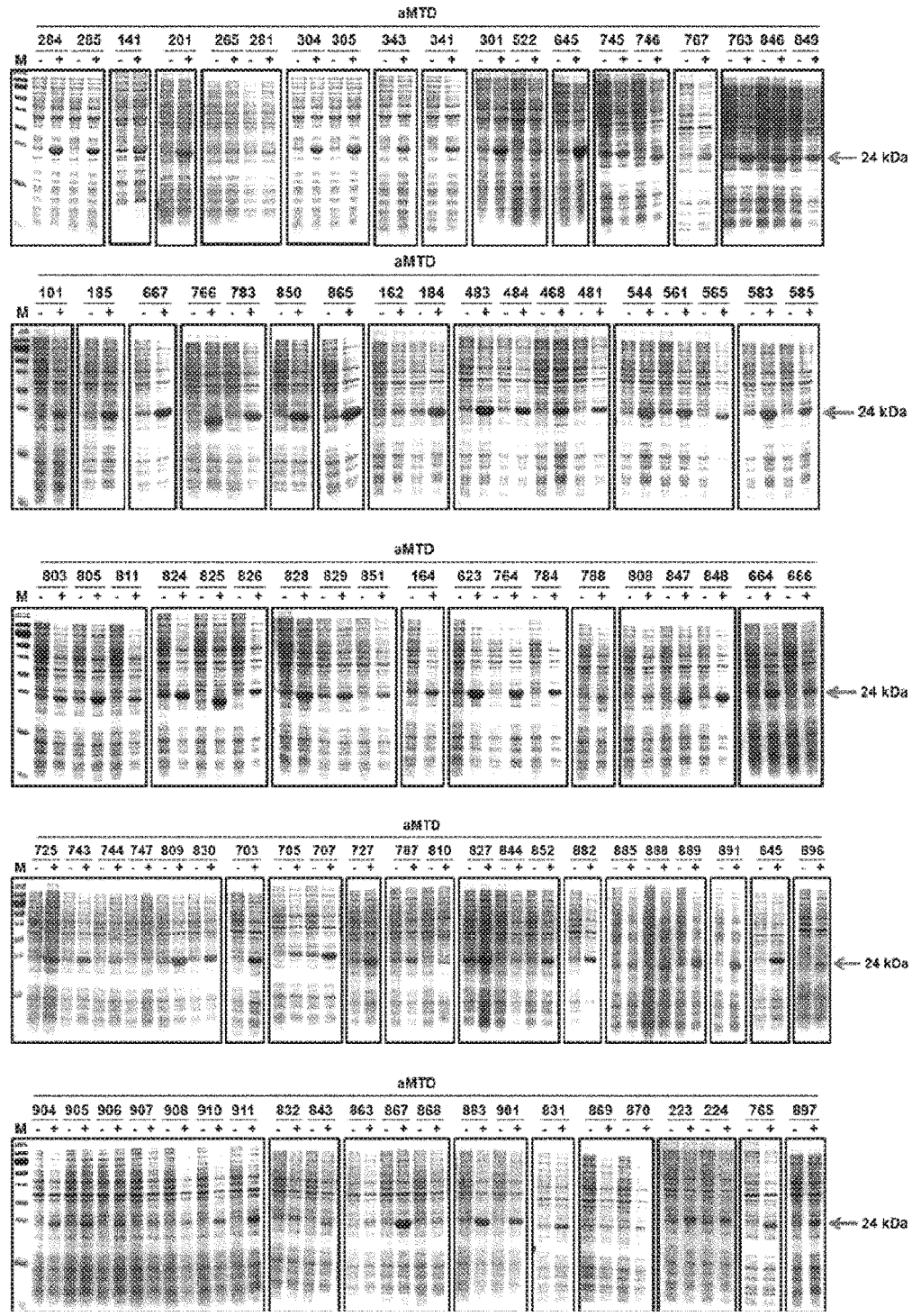

[Fig. 3c]
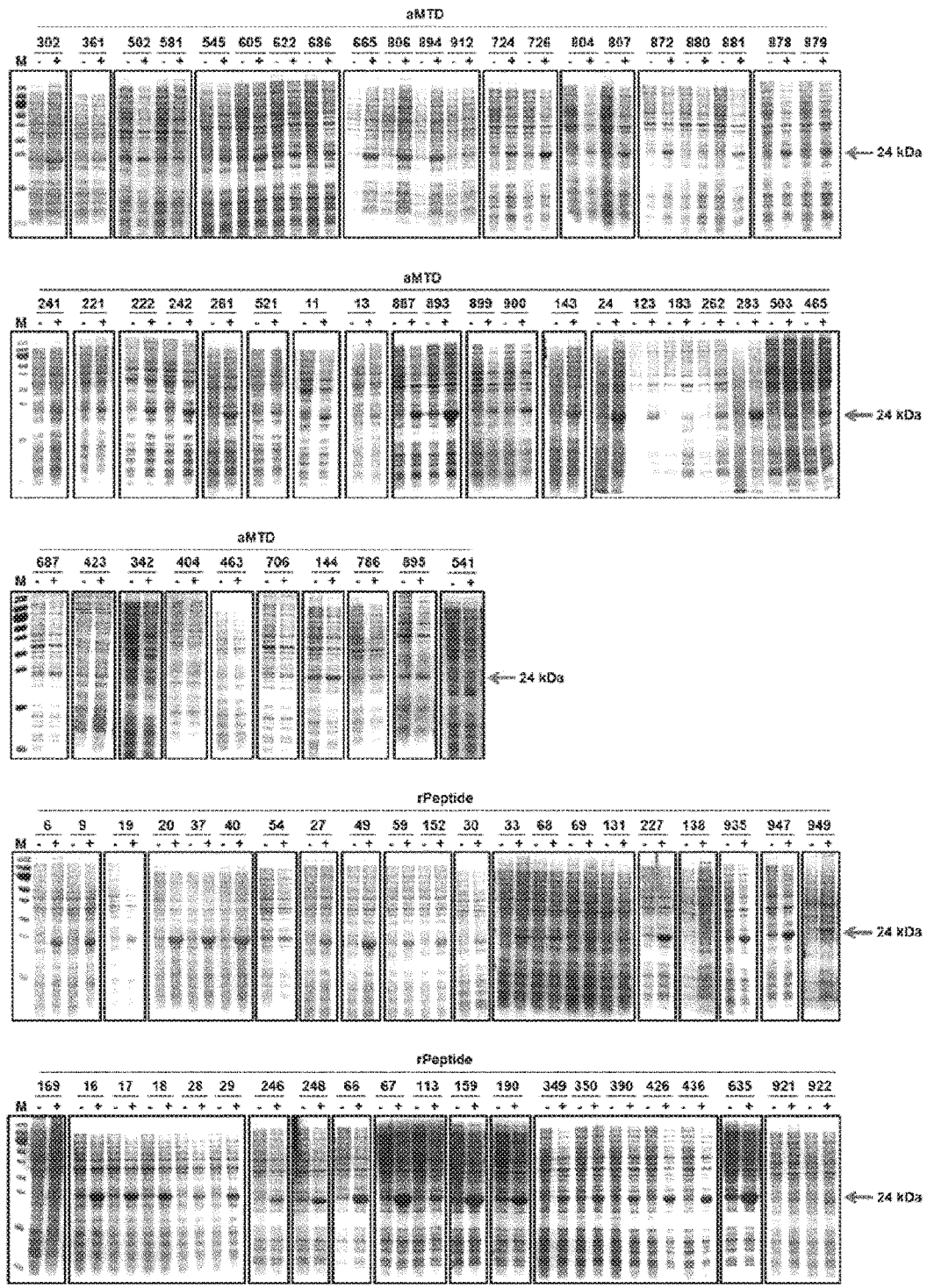

[Fig. 3d]
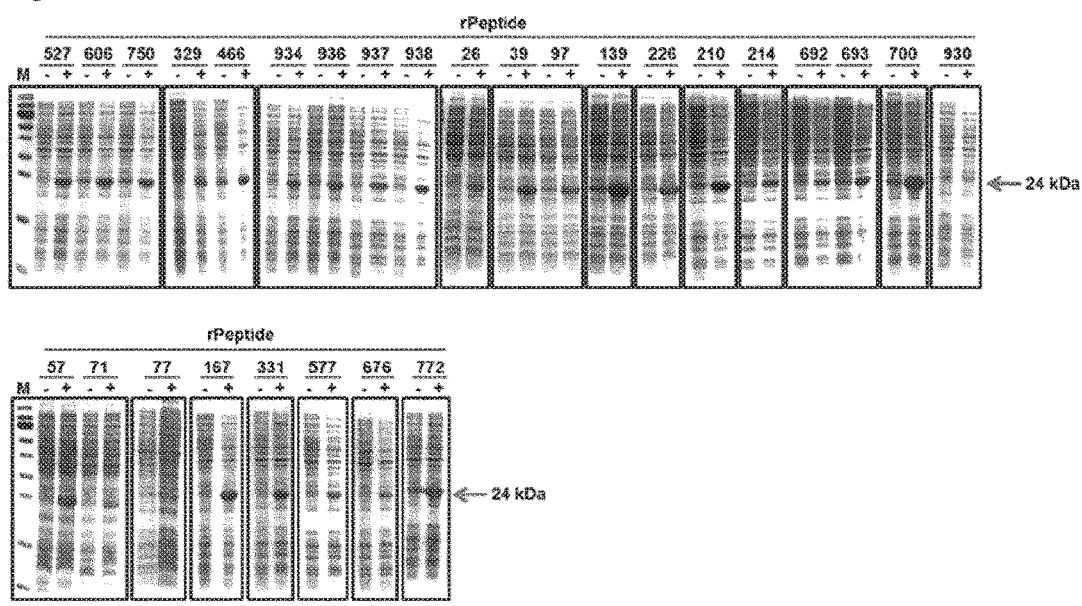

[Fig. 4a]
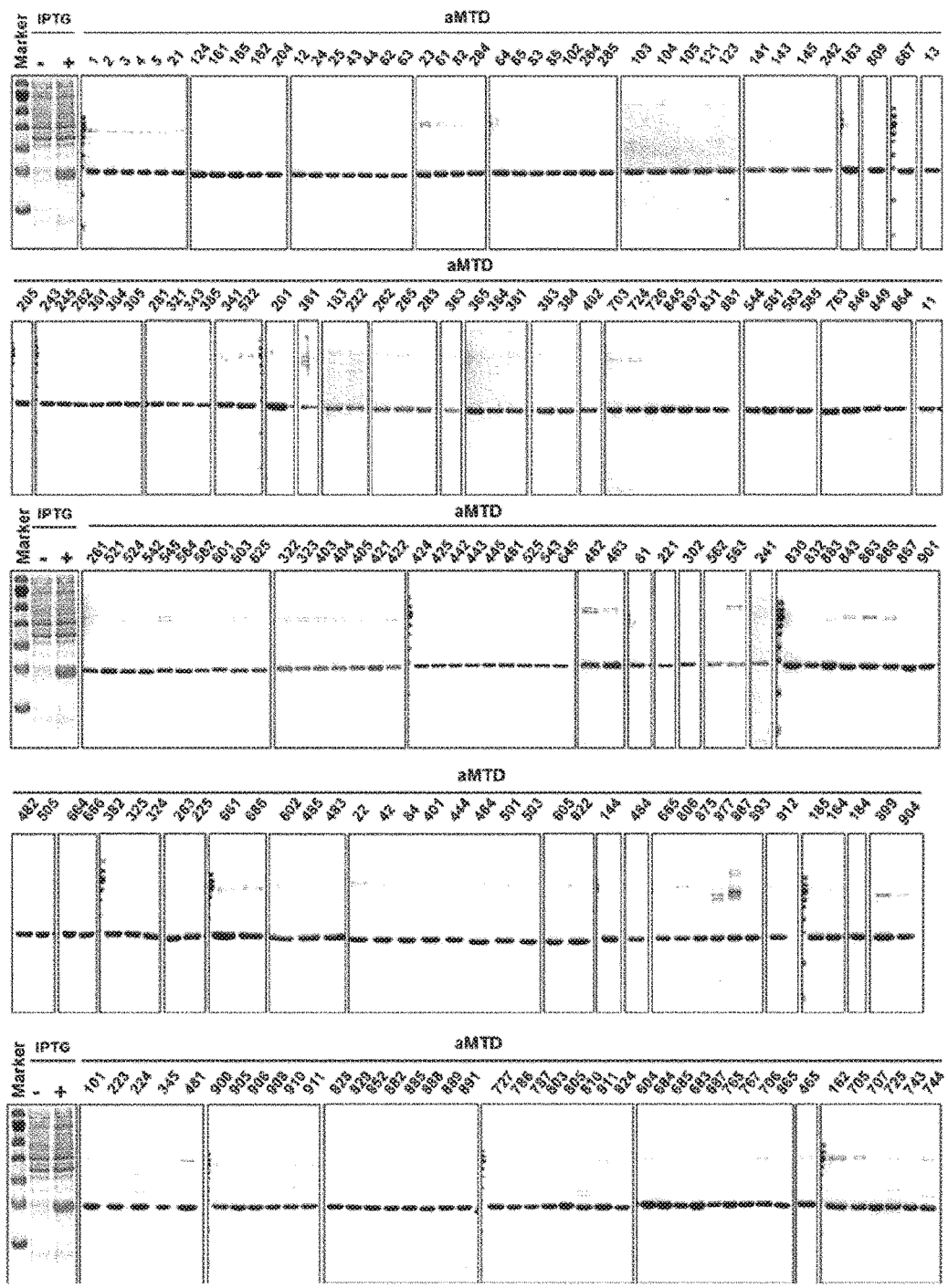

[Fig. 4b]
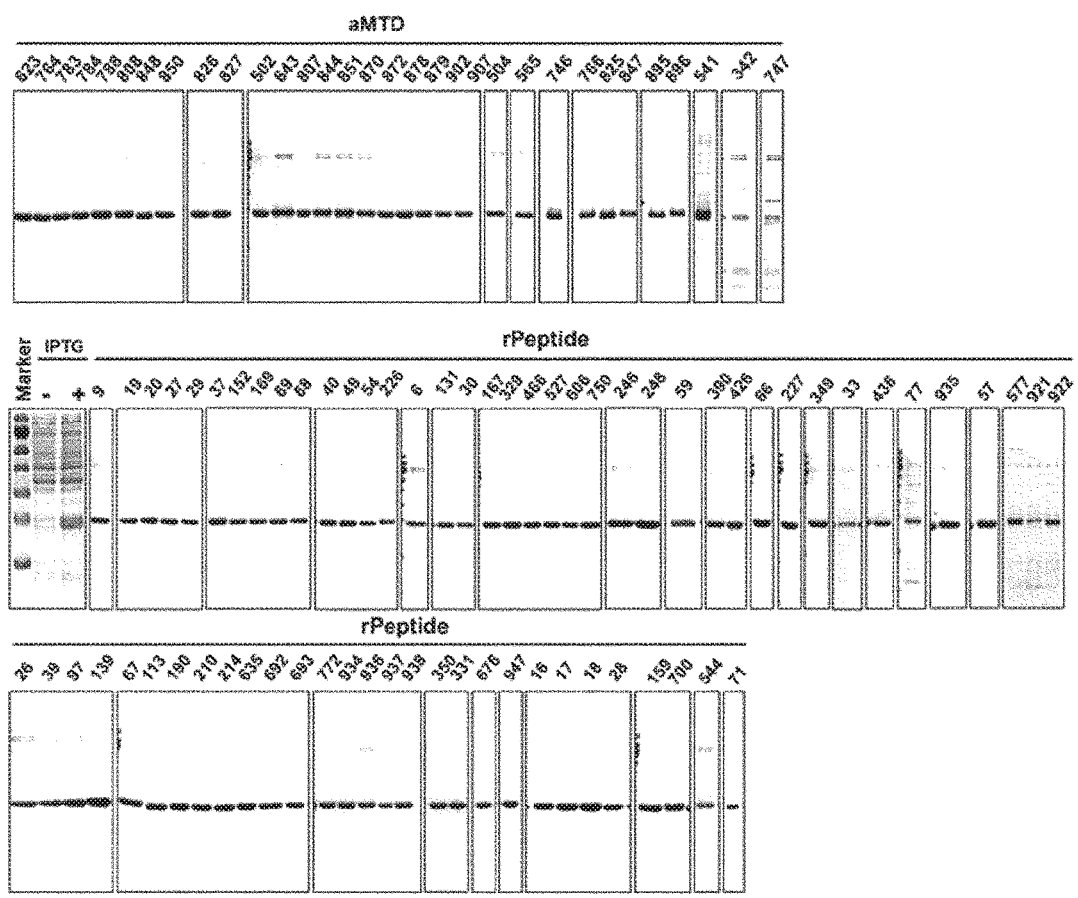

[Fig. 5a]
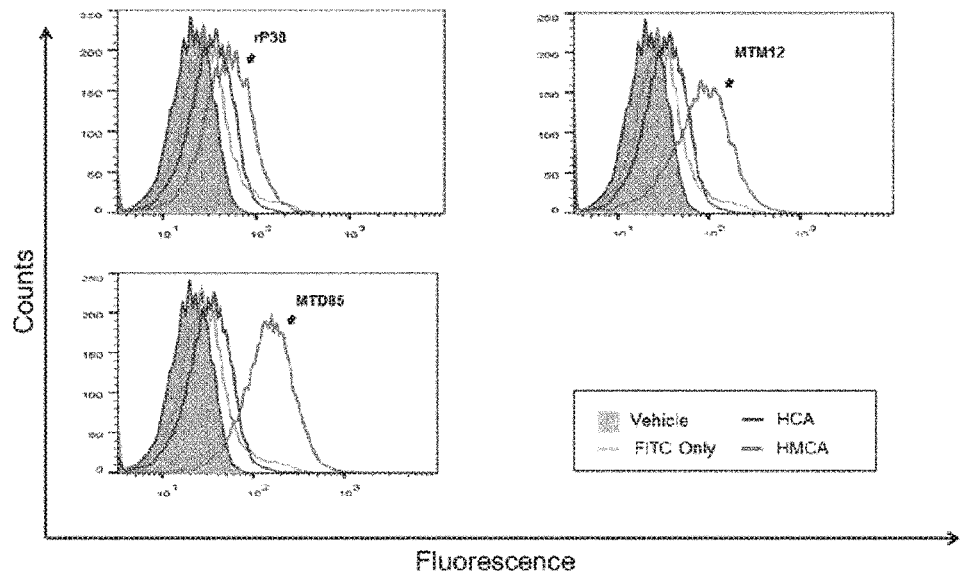
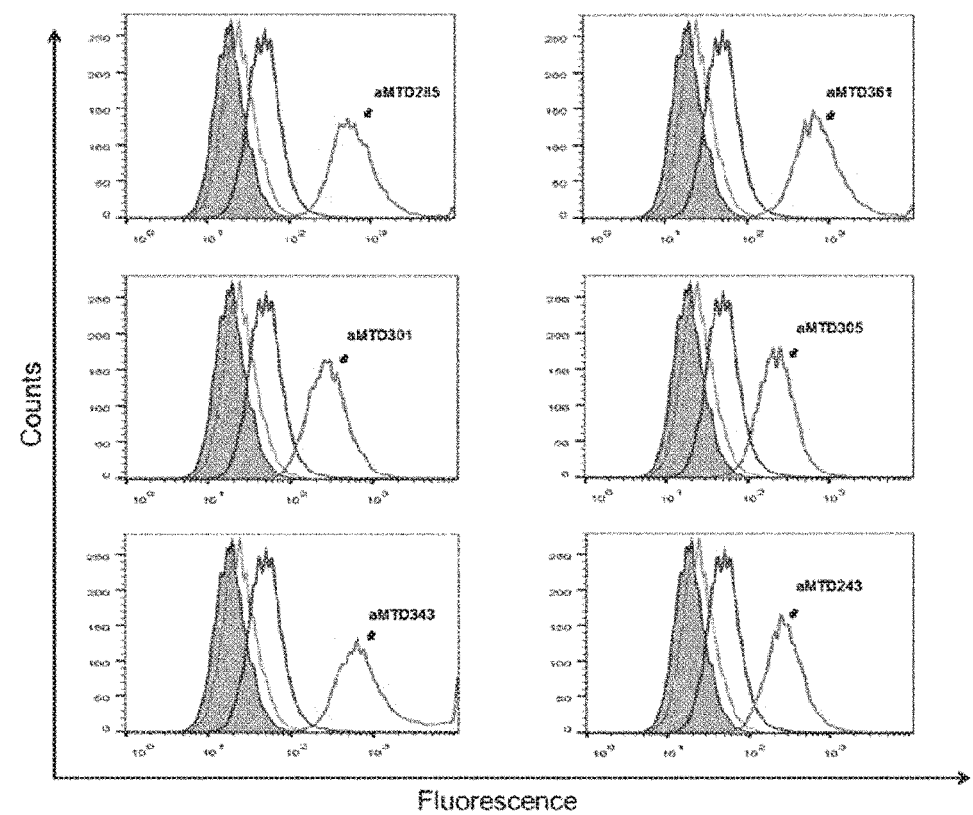

[Fig. 5b]
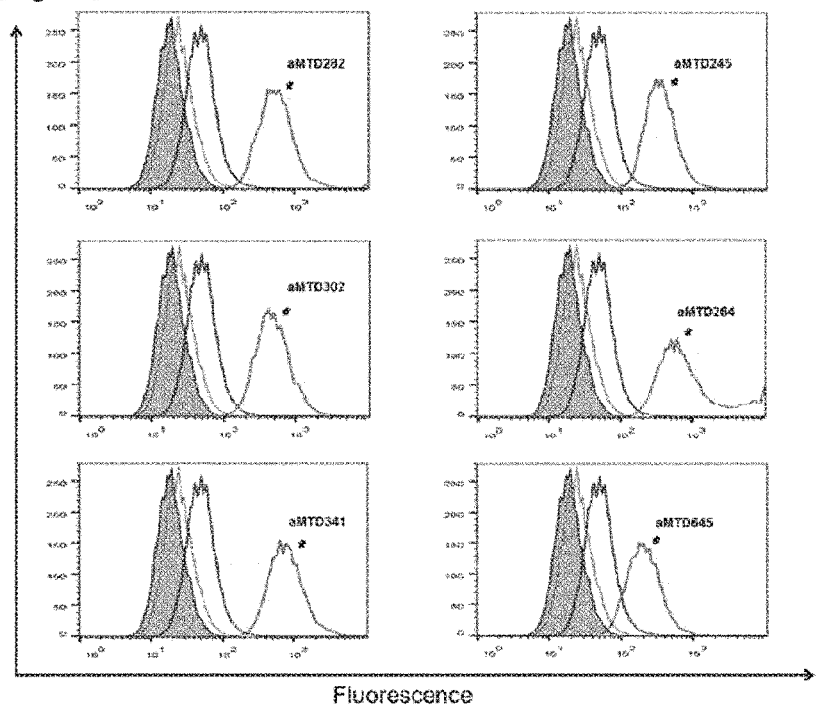
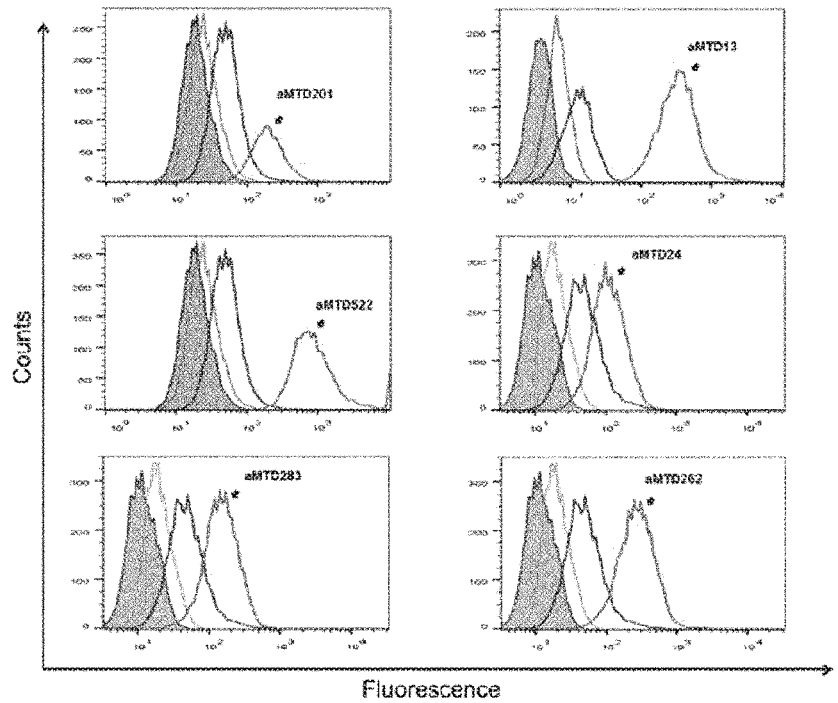

[Fig. 5c]
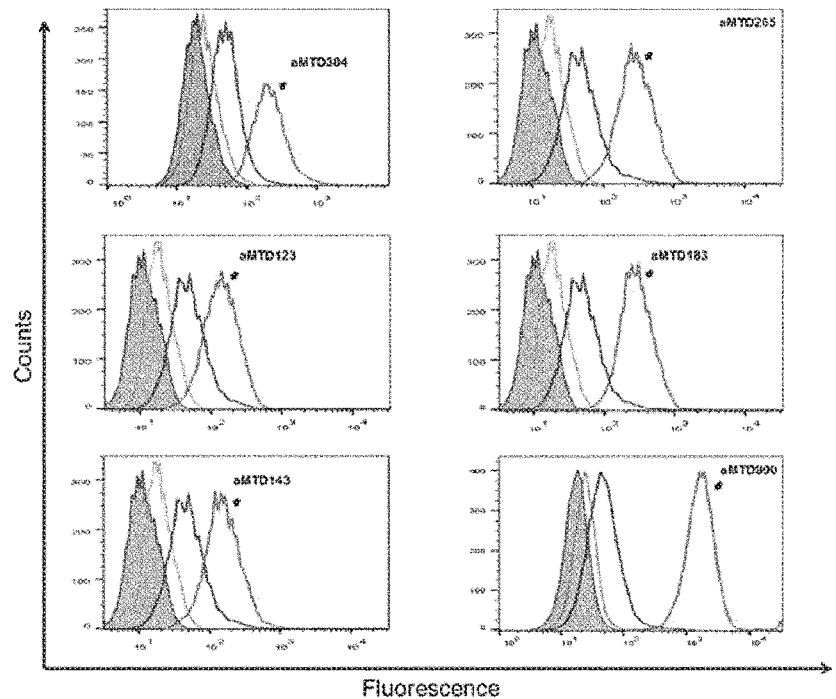
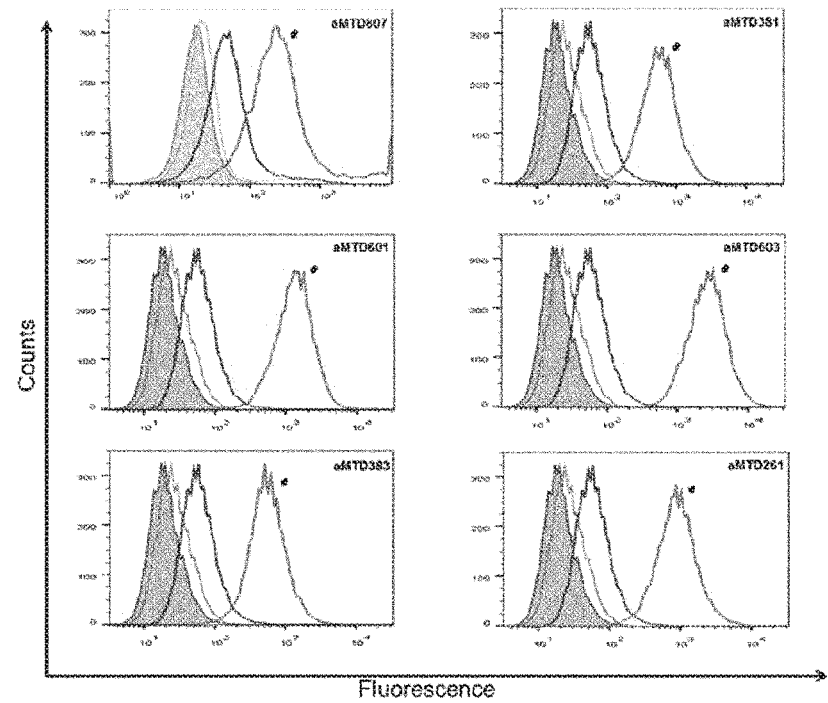

[Fig. 5d]
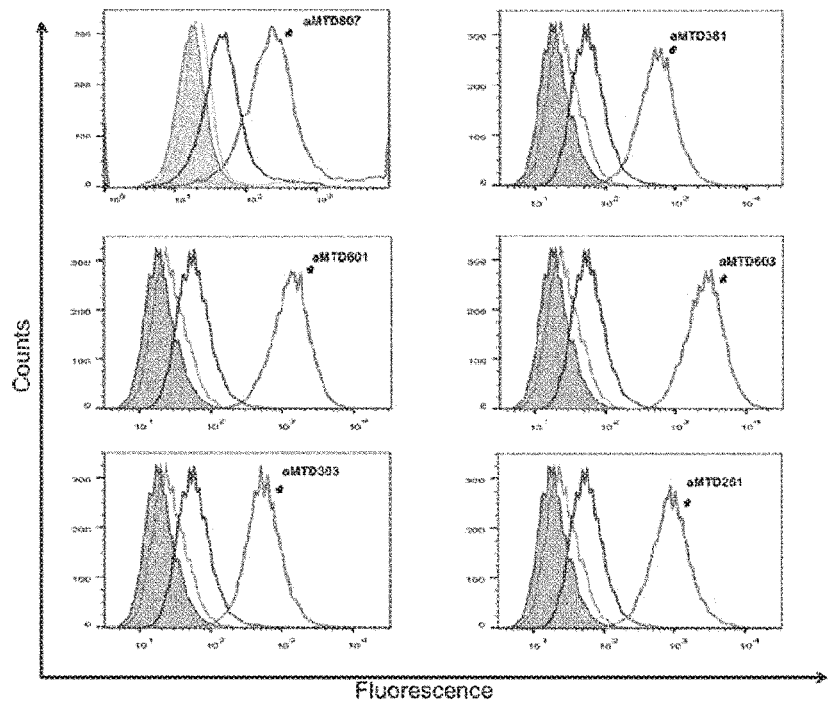
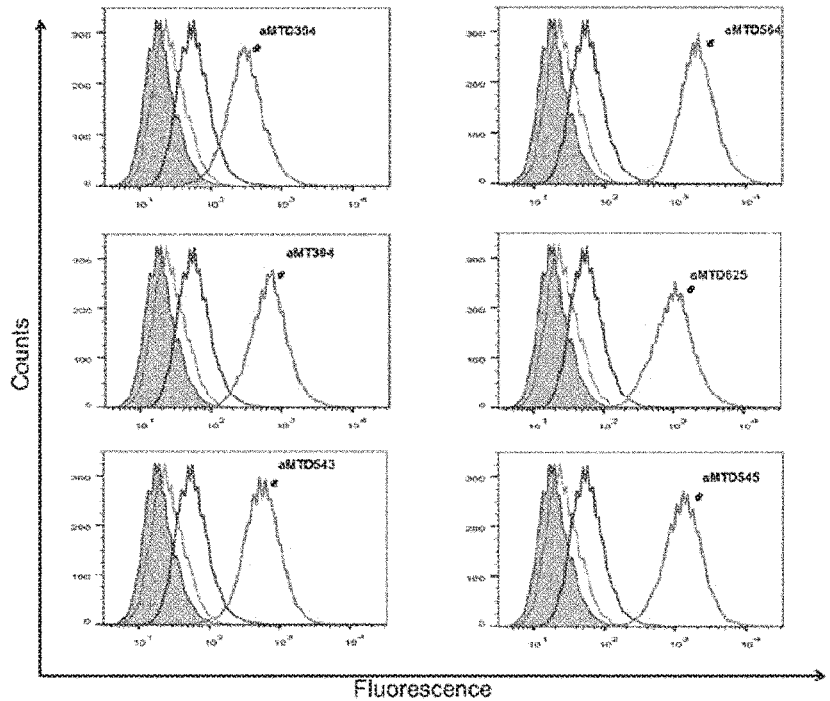

[Fig. 5e]
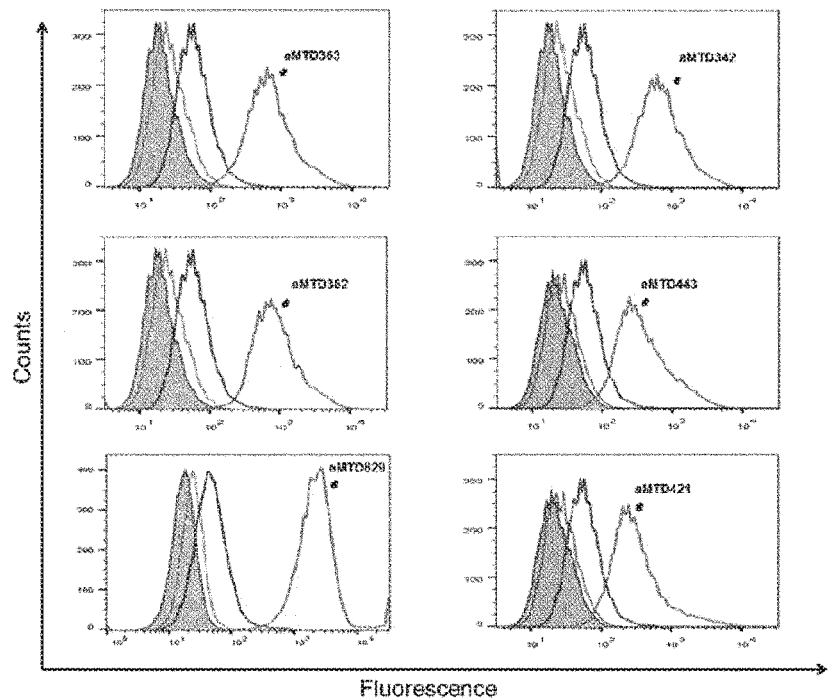
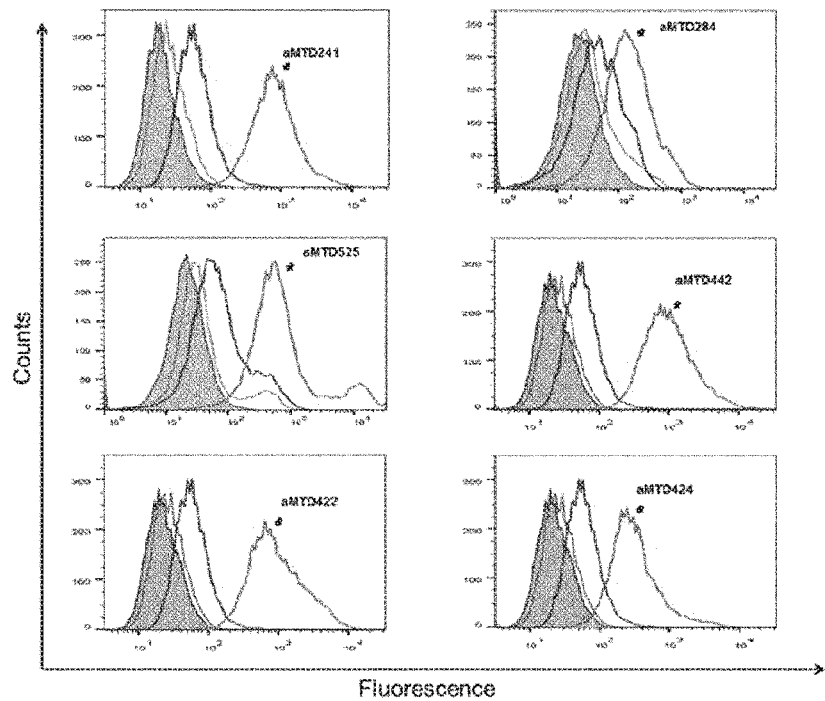

[Fig. 5f]
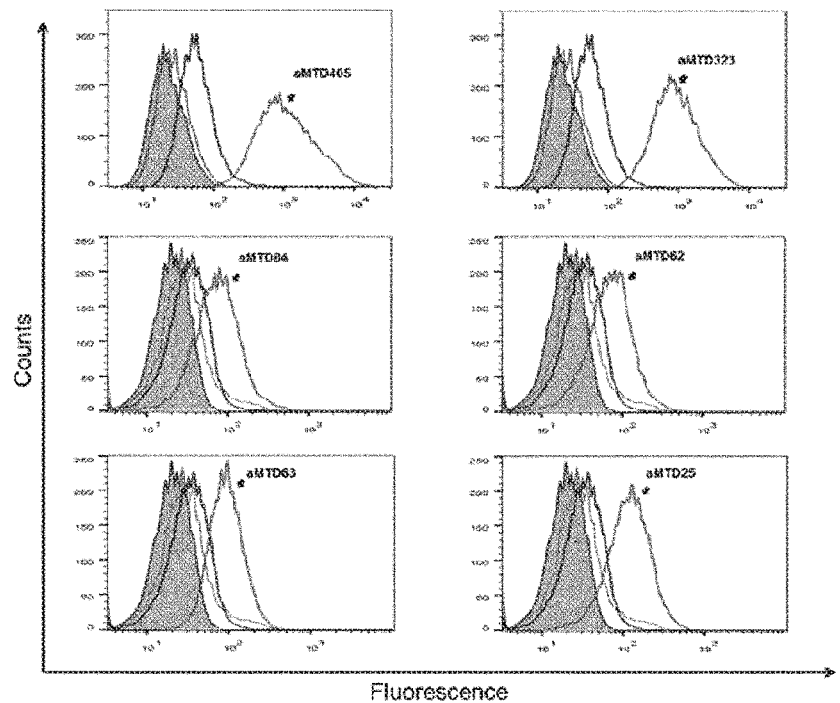
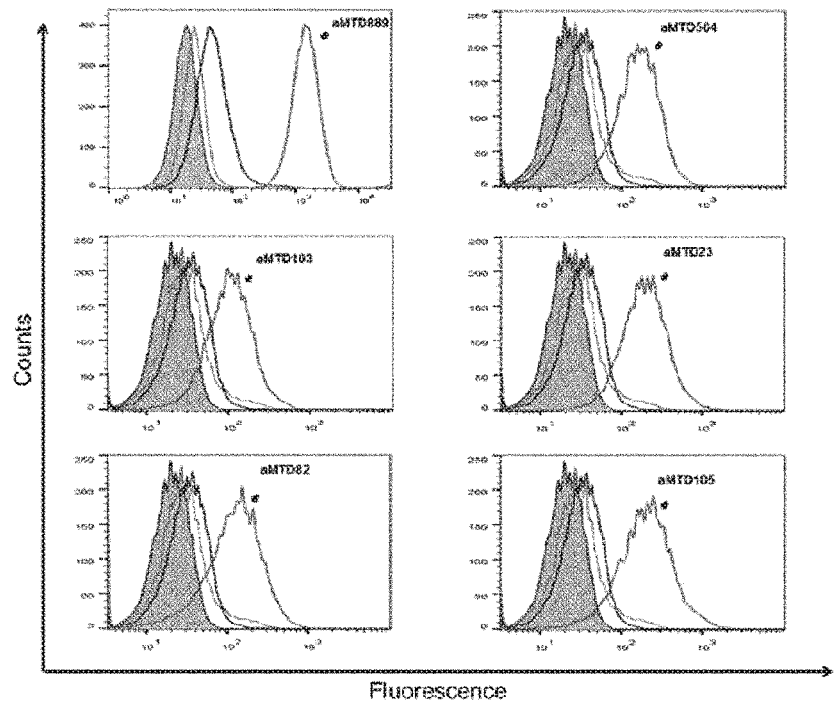

[Fig. 5g]
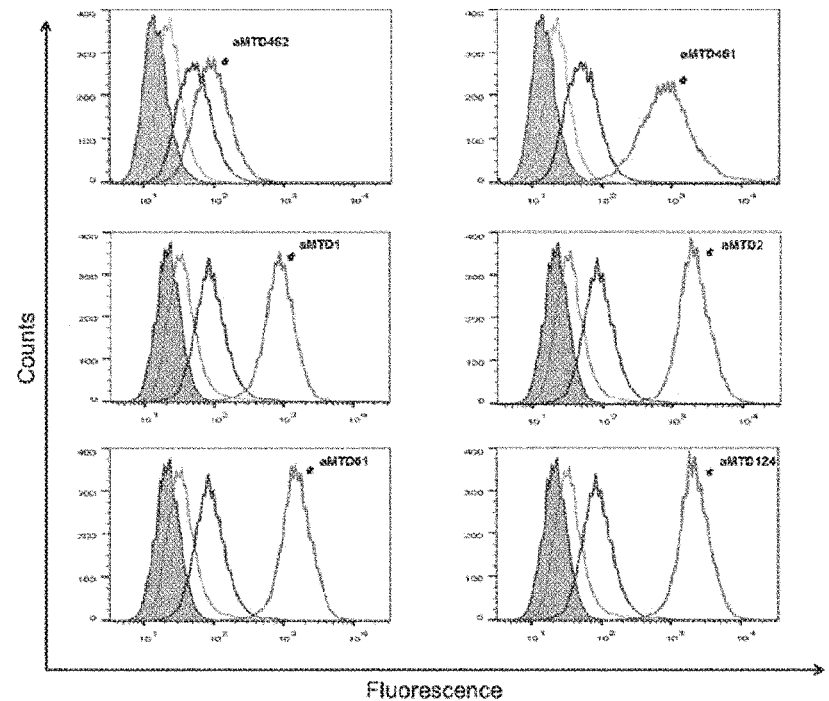
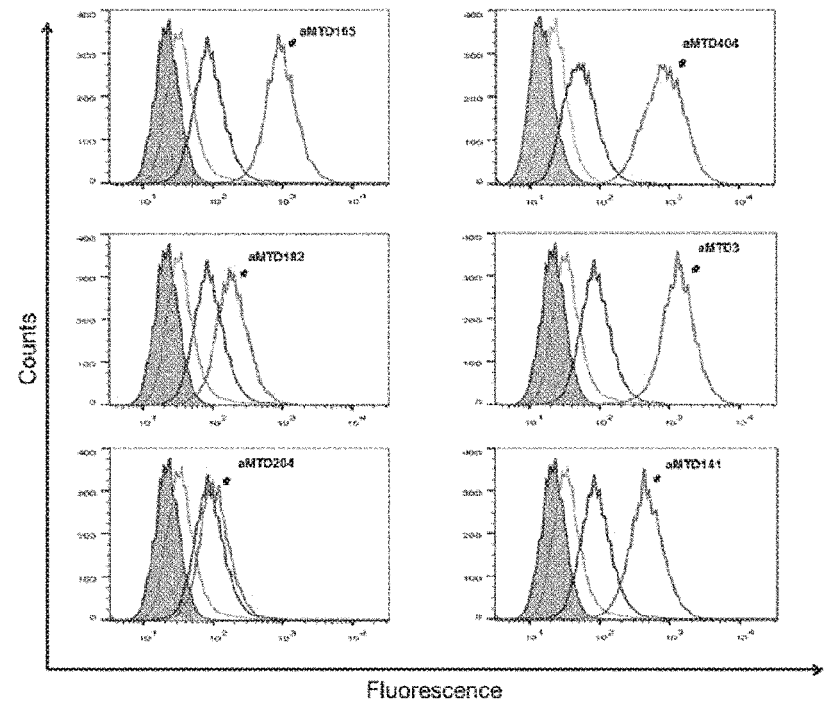

[Fig. 5h]
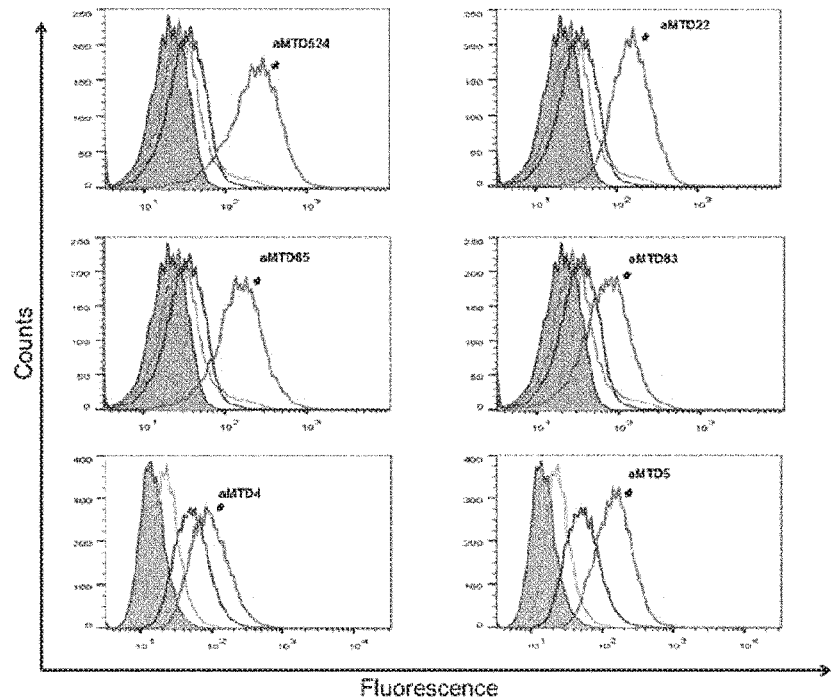
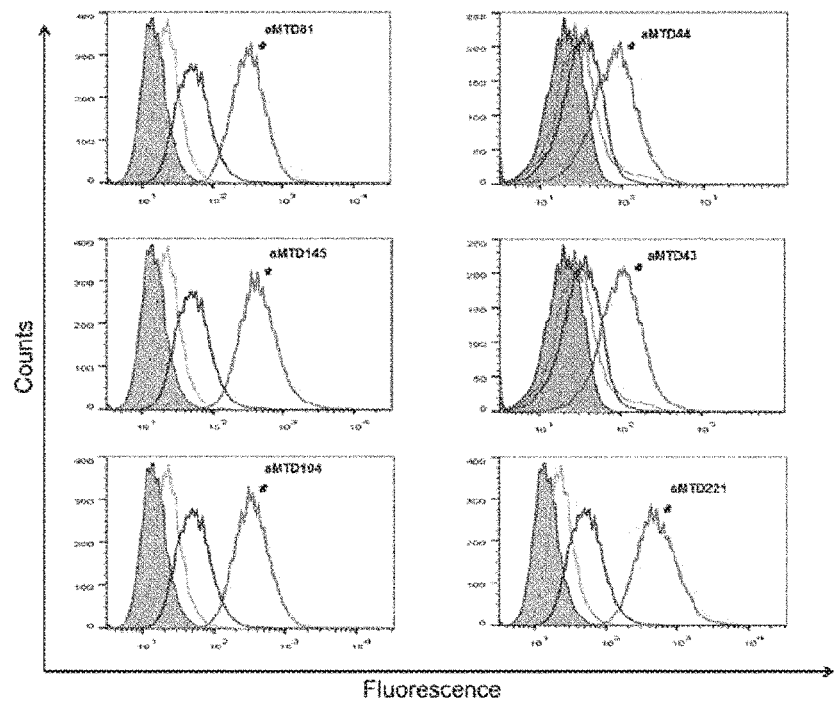

[Fig. 5i]
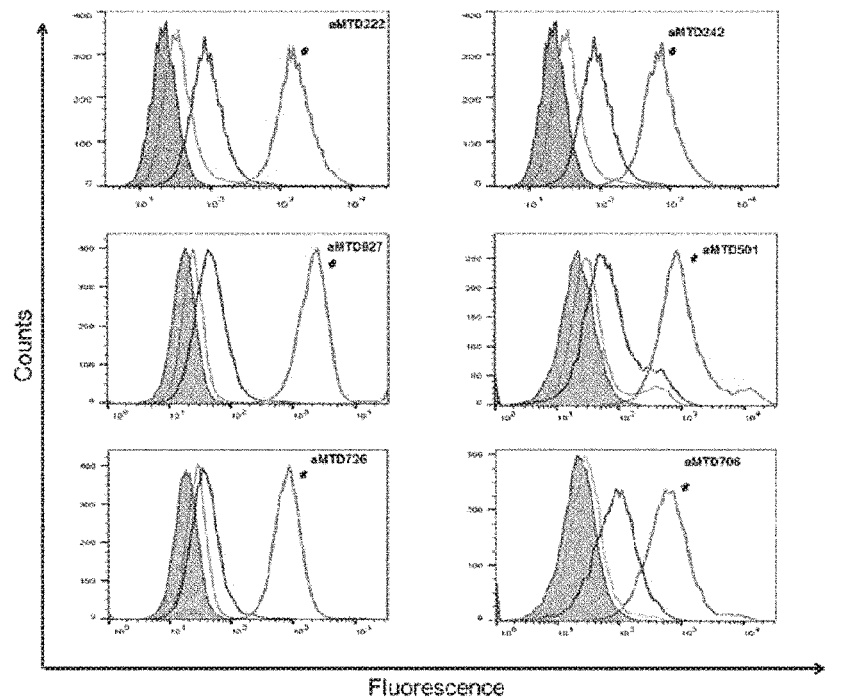
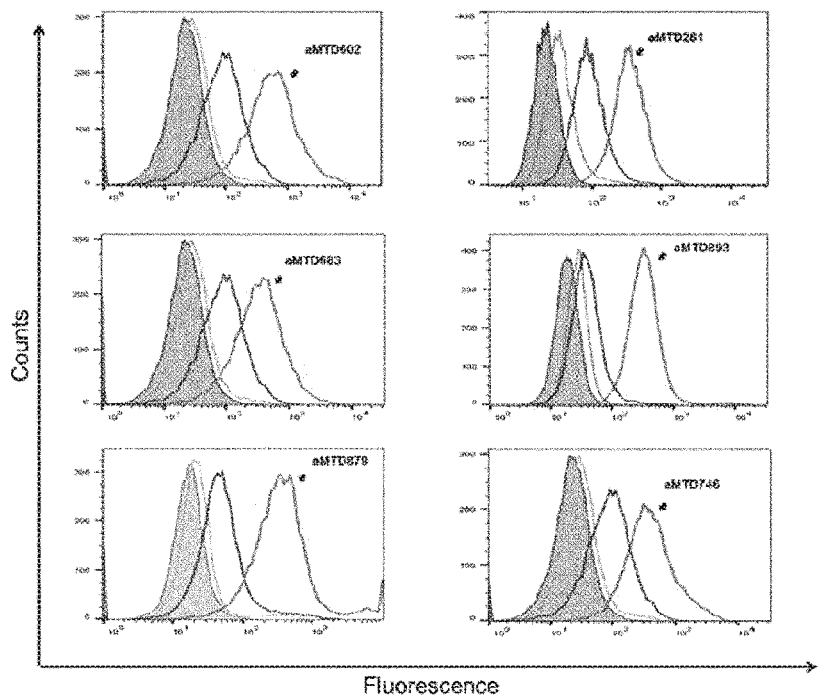

[Fig. 5j]
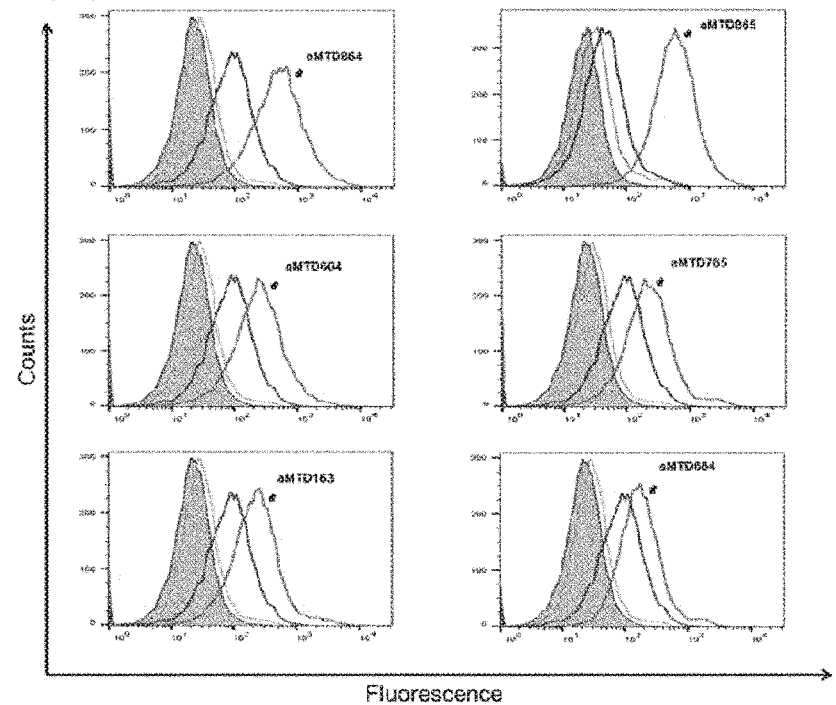
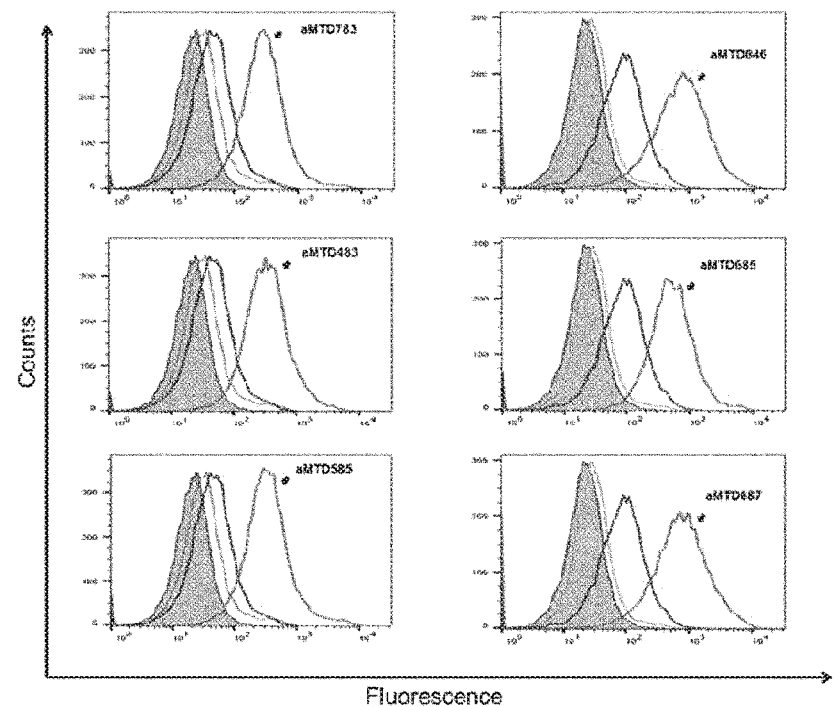

[Fig. 5k]
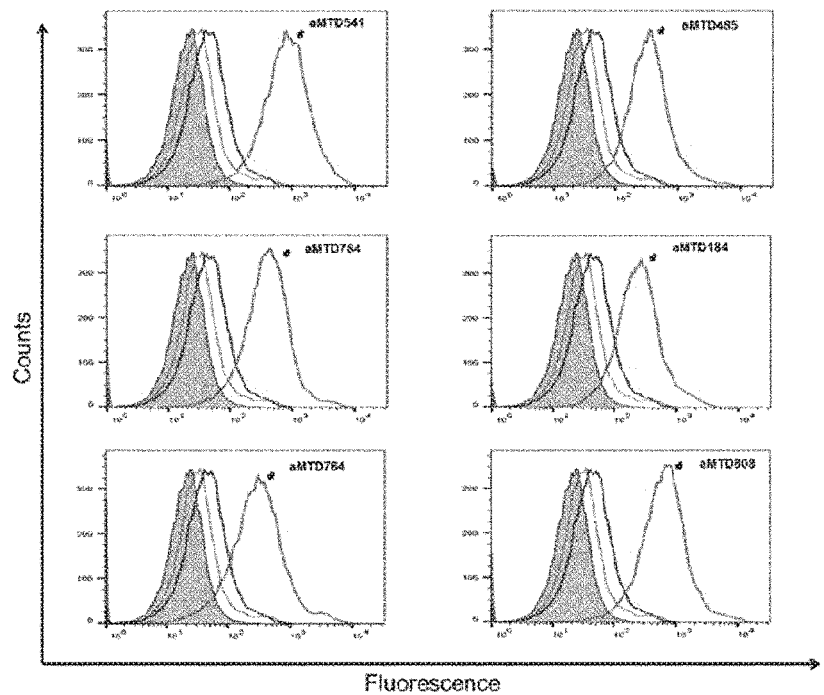
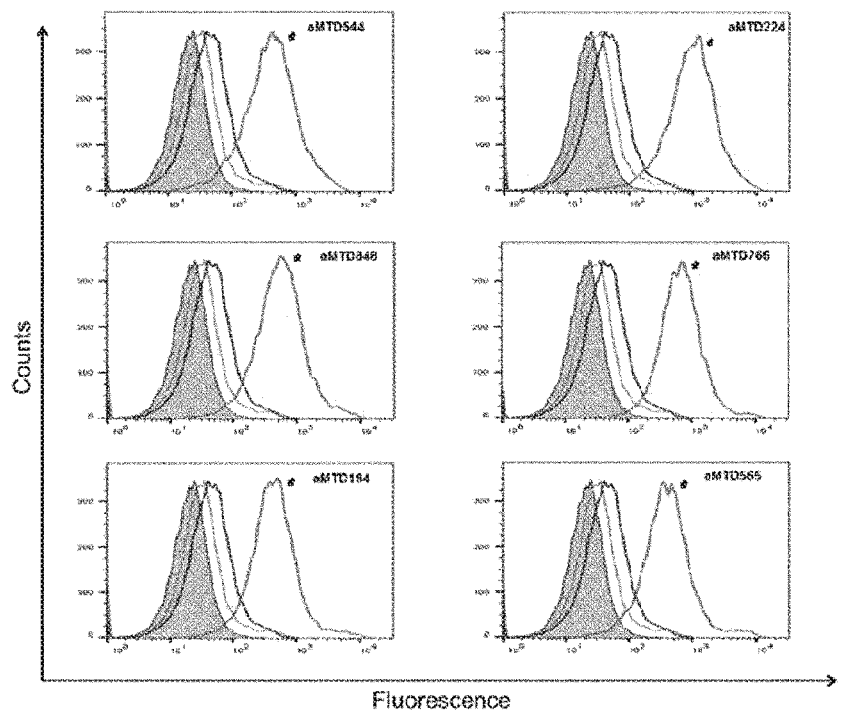

[Fig. 5I]
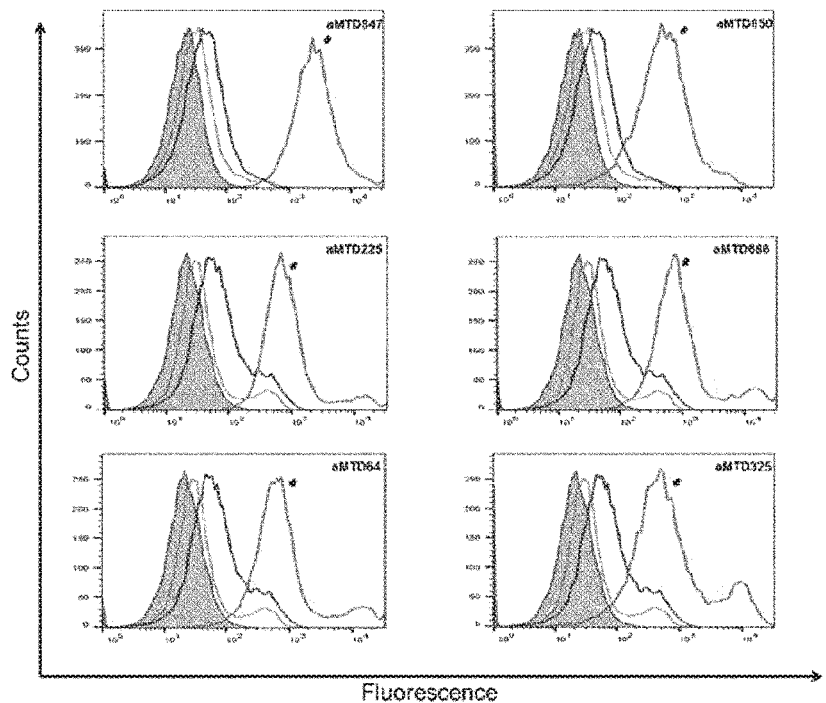
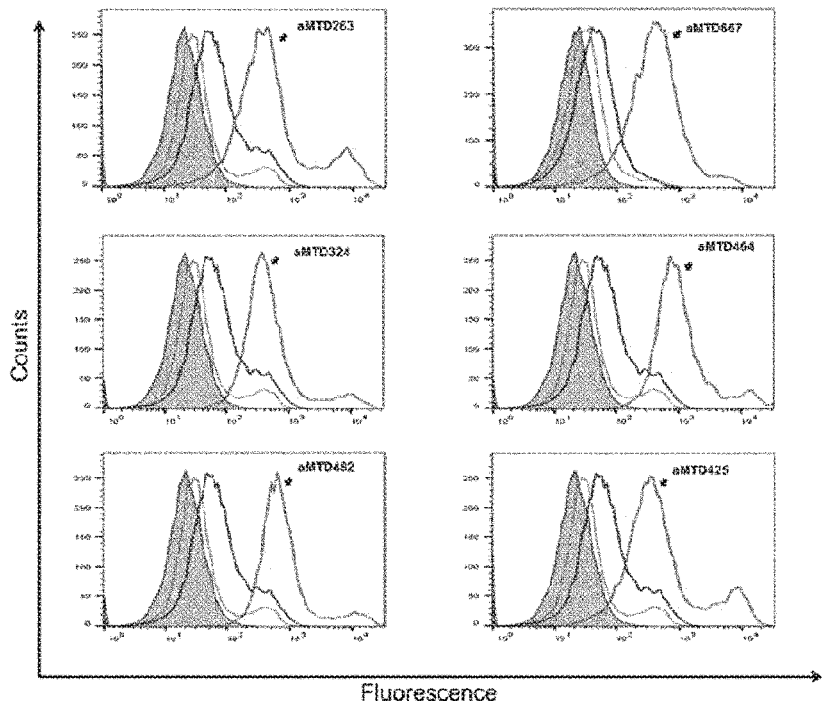

[Fig. 5m]
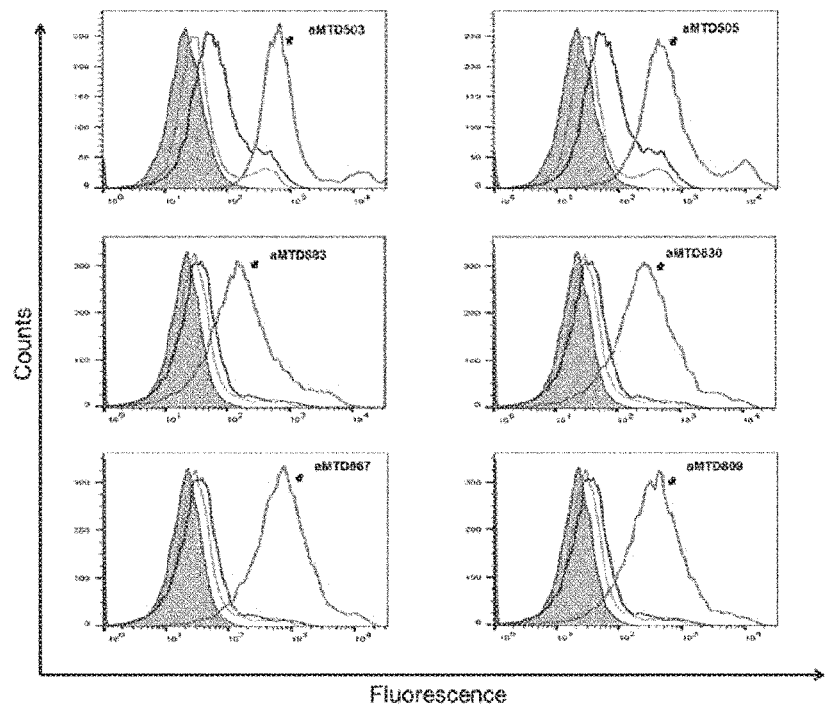
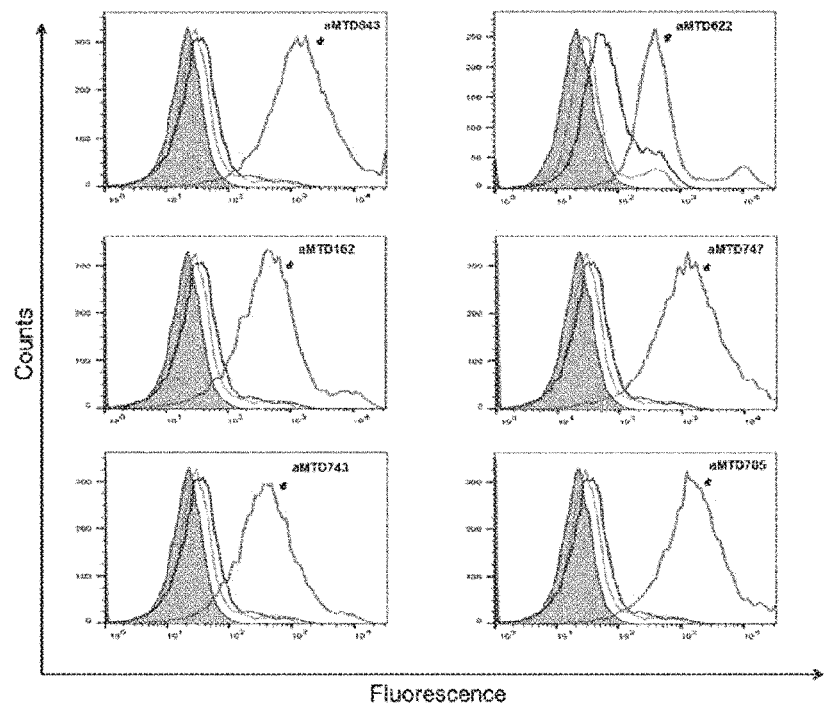

[Fig. 5n]
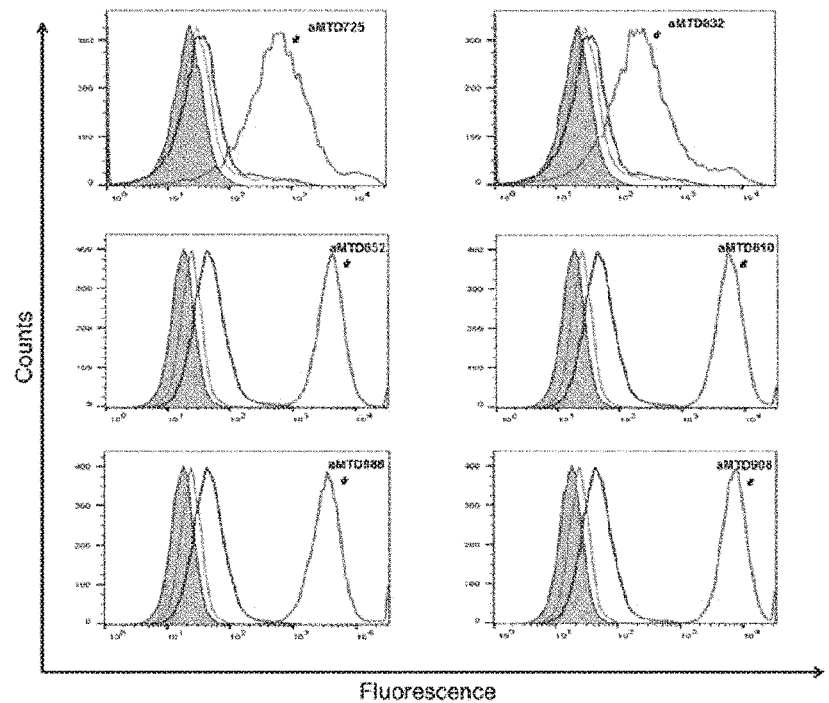
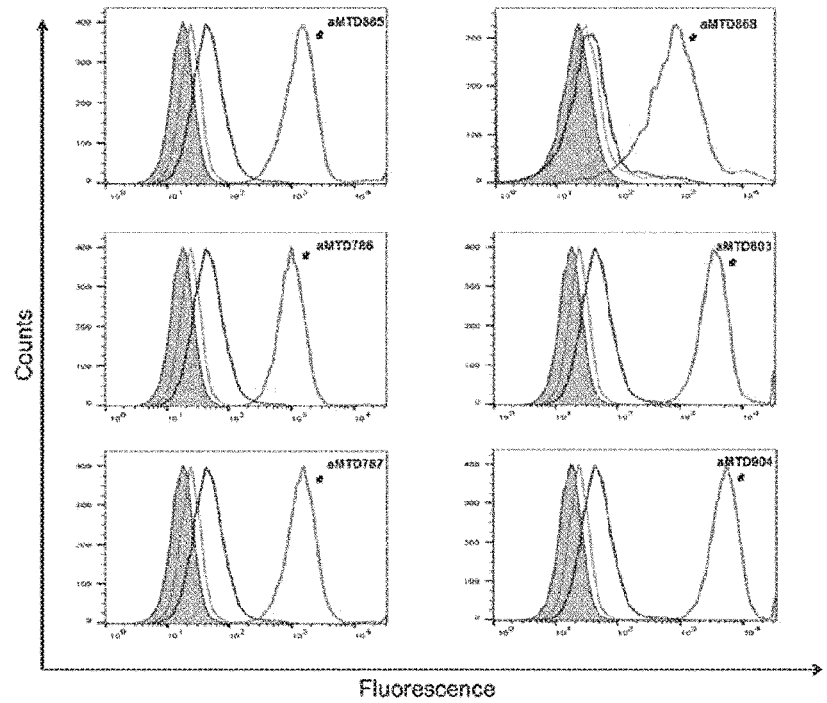

[Fig. 5o]
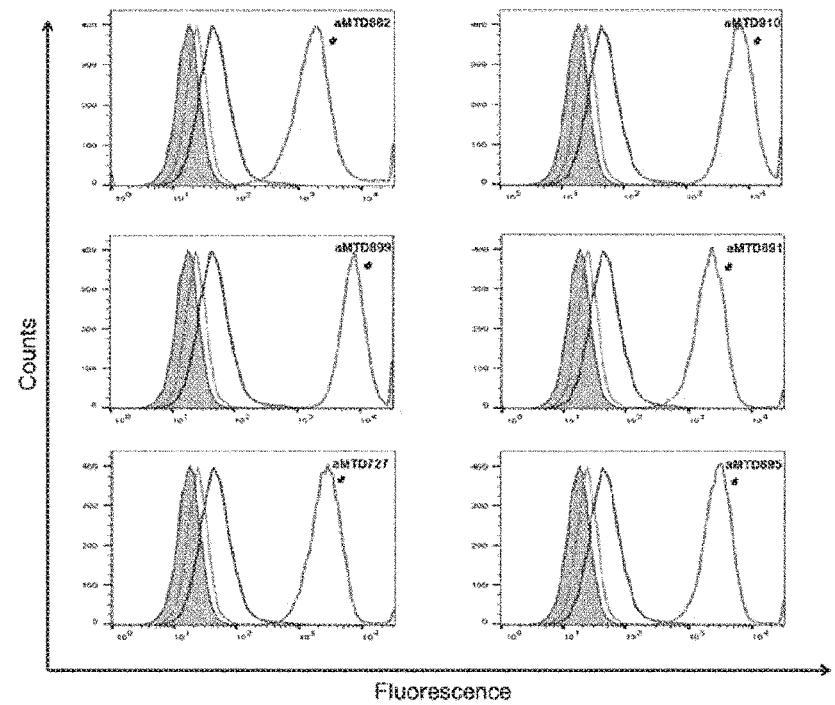
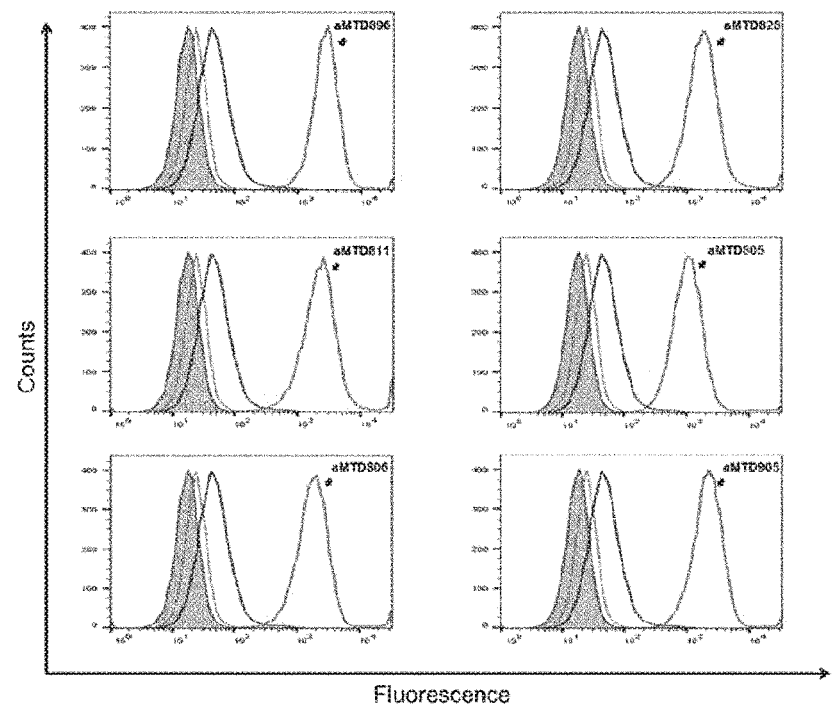

[Fig. 5p]
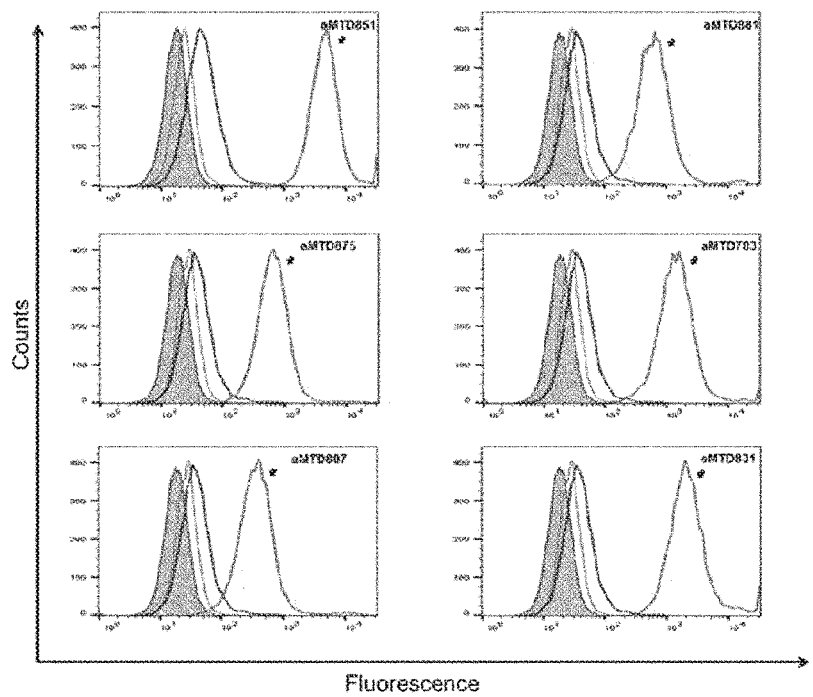
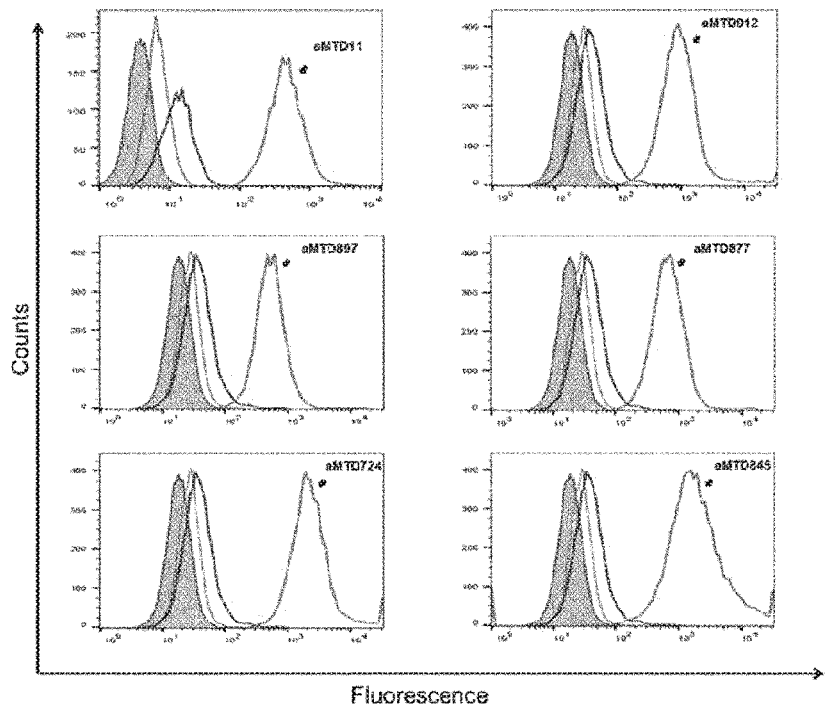

[Fig. 5q]
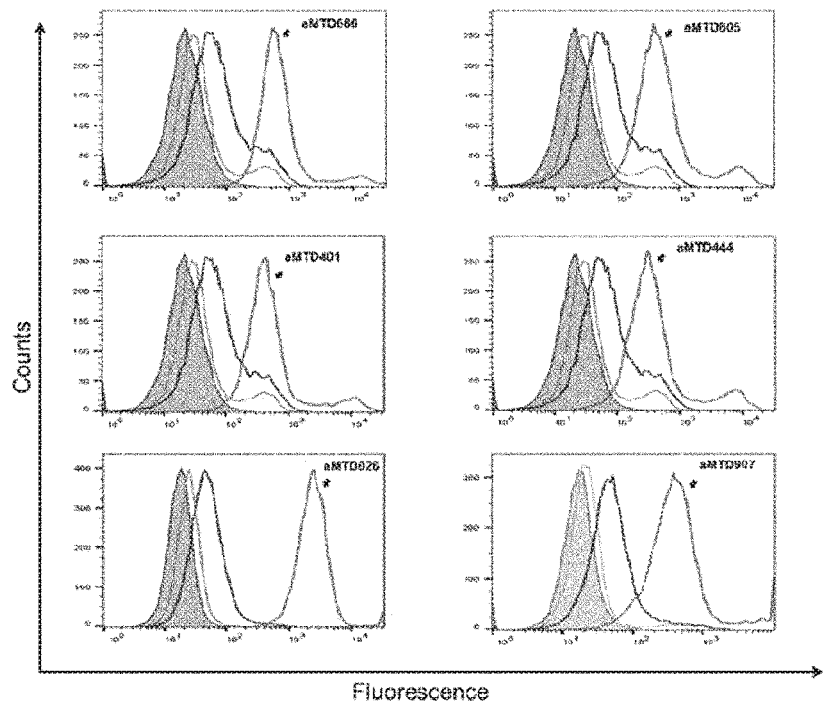
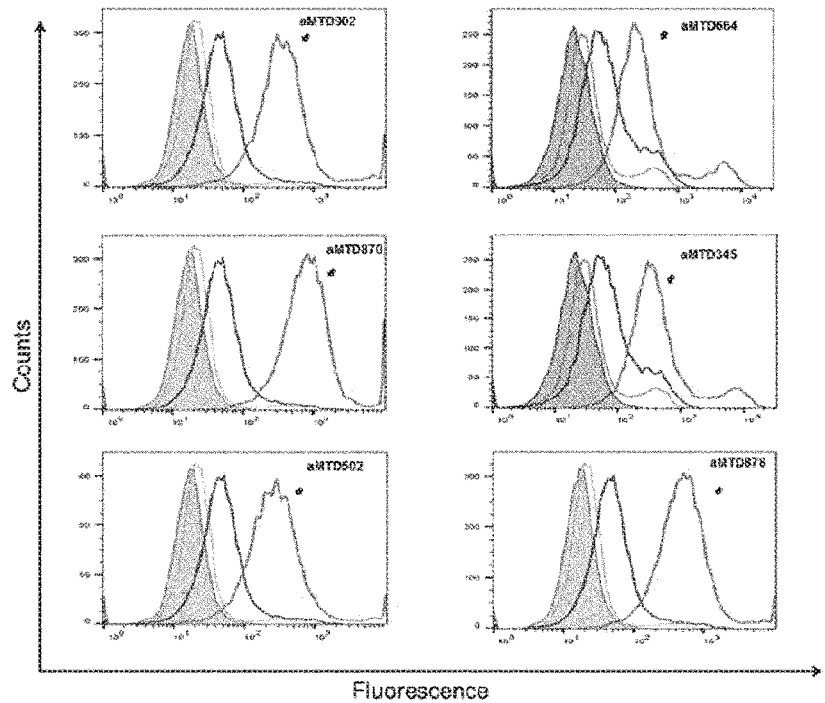

[Fig. 5r]
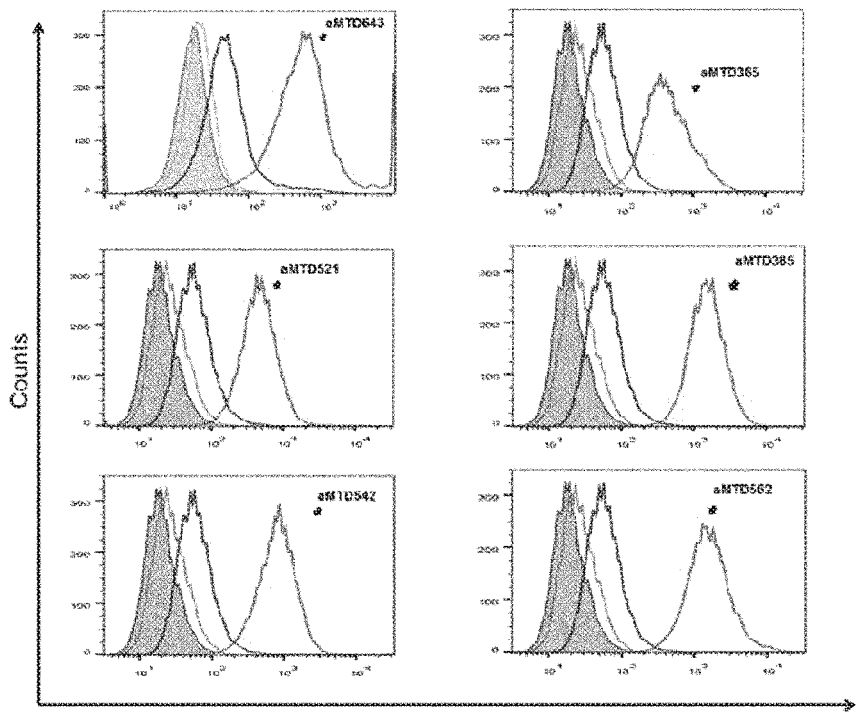
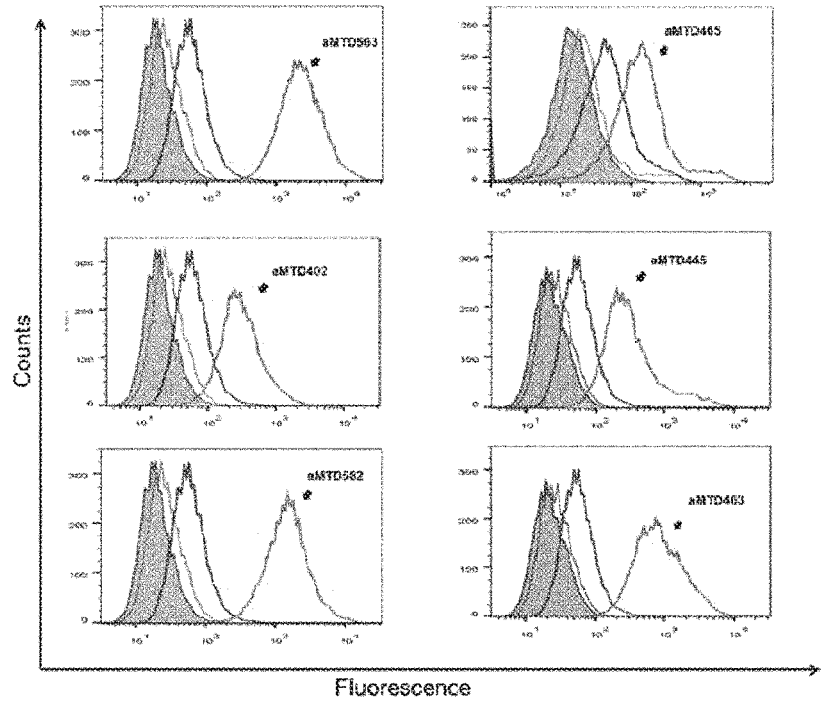

[Fig. 5s]
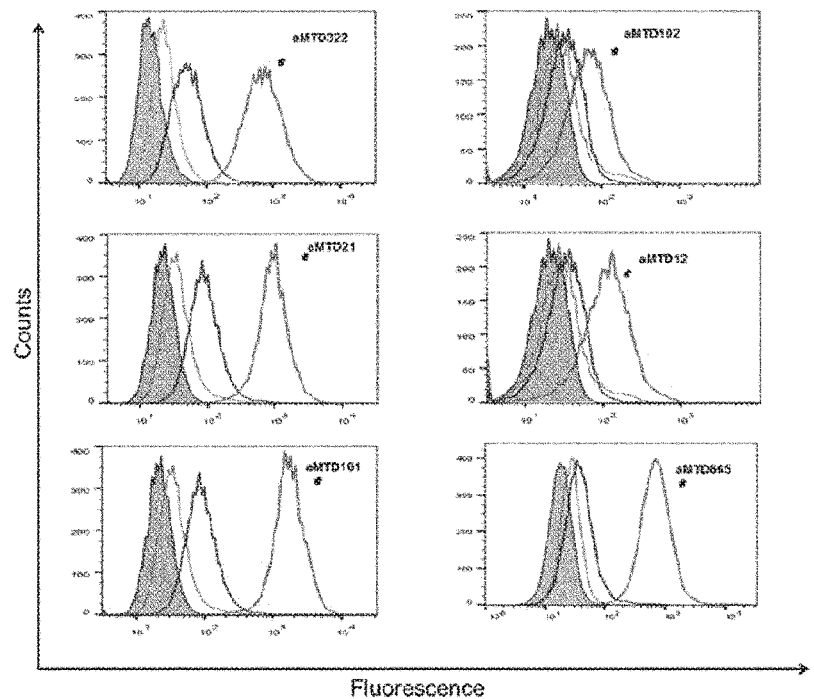
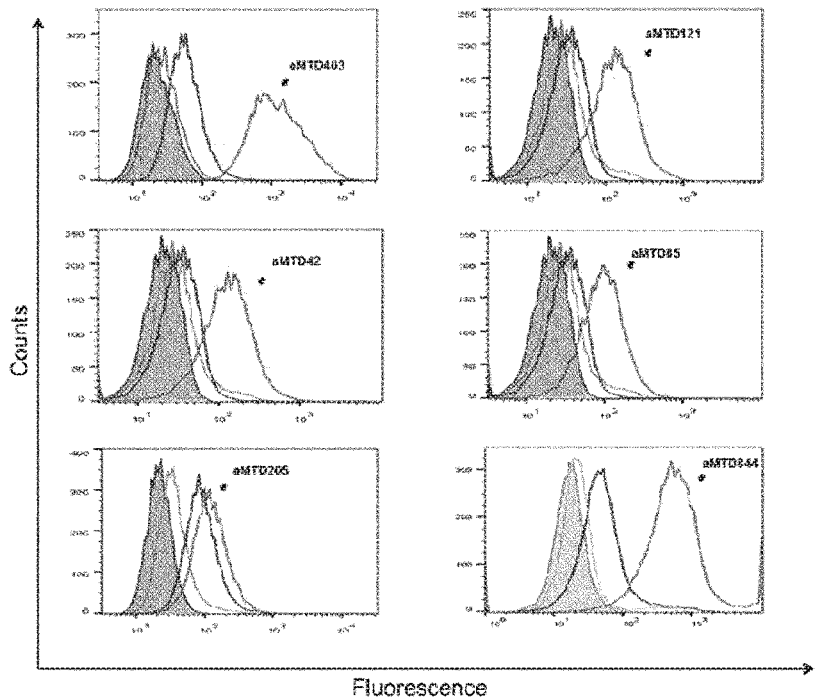

[Fig. 5t]
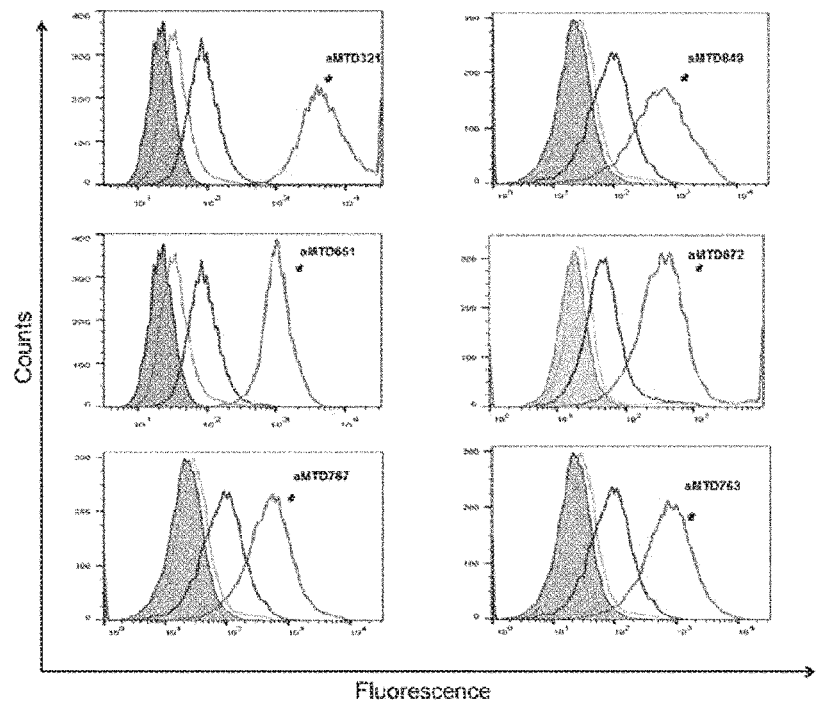
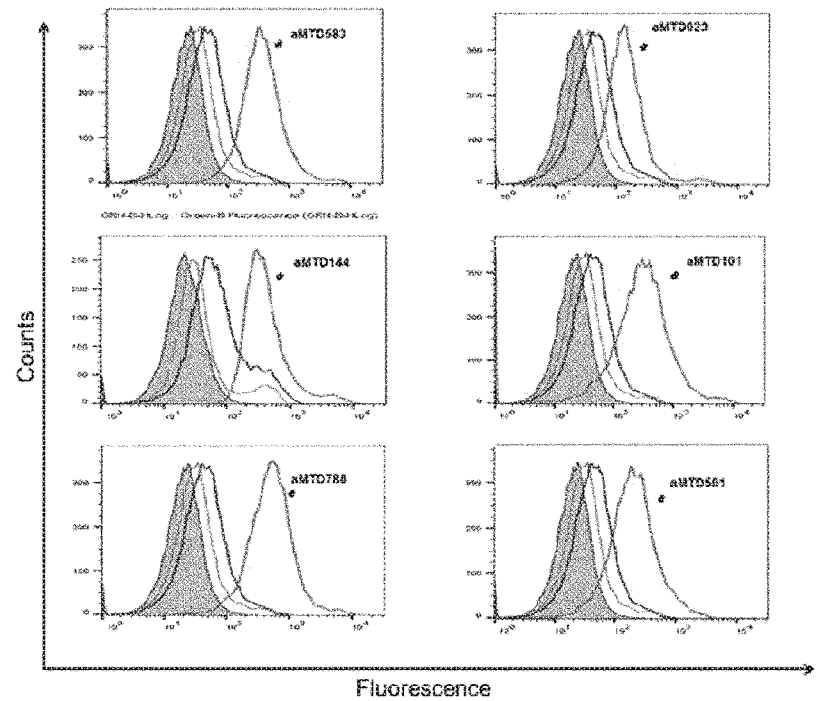

[Fig. 5u]
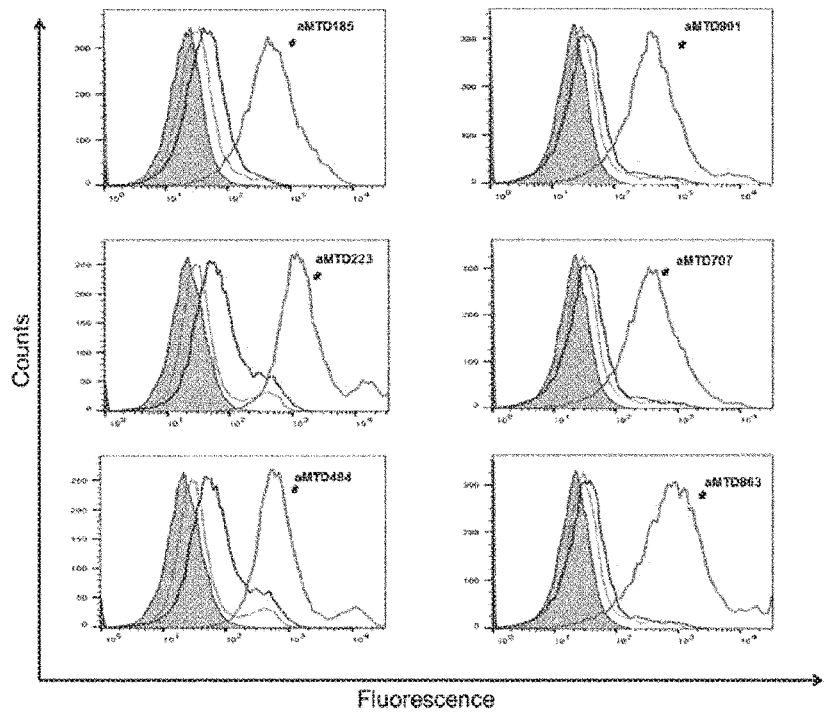
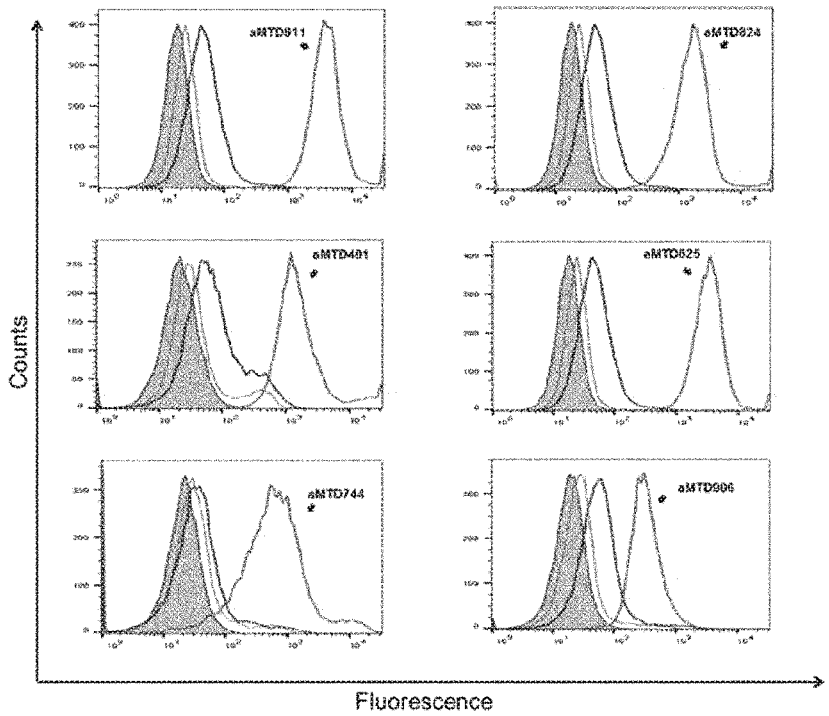

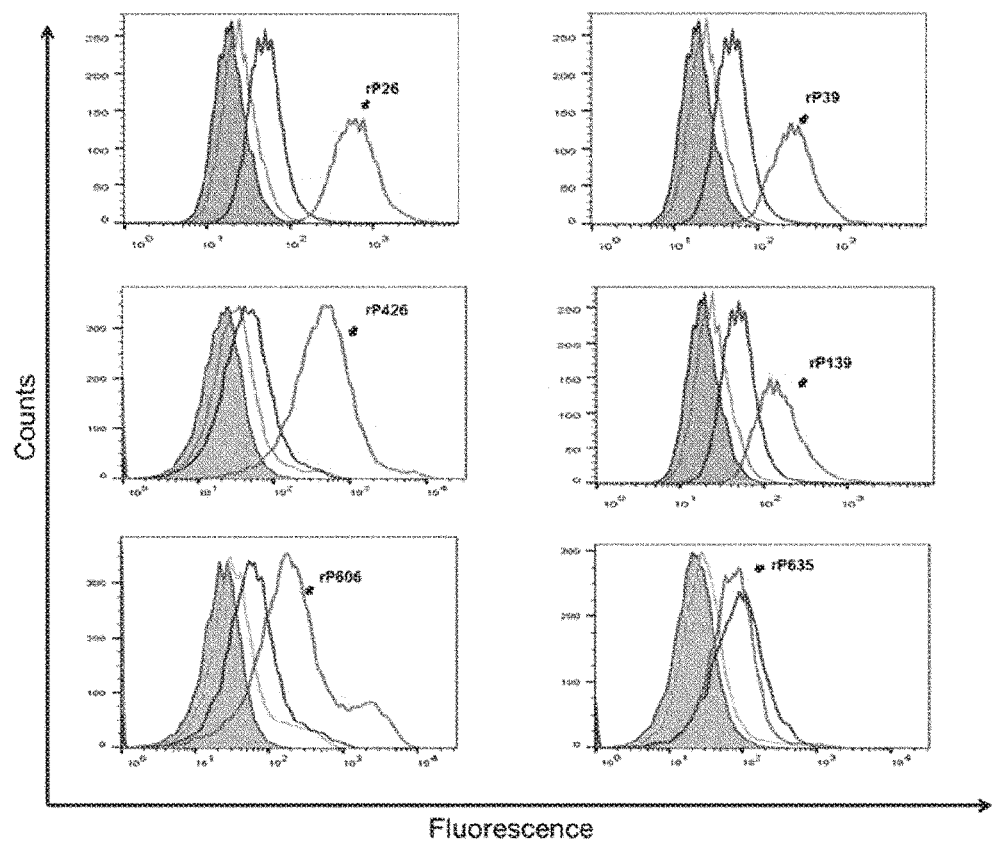
[Fig. 6a]

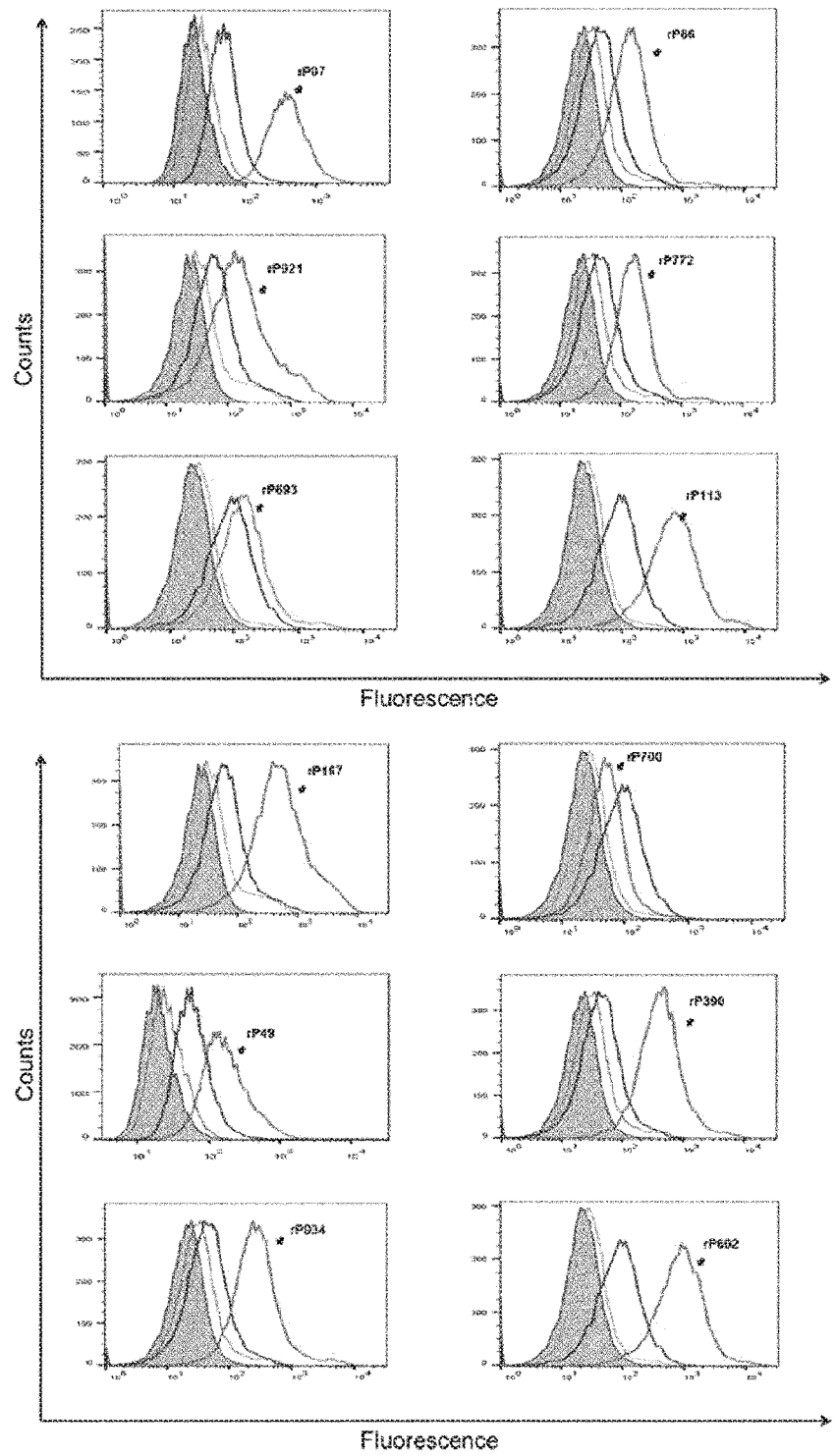

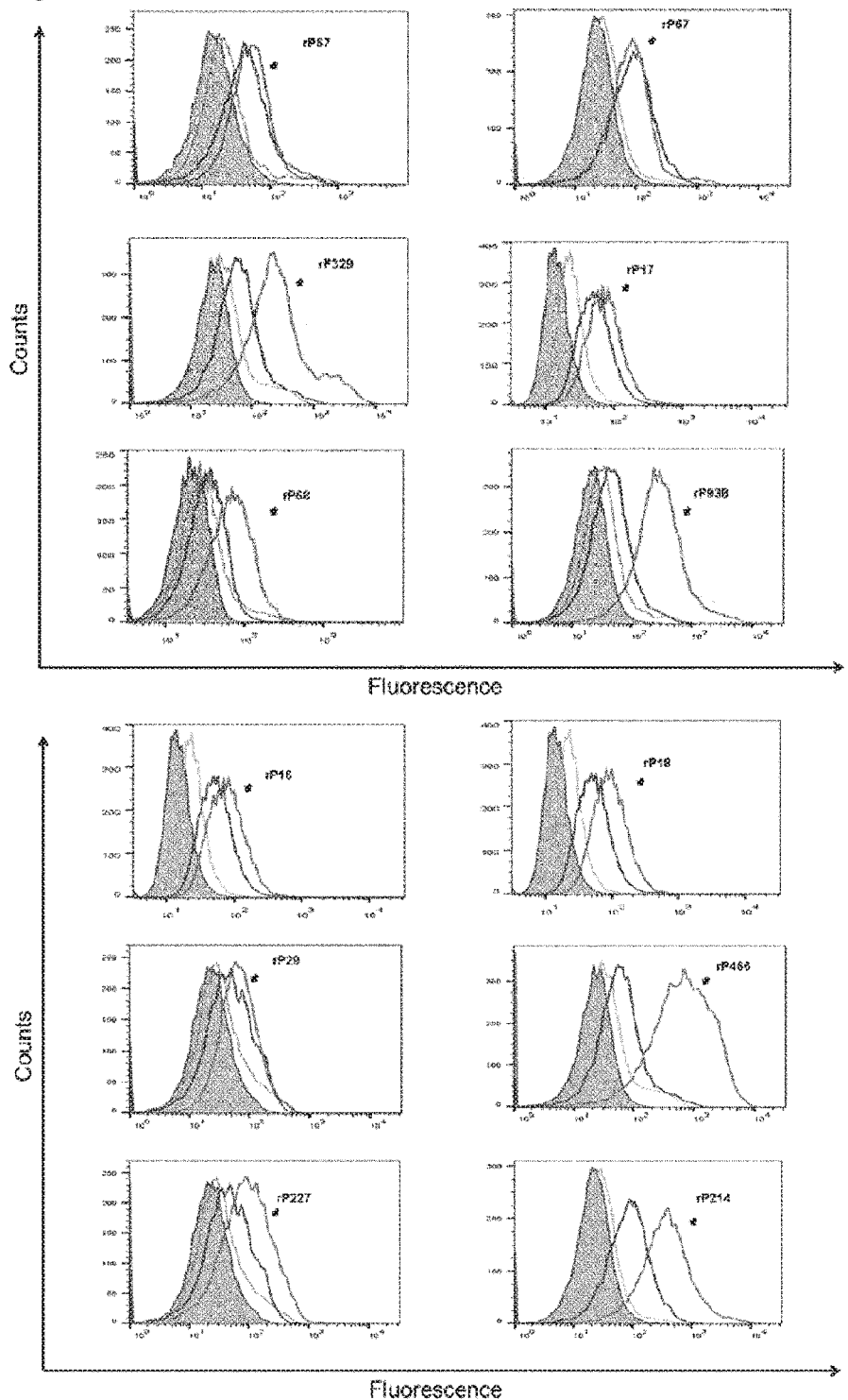

[Fig. 7a]
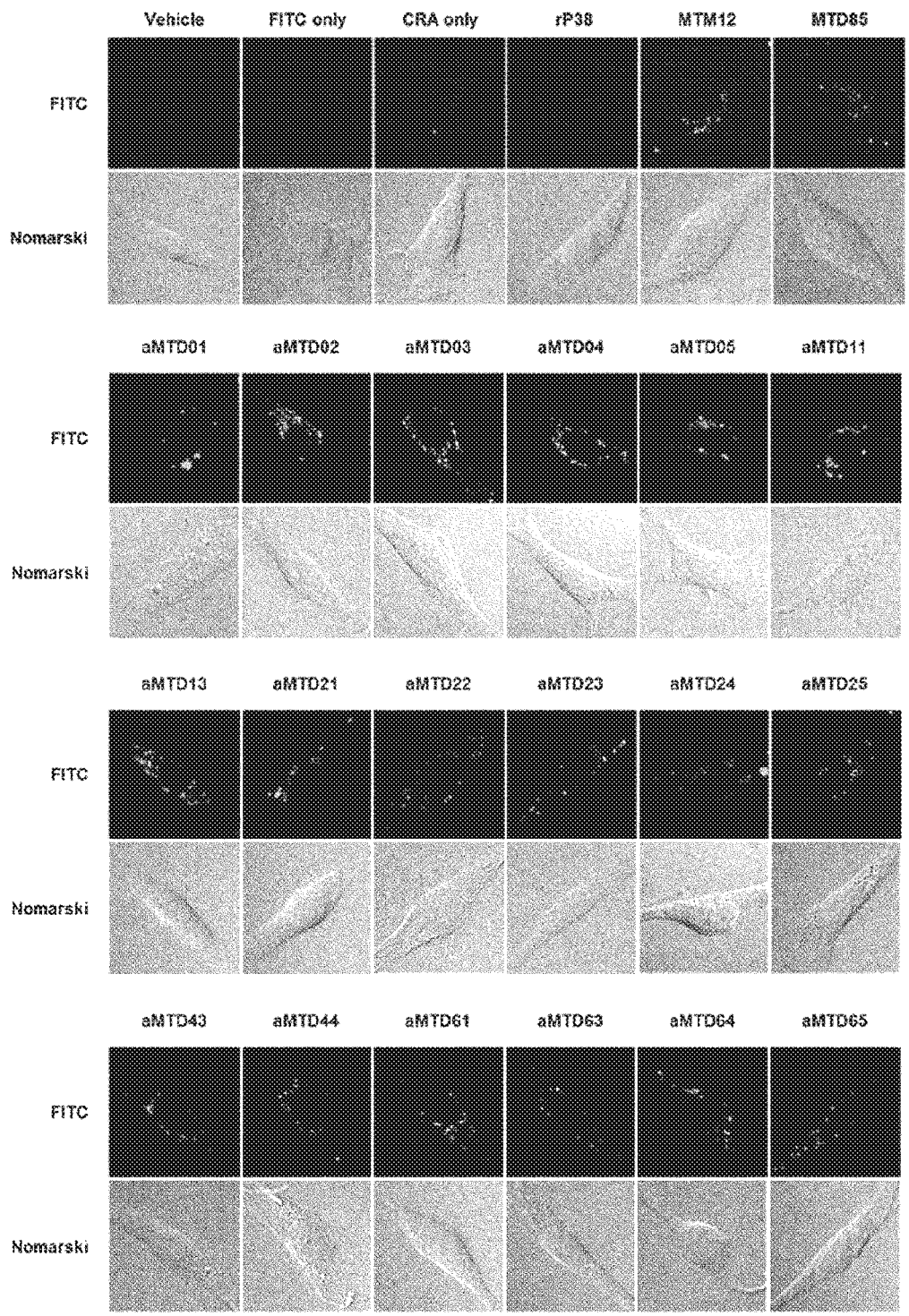

[Fig. 7b]
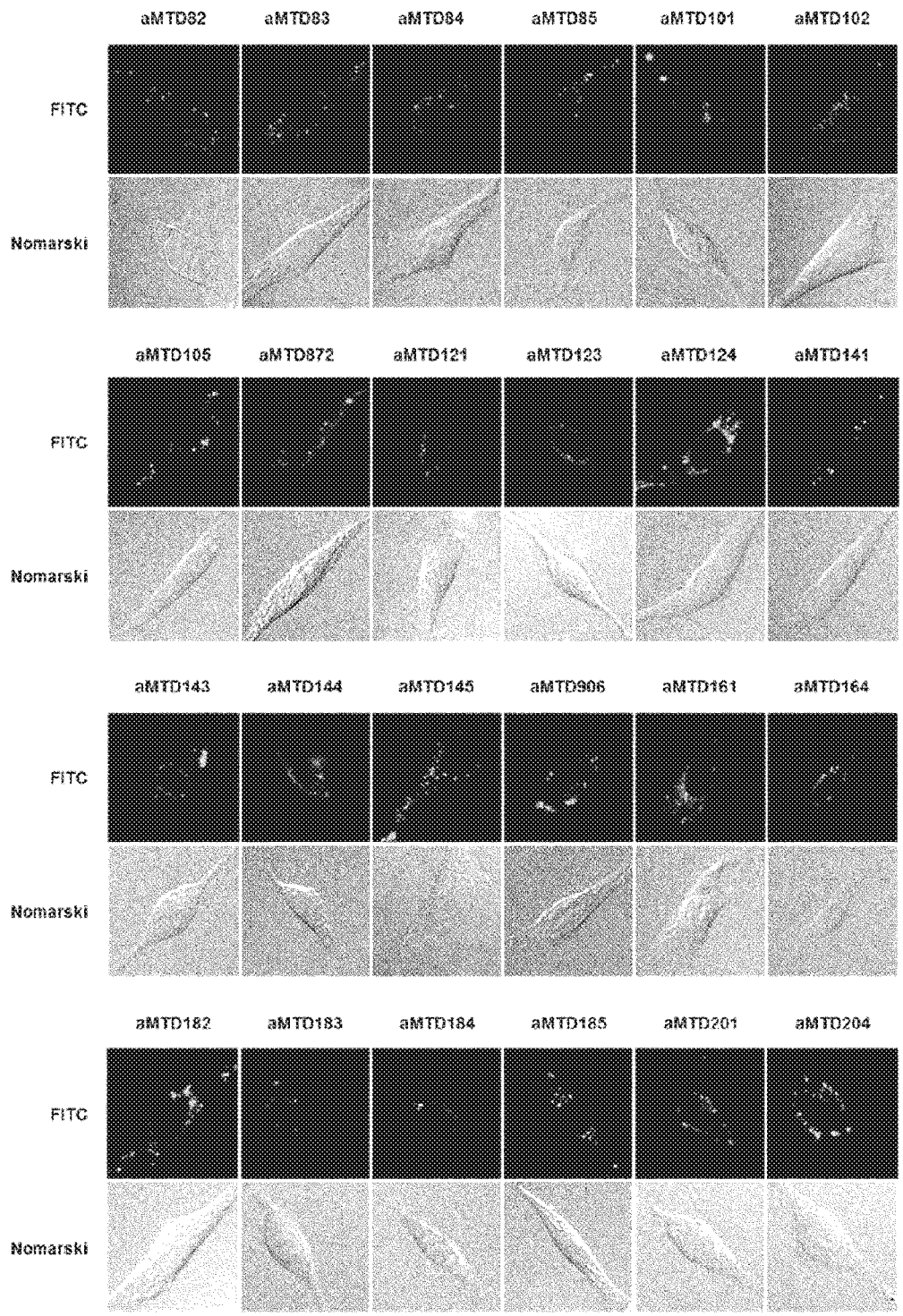

[Fig. 7c]
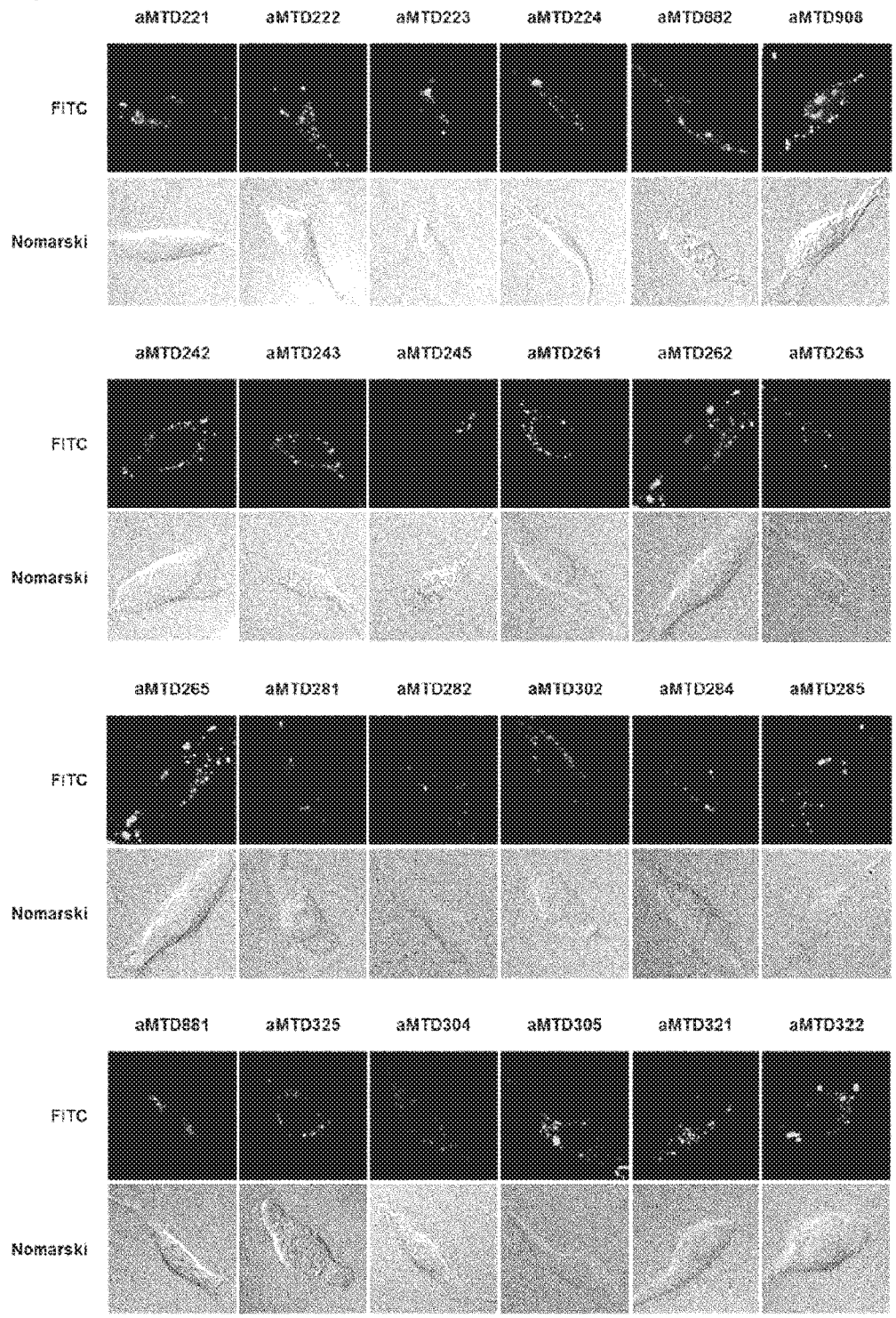

[Fig. 7d]
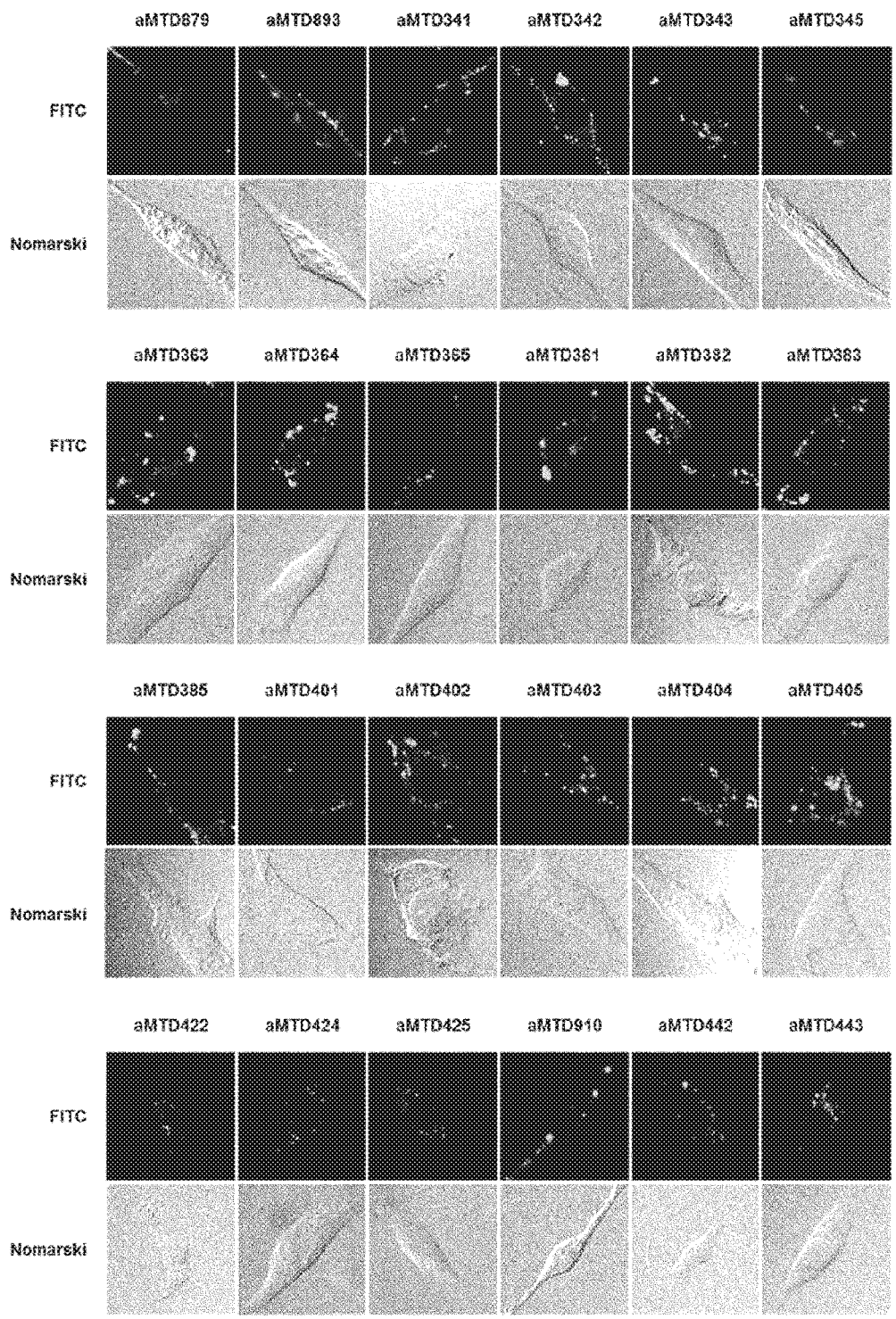

[Fig. 7e]
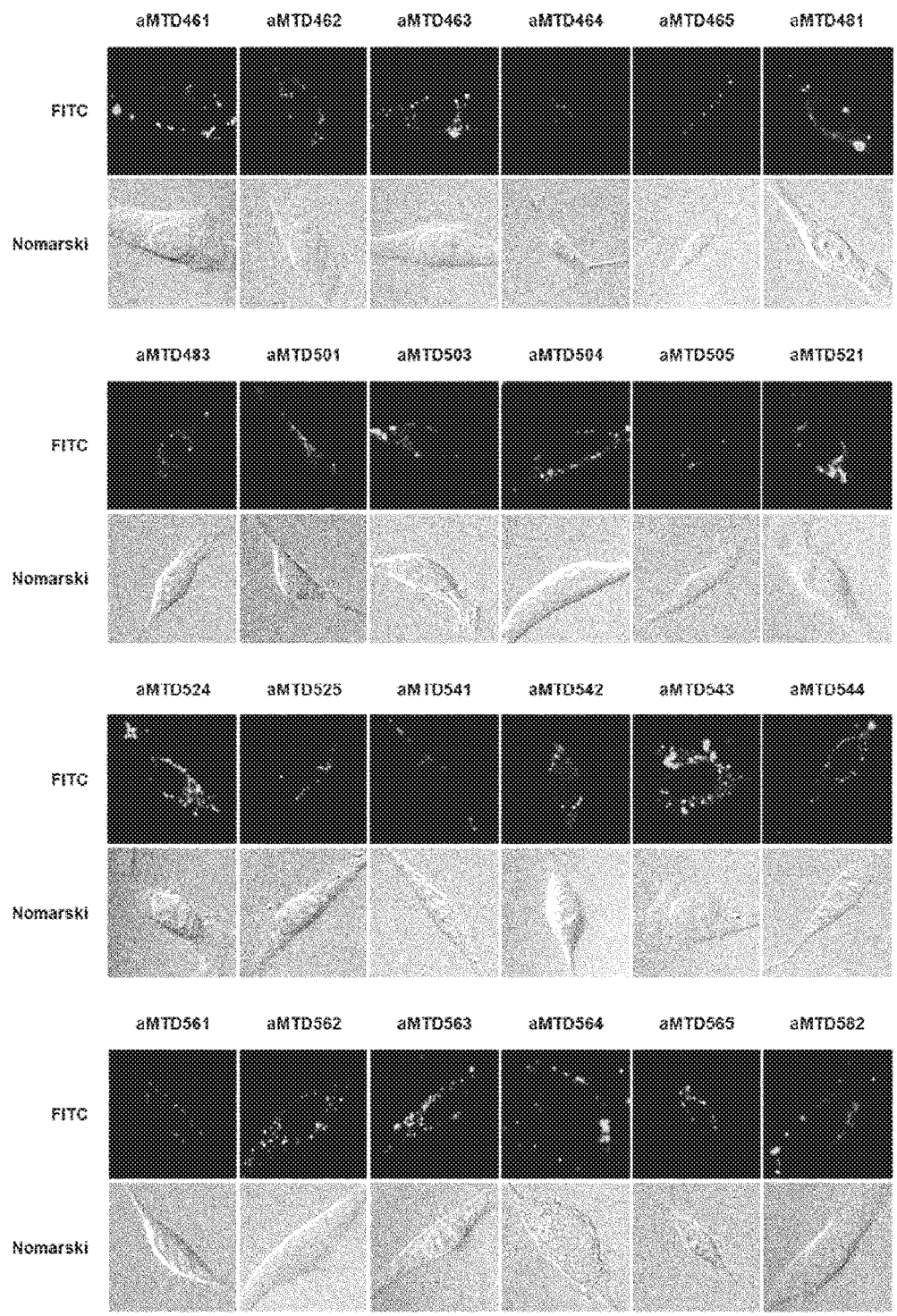

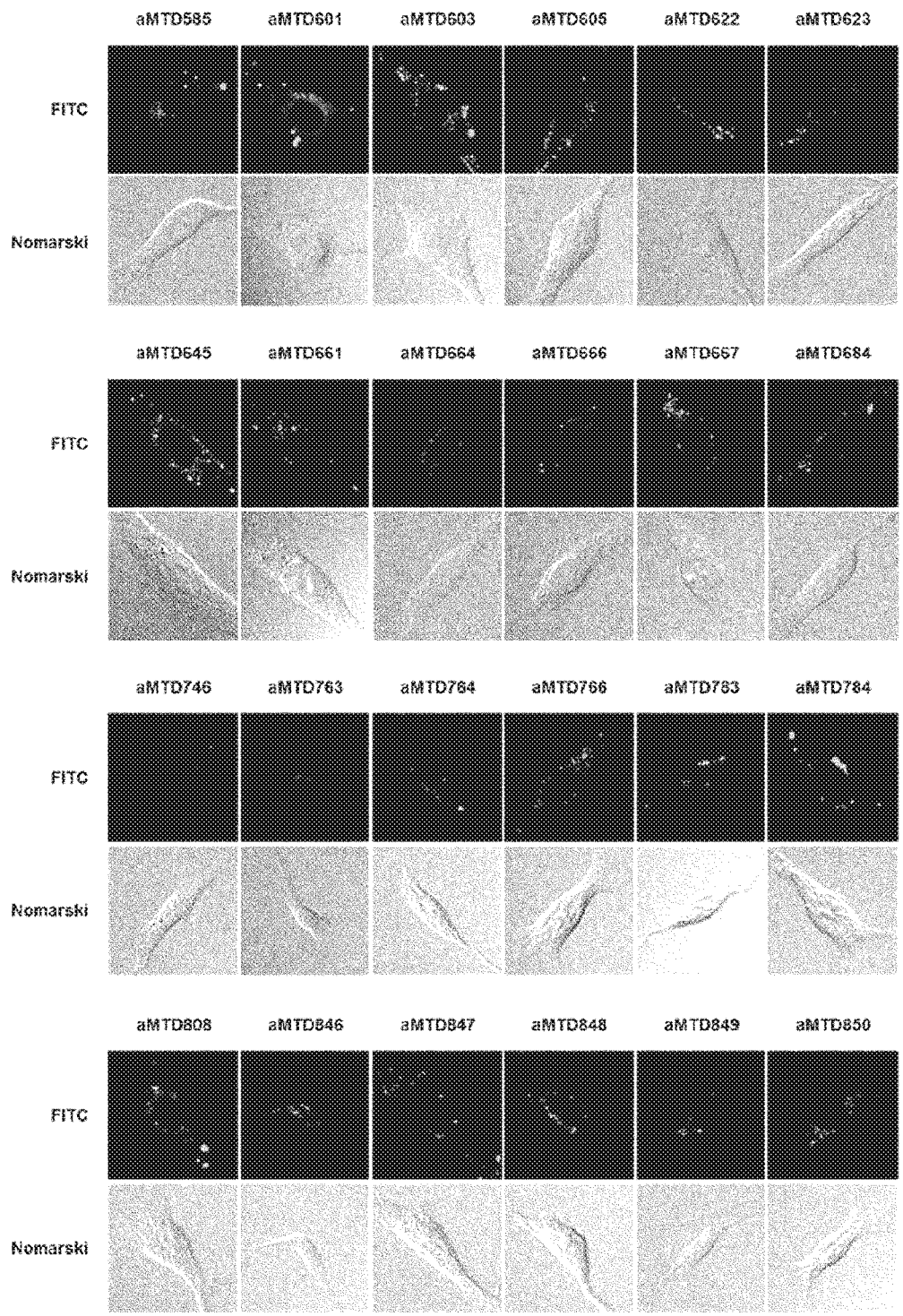
[Fig. 7f]

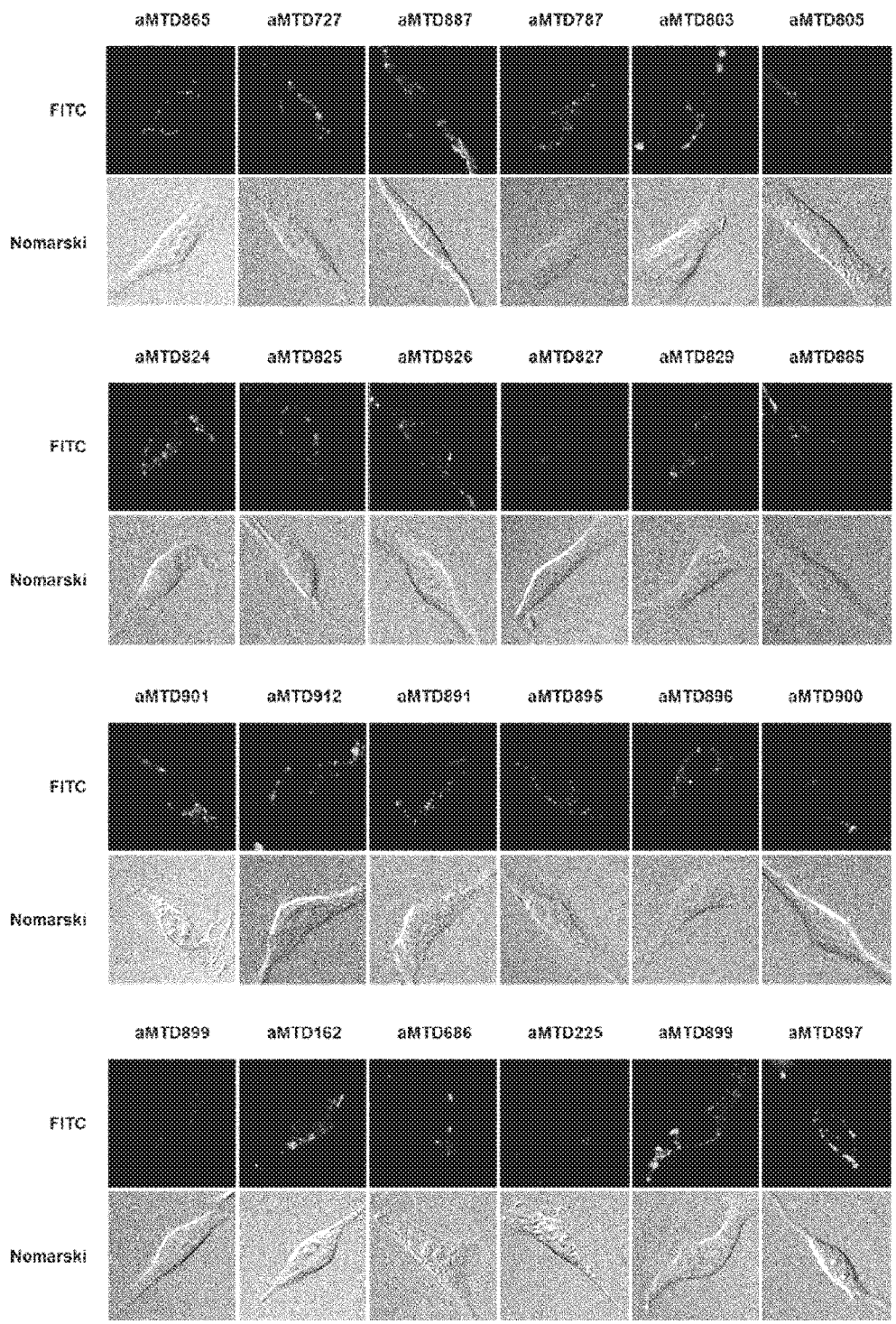
[Fig. 7g]

[Fig. 7h]
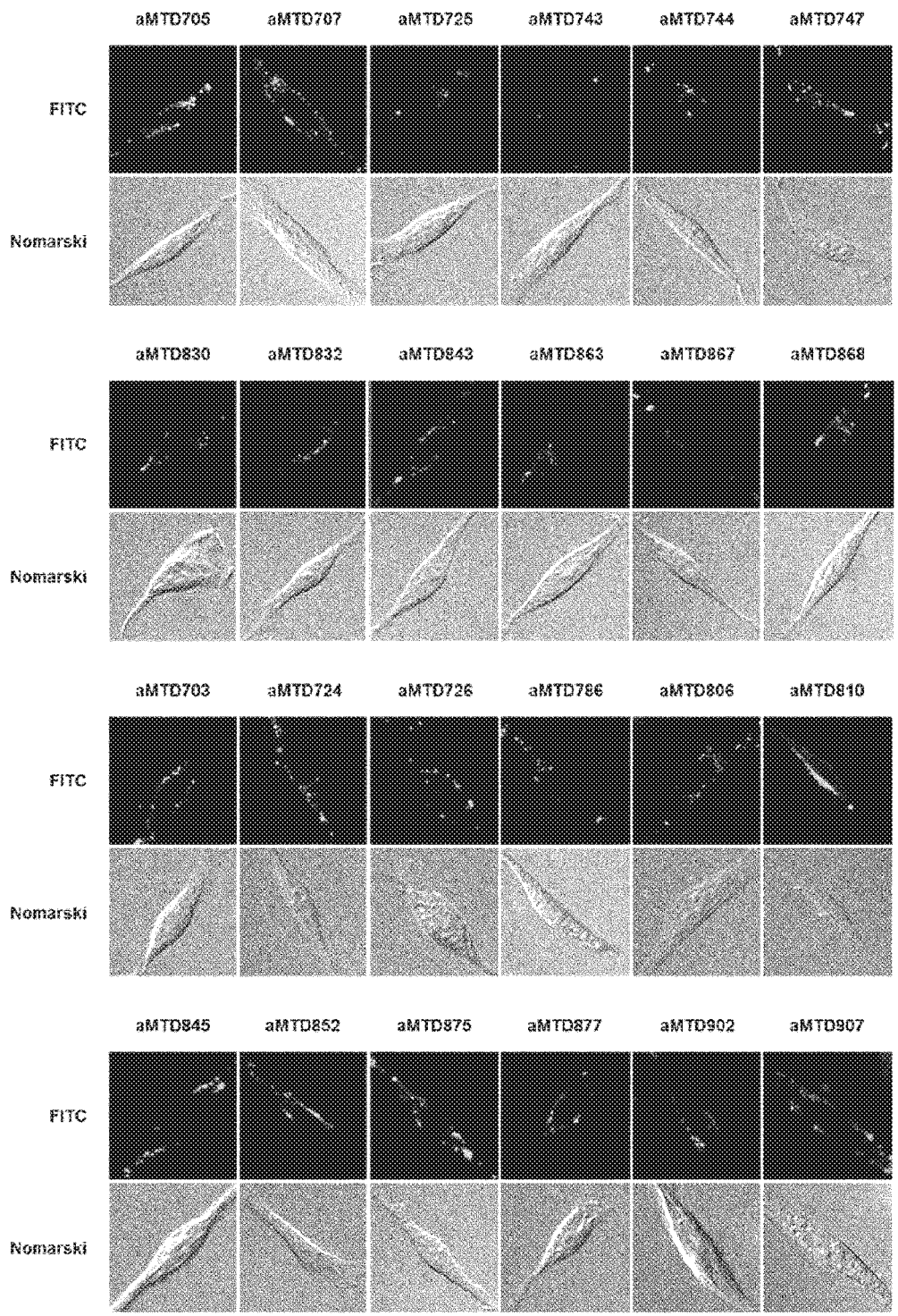

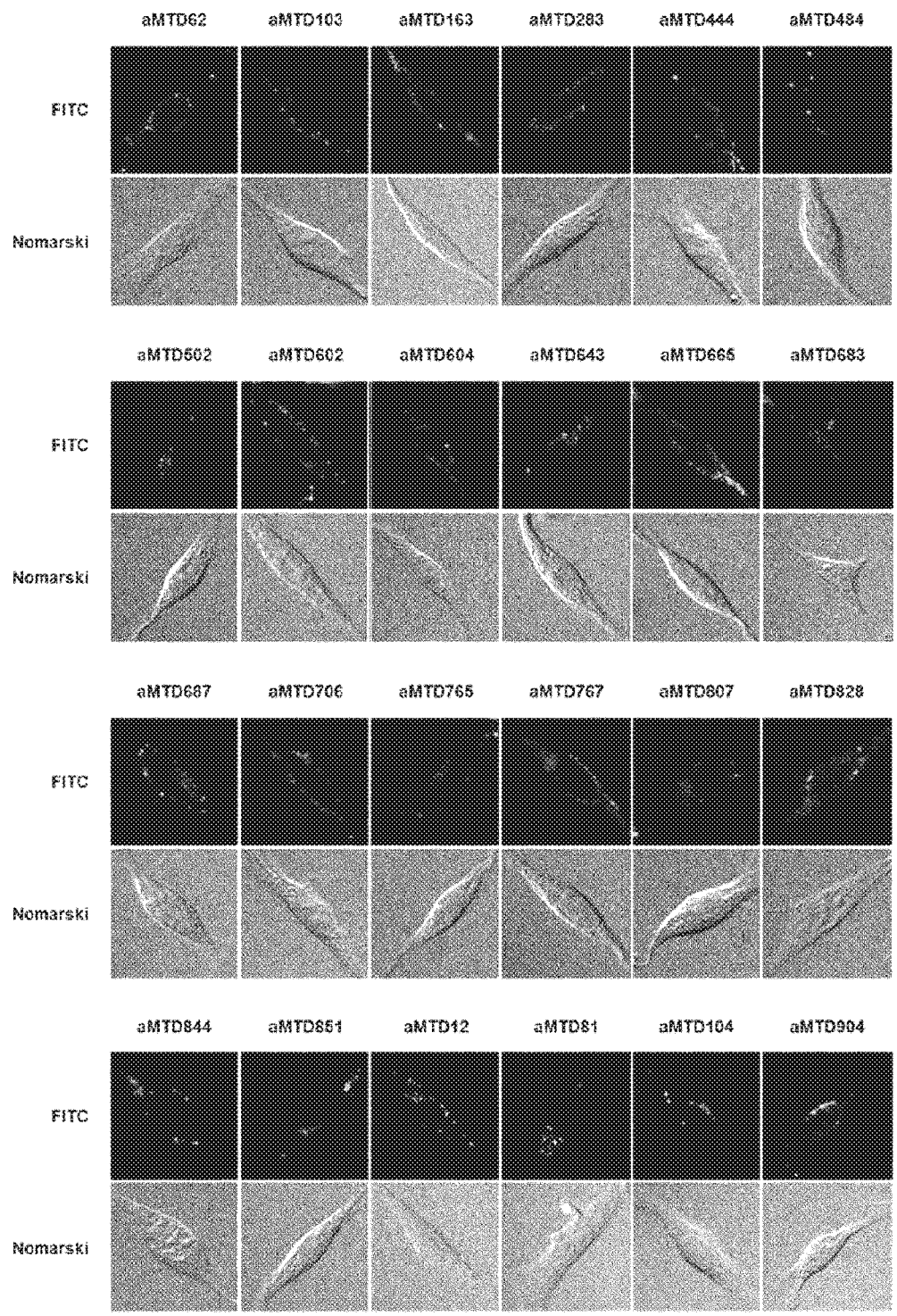
[Fig. 7i]

[Fig. 7j]
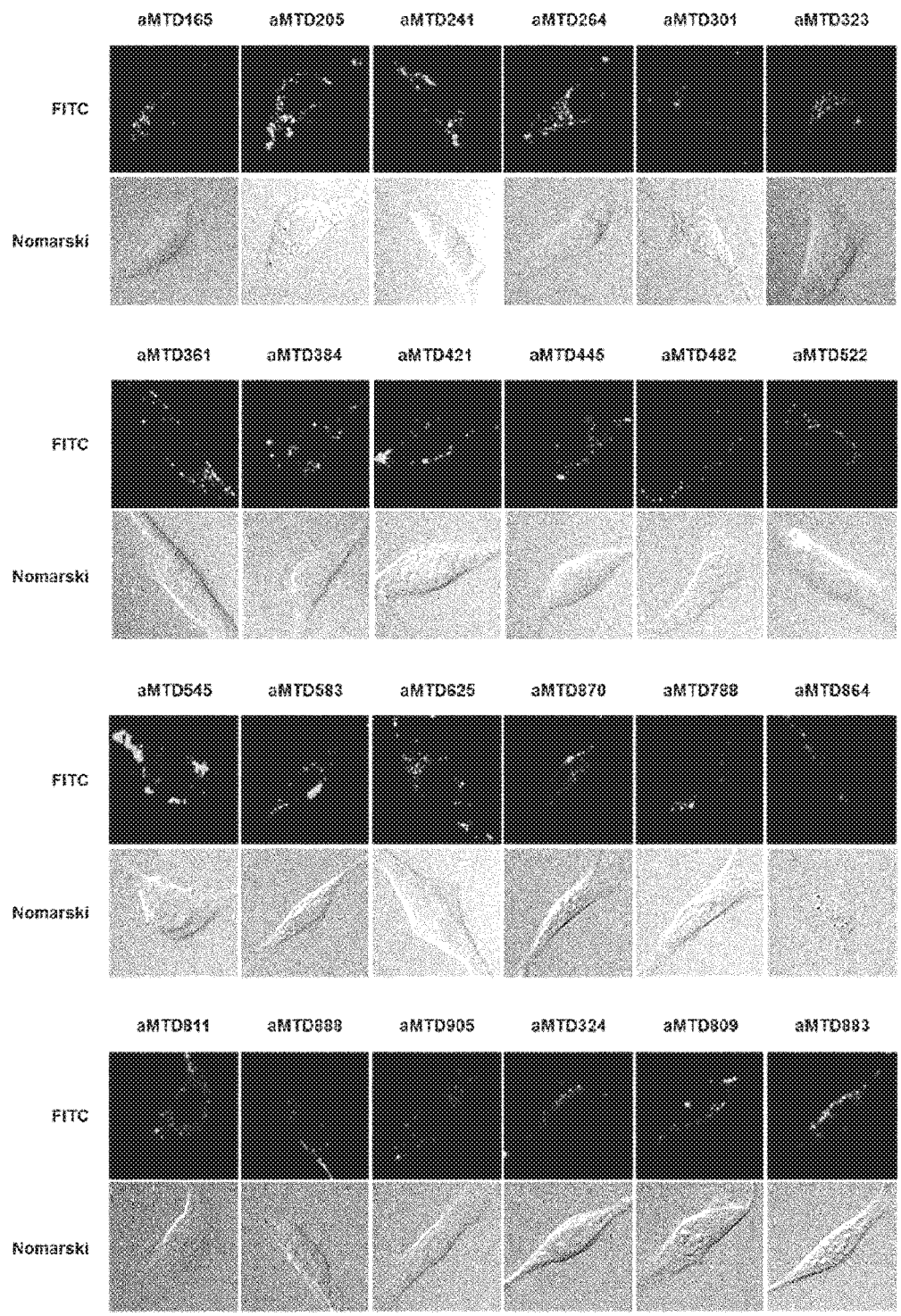

[Fig. 7k]
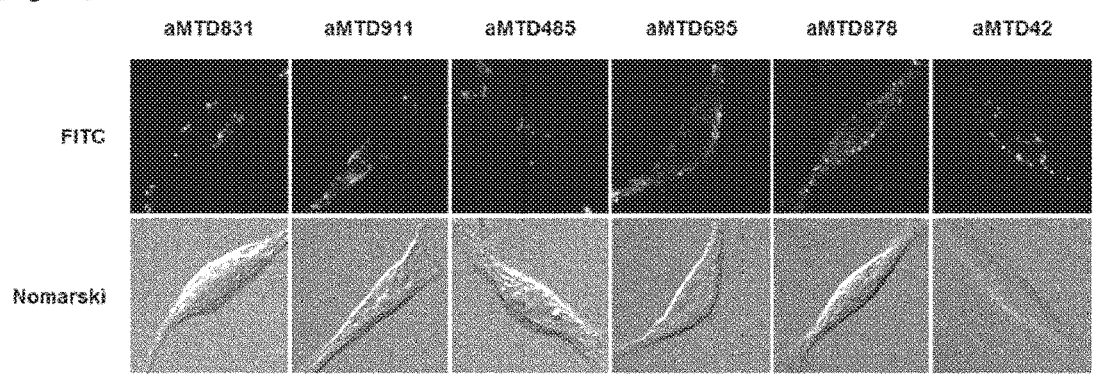

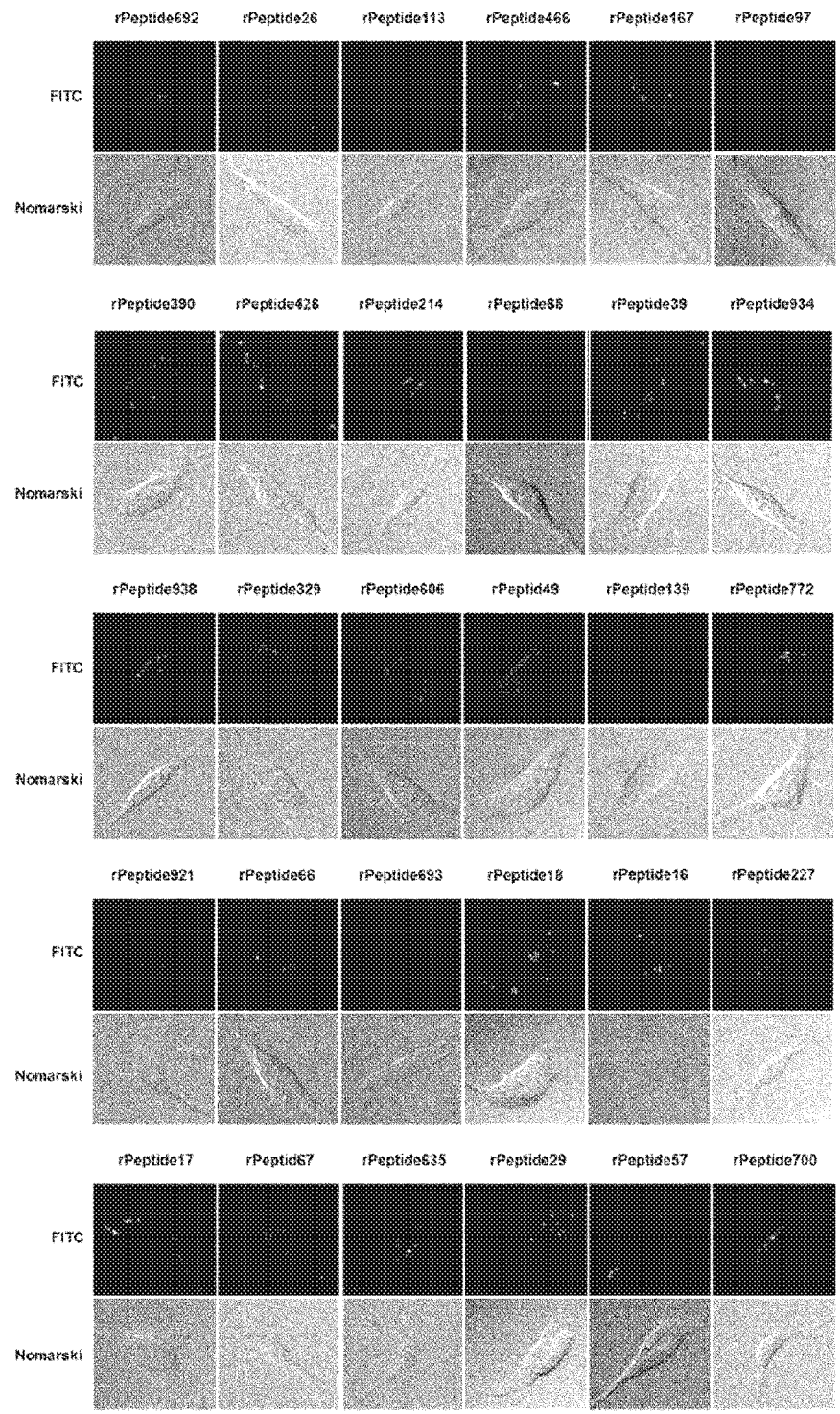

[Fig. 9a]
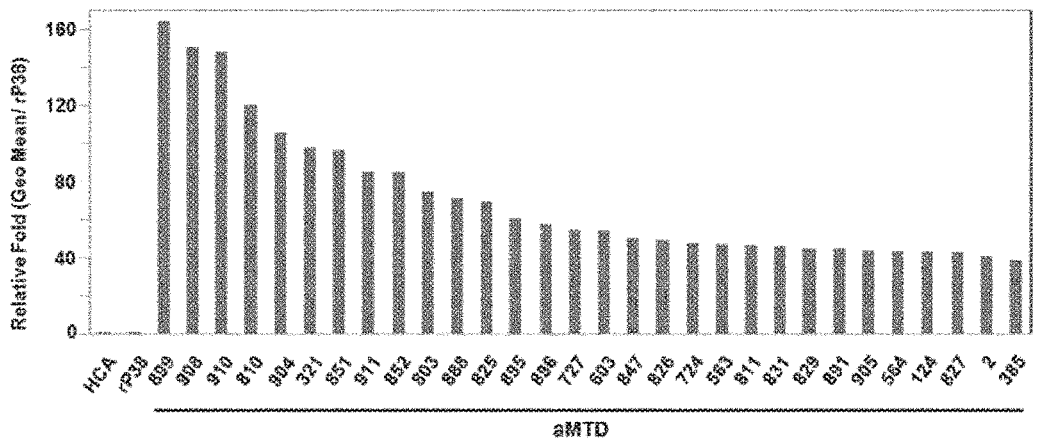
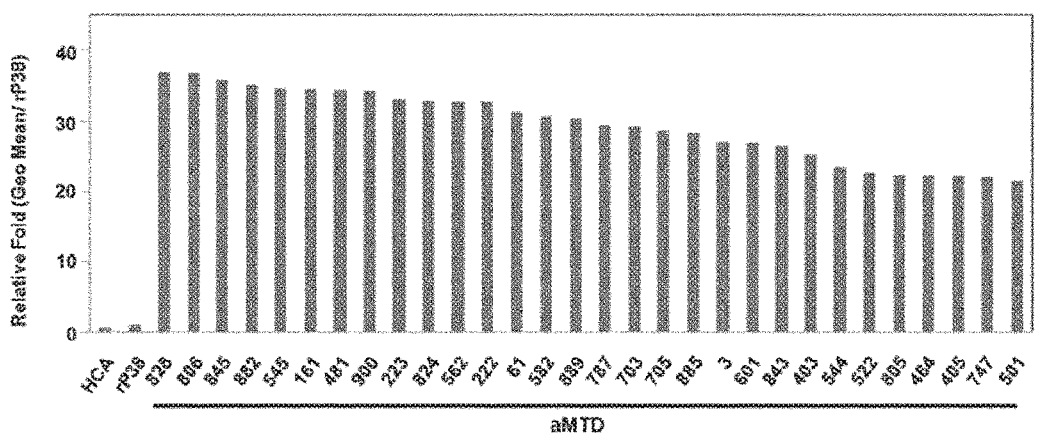
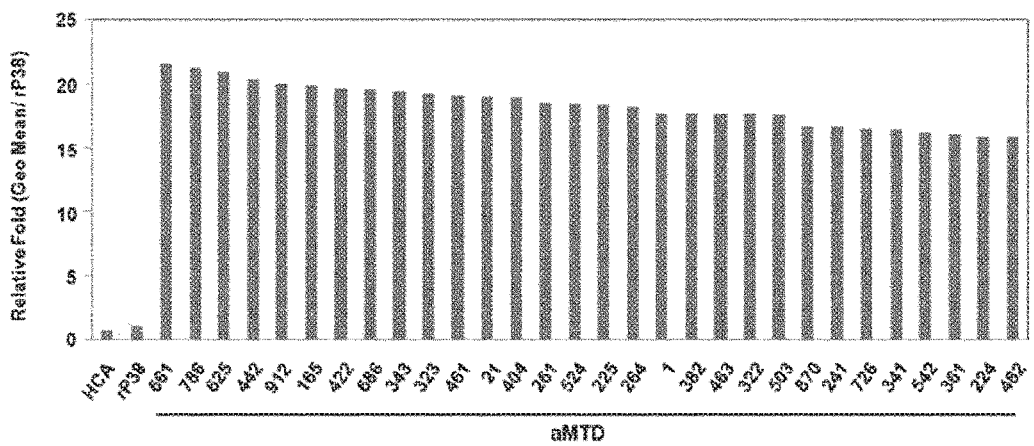

[Fig. 9b]
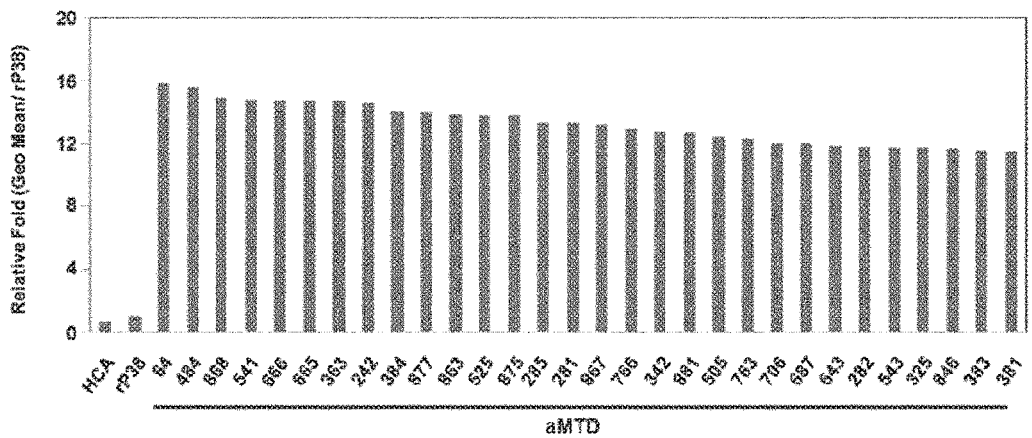
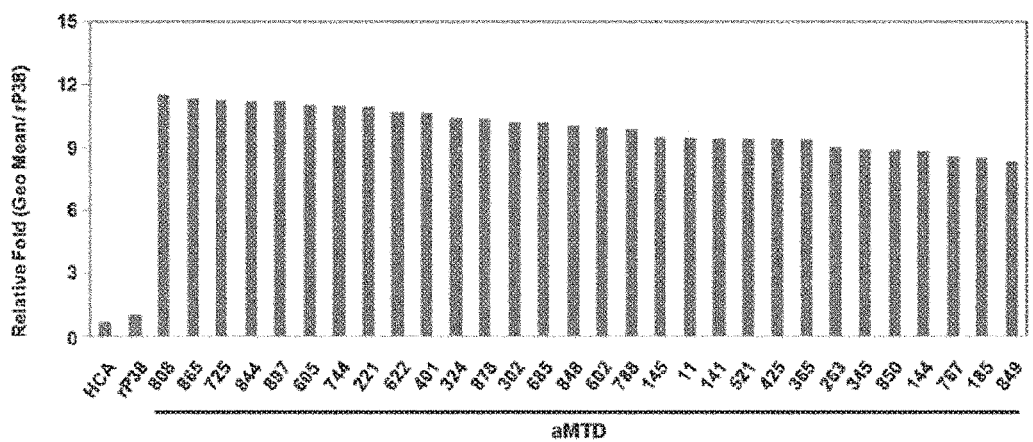
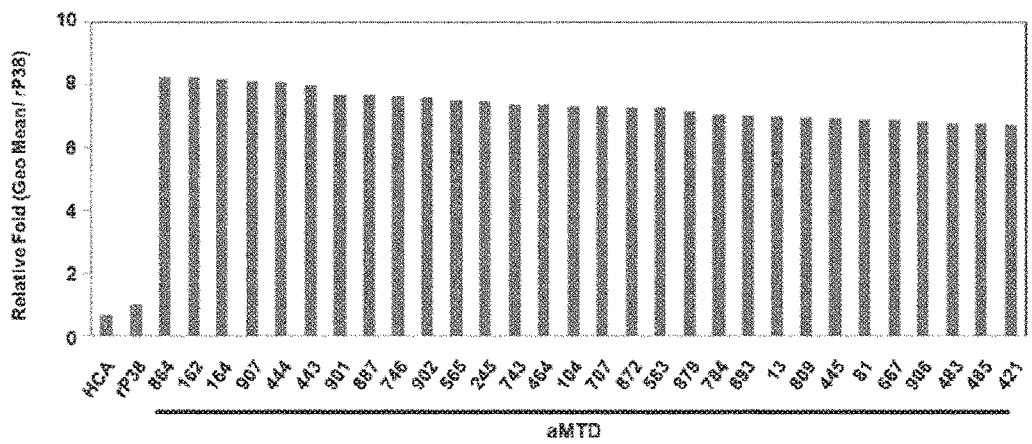

[Fig. 9c]
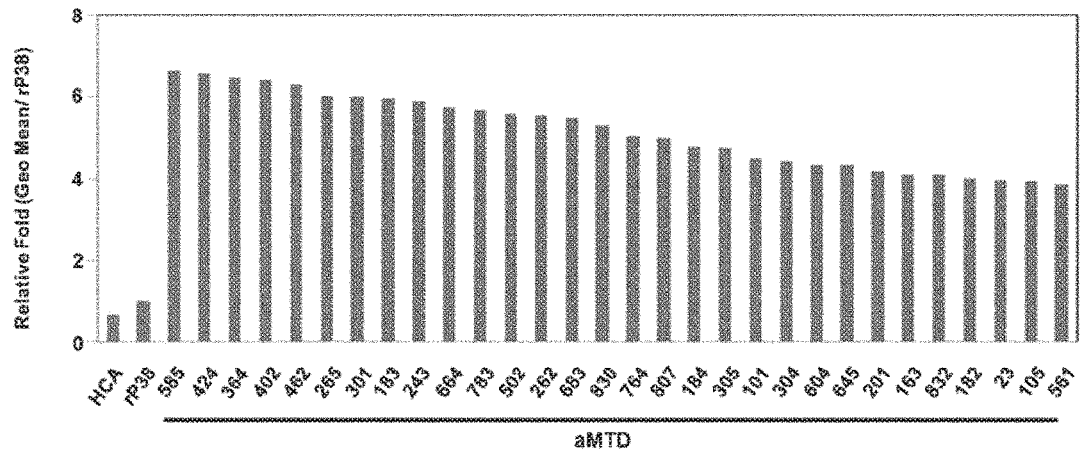
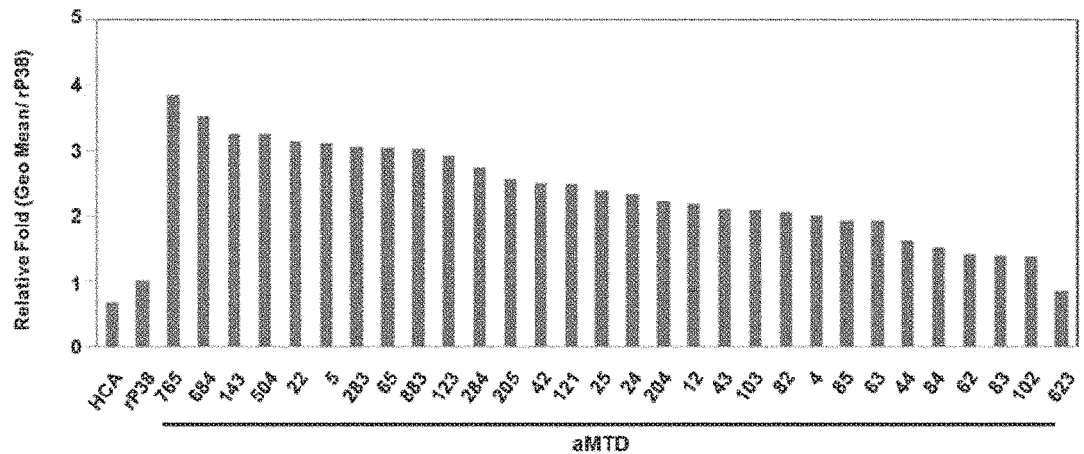

[Fig. 10a]
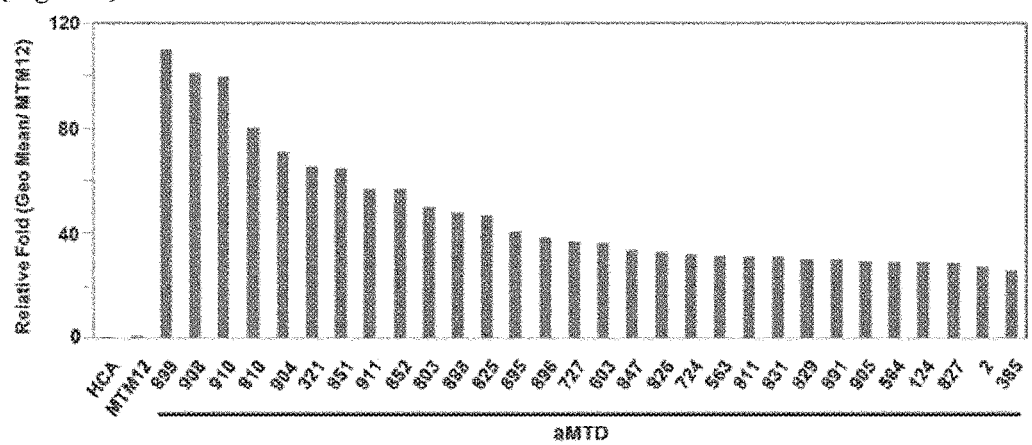
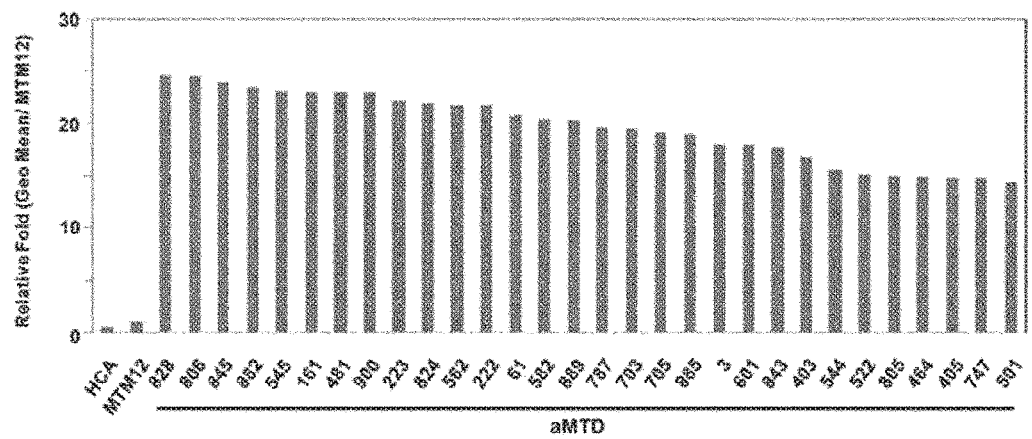
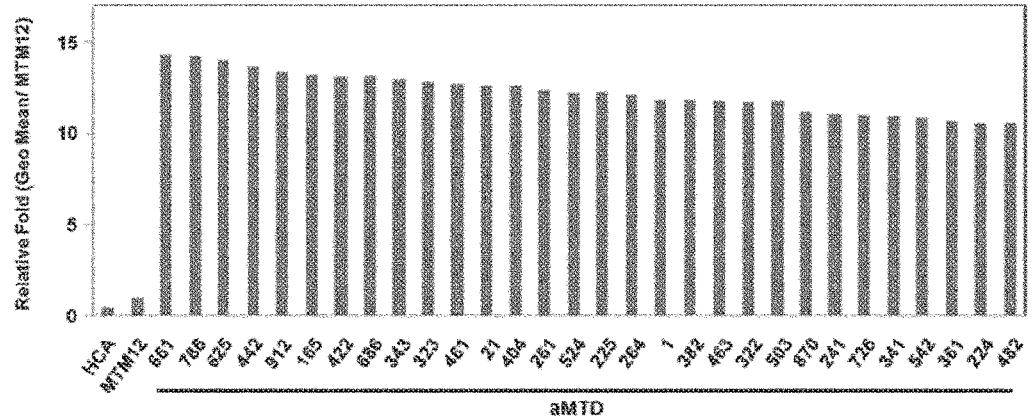

[Fig. 10b]
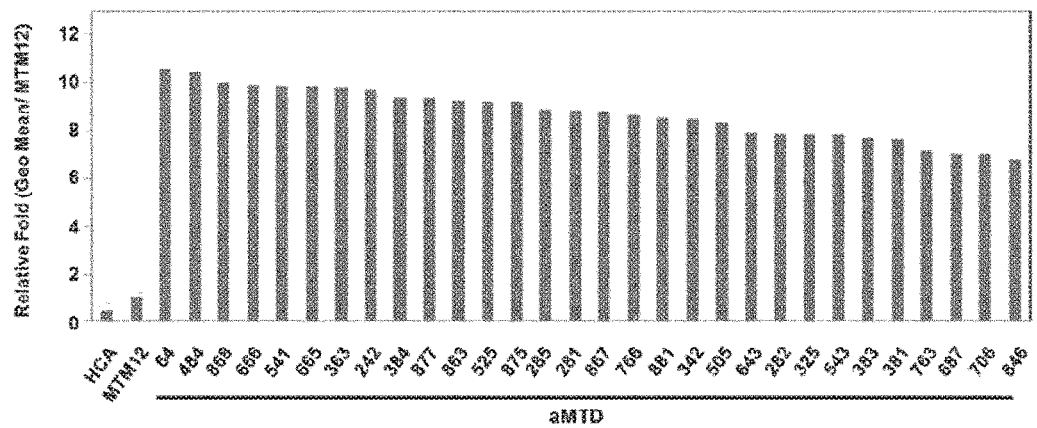
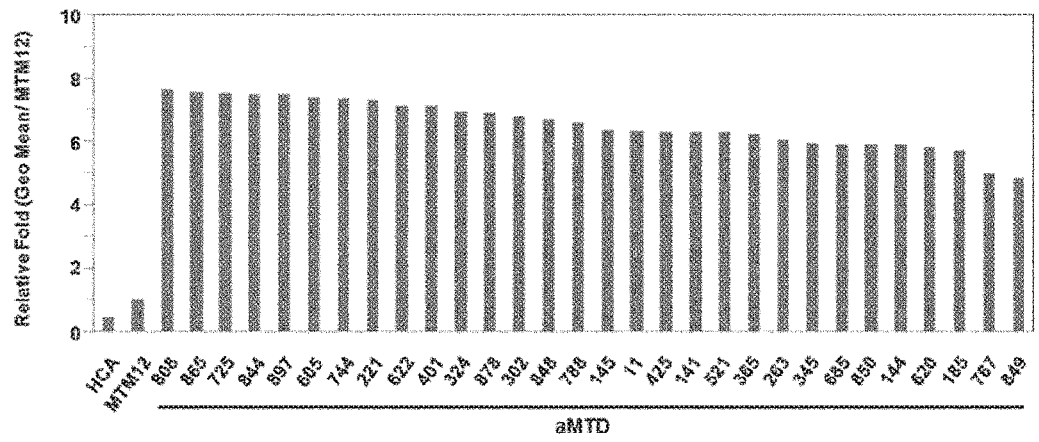
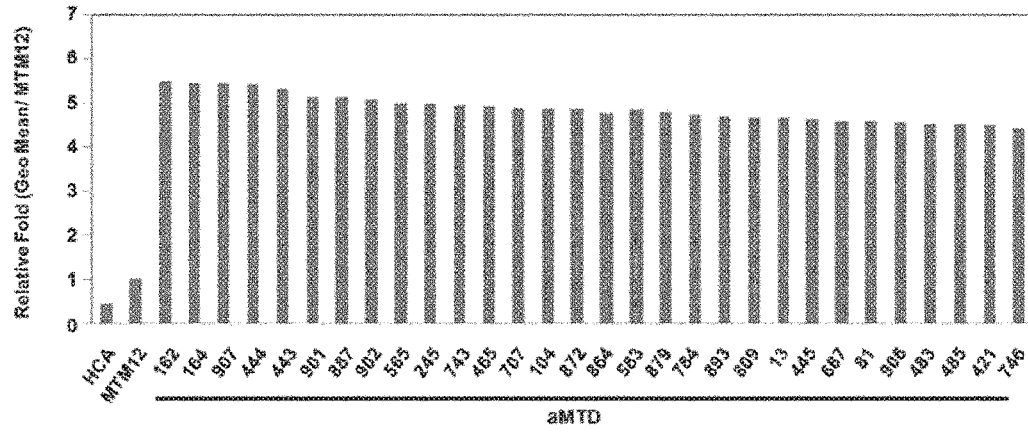

[Fig. 10c]
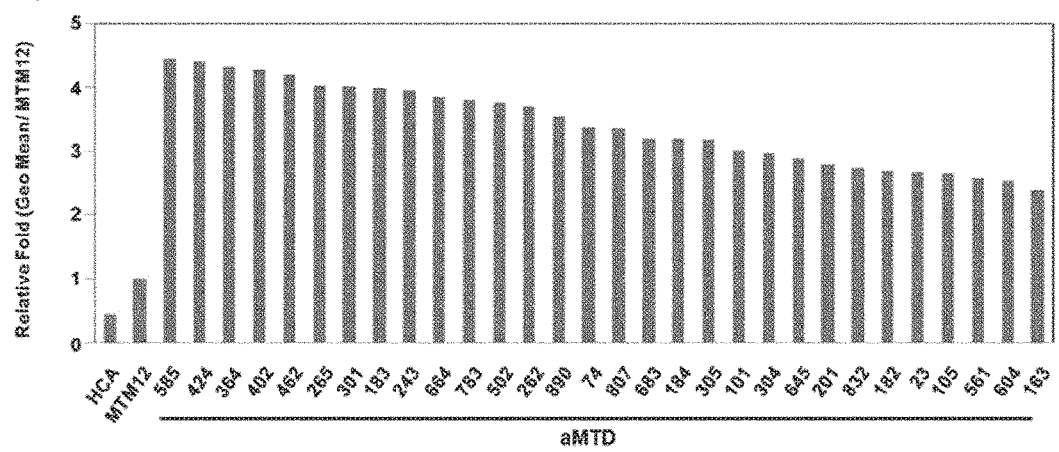
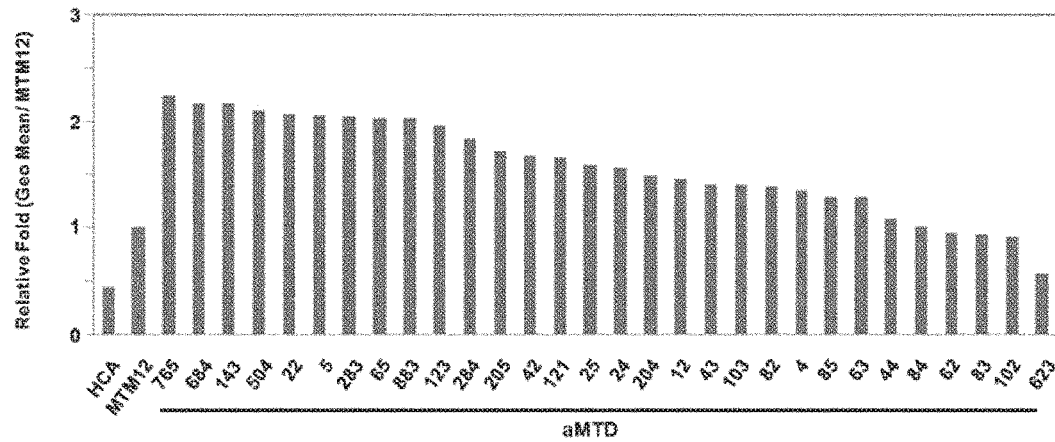

[Fig. 11a]
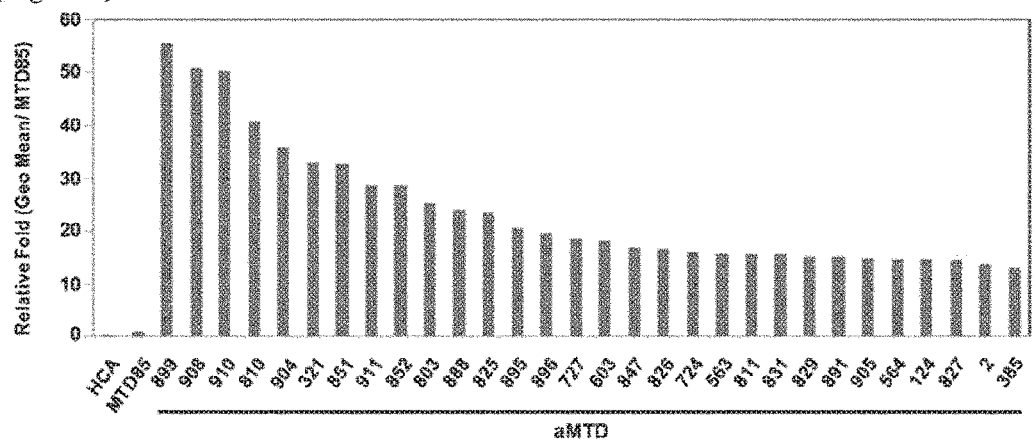
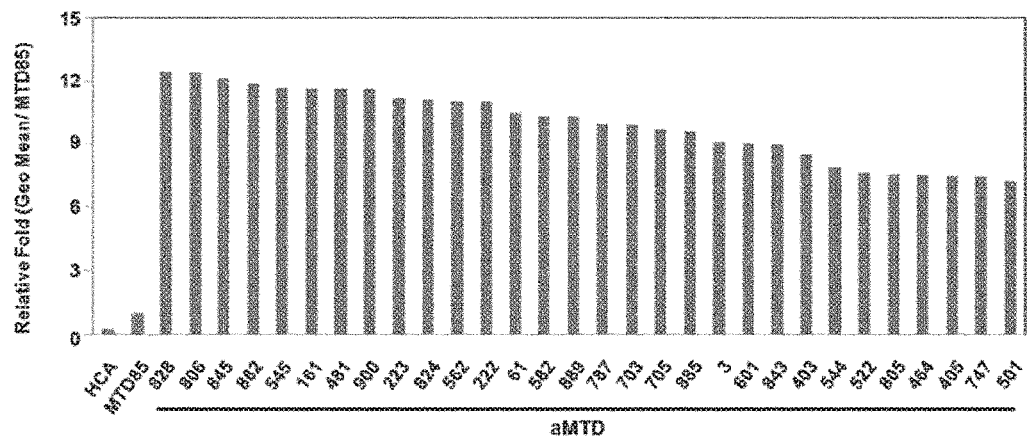
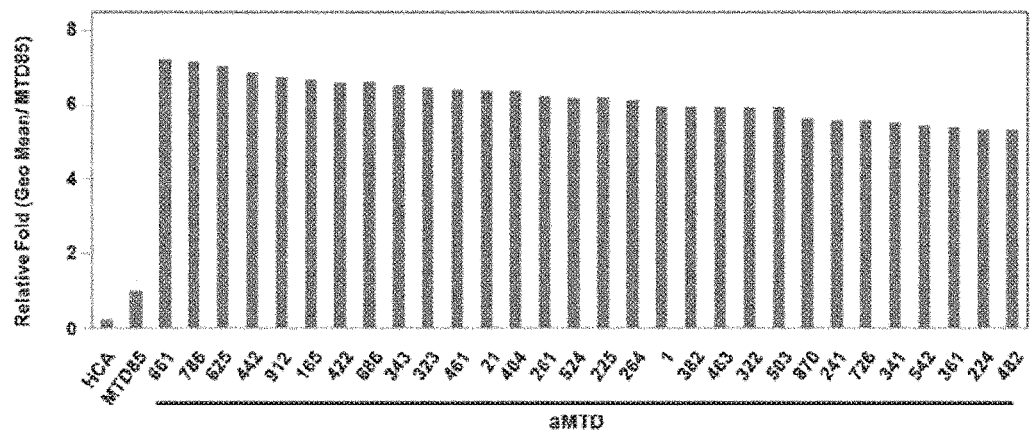

[Fig. 11b]
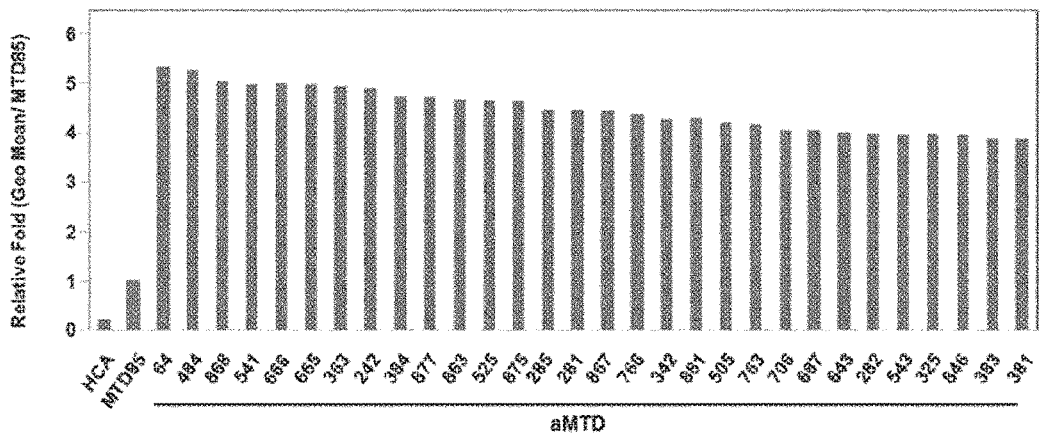
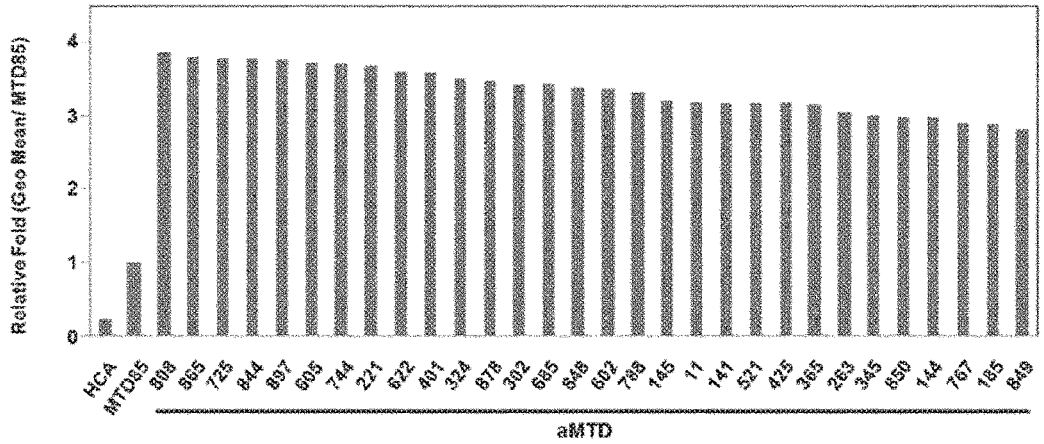
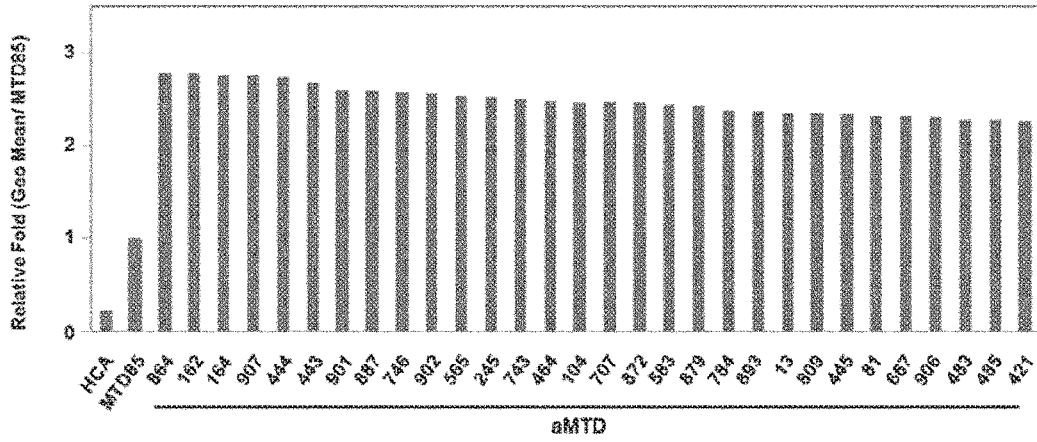

[Fig. 11c]
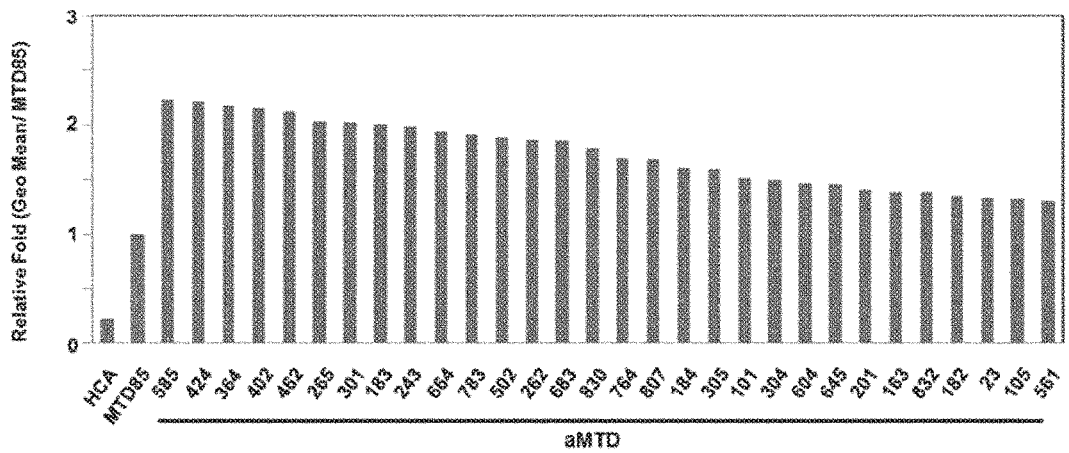
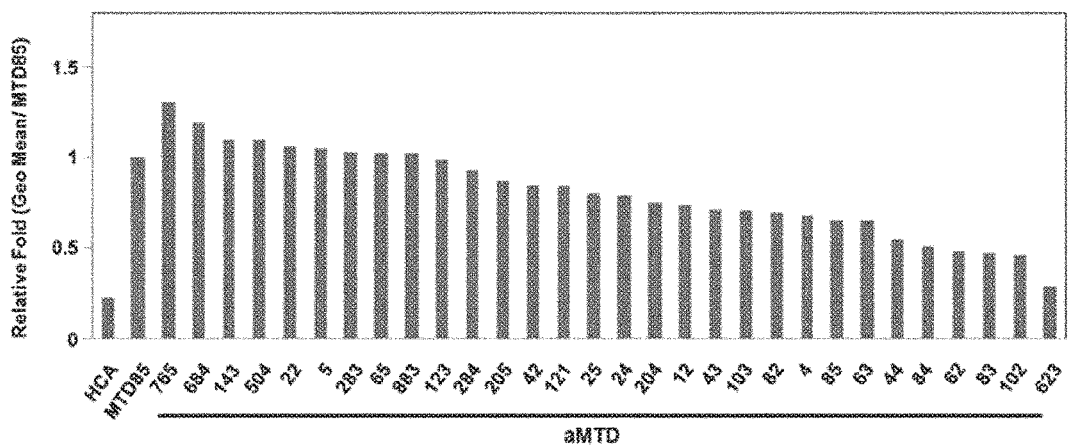
[Fig. 12]
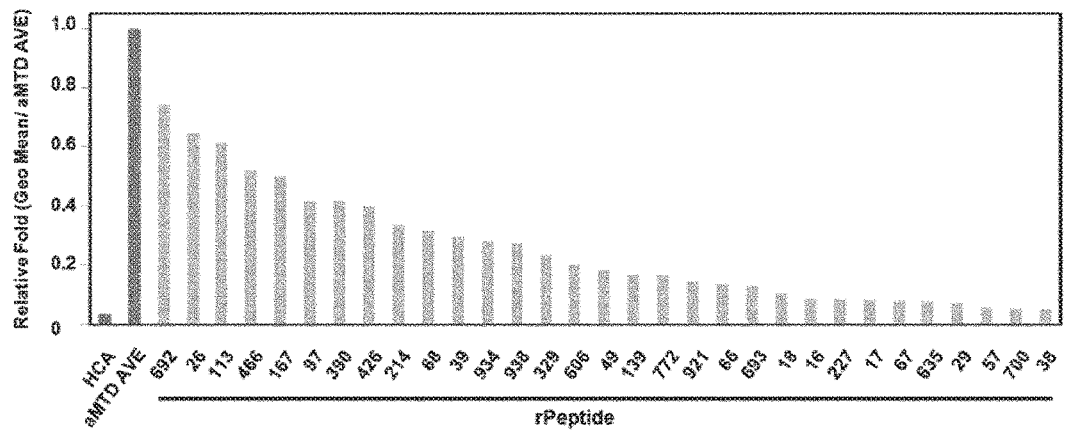

[Fig. 13a]
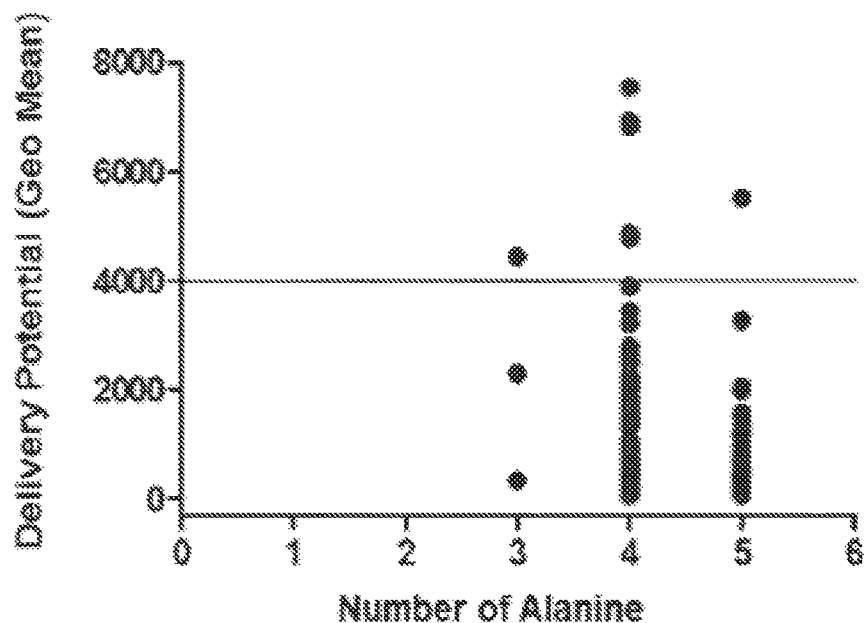
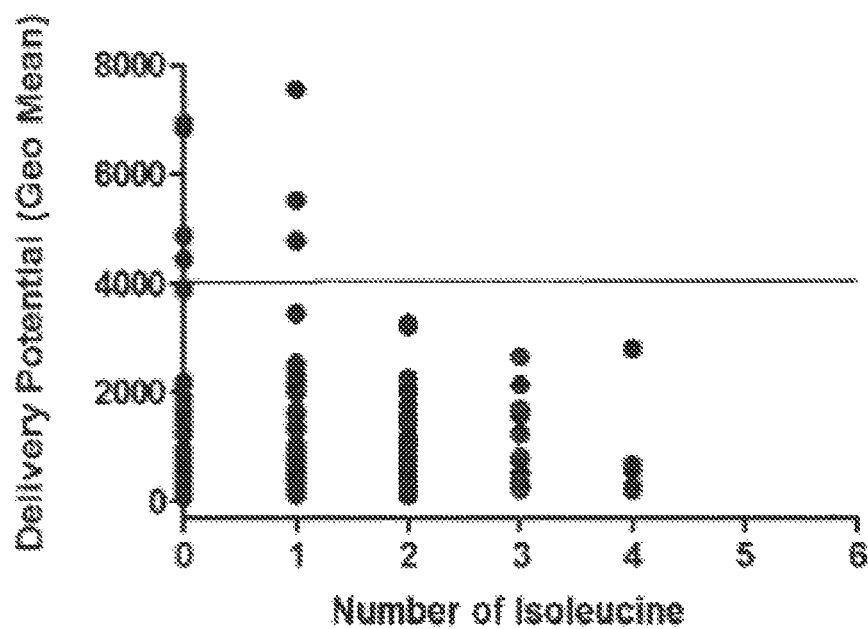

[Fig. 13b]
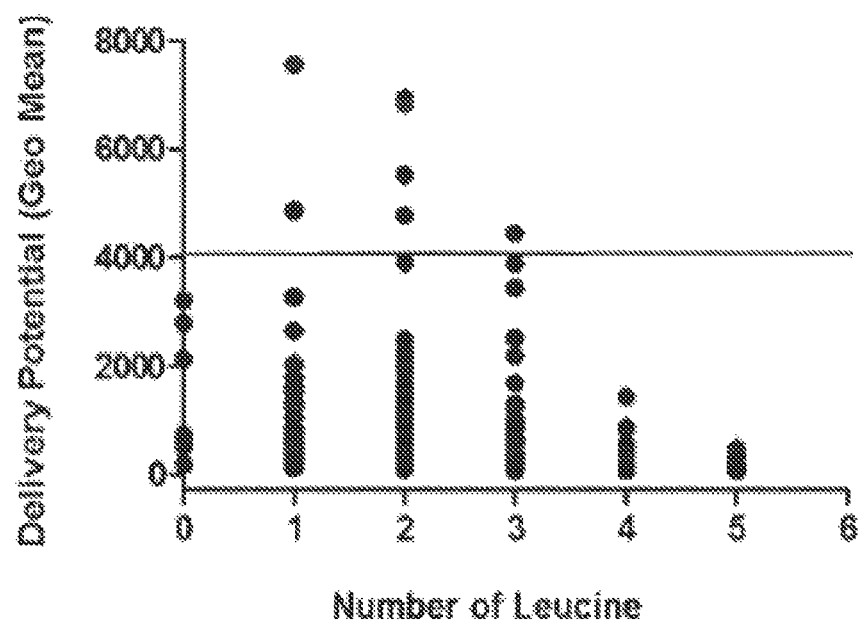
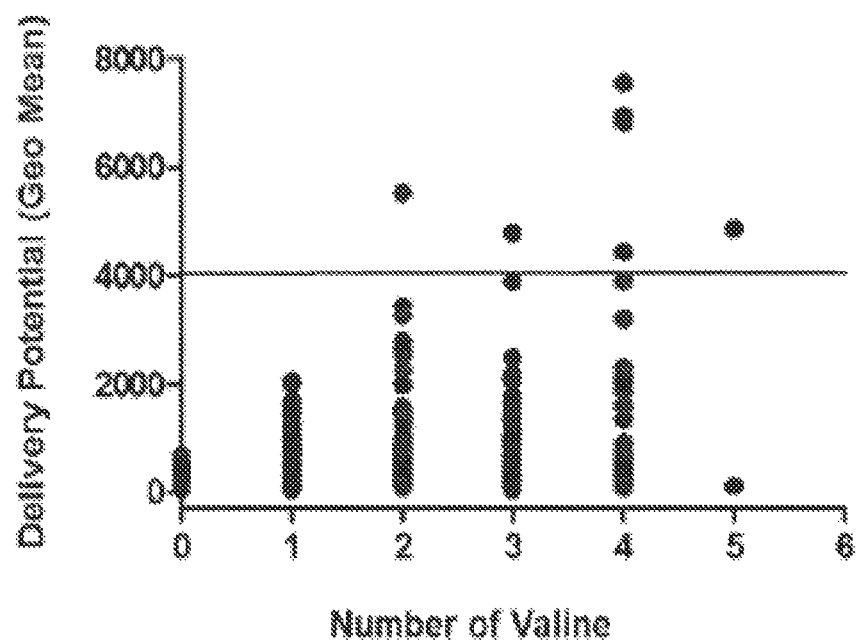

[Fig. 14a]
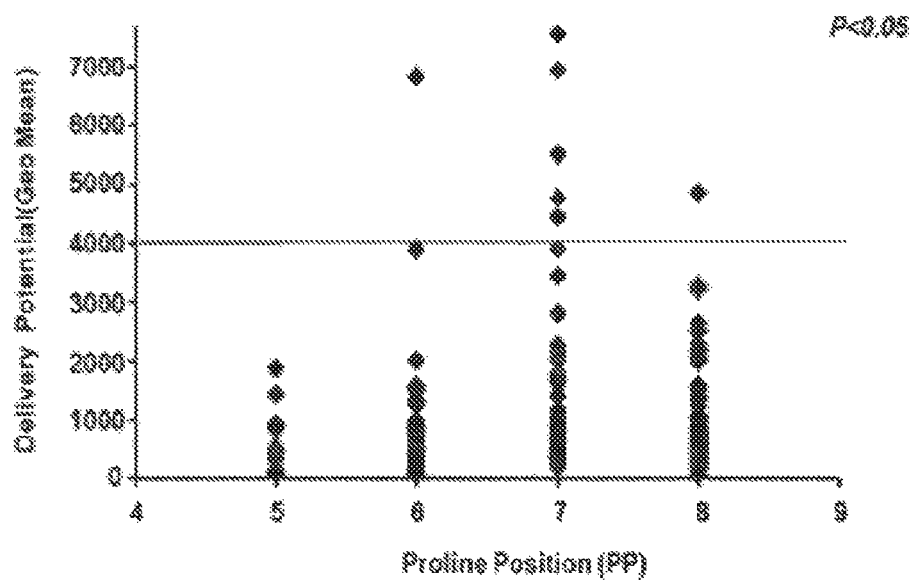
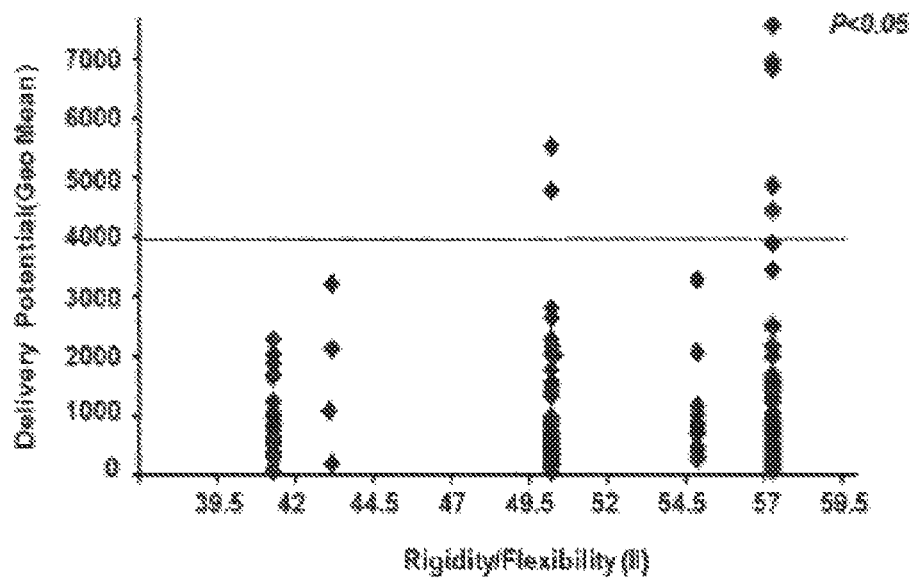

[Fig. 14b]
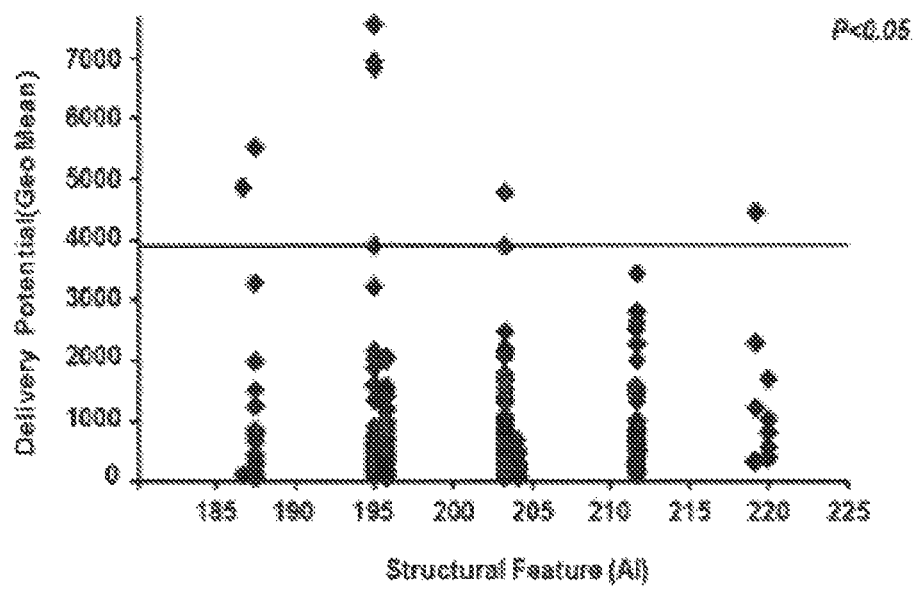
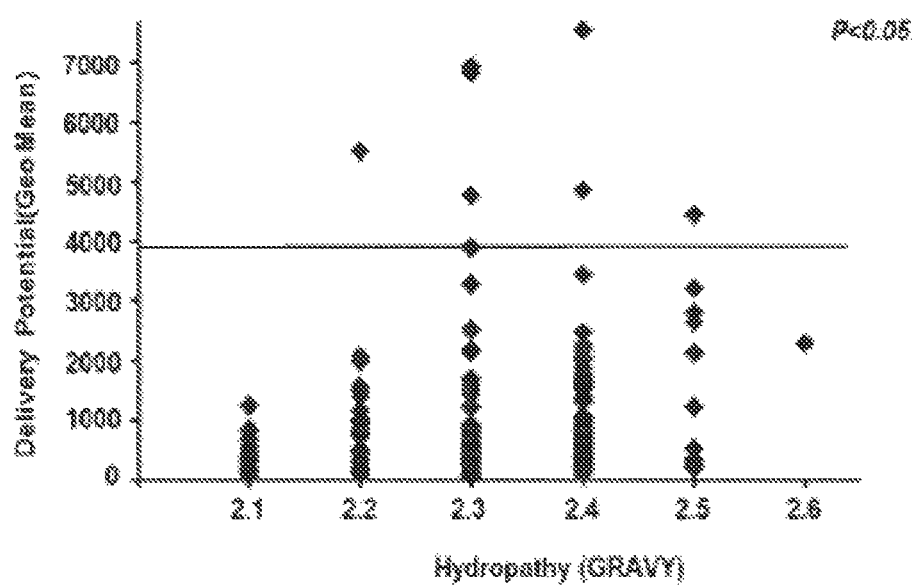

[Fig. 15a]
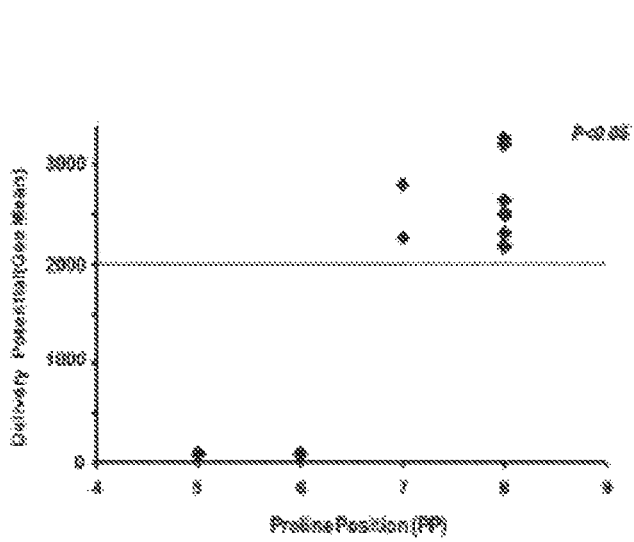
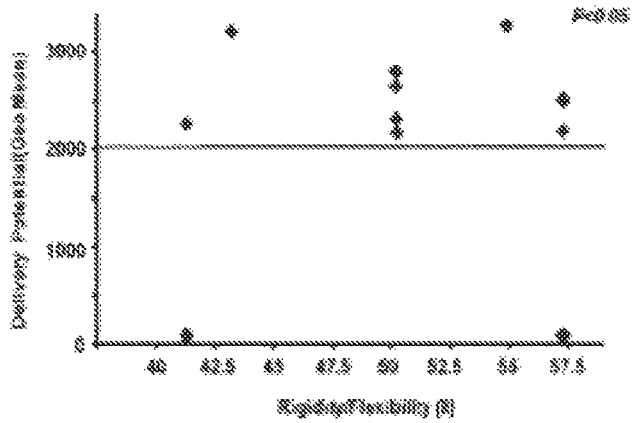

[Fig. 15b]
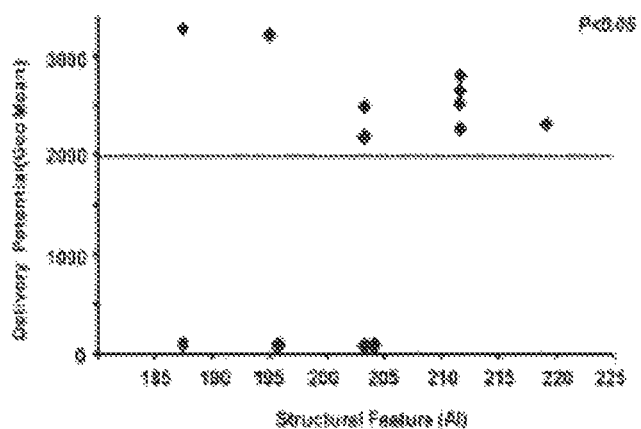
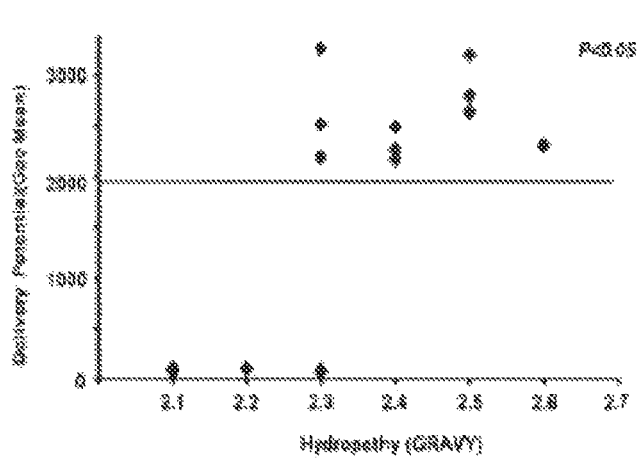

[Fig. 16]
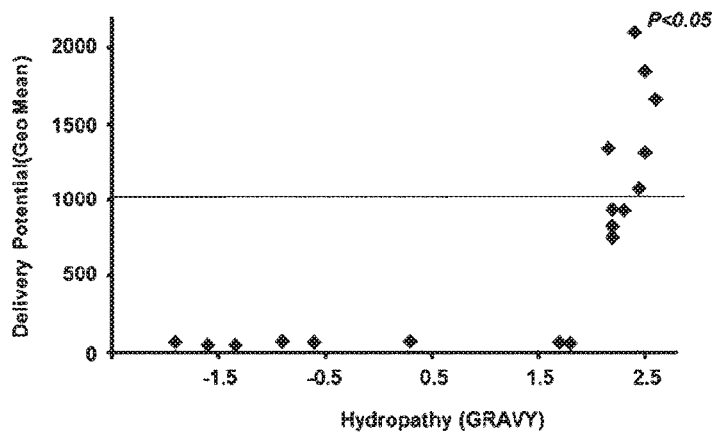

SEQUENCE LISTING

```
<160> NUMBER OF SEQ ID NOS: 480

<210> SEQ ID NO 1
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 1

Ala Ala Ala Leu Ala Pro Val Val Leu Ala Leu Pro
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Advanced Macromolecule Transduction Domain
```

-continued (aMTD) Sequences for Improvement of Cell-Permeability

<400> SEQUENCE: 2

Ala Ala Ala Val Pro Leu Leu Ala Val Val Val Pro
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 3

Ala Ala Leu Leu Val Pro Ala Ala Val Leu Ala Pro
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 4

Ala Leu Ala Leu Leu Pro Val Ala Ala Leu Ala Pro
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 5

Ala Ala Ala Leu Leu Pro Val Ala Leu Val Ala Pro
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 6

Val Val Ala Leu Ala Pro Ala Leu Ala Ala Leu Pro
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 7

Leu Leu Ala Ala Val Pro Ala Val Leu Leu Ala Pro
 1               5                  10

<210> SEQ ID NO 8

```
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 8

Ala Ala Ala Leu Val Pro Val Val Ala Leu Leu Pro
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 9

Ala Val Ala Leu Leu Pro Ala Leu Leu Ala Val Pro
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 10

Ala Val Val Leu Val Pro Val Leu Ala Ala Ala Pro
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 11

Val Val Leu Val Leu Pro Ala Ala Ala Ala Val Pro
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 12

Ile Ala Leu Ala Ala Pro Ala Leu Ile Val Ala Pro
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 13
```

```
Ile Val Ala Val Ala Pro Ala Leu Val Ala Leu Pro
  1               5                  10

<210> SEQ ID NO 14
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 14

Val Ala Ala Leu Pro Val Val Ala Val Val Ala Pro
  1               5                  10

<210> SEQ ID NO 15
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 15

Leu Leu Ala Ala Pro Leu Val Val Ala Ala Val Pro
  1               5                  10

<210> SEQ ID NO 16
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 16

Ala Leu Ala Val Pro Val Ala Leu Leu Val Ala Pro
  1               5                  10

<210> SEQ ID NO 17
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 17

Val Ala Ala Leu Pro Val Leu Leu Ala Ala Leu Pro
  1               5                  10

<210> SEQ ID NO 18
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 18

Val Ala Leu Leu Ala Pro Val Ala Leu Ala Val Pro
  1               5                  10

<210> SEQ ID NO 19
<211> LENGTH: 12
<212> TYPE: PRT
<213> ORGANISM: Artificial Sequence
<220> FEATURE:
```

<223> OTHER INFORMATION: Advanced Macromolecule Transduction Domain
      (aMTD) Sequences for Improvement of Cell-Permeability

<400> SEQUENCE: 19

Ala Ala Leu Leu Val Pro Ala Leu Val Ala Val Pro
 1               5                   10

<210> SEQ ID NO 20
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 20

Ala Ile Val Ala Leu Pro Val Ala Val Leu Ala Pro
 1               5                   10

<210> SEQ ID NO 21
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 21

Ile Ala Ile Val Ala Pro Val Val Ala Leu Ala Pro
 1               5                   10

<210> SEQ ID NO 22
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 22

Ala Ala Leu Leu Pro Ala Leu Ala Ala Leu Leu Pro
 1               5                   10

<210> SEQ ID NO 23
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 23

Ala Val Val Leu Ala Pro Val Ala Ala Val Leu Pro
 1               5                   10

<210> SEQ ID NO 24
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 24

Leu Ala Val Ala Ala Pro Leu Ala Leu Ala Leu Pro
 1               5                   10

-continued

```
<210> SEQ ID NO 25
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 25

Ala Ala Val Ala Ala Pro Leu Leu Leu Ala Leu Pro
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 26

Leu Leu Val Leu Pro Ala Ala Ala Leu Ala Ala Pro
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 27

Leu Val Ala Leu Ala Pro Val Ala Ala Val Leu Pro
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 28

Leu Ala Leu Ala Pro Ala Ala Leu Ala Leu Leu Pro
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 29

Ala Leu Ile Ala Ala Pro Ile Leu Ala Leu Ala Pro
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 30
```

Ala Val Val Ala Ala Pro Leu Val Leu Ala Leu Pro
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 31

Leu Leu Ala Leu Ala Pro Ala Ala Leu Leu Ala Pro
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 32

Ala Ile Val Ala Leu Pro Ala Leu Ala Leu Ala Pro
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 33

Ala Ala Ile Ile Val Pro Ala Ala Leu Leu Ala Pro
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 34

Ile Ala Val Ala Leu Pro Ala Leu Ile Ala Ala Pro
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 35

Ala Val Ile Val Leu Pro Ala Leu Ala Val Ala Pro
 1               5                  10

<210> SEQ ID NO 36
<211> LENGTH: 12
<212> TYPE: PRT
<213> ORGANISM: Artificial Sequence

```
<220> FEATURE:
<223> OTHER INFORMATION: Advanced Macromolecule Transduction Domain
      (aMTD) Sequences for Improvement of Cell-Permeability

<400> SEQUENCE: 36

Ala Val Leu Ala Val Pro Ala Val Leu Val Ala Pro
 1               5                  10

<210> SEQ ID NO 37
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 37

Val Leu Ala Ile Val Pro Ala Val Ala Leu Ala Pro
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 38

Leu Leu Ala Val Val Pro Ala Val Ala Leu Ala Pro
 1               5                  10

<210> SEQ ID NO 39
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 39

Ala Val Ile Ala Leu Pro Ala Leu Ile Ala Ala Pro
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 40

Ala Val Val Ala Leu Pro Ala Ala Leu Ile Val Pro
 1               5                  10

<210> SEQ ID NO 41
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 41

Leu Ala Leu Val Leu Pro Ala Ala Leu Ala Ala Pro
 1               5                  10
```

<210> SEQ ID NO 42
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 42

Leu Ala Ala Val Leu Pro Ala Leu Leu Ala Ala Pro
 1               5                  10

<210> SEQ ID NO 43
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 43

Ala Leu Ala Val Pro Val Ala Leu Ala Ile Val Pro
 1               5                  10

<210> SEQ ID NO 44
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 44

Ala Leu Ile Ala Pro Val Val Ala Leu Val Ala Pro
 1               5                  10

<210> SEQ ID NO 45
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 45

Leu Leu Ala Ala Pro Val Val Ile Ala Leu Ala Pro
 1               5                  10

<210> SEQ ID NO 46
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 46

Leu Ala Ala Ile Val Pro Ala Ile Ile Ala Val Pro
 1               5                  10

<210> SEQ ID NO 47
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

```
<400> SEQUENCE: 47

Ala Ala Leu Val Leu Pro Leu Ile Ile Ala Ala Pro
  1               5                  10

<210> SEQ ID NO 48
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 48

Leu Ala Leu Ala Val Pro Ala Leu Ala Ala Leu Pro
  1               5                  10

<210> SEQ ID NO 49
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 49

Leu Ile Ala Ala Leu Pro Ala Val Ala Ala Leu Pro
  1               5                  10

<210> SEQ ID NO 50
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 50

Ala Leu Ala Leu Val Pro Ala Ile Ala Ala Leu Pro
  1               5                  10

<210> SEQ ID NO 51
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 51

Ala Ala Ile Leu Ala Pro Ile Val Ala Leu Ala Pro
  1               5                  10

<210> SEQ ID NO 52
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 52

Ala Leu Leu Ile Ala Pro Ala Ala Val Ile Ala Pro
  1               5                  10

<210> SEQ ID NO 53
<211> LENGTH: 12
<212> TYPE: PRT
```

```
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 53

Ala Ile Leu Ala Val Pro Ile Ala Val Val Ala Pro
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 54

Ile Leu Ala Ala Val Pro Ile Ala Leu Ala Ala Pro
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 55

Val Ala Ala Leu Leu Pro Ala Ala Ala Val Leu Pro
 1               5                  10

<210> SEQ ID NO 56
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 56

Ala Ala Ala Val Val Pro Val Leu Leu Val Ala Pro
 1               5                  10

<210> SEQ ID NO 57
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 57

Ala Ala Leu Leu Val Pro Ala Leu Val Ala Ala Pro
 1               5                  10

<210> SEQ ID NO 58
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 58

Ala Ala Val Leu Leu Pro Val Ala Leu Ala Ala Pro
 1               5                  10
```

<210> SEQ ID NO 59
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 59

Ala Ala Ala Leu Ala Pro Val Leu Ala Leu Val Pro
 1               5                  10

<210> SEQ ID NO 60
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 60

Leu Val Leu Val Pro Leu Leu Ala Ala Ala Ala Pro
 1               5                  10

<210> SEQ ID NO 61
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 61

Ala Leu Ile Ala Val Pro Ala Ile Ile Val Ala Pro
 1               5                  10

<210> SEQ ID NO 62
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 62

Ala Leu Ala Val Ile Pro Ala Ala Ala Ile Leu Pro
 1               5                  10

<210> SEQ ID NO 63
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 63

Leu Ala Ala Ala Pro Val Val Ile Val Ile Ala Pro
 1               5                  10

<210> SEQ ID NO 64
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

```
<400> SEQUENCE: 64

Val Leu Ala Ile Ala Pro Leu Leu Ala Ala Val Pro
 1               5                  10

<210> SEQ ID NO 65
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 65

Ala Leu Ile Val Leu Pro Ala Ala Val Ala Val Pro
 1               5                  10

<210> SEQ ID NO 66
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 66

Val Leu Ala Val Ala Pro Ala Leu Ile Val Ala Pro
 1               5                  10

<210> SEQ ID NO 67
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 67

Ala Ala Leu Leu Ala Pro Ala Leu Ile Val Ala Pro
 1               5                  10

<210> SEQ ID NO 68
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 68

Ala Leu Ile Ala Pro Ala Val Ala Leu Ile Val Pro
 1               5                  10

<210> SEQ ID NO 69
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 69

Ala Ile Val Leu Leu Pro Ala Ala Val Val Ala Pro
 1               5                  10

<210> SEQ ID NO 70
<211> LENGTH: 12
```

```
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 70

Val Ile Ala Ala Pro Val Leu Ala Val Leu Ala Pro
 1

<210> SEQ ID NO 76
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 76

Ile Val Ala Val Ala Leu Pro Val Ala Leu Ala Pro
 1               5                  10

<210> SEQ ID NO 77
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 77

Ile Val Ala Val Ala Leu Pro Ala Ala Leu Val Pro
 1               5                  10

<210> SEQ ID NO 78
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 78

Ile Val Ala Val Ala Leu Pro Ala Val Ala Leu Pro
 1               5                  10

<210> SEQ ID NO 79
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 79

Ile Val Ala Val Ala Leu Pro Ala Val Leu Ala Pro
 1               5                  10

<210> SEQ ID NO 80
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 80

Val Ile Val Ala Leu Ala Pro Ala Val Leu Ala Pro
 1               5                  10

<210> SEQ ID NO 81
<211> LENGTH: 12
<212> TYPE: PRT
<213> ORGANISM: Artificial Sequence
<220> FEATURE:
<223> OTHER INFORMATION: Advanced Macromolecule Transduction Domain (aMTD) Sequences for Improvement of Cell-Permeability

<400> SEQUENCE: 81

Ile Val Ala Val Ala Leu Pro Ala Leu Val Ala Pro
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 82

Ala Leu Leu Ile Val Ala Pro Val Ala Val Ala Pro
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 83

Ala Val Val Ile Val Ala Pro Ala Val Ile Ala Pro
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 84

Ala Val Leu Ala Val Ala Pro Ala Leu Ile Val Pro
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 85

Leu Val Ala Ala Val Ala Pro Ala Leu Ile Val Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 86

Ala Val Ile Val Val Ala Pro Ala Leu Leu Ala Pro
1               5                   10

<210> SEQ ID NO 87

```
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 87

Val Val Ala Ile Val Leu Pro Ala Val Ala Ala Pro
  1               5                  10

<210> SEQ ID NO 88
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 88

Ala Ala Ala Leu Val Ile Pro Ala Ile Leu Ala Pro
  1               5                  10

<210> SEQ ID NO 89
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 89

Val Ile Val Ala Leu Ala Pro Ala Leu Leu Ala Pro
  1               5                  10

<210> SEQ ID NO 90
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 90

Val Ile Val Ala Ile Ala Pro Ala Leu Leu Ala Pro
  1               5                  10

<210> SEQ ID NO 91
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 91

Ile Val Ala Ile Ala Val Pro Ala Leu Val Ala Pro
  1               5                  10

<210> SEQ ID NO 92
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 92
```

```
Ala Ala Leu Ala Val Ile Pro Ala Ala Ile Leu Pro
1               5                   10
```

<210> SEQ ID NO 93
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 93

```
Ala Leu Ala Ala Val Ile Pro Ala Ala Ile Leu Pro
1               5                   10
```

<210> SEQ ID NO 94
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 94

```
Ala Ala Ala Leu Val Ile Pro Ala Ala Ile Leu Pro
1               5                   10
```

<210> SEQ ID NO 95
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 95

```
Leu Ala Ala Ala Val Ile Pro Ala Ala Ile Leu Pro
1               5                   10
```

<210> SEQ ID NO 96
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 96

```
Leu Ala Ala Ala Val Ile Pro Val Ala Ile Leu Pro
1               5                   10
```

<210> SEQ ID NO 97
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 97

```
Ala Ala Ile Leu Ala Ala Pro Leu Ile Ala Val Pro
1               5                   10
```

<210> SEQ ID NO 98
<211> LENGTH: 12
<212> TYPE: PRT
<213> ORGANISM: Artificial Sequence
<220> FEATURE:

<223> OTHER INFORMATION: Advanced Macromolecule Transduction Domain
     (aMTD) Sequences for Improvement of Cell-Permeability

<400> SEQUENCE:

```
<210> SEQ ID NO 104
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 104

Ala Leu Ala Ala Leu Val Pro Ala Leu Val Val Pro
 1               5                  10

<210> SEQ ID NO 105
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 105

Ile Ala Ala Val Ile Val Pro Ala Val Ala Leu Pro
 1               5                  10

<210> SEQ ID NO 106
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 106

Ile Ala Ala Val Leu Val Pro Ala Val Ala Leu Pro
 1               5                  10

<210> SEQ ID NO 107
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 107

Ala Val Ala Ile Leu Val Pro Leu Leu Ala Ala Pro
 1               5                  10

<210> SEQ ID NO 108
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 108

Ala Val Val Ile Leu Val Pro Leu Ala Ala Ala Pro
 1               5                  10

<210> SEQ ID NO 109
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 109
```

```
Ile Ala Ala Val Ile Val Pro Val Ala Ala Leu Pro
 1               5                  10
```

<210> SEQ ID NO 110
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 110

```
Ala Ile Ala Ile Ala Ile Val Pro Val Ala Leu Pro
 1               5                  10
```

<210> SEQ ID NO 111
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 111

```
Ile Leu Ala Val Ala Ala Ile Pro Val Ala Val Pro
 1               5                  10
```

<210> SEQ ID NO 112
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 112

```
Ile Leu Ala Ala Ala Ile Ile Pro Ala Ala Leu Pro
 1               5                  10
```

<210> SEQ ID NO 113
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 113

```
Leu Ala Val Val Leu Ala Ala Pro Ala Ile Val Pro
 1               5                  10
```

<210> SEQ ID NO 114
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 114

```
Ala Ile Leu Ala Ala Ile Val Pro Leu Ala Val Pro
 1               5                  10
```

<210> SEQ ID NO 115
<211> LENGTH: 12
<212> TYPE: PRT
<213> ORGANISM: Artificial Sequence

```
<220> FEATURE:
<223> OTHER INFORMATION: Advanced Macromolecule Transduction Domain
      (aMTD) Sequences for Improvement of Cell-Permeability

<400> SEQUENCE: 115

Val Ile Val Ala Leu Ala Val Pro Ala Leu Ala Pro
 1               5                  10

<210> SEQ ID NO 116
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 116

Ala Ile Val Ala Leu Ala Val Pro Val Leu Ala Pro
 1               5                  10

<210> SEQ ID NO 117
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 117

Ala Ala Ile Ile Ile Val Leu Pro Ala Ala Leu Pro
 1               5                  10

<210> SEQ ID NO 118
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 118

Leu Ile Val Ala Leu Ala Val Pro Ala Leu Ala Pro
 1               5                  10

<210> SEQ ID NO 119
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 119

Ala Ile Ile Ile Val Ile Ala Pro Ala Ala Ala Pro
 1               5                  10

<210> SEQ ID NO 120
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 120

Leu Ala Ala Leu Ile Val Val Pro Ala Val Ala Pro
 1               5                  10
```

<210> SEQ ID NO 121
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 121

Ala Leu Leu Val Ile Ala Val Pro Ala Val Ala Pro
 1               5                  10

<210> SEQ ID NO 122
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 122

Ala Val Ala Leu Ile Val Val Pro Ala Leu Ala Pro
 1               5                  10

<210> SEQ ID NO 123
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 123

Ala Leu Ala Ile Val Val Ala Pro Val Ala Val Pro
 1               5                  10

<210> SEQ ID NO 124
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 124

Leu Leu Ala Leu Ile Ile Ala Pro Ala Ala Ala Pro
 1               5                  10

<210> SEQ ID NO 125
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 125

Ala Leu Ala Leu Ile Ile Val Pro Ala Val Ala Pro
 1               5                  10

<210> SEQ ID NO 126
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

```
<400> SEQUENCE: 126

Leu Leu Ala Ala Leu Ile Ala Pro Ala Ala Leu Pro
 1               5                  10

<210> SEQ ID NO 127
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 127

Ile Val Ala Leu Ile Val Ala Pro Ala Ala Val Pro
 1               5                  10

<210> SEQ ID NO 128
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 128

Val Val Leu Val Leu Ala Ala Pro Ala Ala Val Pro
 1               5                  10

<210> SEQ ID NO 129
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 129

Ala Ala Val Ala Ile Val Leu Pro Ala Val Val Pro
 1               5                  10

<210> SEQ ID NO 130
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 130

Ala Leu Ile Ala Ala Ile Val Pro Ala Leu Val Pro
 1               5                  10

<210> SEQ ID NO 131
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 131

Ala Leu Ala Val Ile Val Val Pro Ala Leu Ala Pro
 1               5                  10

<210> SEQ ID NO 132
<211> LENGTH: 12
<212> TYPE: PRT
```

```
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 132

Val Ala Ile Ala Leu Ile Val Pro Ala Leu Ala Pro
 1               5                  10

<210> SEQ ID NO 133
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 133

Val Ala Ile Val Leu Val Ala Pro Ala Val Ala Pro
 1               5                  10

<210> SEQ ID NO 134
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 134

Val Ala Val Ala Leu Ile Val Pro Ala Leu Ala Pro
 1               5                  10

<210> SEQ ID NO 135
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 135

Ala Val Ile Leu Ala Leu Ala Pro Ile Val Ala Pro
 1               5                  10

<210> SEQ ID NO 136
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 136

Ala Leu Ile Val Ala Ile Ala Pro Ala Leu Val Pro
 1               5                  10

<210> SEQ ID NO 137
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 137

Ala Ala Ile Leu Ile Ala Val Pro Ile Ala Ala Pro
 1               5                  10
```

```
<210> SEQ ID NO 138
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 138

Val Ile Val Ala Leu Ala Ala Pro Val Leu Ala Pro
 1               5                  10

<210> SEQ ID NO 139
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 139

Val Leu Val Ala Leu Ala Ala Pro Val Ile Ala Pro
 1               5                  10

<210> SEQ ID NO 140
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 140

Val Ala Leu Ile Ala Val Ala Pro Ala Val Val Pro
 1               5                  10

<210> SEQ ID NO 141
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 141

Val Ile Ala Ala Val Leu Ala Pro Val Ala Val Pro
 1               5                  10

<210> SEQ ID NO 142
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 142

Ala Leu Ile Val Leu Ala Ala Pro Val Ala Val Pro
 1               5                  10

<210> SEQ ID NO 143
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability
```

<400> SEQUENCE: 143

Val Ala Ala Ala Ile Ala Leu Pro Ala Ile Val Pro
 1               5                   10

<210> SEQ ID NO 144
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 144

Ile Leu Ala Ala Ala Ala Ala Pro Leu Ile Val Pro
 1               5                   10

<210> SEQ ID NO 145
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 145

Leu Ala Leu Val Leu Ala Ala Pro Ala Ile Val Pro
 1               5                   10

<210> SEQ ID NO 146
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 146

Ala Leu Ala Val Val Ala Leu Pro Ala Ile Val Pro
 1               5                   10

<210> SEQ ID NO 147
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 147

Ala Ala Ile Leu Ala Pro Ile Val Ala Ala Leu Pro
 1               5                   10

<210> SEQ ID NO 148
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 148

Ile Leu Ile Ala Ile Ala Ile Pro Ala Ala Ala Pro
 1               5                   10

<210> SEQ ID NO 149
<211> LENGTH: 12

```
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 149

Leu Ala Ile Val Leu Ala Ala Pro Val Ala Val Pro
 1               5                  10

<210> SEQ ID NO 150
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 150

Ala Ala Ile Ala Ile Ile Ala Pro Ala Ile Val Pro
 1               5                  10

<210> SEQ ID NO 151
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 151

Leu Ala Val Ala Ile Val Ala Pro Ala Leu Val Pro
 1               5                  10

<210> SEQ ID NO 152
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 152

Leu Ala Ile Val Leu Ala Ala Pro Ala Val Leu Pro
 1               5                  10

<210> SEQ ID NO 153
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 153

Ala Ala Ile Val Leu Ala Leu Pro Ala Val Leu Pro
 1               5                  10

<210> SEQ ID NO 154
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 154

Ala Leu Leu Val Ala Val Leu Pro Ala Ala Leu Pro
```

```
<210> SEQ ID NO 155
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 155

Ala Ala Leu Val Ala Val Leu Pro Val Ala Leu Pro
  1               5                  10

<210> SEQ ID NO 156
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 156

Ala Ile Leu Ala Val Ala Leu Pro Leu Leu Ala Pro
  1               5                  10

<210> SEQ ID NO 157
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 157

Ile Val Ala Val Ala Leu Val Pro Ala Leu Ala Pro
  1               5                  10

<210> SEQ ID NO 158
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 158

Ile Val Ala Val Ala Leu Leu Pro Ala Leu Ala Pro
  1               5                  10

<210> SEQ ID NO 159
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 159

Ile Val Ala Val Ala Leu Leu Pro Ala Val Ala Pro
  1               5                  10

<210> SEQ ID NO 160
<211> LENGTH: 12
<212> TYPE: PRT
<213> ORGANISM: Artificial Sequence
<220> FEATURE:
<223> OTHER INFORMATION: Advanced Macromolecule Transduction Domain
```

(aMTD) Sequences for Improvement of Cell-Permeability

<400> SEQUENCE: 160

Ile Val Ala Leu Ala Val Leu Pro Ala Val Ala Pro
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 161

Val Ala Val Leu Ala Val Leu Pro Ala Leu Ala Pro
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 162

Ile Ala Val Leu Ala Val Ala Pro Ala Val Leu Pro
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 163

Leu Ala Val Ala Ile Ile Ala Pro Ala Val Ala Pro
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 164

Val Ala Leu Ala Ile Ala Leu Pro Ala Val Leu Pro
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 165

Ala Ile Ala Ile Ala Leu Val Pro Val Ala Leu Pro
1               5                   10

<210> SEQ ID NO 166

```
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 166

Ala Ala Val Val Ile Val Ala Pro Val Ala Leu Pro
 1               5                  10

<210> SEQ ID NO 167
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 167

Val Ala Ile Ile Val Val Ala Pro Ala Leu Ala Pro
 1               5                  10

<210> SEQ ID NO 168
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 168

Val Ala Leu Leu Ala Ile Ala Pro Ala Leu Ala Pro
 1               5                  10

<210> SEQ ID NO 169
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 169

Val Ala Val Leu Ile Ala Val Pro Ala Leu Ala Pro
 1               5                  10

<210> SEQ ID NO 170
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 170

Ala Val Ala Leu Ala Val Leu Pro Ala Val Val Pro
 1               5                  10

<210> SEQ ID NO 171
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 171
```

```
Ala Val Ala Leu Ala Val Val Pro Ala Val Leu Pro
 1               5                  10

<210> SEQ ID NO 172
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 172

Ile Val Val Ile Ala Val Ala Pro Ala Val Ala Pro
 1               5                  10

<210> SEQ ID NO 173
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 173

Ile Val Val Ala Ala Val Val Pro Ala Leu Ala Pro
 1               5                  10

<210> SEQ ID NO 174
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 174

Ile Val Ala Leu Val Pro Ala Val Ala Ile Ala Pro
 1               5                  10

<210> SEQ ID NO 175
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 175

Val Ala Ala Leu Pro Ala Val Ala Leu Val Val Pro
 1               5                  10

<210> SEQ ID NO 176
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 176

Leu Val Ala Ile Ala Pro Leu Ala Val Leu Ala Pro
 1               5                  10

<210> SEQ ID NO 177
<211> LENGTH: 12
<212> TYPE: PRT
<213> ORGANISM: Artificial Sequence
<220> FEATURE:
```

<223> OTHER INFORMATION: Advanced Macromolecule Transduction Domain
      (aMTD) Sequences for Improvement of Cell-Permeability

<400> SEQUENCE: 177

Ala Val Ala Leu Val Pro Val Ile Val Ala Ala Pro
 1               5                   10

<210> SEQ ID NO 178
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 178

Ala Ile Ala Val Ala Ile Ala Pro Val Ala Leu Pro
 1               5                   10

<210> SEQ ID NO 179
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 179

Ala Ile Ala Leu Ala Val Pro Val Leu Ala Leu Pro
 1               5                   10

<210> SEQ ID NO 180
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 180

Leu Val Leu Ile Ala Ala Ala Pro Ile Ala Leu Pro
 1               5                   10

<210> SEQ ID NO 181
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 181

Leu Val Ala Leu Ala Val Pro Ala Ala Val Leu Pro
 1               5                   10

<210> SEQ ID NO 182
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 182

Ala Val Ala Leu Ala Val Pro Ala Leu Val Leu Pro
 1               5                   10

<210> SEQ ID NO 183
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 183

Leu Val Val Leu Ala Ala Ala Pro Leu Ala Val Pro
 1               5                  10

<210> SEQ ID NO 184
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 184

Leu Ile Val Leu Ala Ala Pro Ala Leu Ala Ala Pro
 1               5                  10

<210> SEQ ID NO 185
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 185

Val Ile Val Leu Ala Ala Pro Ala Leu Ala Ala Pro
 1               5                  10

<210> SEQ ID NO 186
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 186

Ala Val Val Leu Ala Val Pro Ala Leu Ala Val Pro
 1               5                  10

<210> SEQ ID NO 187
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 187

Leu Ile Ile Val Ala Ala Ala Pro Ala Val Ala Pro
 1               5                  10

<210> SEQ ID NO 188
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 188

Ile Val Ala Val Ile Val Ala Pro Ala Val Ala Pro
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 189

Leu Val Ala Leu Ala Ala Pro Ile Ile Ala Val Pro
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 190

Ile Ala Ala Val Leu Ala Ala Pro Ala Leu Val Pro
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 191

Ile Ala Leu Leu Ala Ala Pro Ile Ile Ala Val Pro
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 192

Ala Ala Leu Ala Leu Val Ala Pro Val Ile Val Pro
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 193

Ile Ala Leu Val Ala Ala Pro Val Ala Leu Val Pro
1               5                   10

<210> SEQ ID NO 194
<211> LENGTH: 12
<212> TYPE: PRT
<213> ORGANISM: Artificial Sequence -continued

```
<220> FEATURE:
<223> OTHER INFORMATION: Advanced Macromolecule Transduction Domain
      (aMTD) Sequences for Improvement of Cell-Permeability

<400> SEQUENCE: 194

Ile Ile Val Ala Val Ala Pro Ala Ala Ile Val Pro
 1               5                  10

<210> SEQ ID NO 195
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 195

Ala Val Ala Ala Ile Val Pro Val Ile Val Ala Pro
 1               5                  10

<210> SEQ ID NO 196
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 196

Ala Val Leu Val Leu Val Ala Pro Ala Ala Ala Pro
 1               5                  10

<210> SEQ ID NO 197
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 197

Val Val Ala Leu Leu Ala Pro Leu Ile Ala Ala Pro
 1               5                  10

<210> SEQ ID NO 198
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 198

Ala Ala Val Val Ile Ala Pro Leu Leu Ala Val Pro
 1               5                  10

<210> SEQ ID NO 199
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 199

Ile Ala Val Ala Val Ala Ala Pro Leu Leu Val Pro
 1               5                  10
```

```
<210> SEQ ID NO 200
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 200

Leu Val Ala Ile Val Val Leu Pro Ala Val Ala Pro
  1               5                  10

<210> SEQ ID NO 201
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 201

Ala Val Ala Ile Val Val Leu Pro Ala Val Ala Pro
  1               5                  10

<210> SEQ ID NO 202
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 202

Ala Val Ile Leu Leu Ala Pro Leu Ile Ala Ala Pro
  1               5                  10

<210> SEQ ID NO 203
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 203

Leu Val Ile Ala Leu Ala Ala Pro Val Ala Leu Pro
  1               5                  10

<210> SEQ ID NO 204
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 204

Val Leu Ala Val Val Leu Pro Ala Val Ala Leu Pro
  1               5                  10

<210> SEQ ID NO 205
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability
```

-continued

<400> SEQUENCE: 205

Val Leu Ala Val Ala Ala Pro Ala Val Leu Leu Pro
  1               5                   10

<210> SEQ ID NO 206
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 206

Ala Ala Val Val Leu Leu Pro Ile Ile Ala Ala Pro
  1               5                   10

<210> SEQ ID NO 207
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 207

Ala Leu Leu Val Ile Ala Pro Ala Ile Ala Val Pro
  1               5                   10

<210> SEQ ID NO 208
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 208

Ala Val Leu Val Ile Ala Val Pro Ala Ile Ala Pro
  1               5                   10

<210> SEQ ID NO 209
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 209

Ala Leu Leu Val Val Ile Ala Pro Leu Ala Ala Pro
  1               5                   10

<210> SEQ ID NO 210
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 210

Val Leu Val Ala Ala Ile Leu Pro Ala Ala Ile Pro
  1               5                   10

<210> SEQ ID NO 211
<211> LENGTH: 12
<212> TYPE: PRT

<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 211

Val Leu Val Ala Ala Val Leu Pro Ile Ala Ala Pro
  1               5                  10

<210> SEQ ID NO 212
<211> LENGTH: 12
<212> TYPE: PRT
<213> ORGANISM: Artificial Sequence
<220> FEATURE:
<223> OTHER INFORMATION: Advanced Macromolecule Transduction Domain (aMTD) Sequences for Improvement of Cell-Permeability

<400> SEQUENCE: 212

Val Leu Ala Ala Ala Val Leu Pro Leu Val Val Pro
1 5 10

<210> SEQ ID NO 213
<211> LENGTH: 12
<212> TYPE: PRT
<213> ORGANISM: Artificial Sequence
<220> FEATURE:
<223> OTHER INFORMATION: Advanced Macromolecule Transduction Domain (aMTD) Sequences for Improvement of Cell-Permeability

<400> SEQUENCE: 213

Ala Ile Ala Ile Val Val Pro Ala Val Ala Val Pro
1 5 10

<210> SEQ ID NO 214
<211> LENGTH: 12
<212> TYPE: PRT
<213> ORGANISM: Artificial Sequence
<220> FEATURE:
<223> OTHER INFORMATION: Advanced Macromolecule Transduction Domain (aMTD) Sequences for Improvement of Cell-Permeability

<400> SEQUENCE: 214

Val Ala Ile Ile Ala Val Pro Ala Val Val Ala Pro
1 5 10

<210> SEQ ID NO 215
<211> LENGTH: 12
<212> TYPE: PRT
<213> ORGANISM: Artificial Sequence
<220> FEATURE:
<223> OTHER INFORMATION: Advanced Macromolecule Transduction Domain (aMTD) Sequences for Improvement of Cell-Permeability

<400> SEQUENCE: 215

Ile Val Ala Leu Val Ala Pro Ala Ala Val Val Pro
1 5 10

<210> SEQ ID NO 216
<211> LENGTH: 12
<212> TYPE: PRT
<213> ORGANISM: Artificial Sequence
<220> FEATURE:
<223> OTHER INFORMATION: Advanced Macromolecule Transduction Domain (aMTD) Sequences for Improvement of Cell-Permeability

<400> SEQUENCE: 216

Ala Ala Ile Val Leu Leu Pro Ala Val Val Val Pro
1 5 10

<210> SEQ ID NO 217
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 217

Ala Ala Leu Ile Val Val Pro Ala Val Ala Val Pro
  1               5                  10

<210> SEQ ID NO 218
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 218

Ala Ile Ala Leu Val Val Pro Ala Val Ala Val Pro
  1               5                  10

<210> SEQ ID NO 219
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 219

Leu Ala Ile Val Pro Ala Ala Ile Ala Ala Leu Pro
  1               5                  10

<210> SEQ ID NO 220
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 220

Leu Val Ala Ile Ala Pro Ala Val Ala Val Leu Pro
  1               5                  10

<210> SEQ ID NO 221
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 221

Val Leu Ala Val Ala Pro Ala Val Ala Val Leu Pro
  1               5                  10

<210> SEQ ID NO 222
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

```
<400> SEQUENCE: 222

Ile Leu Ala Val Val Ala Ile Pro Ala Ala Ala Pro
1               5                   10

<210> SEQ ID NO 223
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 223

Ile Leu Val Ala Ala Ala Pro Ile Ala Ala Leu Pro
1               5                   10

<210> SEQ ID NO 224
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 224

Ile Leu Ala Val Ala Ala Ile Pro Ala Ala Leu Pro
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 225

Val Ile Ala Ile Pro Ala Ile Leu Ala Ala Ala Pro
1               5                   10

<210> SEQ ID NO 226
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 226

Ala Ile Ile Ile Val Val Pro Ala Ile Ala Ala Pro
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 227

Ala Ile Leu Ile Val Val Ala Pro Ile Ala Ala Pro
1               5                   10

<210> SEQ ID NO 228
<211> LENGTH: 12
```

<212> TYPE: PRT
<213> ORGANISM: Artificial Sequence
<220> FEATURE:
<223> OTHER INFORMATION: Advanced Macromolecule Transduction Domain
(aMTD) Sequences for Improvement of Cell-Permeability

<400> SEQUENCE: 228

Ala Val Ile Val Pro Val Ala Ile Ile Ala Ala Pro
1 5 10

<210> SEQ ID NO 229
<211> LENGTH: 12
<212> TYPE: PRT
<213> ORGANISM: Artificial Sequence
<220> FEATURE:
<223> OTHER INFORMATION: Advanced Macromolecule Transduction Domain
(aMTD) Sequences for Improvement of Cell-Permeability

<400> SEQUENCE: 229

Ala Val Val Ile Ala Leu Pro Ala Val Val Ala Pro
1 5 10

<210> SEQ ID NO 230
<211> LENGTH: 12
<212> TYPE: PRT
<213> ORGANISM: Artificial Sequence
<220> FEATURE:
<223> OTHER INFORMATION: Advanced Macromolecule Transduction Domain
(aMTD) Sequences for Improvement of Cell-Permeability

<400> SEQUENCE: 230

Ala Leu Val Ala Val Ile Ala Pro Val Val Ala Pro
1 5 10

<210> SEQ ID NO 231
<211> LENGTH: 12
<212> TYPE: PRT
<213> ORGANISM: Artificial Sequence
<220> FEATURE:
<223> OTHER INFORMATION: Advanced Macromolecule Transduction Domain
(aMTD) Sequences for Improvement of Cell-Permeability

<400> SEQUENCE: 231

Ala Leu Val Ala Val Leu Pro Ala Val Ala Val Pro
1 5 10

<210> SEQ ID NO 232
<211> LENGTH: 12
<212> TYPE: PRT
<213> ORGANISM: Artificial Sequence
<220> FEATURE:
<223> OTHER INFORMATION: Advanced Macromolecule Transduction Domain
(aMTD) Sequences for Improvement of Cell-Permeability

<400> SEQUENCE: 232

Ala Leu Val Ala Pro Leu Leu Ala Val Ala Val Pro
1 5 10

<210> SEQ ID NO 233
<211> LENGTH: 12
<212> TYPE: PRT
<213> ORGANISM: Artificial Sequence
<220> FEATURE:
<223> OTHER INFORMATION: Advanced Macromolecule Transduction Domain
(aMTD) Sequences for Improvement of Cell-Permeability

<400> SEQUENCE: 233

Ala Val Leu Ala Val Val Ala Pro Val Val Ala Pro

```
                1               5                    10

<210> SEQ ID NO 234
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 234

Ala Val Ile Ala Val Ala Pro Leu Val Val Ala Pro
  1               5                    10

<210> SEQ ID NO 235
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 235

Ala Val Ile Ala Leu Ala Pro Val Val Val Ala Pro
  1               5                    10

<210> SEQ ID NO 236
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 236

Val Ala Ile Ala Leu Ala Pro Val Val Val Ala Pro
  1               5                    10

<210> SEQ ID NO 237
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 237

Val Ala Leu Ala Leu Ala Pro Val Val Val Ala Pro
  1               5                    10

<210> SEQ ID NO 238
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 238

Val Ala Ala Leu Leu Pro Ala Val Val Val Ala Pro
  1               5                    10

<210> SEQ ID NO 239
<211> LENGTH: 12
<212> TYPE: PRT
<213> ORGANISM: Artificial Sequence
<220> FEATURE:
<223> OTHER INFORMATION: Advanced Macromolecule Transduction Domain
```

(aMTD) Sequences for Improvement of Cell-Permeability

<400> SEQUENCE: 239

Val Ala Leu Ala Leu Pro Ala Val Val Val Ala Pro
 1               5                  10

<210> SEQ ID NO 240
<211> LENGTH: 12
<212> TYPE: PRT
<213> ORGANISM: Artificial Sequence
<220> FEATURE:
<223> OTHER INFORMATION: Advanced Macromolecule Transduction Domain
      (aMTD) Sequences for Improvement of Cell-Permeability

<400> SEQUENCE: 240

Val Ala Leu Leu Ala Pro Ala Val Val Val Ala Pro
 1               5                  10

<210> SEQ ID NO 241
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 241
gcggcggcgc tggcgccggt ggtgctggcg ctgccg                         36

<210> SEQ ID NO 242
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 242
gcggcggcgg tgccgctgct ggcggtggtg gtgccg                         36

<210> SEQ ID NO 243
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 243
gcggcgctgc tggtgccggc ggcggtgctg gcgccg                         36

<210> SEQ ID NO 244
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 244
gcgctggcgc tgctgccggt ggcggcgctg gcgccg                         36

<210> SEQ ID NO 245

```
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 245
gcggcggcgc tgctgccggt ggcgctggtg gcgccg                               36

<210> SEQ ID NO 246
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 246
gtggtggcgc tggcgccggc gctggcggcg ctgccg                               36

<210> SEQ ID NO 247
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 247
ctgctggcgg cggtgccggc ggtgctgctg gcgccg                               36

<210> SEQ ID NO 248
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 248
gcggcggcgc tggtgccggt ggtggcgctg ctgccg                               36

<210> SEQ ID NO 249
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 249
gcggtggcgc tgctgccggc gctgctggcg gtgccg                               36

<210> SEQ ID NO 250
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 250
```
gcggtggtgc tggtgccggt gctggcggcg gcgccg				36

<210> SEQ ID NO 251
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 251
gtggtgctgg tgctgccggc ggcggcggcg gtgccg				36

<210> SEQ ID NO 252
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 252
attgcgctgg cggcgccggc gctgattgtg gcgccg				36

<210> SEQ ID NO 253
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 253
attgtggcgg tggcgccggc gctggtggcg ctgccg				36

<210> SEQ ID NO 254
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 254
gtggcggcgc tgccggtggt ggcggtggtg gcgccg				36

<210> SEQ ID NO 255
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 255
ctgctggcgg cgccgctggt ggtggcggcg gtgccg				36

<210> SEQ ID NO 256
<211> LENGTH: 36
<212> TYPE: DNA
<213> ORGANISM: Artificial Sequence
<220> FEATURE:

<223> OTHER INFORMATION: The polynucleotide sequence that encodes
      advanced Macromolecule Transduction Domain (aMTD) peptide for
      Improvement of Cell-Permeability

<400> SEQUENCE:

<210> SEQ ID NO 262
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 262
gcggcgctgc tgccggcgct ggcggcgctg ctgccg      36

<210> SEQ ID NO 263
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 263
gcggtggtgc tggcgccggt ggcggcggtg ctgccg      36

<210> SEQ ID NO 264
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 264
ctggcggtgg cggcgccgct ggcgctggcg ctgccg      36

<210> SEQ ID NO 265
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 265
gcggcggtgg cggcgccgct gctgctggcg ctgccg      36

<210> SEQ ID NO 266
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 266
ctgctggtgc tgccggcggc ggcgctggcg gcgccg      36

<210> SEQ ID NO 267
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

```
<400> SEQUENCE: 267
ctggtggcgg tggcgccggt ggcggcggtg ctgccg                          36

<210> SEQ ID NO 268
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 268
ctggcgctgg cgccggcggc gctggcgctg ctgccg                          36

<210> SEQ ID NO 269
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 269
gcgctgattg cggcgccgat tctggcgctg gcgccg                          36

<210> SEQ ID NO 270
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 270
gcggtggtgg cggcgccgct ggtgctggcg ctgccg                          36

<210> SEQ ID NO 271
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 271
ctgctggcgc tggcgccggc ggcgctgctg gcgccg                          36

<210> SEQ ID NO 272
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 272
gcgattgtgg cgctgccggc gctggcgctg gcgccg                          36

<210> SEQ ID NO 273
<211> LENGTH: 36
<212> TYPE: DNA
<213> ORGANISM: Artificial Sequence
```

```
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 273
gcggcgatta ttgtgccggc ggcgctgctg gcgccg                                 36

<210> SEQ ID NO 274
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 274
attgcggtgg cgctgccggc gctgattgcg gcgccg                                 36

<210> SEQ ID NO 275
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement

```
<210> SEQ ID NO 279
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 279
gcggtgattg cgctgccggc gctgattgcg gcgccg                                 36

<210> SEQ ID NO 280
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 280
gcggtggtgg cgctgccggc ggcgctgatt gtgccg                                 36

<210> SEQ ID NO 281
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 281
ctggcgctgg tgctgccggc ggcgctggcg gcgccg                                 36

<210> SEQ ID NO 282
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 282
ctggcggcgg tgctgccggc gctgctggcg gcgccg                                 36

<210> SEQ ID NO 283
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 283
gcgctggcgg tgccggtggc gctggcgatt gtgccg                                 36

<210> SEQ ID NO 284
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability
```

<400> SEQUENCE: 284
gcgctgattg cgccggtggt ggcgctggtg gcgccg            36

<210> SEQ ID NO 285
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 285
ctgctggcgg cgccggtggt gattgcgctg gcgccg            36

<210> SEQ ID NO 286
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 286
ctggcggcga ttgtgccggc gattattgcg gtgccg            36

<210> SEQ ID NO 287
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 287
gcggcgctgg tgctgccgct gattattgcg gcgccg            36

<210> SEQ ID NO 288
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 288
ctggcgctgg cggtgccggc gctggcggcg ctgccg            36

<210> SEQ ID NO 289
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 289
ctgattgcgg cgctgccggc ggtggcggcg ctgccg            36

<210> SEQ ID NO 290
<211> LENGTH: 36
<212> TYPE: DNA

```
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 290
gcgctggcgc tggtgccggc gattgcggcg ctgccg                                    36

<210> SEQ ID NO 291
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 291
gcggcgattc tggcgccgat tgtggcgctg gcgccg                                    36

<210> SEQ ID NO 292
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 292
gcgctgctga ttgcgccggc ggcggtgatt gcgccg                                    36

<210> SEQ ID NO 293
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 293
gcgattctgg cggtgccgat tgcggtggtg gcgccg                                    36

<210> SEQ ID NO 294
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 294
attctggcgg cggtgccgat tgcgctggcg gcgccg                                    36

<210> SEQ ID NO 295
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 295
gtggcggcgc tgctgccggc ggcggcggtg ctgccg                                    36
```

<210> SEQ ID NO 296
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 296
gcggcggcgg tggtgccggt gctgctggtg gcgccg                                36

<210> SEQ ID NO 297
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 297
gcggcgctgc tggtgccggc gctggtggcg gcgccg                                36

<210> SEQ ID NO 298
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 298
gcggcggtgc tgctgccggt ggcgctggcg gcgccg                                36

<210> SEQ ID NO 299
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 299
gcggcggcgc tggcgccggt gctggcgctg gtgccg                                36

<210> SEQ ID NO 300
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 300
ctggtgctgg tgccgctgct ggcggcggcg gcgccg                                36

<210> SEQ ID NO 301
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for -continued Improvement of Cell-Permeability

<400> SEQUENCE: 301
gcgctgattg cggtgccggc gattattgtg gcgccg                                   36

<210> SEQ ID NO 302
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 302
gcgctggcgg tgattccggc ggcggcgatt ctgccg                                   36

<210> SEQ ID NO 303
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 303
ctggcggcgg cgccggtggt gattgtgatt gcgccg                                   36

<210> SEQ ID NO 304
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 304
gtgctggcga ttgcgccgct gctggcggcg gtgccg                                   36

<210> SEQ ID NO 305
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 305
gcgctgattg tgctgccggc ggcggtggcg gtgccg                                   36

<210> SEQ ID NO 306
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 306
gtgctggcgg tggcgccggc gctgattgtg gcgccg                                   36

<210> SEQ ID NO 307
<211> LENGTH: 36

<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 307
gcggcgctgc tggcgccggc gctgattgtg gcgccg                36

<210> SEQ ID NO 308
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 308
gcgctgattg cgccggcggt ggcgctgatt gtgccg                36

<210> SEQ ID NO 309
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 309
gcgattgtgc tgctgccggc ggcggtggtg gcgccg                36

<210> SEQ ID NO 310
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 310
gtgattgcgg cgccggtgct ggcggtgctg gcgccg                36

<210> SEQ ID NO 311
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 311
ctggcgctgg cgccggcgct ggcgctgctg gcgccg                36

<210> SEQ ID NO 312
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 312
gcgattattc tggcgccgat tgcggcgatt gcgccg        36

<210> SEQ ID NO 313
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 313
attgcgctgg cggcgccgat tctgctggcg gcgccg        36

<210> SEQ ID NO 314
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 314
attgtggcgg tggcgctgcc ggcgctggcg gtgccg        36

<210> SEQ ID NO 315
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 315
gtggtggcga ttgtgctgcc ggcgctggcg gcgccg        36

<210> SEQ ID NO 316
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 316
attgtggcgg tggcgctgcc ggtggcgctg gcgccg        36

<210> SEQ ID NO 317
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 317
attgtggcgg tggcgctgcc ggcggcgctg gtgccg        36

<210> SEQ ID NO 318
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for
Improvement of Cell-Permeability

<400> SEQUENCE: 318
attgtggcgg tggcgctgcc ggcggtggcg ctgccg                    36

<210> SEQ ID NO 319
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 319
attgtggcgg tggcgctgcc ggcggtgctg gcgccg                    36

<210> SEQ ID NO 320
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 320
gtgattgtgg cgctggcgcc ggcggtgctg gcgccg                    36

<210> SEQ ID NO 321
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 321
attgtggcgg tggcgctgcc ggcgctggtg gcgccg                    36

<210> SEQ ID NO 322
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 322
gcgctgctga ttgtggcgcc ggtggcggtg gcgccg                    36

<210> SEQ ID NO 323
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 323
gcggtggtga ttgtggcgcc ggcggtgatt gcgccg                    36

<210> SEQ ID NO 324

```
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 324
gcggtgctgg cggtggcgcc ggcgctgatt gtgccg                            36

<210> SEQ ID NO 325
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 325
ctggtggcgg cggtggcgcc ggcgctgatt gtgccg                            36

<210> SEQ ID NO 326
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 326
gcggtgattg tggtggcgcc ggcgctgctg gcgccg                            36

<210> SEQ ID NO 327
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 327
gtggtggcga ttgtgctgcc ggcggtggcg gcgccg                            36

<210> SEQ ID NO 328
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 328
gcggcggcgc tggtgattcc ggcgattctg gcgccg                            36

<210> SEQ ID NO 329
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 329
```

```
gtgattgtgg cgctggcgcc ggcgctgctg gcgccg                                  36
```

<210> SEQ ID NO 330
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 330

```
gtgattgtgg cgattgcgcc ggcgctgctg gcgccg                                  36
```

<210> SEQ ID NO 331
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 331

```
attgtggcga ttgcggtgcc ggcgctggtg gcgccg                                  36
```

<210> SEQ ID NO 332
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 332

```
gcggcgctgg cggtgattcc ggcggcgatt ctgccg                                  36
```

<210> SEQ ID NO 333
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 333

```
gcgctggcgg cggtgattcc ggcggcgatt ctgccg                                  36
```

<210> SEQ ID NO 334
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 334

```
gcggcggcgc tggtgattcc ggcggcgatt ctgccg                                  36
```

<210> SEQ ID NO 335
<211> LENGTH: 36
<212> TYPE: DNA
<213> ORGANISM: Artificial Sequence
<220> FEATURE:

```
<223> OTHER INFORMATION: The polynucleotide sequence that encodes
      advanced Macromolecule Transduction Domain (aMTD) peptide for
      Improvement of Cell-Permeability

<400>

<210> SEQ ID NO 341
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 341
gcgctggcgg cgctggtgcc ggcggtgctg gtgccg                              36

<210> SEQ ID NO 342
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 342
gcgctggcgg cgctggtgcc ggtggcgctg gtgccg                              36

<210> SEQ ID NO 343
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 343
ctggcggcgg cgctggtgcc ggtggcgctg gtgccg                              36

<210> SEQ ID NO 344
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 344
gcgctggcgg cgctggtgcc ggcgctggtg gtgccg                              36

<210> SEQ ID NO 345
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 345
attgcggcgg tgattgtgcc ggcggtggcg ctgccg                              36

<210> SEQ ID NO 346
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

```
<400> SEQUENCE: 346
attgcggcgg tgctggtgcc ggcggtggcg ctgccg                                    36

<210> SEQ ID NO 347
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 347
gcggtggcga ttctggtgcc gctgctggcg gcgccg                                    36

<210> SEQ ID NO 348
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 348
gcggtggtga ttctggtgcc gctggcggcg gcgccg                                    36

<210> SEQ ID NO 349
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 349
attgcggcgg tgattgtgcc ggtggcggcg ctgccg                                    36

<210> SEQ ID NO 350
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 350
gcgattgcga ttgcgattgt gccggtggcg ctgccg                                    36

<210> SEQ ID NO 351
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 351
attctggcgg tggcggcgat tccggtggcg gtgccg                                    36

<210> SEQ ID NO 352
<211> LENGTH: 36
<212> TYPE: DNA
<213> ORGANISM: Artificial Sequence
```

```
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 352
attctggcgg cggcgattat tccggcggcg ctgccg                              36

<210> SEQ ID NO 353
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 353
ctggcggtgg tgctggcggc gccggcgatt gtgccg                              36

<210> SEQ ID NO 354
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 354
gcgattctgg cggcgattgt gccgctggcg gtgccg                              36

<210> SEQ ID NO 355
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 355
gtgattgtgg cgctggcggt gccggcgctg gcgccg                              36

<210> SEQ ID NO 356
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 356
gcgattgtgg cgctggcggt gccggtgctg gcgccg                              36

<210> SEQ ID NO 357
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 357
gcggcgatta ttattgtgct gccggcggcg ctgccg                              36
```

<210> SEQ ID NO 358
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 358
ctgattgtgg cgctggcggt gccggcgctg gcgccg                              36

<210> SEQ ID NO 359
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 359
gcgattatta ttgtgattgc gccggcggcg gcgccg                              36

<210> SEQ ID NO 360
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 360
ctggcggcgc tgattgtggt gccggcggtg gcgccg                              36

<210> SEQ ID NO 361
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 361
gcgctgctgg tgattgcggt gccggcggtg gcgccg                              36

<210> SEQ ID NO 362
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 362
gcggtggcgc tgattgtggt gccggcgctg gcgccg                              36

<210> SEQ ID NO 363
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 363
gcgctggcga ttgtggtggc gccggtggcg gtgccg                                36

<210> SEQ ID NO 364
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 364
ctgctggcgc tgattattgc gccggcggcg gcgccg                                36

<210> SEQ ID NO 365
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 365
gcgctggcgc tgattattgt gccggcggtg gcgccg                                36

<210> SEQ ID NO 366
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 366
ctgctggcgg cgctgattgc gccggcggcg ctgccg                                36

<210> SEQ ID NO 367
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 367
attgtggcgc tgattgtggc gccggcggcg gtgccg                                36

<210> SEQ ID NO 368
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 368
gtggtgctgg tgctggcggc gccggcggcg gtgccg                                36

<210> SEQ ID NO 369
<211> LENGTH: 36
<212> TYPE: DNA

```
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 369
gcggcggtgg cgattgtgct gccggcggtg gtgccg                                    36

<210> SEQ ID NO 370
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 370
gcgctgattg cggcgattgt gccggcgctg gtgccg                                    36

<210> SEQ ID NO 371
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 371
gcgctggcgg tgattgtggt gccggcgctg gcgccg                                    36

<210> SEQ ID NO 372
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 372
gtggcgattg cgctgattgt gccggcgctg gcgccg                                    36

<210> SEQ ID NO 373
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 373
gtggcgattg tgctggtggc gccggcggtg gcgccg                                    36

<210> SEQ ID NO 374
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 374
gtggcggtgg cgctgattgt gccggcgctg gcgccg                                    36
```

<210> SEQ ID NO 375
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 375
gcggtgattc tggcgctggc gccgattgtg gcgccg                                    36

<210> SEQ ID NO 376
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 376
gcgctgattg tggcgattgc gccggcgctg gtgccg                                    36

<210> SEQ ID NO 377
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 377
gcggcgattc tgattgcggt gccgattgcg gcgccg                                    36

<210> SEQ ID NO 378
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 378
gtgattgtgg cgctggcggc gccggtgctg gcgccg                                    36

<210> SEQ ID NO 379
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 379
gtgctggtgg cgctggcggc gccggtgatt gcgccg                                    36

<210> SEQ ID NO 380
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for Improvement of Cell-Permeability

<400> SEQUENCE: 380
gtggcgctga ttgcggtggc gccggcggtg gtgccg        36

<210> SEQ ID NO 381
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 381
gtgattgcgg cggtgctggc gccggtggcg gtgccg        36

<210> SEQ ID NO 382
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 382
gcgctgattg tgctggcggc gccggtggcg gtgccg        36

<210> SEQ ID NO 383
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 383
gtggcggcgg cgattgcgct gccggcgatt gtgccg        36

<210> SEQ ID NO 384
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 384
attctggcgg cggcggcggc gccgctgatt gtgccg        36

<210> SEQ ID NO 385
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 385
ctggcgctgg tgctggcggc gccggcgatt gtgccg        36

<210> SEQ ID NO 386
<211> LENGTH: 36

```
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 386
gcgctggcgg tggtggcgct gccggcgatt gtgccg                             36

<210> SEQ ID NO 387
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 387
gcggcgattc tggcgccgat tgtggcggcg ctgccg                             36

<210> SEQ ID NO 388
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 388
attctgattg cgattgcgat tccggcggcg gcgccg                             36

<210> SEQ ID NO 389
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 389
ctggcgattg tgctggcggc gccggtggcg gtgccg                             36

<210> SEQ ID NO 390
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 390
gcggcgattg cgattattgc gccggcgatt gtgccg                             36

<210> SEQ ID NO 391
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 391
```
ctggcggtgg cgattgtggc gccggcgctg gtgccg 36

<210> SEQ ID NO 392
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 392
ctggcgattg tgctggcggc gccggcggtg ctgccg 36

<210> SEQ ID NO 393
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 393
gcggcgattg tgctggcgct gccggcggtg ctgccg 36

<210> SEQ ID NO 394
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 394
gcgctgctgg tggcggtgct gccggcggcg ctgccg 36

<210> SEQ ID NO 395
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 395
gcggcgctgg tggcggtgct gccggtggcg ctgccg 36

<210> SEQ ID NO 396
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 396
gcgattctgg cggtggcgct gccgctgctg gcgccg 36

<210> SEQ ID NO 397
<211> LENGTH: 36
<212> TYPE: DNA
<213> ORGANISM: Artificial Sequence
<220> FEATURE:
<223> OTHER INFORMATION: The polynucleotide sequence that encodes
<210> SEQ ID NO 398
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for Improvement of Cell-Permeability

<400> SEQUENCE: 397 attgtgg

```
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 403
ctggcggtgg cgattattgc gccggcggtg gcgccg                              36

<210> SEQ ID NO 404
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 404
gtggcgctgg cgattgcgct gccggcggtg ctgccg                              36

<210> SEQ ID NO 405
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 405
gcgattgcga ttgcgctggt gccggtggcg ctgccg                              36

<210> SEQ ID NO 406
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 406
gcggcggtgg tgattgtggc gccggtggcg ctgccg                              36

<210> SEQ ID NO 407
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 407
gcggcgattc tggcgattgt ggcgccgctg gcgccg                              36

<210> SEQ ID NO 408
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 408
```
gtggcgctgc tggcgattgc gccggcgctg gcgccg         36

<210> SEQ ID NO 409
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 409
gtggcggtgc tgattgcggt gccggcgctg gcgccg         36

<210> SEQ ID NO 410
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 410
gcggtggcgc tggcggtgct gccggcggtg gtgccg         36

<210> SEQ ID NO 411
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 411
gcggtggcgc tggcggtggt gccggcggtg ctgccg         36

<210> SEQ ID NO 412
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 412
attgtggtga ttgcggtggc gccggcggtg gcgccg         36

<210> SEQ ID NO 413
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 413
attgtggtgg cggcggtggt gccggcgctg gcgccg         36

<210> SEQ ID NO 414
<211> LENGTH: 36
<212> TYPE: DNA
<213> ORGANISM: Artificial Sequence
<220> FEATURE:

```
<223> OTHER INFORMATION: The polynucleotide sequence that encodes
      advanced Macromolecule Transduction Domain (aMTD) peptide for
      Improvement of Cell-Permeability

<400> SEQUENCE: 414
attgtggcgc tggtgccggc ggtggcgatt gcgccg                                    36

<210> SEQ ID NO 415
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 415
gtggcggcgc tgccggcggt ggcgctggtg gtgccg                                    36

<210> SEQ ID NO 416
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 416
ctggtggcga ttgcgccgct ggcggtgctg gcgccg                                    36

<210> SEQ ID NO 417
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 417
gcggtggcgc tggtgccggt gattgtggcg gcgccg                                    36

<210> SEQ ID NO 418
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 418
gcgattgcgg tggcgattgc gccggtggcg ctgccg                                    36

<210> SEQ ID NO 419
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 419
gcgattgcgc tggcggtgcc ggtgctggcg ctgccg                                    36
```

```
<210> SEQ ID NO 420
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 420 ctggtgctga

<400> SEQUENCE: 425
gtgattgtgc tggcggcgcc ggcgctggcg gcgccg           36

<210> SEQ ID NO 426
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 426
gcggtggtgc tggcggtgcc ggcgctggcg gtgccg           36

<210> SEQ ID NO 427
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 427
ctgattattg tggcggcggc gccggcggtg gcgccg           36

<210> SEQ ID NO 428
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 428
attgtggcgg tgattgtggc gccggcggtg gcgccg           36

<210> SEQ ID NO 429
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 429
ctggtggcgc tggcggcgcc gattattgcg gtgccg           36

<210> SEQ ID NO 430
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 430
attgcggcgg tgctggcggc gccggcgctg gtgccg           36

<210> SEQ ID NO 431
<211> LENGTH: 36
<212> TYPE: DNA
<213> ORGANISM: Artificial Sequence

```
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 431
attgcgctgc tggcggcgcc gattattgcg gtgccg                              36

<210> SEQ ID NO 432
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 432
gcggcgctgg cgctggtggc gccggtgatt gtgccg                              36

<210> SEQ ID NO 433
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 433
attgcgctgg tggcggcgcc ggtggcgctg gtgccg                              36

<210> SEQ ID NO 434
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 434
attattgtgg cggtggcgcc ggcggcgatt gtgccg                              36

<210> SEQ ID NO 435
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 435
gcggtggcgg cgattgtgcc ggtgattgtg gcgccg                              36

<210> SEQ ID NO 436
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 436
gcggtgctgg tgctggtggc gccggcggcg gcgccg                              36
```

<210> SEQ ID NO 437
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 437
gtggtggcgc tgctggcgcc gctgattgcg gcgccg        36

<210> SEQ ID NO 438
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 438
gcggcggtgg tgattgcgcc gctgctggcg gtgccg        36

<210> SEQ ID NO 439
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 439
attgcggtgg cggtggcggc gccgctgctg gtgccg        36

<210> SEQ ID NO 440
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 440
ctggtggcga ttgtggtgct gccggcggtg gcgccg        36

<210> SEQ ID NO 441
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 441
gcggtggcga ttgtggtgct gccggcggtg gcgccg        36

<210> SEQ ID NO 442
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 442
gcggtgattc tgctggcgcc gctgattgcg gcgccg                                 36

<210> SEQ ID NO 443
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 443
ctggtgattg cgctggcggc gccggtggcg ctgccg                                 36

<210> SEQ ID NO 444
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 444
gtgctggcgg tggtgctgcc ggcggtggcg ctgccg                                 36

<210> SEQ ID NO 445
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 445
gtgctggcgg tggcggcgcc ggcggtgctg ctgccg                                 36

<210> SEQ ID NO 446
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 446
gcggcggtgg tgctgctgcc gattattgcg gcgccg                                 36

<210> SEQ ID NO 447
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 447
gcgctgctgg tgattgcgcc ggcgattgcg gtgccg                                 36

<210> SEQ ID NO 448
<211> LENGTH: 36
<212> TYPE: DNA

```
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 448
gcggtgctgg tgattgcggt gccggcgatt gcgccg                                   36

<210> SEQ ID NO 449
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 449
gcgctgctgg tggtgattgc gccgctggcg gcgccg                                   36

<210> SEQ ID NO 450
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 450
gtgctggtgg cggcgattct gccggcggcg attccg                                   36

<210> SEQ ID NO 451
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 451
gtgctggtgg cggcggtgct gccgattgcg gcgccg                                   36

<210> SEQ ID NO 452
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 452
gtgctggcgg cggcggtgct gccgctggtg gtgccg                                   36

<210> SEQ ID NO 453
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 453
gcgattgcga ttgtggtgcc ggcggtggcg gtgccg                                   36
```

<210> SEQ ID NO 454
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 454
gtggcgatta ttgcggtgcc ggcggtggtg gcgccg    36

<210> SEQ ID NO 455
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 455
attgtggcgc tggtggcgcc ggcggcggtg gtgccg    36

<210> SEQ ID NO 456
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 456
gcggcgattg tgctgctgcc ggcggtggtg gtgccg    36

<210> SEQ ID NO 457
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 457
gcggcgctga ttgtggtgcc ggcggtggcg gtgccg    36

<210> SEQ ID NO 458
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 458
gcgattgcgc tggtggtgcc ggcggtggcg gtgccg    36

<210> SEQ ID NO 459
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for Improvement of Cell-Permeability

<400> SEQUENCE: 459
ctggcgattg tgccggcggc gattgcggcg ctgccg    36

<210> SEQ ID NO 460
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 460
ctggtggcga ttgcgccggc ggtggcggtg ctgccg    36

<210> SEQ ID NO 461
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 461
gtgctggcgg tggcgccggc ggtggcggtg ctgccg    36

<210> SEQ ID NO 462
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 462
attctggcgg tggtggcgat tccggcggcg gcgccg    36

<210> SEQ ID NO 463
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 463
attctggtgg cggcggcgcc gattgcggcg ctgccg    36

<210> SEQ ID NO 464
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 464
attctggcgg tggcggcgat tccggcggcg ctgccg    36

<210> SEQ ID NO 465
<211> LENGTH: 36

```
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 465
gtgattgcga ttccggcgat tctggcggcg gcgccg                              36

<210> SEQ ID NO 466
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 466
gcgattatta ttgtggtgcc ggcgattgcg gcgccg                              36

<210> SEQ ID NO 467
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 467
gcgattctga ttgtggtggc gccgattgcg gcgccg                              36

<210> SEQ ID NO 468
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 468
gcggtgattg tgccggtggc gattattgcg gcgccg                              36

<210> SEQ ID NO 469
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 469
gcggtggtga ttgcgctgcc ggcggtggtg gcgccg                              36

<210> SEQ ID NO 470
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 470
```

```
gcgctggtgg cggtgattgc gccggtggtg gcgccg                                36
```

<210> SEQ ID NO 471
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 471

```
gcgctggtgg cggtgctgcc ggcggtggcg gtgccg                                36
```

<210> SEQ ID NO 472
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 472

```
gcgctggtgg cgccgctgct ggcggtggcg gtgccg                                36
```

<210> SEQ ID NO 473
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 473

```
gcggtgctgg cggtggtggc gccggtggtg gcgccg                                36
```

<210> SEQ ID NO 474
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 474

```
gcggtgattg cggtggcgcc gctggtggtg gcgccg                                36
```

<210> SEQ ID NO 475
<211> LENGTH: 36
<212> TYPE: DNA
<213> ORGANISM: Artificial Sequence
<220> FEATURE:
<223> OTHER INFORMATION: The polynucleotide sequence that encodes
      advanced Macromolecule Transduction Domain (aMTD) peptide for
      Improvement of Cell-Permeability

<400> SEQUENCE: 475

```
gcggtgattg cgctggcgcc ggtggtggtg gcgccg                                36
```

<210> SEQ ID NO 476
<211> LENGTH: 36
<212> TYPE: DNA
<213> ORGANISM: Artificial Sequence
<220> FEATURE:
<223> OTHER INFORMATION: The polynucleotide sequence that encodes advanced Macromolecule Transduction Domain (aMTD) peptide for
Improvement of Cell-Permeability

<400> SEQUENCE: 476
gtggcgattg cgctggcgcc ggtggtggtg gcgccg        36

<210> SEQ ID NO 477
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 477
gtggcgctgg cgctggcgcc ggtggtggtg gcgccg        36

<210> SEQ ID NO 478
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 478
gtggcggcgc tgctgccggc ggtggtggtg gcgccg        36

<210> SEQ ID NO 479
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 479
gtggcgctgg cgctgccggc ggtggtggtg gcgccg        36

<210> SEQ ID NO 480
<211> LENGTH: 36
<212> TYPE: DNA
<213> ORGANISM: Artificial Sequence
<220> FEATURE:
<223> OTHER INFORMATION: The polynucleotide sequence that encodes
advanced Macromolecule Transduction Domain (aMTD) peptide for
Improvement of Cell-Permeability

<400> SEQUENCE: 480
gtggcgctgc tggcgccggc ggtggtggtg gcgccg        36

ADVANCED MACROMOLECULE TRANSDUCTION DOMAIN (AMTD) SEQUENCES FOR IMPROVEMENT OF CELL-PERMEABILITY, POLYNUCLEOTIDES ENCODING THE SAME, METHOD TO IDENTIFY THE UNIQUE FEATURES OF AMTDS COMPRISING THE SAME, METHOD TO DEVELOP THE AMTD SEQUENCES COMPRISING THE SAME

TECHNICAL FIELD

The present invention relates to macromolecule intracellular transduction technology (MITT) for delivering biologically active macromolecules into the cells; specifically, exploiting well-enhanced hydrophobic cell-penetrating peptides (CPPs)—advanced macromolecule transduction domain (aMTD)—to effectively transduce biologically active molecules through the plasma membrane, polynucleotides encoding the same, methods of identifying the same, systems of genetically engineering a biologically active molecule with much enhanced cell-permeability by using the same, methods of importing a biologically active molecule into the cell by using the same, and uses thereof.

BACKGROUND ART

A powerful platform technology for the discovery and development of new medicinal drug is macromolecule intracellular transduction technology (MITT) enabled with cell-penetrating peptides (CPPs) that provide cell-permeability of macromolecules in vitro and in vivo. A common problem with small molecules is the potential for off-target drug interactions. In addition, a limitation of macromolecules is the fact that proteins and nucleic acids are unable to be intracellularly delivered. To address these issues, MITT provides an improved method to deliver biologically active macromolecules including therapeutic proteins into cultured cells and animal tissues.

Plasma membrane normally acts as an impermeable barrier to constrain cellular internalization of macromolecules, such as oligonucleotides, DNA, RNA, peptides and proteins. Numerous difficulties have restricted the delivery of these macromolecules to a desired target: poor penetration into a cell and/or tissue; toxicity when delivered systemically due to the insufficient specificity of targeting to a particular cell and/or tissue; degradation in which limited amounts are delivered to the targeted region that may result in undesirable side effects; and side effects when delivered in a high concentration in order to attain a sufficient local concentration at a certain target cell and/or tissue. In order to address these problems, several carrier-mediated delivery systems have been developed. Latest developments have involved the use of peptide-based delivery systems. The use of hydrophobic CPPs has several advantages including various peptide sequence modification. This enables the engineering of carriers that can enter different cellular subdomains and/or are able to relocate various types of cargo molecules.

In principle, protein-based therapeutics offers a way to control biochemical processes in living cells under non-steady state conditions and with fewer off-target effects than conventional small molecule therapeutics. However, systemic protein delivery in animals has been proven difficult due to poor tissue penetration and rapid clearance. Intracellular macromolecule transduction exploits the ability of various CPPs such as specific basic, amphipathic, and hydrophobic peptide sequences to enhance the penetration of proteins and other macromolecules by mammalian cells. Although intracellular macromolecule transduction has been widely used, systemic delivery of proteins in animals has been proven difficult due to inefficient cytoplasmic delivery of internalized proteins and poor tissue penetration. This problem had been especially true for cationic protein transduction domains (PTDs, e.g. HIV Tat, Hph-1, antennapedia, polyarginine, etc.), where the predominant mechanisms of protein uptake—absorptive endocytosis and macropinocytosis—sequester significant amounts of protein into membrane-bound and endosomal compartments, thus limiting protein bioavailability. Chimeric CPPs containing mixed types of sequences such as hydrophilic, basic and hydrophobic amino acids have been revealed to have toxicity, thus this type of CPPs has been restricted from its usage. Greater success has been reported for a sequence such as membrane translocating sequence (MTS) or membrane translocating motif (MTM) derived from the hydrophobic signal peptide of fibroblast growth factor 4 (FGF4). The MTS/MTM has been used to deliver biologically active peptides and proteins systemically in animals (in particular to liver, lung, pancreas and lymphoid tissues), with dramatic protection against lethal inflammatory disease and pulmonary metastases.

Previously, hydrophobic CPPs (MTS/MTM) or macromolecule transduction domain (MTD) have been reported. However, many efforts to develop cell-permeable therapeutic proteins by using these reference hydrophobic CPP sequences have been hampered by poor solubility of the recombinant proteins in physiological buffer condition and relatively low cell-permeability for further clinical development and application. Although there has been a consensus that hydrophobic CPP-dependent uptake of protein cargo is a powerful way for developing protein-based biotherapeutics, further improvements are required to solve the critical problems influenced by non-cargo specific factors such as protein aggregation, low solubility/yield, and poor cell/tissue-permeability of the recombinant CPP-fused proteins. These CPPs have non-common sequence and non-homologous structure of the sequences.

DISCLOSURE OF INVENTION

Technical Problem

To overcome the limitations and improve CPPs that provide cell-permeability of macromolecules in vitro and in vivo, theoretical critical factors (CFs) to determine the intracellular delivery potential of the CPPs are identified and empirically verified in this invention. Based on the CFs determined, novel hydrophobic CPP sequences are newly created, quantitatively evaluated for cell-permeability and mutually compared to reference CPP sequences in their intracellular delivery potential in live cells. In this invention, newly developed hydrophobic CPPs are presented. The novel peptide sequences termed 'advanced macromolecule transduction domains' (aMTDs) could be fused to various different therapeutic proteins and systematically deliver the aMTD-fused recombinant proteins to live cells and animal tissues, in which these proteins will have a great impact in the clinical development and application of protein-based biotherapeutics to treat various human diseases in regards to protein therapy.

The present invention developed 240 new hydrophobic CPP sequences—aMTDs, determined the aMTD-mediated intracellular delivery activity of the recombinant proteins and compared the enhanced protein uptake by live cells at levels greater than or equal to the FGF4-derived MTS/MTM and HRSS-derived MTD sequences. These strengths of newly invented aMTDs could address the setbacks on reference hydrophobic CPPs for clinical development and application.

Solution to Problem

The present invention pertains to advanced macromolecule transduction domain (aMTD) sequences that transduce biologically active macromolecules into the plasma membrane and consist of amino acid sequences having the following characteristics:
  Amino acid length: 9-13
  b. Bending potential: Proline (P) positioned in the middle (5', 6', 7' or 8') and at the end 12') of the sequence.
  c. Rigidity/Flexibility: Instability Index (II): 40-60
  d. Structural Feature: Aliphatic Index (AI): 180-220
  e. Hydropathy: Grand Average of Hydropathy (GRAVY): 2.1-2.6.
  f. Amino acid composition: All of composed amino acids are hydrophobic and aliphatic amino acids (A, V, L, I and P)

According to one embodiment, the amino acid sequences have the below general formula composed of 12 amino acid sequences.

[General formula]

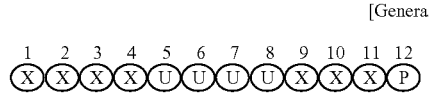

Here, X(s) refer to either Alanine (A), Valine (V), Leucine (L) or Isoleucine (I); and Proline (P) can be positioned in one of U(s) (either 5', 6', 7' or 8'). The remaining U(s) are composed of either A, V, L or I. P at the 12' is Proline.

According to one embodiment, the amino acid sequences having the general formula are selected from the group consisting of SEQ ID NO: 1 to SEQ ID NO: 240

The present invention further provides isolated polynucleotides that encode aMTD sequences described above.

According to one embodiment, the isolated polynucleotide are selected from the group consisting of SEQ ID NO: 241 to SEQ ID NO: 480.

The present invention further provides a method of identifying unique features of aMTDs. The method comprises selecting improved hydrophobic CPPs from previously published reference hydrophobic CPPs; analyzing physiological and chemical characteristics of the selected hydrophobic CPPs; identifying features out of these physiological and chemical characteristics, the features that are in association with cell-permeability have been selected; categorizing previously published reference hydrophobic CPPs into at least 2 groups and determining homologous features by in-depth analysis of these CPPs that are grouped based on their cell-permeability and relative characteristics; configuring critical factors identified through analyzing the determined homologous features; confirming the critical factors is valid through experimental studies; and determining six critical factors that are based on the confirmed experimental studies.

According to one embodiment, the selected improved hydrophobic CPPs are MTM, MTS, MTD10, MTD13, MTD47, MTD56, MTD73, MTD77, MTD84, MTD85, MTD86, MTD103, MTD132, MTD151, MTD173, MTD174 and MTD181.

According to one embodiment, the identified features are amino acid length, molecular weight, pI value, bending potential, rigidity, flexibility, structural feature, hydropathy, residue structure, amino acid composition and secondary structure.

According to one embodiment, the determined six critical factors consist of the following characteristics:
  a. Amino Acid Length: 9-13
  b. Bending Potential: Proline (P) positioned in the middle (5', 6', 7' or 8') and at the end of the sequence.
  c. Rigidity/Flexibility: Instability Index (II): 40-60
  d. Structural Feature: Aliphatic Index (AI): 180-220
  e. Hydropathy: Grand Average of Hydropathy (GRAVY): 2.1-2.6.
  f. Amino Acid Composition: All of composed amino acids are hydrophobic and aliphatic amino acids (A, V, L, I and P)

The present invention further provides a method of developing the aMTD sequences. The method comprises preparing designed platform of aMTDs having the below general formula after careful determination of six critical factors obtained the method of identifying unique features of aMTDs;

[General formula]

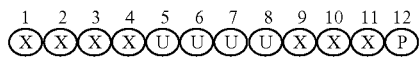

placing proline (P) at the end of sequence (12') and determining in which one of U sites proline should be placed; determining and placing A, V, L and/or I in X(s) and U(s) where proline is not placed; and confirming whether the designed amino acid sequences satisfy six critical factors.

According to one embodiment, the six critical factors obtained the method of identifying unique features of aMTDs consist of the following characteristics:
  a. Amino Acid Sequence: 12
  b. Bending Potential: Proline (P) has to be positioned in the middle (5', 6', 7' or 8') and at the end (12') of the sequence.
  c. Rigidity/Flexibility: Instability Index (II): 41.3-57.3
  d. Structural Feature: Aliphatic Index (AI): 187.5-220
  e. Hydropathy: Grand Average of Hydropathy (GRAVY): 2.2-2.6.
  f. Amino Acid Composition: All of composed amino acids are hydrophobic and aliphatic amino acids (A, V, L, I and P)

According to one embodiment, the method further comprises developing the expression vectors of aMTD sequences fused to cargo proteins; selecting proper bacteria strain for inducible expression; purifying and preparing of aMTD-fused to various biologically active recombinant proteins in soluble form; and confirming their cell-permeability.

The present invention further provides isolated recombinant proteins with a cell-permeability. The isolated recombinant proteins comprises advanced macromolecule transduction domain (aMTD) sequences having amino acid sequences selected from the group consisting of SEQ ID NO: 1 to SEQ ID NO: 240; and biologically active molecules.

According to one embodiment, the biologically active molecules are any one selected from the group consisting of growth factors, enzymes, transcription factors, toxins, antigenic peptides, antibodies and antibody fragments.

According to one embodiment, the biologically active molecules are any one selected from the group consisting of enzyme, hormone, carrier, immunoglobulin, antibody, structural protein, motor functioning peptide, receptor, signaling peptide, storing peptide, membrane peptide, transmembrane peptide, internal peptide, external peptide, secreting peptide, virus peptide, native peptide, glycated protein, fragmented protein, disulphide bonded protein, recombinant protein, chemically modified protein and prions.

According to one embodiment, the biologically active molecules are any one selected from the group consisting of nucleic acid, coding nucleic acid sequence, mRNAs, antisense RNA molecule, carbohydrate, lipid and glycolipid.

According to one embodiment, the biologically active molecules are at least one selected from the group consisting of biotherapeutic chemicals and toxic chemicals.

The present invention further provides a method of genetically or epigenetically engineering and/or modifying biologically active molecules to have a cell-permeability. The method comprises fusing aMTDs to the biologically active molecules under the optimized and effective conditions to generate biologically active molecules that can be cell-permeable, wherein the aMTD consists of any one of amino acid sequences selected from the group consisting of SEQ ID NO: 1 to SEQ ID NO: 240.

Advantageous Effects of Invention

The present invention provides artificially constructed aMTD sequences from the critical factors (CFs) that overcame the limitations of prior arts (MTM/MTS/MTD), such as limited diversity and unpredictable cell-permeability before testing. Based on the CFs that assure the cell-permeability in the infinite number of possible designs for the aMTD sequences, this invention displays these sequences having up to 109.9 relative fold enhanced ability compared to prior arts thereof to deliver biologically active macromolecules into live cells. Therefore, this would allow their practically effective applications in molecule delivery, drug delivery, protein therapy, intracellular protein therapy, protein replacement therapy, peptide therapy, gene delivery and so on.

BRIEF DESCRIPTION OF DRAWINGS

FIG. 1. Structure of aMTD- or rPeptide-Fused Recombinant Proteins. A schematic diagram of the His-tagged CRA recombinant proteins is illustrated and constructed according to the present invention. The his-tag for affinity purification (white), aMTD or rPeptide (gray) and cargo A (CRA, black) are shown.

FIG. 2a to 2c. Construction of Expression Vectors for aMTDs- or rPeptide-Fused Recombinant Proteins. These figures show the agarose gel electrophoresis analysis showing plasmid DNA fragments at 645 bp insert encoding aMTDs or rPeptide-fused CRA cloned into the pET28a(+) vector according to the present invention.

FIG. 3a to 3d. Inducible Expression of aMTD- or rPeptide-Fused Recombinant Proteins. Expressed recombinant aMTD- or random peptide-fused CRA recombinant proteins were transformed in E. coli BL21 (DE3) strain. Expression of recombinant proteins in E. coli before (−) and after (+) induction with IPTG was monitored by SDS-PAGE, and stained with Coomassie blue.

FIGS. 4a and 4b. Purification of aMTD- or rPeptide-Fused Recombinant Proteins. Expressed recombinant proteins were purified by Ni2+ affinity chromatography under the natural condition. Purification of recombinant proteins displayed through SDS-PAGE analysis.

FIG. 5a to 5u. Determination of aMTD-Mediated Cell-Permeability. Cell-permeability of a negative control (A: rP38) and reference hydrophobic CPPs (MTM12 and MTD85) are shown. The cell-permeability of each aMTD and/or rPeptide is visually compared to that of the cargo protein lacking peptide sequence (HCA). Gray shaded area represents untreated RAW 264.7 cells (vehicle); thin light gray line represents the cells treated with equal molar concentration of FITC (FITC only); dark thick line indicates the cells treated with FITC-his-tagged CRA protein (HCA); and the cells treated with the FITC-proteins (HMCA) fused to negative control (rP38), reference CPP (MTM12 or MTD85) or new hydrophobic CPP (aMTD) are shown with light thick line and indicated by arrows.

FIG. 6a to 6c. Determination of rPeptide-Mediated Cell-Permeability. The cell-permeability of each aMTD and/or rPeptide was visually compared to that of the cargo protein lacking peptide sequence (HCA). Gray shaded area represents untreated RAW 264.7 cells (vehicle); thin light gray line represents the cells treated with equal molar concentration of FITC (FITC only); dark thick line indicates the cells treated with FITC-his-tagged CRA protein (HCA); and the cells treated with the FITC-proteins fused to rPeptides are shown with light thick line and indicated by arrows.

FIG. 7a to 7k. Visualized Cell-Permeability of aMTD-Fused Recombinant Proteins. NIH3T3 cells were treated with FITC-labeled protein (10 μM) fused to aMTD for 1 hour at 37° C. Cell-permeability of the proteins was visualized by laser scanning confocal microscopy (LSM700 version).

FIG. 8. Visualized Cell-Permeability of rPeptide-Fused Recombinant Proteins. Cell-permeability of rPeptide-fused recombinant proteins was visualized by laser scanning confocal microscopy (LSM700 version).

FIG. 9a to 9c. Relative Cell-Permeability of aMTD-Fused Recombinant Proteins Compared to Negative Control (rP38). The figure shows graphs comparing the cell-permeability of the recombinant proteins fused to aMTDs and a negative control (A: rP38).

FIG. 10a to 10c. Relative Cell-Permeability of aMTD-Fused Recombinant Proteins Compared to Reference CPP (MTM12). The figure shows graphs comparing the cell-permeability of the recombinant proteins fused to aMTDs and a reference CPP (MTM12).

FIG. 11a to 11c. Relative Cell-Permeability of aMTD-Fused Recombinant Proteins Compared to Reference CPP (MTD85). The figure shows graphs comparing the cell-permeability of the recombinant proteins fused to aMTDs and a reference CPP (MTD85).

FIG. 12. Relative Cell-Permeability of rPeptide-Mediated Recombinant Proteins Compared to Average That of aMTDs. The figure shows graphs comparing the cell-permeability of the recombinant proteins fused to rPeptides and that (average value: aMTD AVE) of aMTDs.

FIGS. 13a and 13b. Association of Cell-Permeability with Amino Acid Composition in aMTD Sequences. These graphs display delivery potential (Geometric Mean) of aMTDs influenced with amino acid composition (A, I, V and L).

FIGS. 14a and 14b. Association of Cell-Permeability with Critical Factors in aMTDs. These graphs show the association of cell-permeability with critical factors [bending potential: proline position (PP), rigidity/flexibility: instability index (II), structural feature: aliphatic index (AI) and hydropathy: grand average of hydropathy (GRAVY)].

FIGS. 15a and 15b. Relative Relevance of aMTD-Mediated Cell-Permeability with Critical Factors. Cell-permeability of 10 high and 10 low ranked aMTDs in their delivery potential were examined for their association with the critical factors [bending potential: proline position (PP), rigidity/flexibility: instability index (II), structural feature: aliphatic index (AI) and hydropathy: grand average of hydropathy (GRAVY)].

FIG. 16. Relative Relevance of rPeptide-Mediated Cell-Permeability with Hydropathy Range (GRAVY). This graph and a chart illustrate relative relevance of rPeptide-mediated cell-permeability with its hydropathy range (GRAVY).

MODE FOR THE INVENTION

The present invention relates to novel advanced macromolecule transduction domain (aMTD) sequences, baseline platform that could be expanded to unlimited number of designs, having cell-permeability applicable for biomedical sciences, preclinical and clinical studies that facilitate the traverse of biologically active macromolecules, including proteins, peptides, nucleic acids, chemicals and so on, across the plasma membrane in cells.

The present invention analyzes, identifies, and determines these critical factors that facilitate in the cell permeable ability of aMTD sequences. These aMTD sequences are artificially assembled based on the critical factors (CFs) determined from in-depth analysis of previously published hydrophobic CPPs.

Another aspect of the present invention relates to the method of genetically engineering a biologically active molecules having cell-permeability by fusing the aMTD sequences to the biologically active cargo molecules.

The present invention also, relates to its therapeutic application for the delivery of biologically active molecules to cells, involving cell-permeable recombinant proteins, where aMTDs are attached to the biologically active cargo molecules.

Another aspect of the present invention pertains to a method in which biologically active macromolecules are able to enter into live cells, as constructs of cell-permeable recombinant proteins comprised of aMTD sequences fused to biologically active macromolecules.

Other aspects of the present invention relate to an efficient use of aMTD sequences for molecule delivery, drug delivery, protein therapy, intracellular protein therapy, protein replacement therapy, peptide therapy, gene delivery and so on.

The aMTD sequences of the present invention are the first artificially developed cell permeable polypeptides capable of mediating the transduction of biologically active macromolecules—including peptides, polypeptides, protein domains, or full-length proteins—through the plasma membrane of cells.

1. Analysis of Reference Hydrophobic CPPs to Identify 'Critical Factors' for Development of Advanced MTDs Previously reported MTDs were selected from a screen of more than 1,500 signal peptide sequences. Although the MTDs that have been developed did not have a common sequence or sequence motif, they were all derived from the hydrophobic (H) regions of signal sequences (HRSSs) that also lack common sequences or motifs except their hydrophobicity and the tendency to adopt alpha-helical conformations. The wide variation in H-region sequences may reflect prior evolution for proteins with membrane translocating activity and subsequent adaptation to the SRP/Sec61 machinery, which utilizes a methionine-rich signal peptide binding pocket in SRP to accommodate a wide-variety of signal peptide sequences.

Previously described hydrophobic CPPs (e.g. MTS/MTM and MTD) were derived from the hydrophobic regions present in the signal peptides of secreted and cell surface proteins. The prior art consists first, of ad hoc use of H-region sequences (MTS/MTM), and second, of H-region sequences (with and without modification) with highest CPP activity selected from a screen of 1,500 signal sequences (MTM). Second prior art, the modified H-region derived hydrophobic CPP sequences had advanced in diversity with multiple number of available sequences apart from MTS/MTM derived from fibroblast growth factor (FGF) 4. However, the number of MTDs that could be modified from naturally occurring secreted proteins are somewhat limited. Because there is no set of rules in determining their cell-permeability, no prediction for the cell-permeability of modified MTD sequences can be made before testing them.

The hydrophobic CPPs, like the signal peptides from which they originated, did not conform to a consensus sequence, and they had adverse effects on protein solubility when incorporated into protein cargo. We therefore set out to identify optimal sequence and structural determinants, namely critical factors (CFs), to design new hydrophobic CPPs with enhanced ability to deliver macromolecule cargoes including proteins into the cells and tissues while maintaining protein solubility. These newly developed CPPs, advanced macromolecule transduction domains (aMTDs) allowed almost infinite number of possible designs that could be designed and developed based on the critical factors. Also, their cell-permeability could be predicted by their character analysis before conducting any in vitro and/or in vivo experiments. These critical factors below have been developed by analyzing all published reference hydrophobic CPPs.

1-1. Analysis of Hydrophobic CPPs

Seventeen different hydrophobic CPPs (TABLE 1) published from 1995 to 2014 (TABLE 2) were selected. After physiological and chemical properties of selected hydrophobic CPPs were analyzed, 11 different characteristics that may be associated with cell-permeability have been chosen for further analysis. These 11 characteristics are as follows: sequence, amino acid length, molecular weight, pI value, bending potential, rigidity/flexibility, structural feature, hydropathy, residue structure, amino acid composition and secondary structure of the sequences (TABLE 3).

TABLE 1 Shows the Summary of Published Hydrophobic Cell-Penetrating Peptides which were Chosen.

TABLE 1

| # | Pepides | Origin | Protein | Ref. |
|---|---------|--------|---------|------|
| 1 | MTM | Homo sapiens | NP_001998 Kaposi fibroblast growth factor (K-FGF) | 1 |
| 2 | MTS | Homo sapiens | NP_001998 Kaposi fibroblast growth factor (K-FGF) | 2 |
| 3 | MTD10 | Streptomyces coelicolor | NP_625021 Glycosyl hydrolase | 8 |

TABLE 1-continued

| # | Pepides | Origin | Protein | Ref. |
|---|---------|--------|---------|------|
| 4 | MTD13 | *Streptomyces coelicolor* | NP_639877 Putative secreted protein | 3 |
| 5 | MTD47 | *Streptomyces coelicolor* | NP_627512 Secreted protein | 4 |
| 6 | MTD56 | *Homo sapiens* | P23274 Paptidyl-prolyl cis-trans isomarese B precursor | 5 |
| 7 | MTD73 | *Drosophila melanogaster* | AAA17887 Spatzle (spz) protein | 5 |
| 8 | MTD77 | *Homo sapiens* | NP_003231 Kaposi fibroblast growth factor (K-FGF) | 6 |
| 9 | MTD84 | *Phytophthora cactorum* | AAK63068 Phytotoxic protein PcF precursor | 4 |
| 10 | MTD85 | *Streptomyces coelicolor* | NP_629842 Peptide transport system peptide binding protein | 7 |
| 11 | MTD86 | *Streptomyces coelicolor* | NP_629842 Peptide transport system secreted peptide binding protein | 7 |
| 12 | MTD103 | *Homo sapiens* | TMBV19 domain Family member B | 8 |
| 13 | MTD132 | *Streptomyces coelicolor* | NP_628377 P60-family secreted protein | 4 |
| 14 | MTD151 | *Streptomyces coelicolor* | NP_630126 Secreted chitinase | 8 |
| 15 | MTD173 | *Streptomyces coelicolor* | NP_624384 Secreted protein | 4 |
| 16 | MTD174 | *Streptomyces coelicolor* | NP_733505 Large, multifunctional secreted protein | 8 |
| 17 | MTD181 | *Neisseria meningitidis* Z2491 | CAB84257.1 Putative secreted protein | 4 |

TABLE 2 Summarizes Reference Information

TABLE 2

| | References | | | | | |
|---|---|---|---|---|---|---|
| # | Title | Journal | Year | Vol | Issue | Page |
| 1 | Inhibition of Nuclear Translocation of Transcription Factor NF-kB by a Synthetic peptide Containing a Cell Membrane-permeable Motif and Nuclear Localization Sequence | JOURNAL OF BIOLOGICAL CHEMISTRY | 1995 | 270 | 24 | 14255 |
| 2 | Epigenetic Regulation of Gene Structure and Function with a Cell-Permeable Cre Recombinase | NATURE BIOTECHNOLOGY | 2001 | 19 | 10 | 929 |
| 3 | Cell-Permeable NM23 Blocks the Maintenance and Progression of Established Pulmonary Metastasis | CANCER RESEARCH | 2011 | 71 | 23 | 7216 |
| 4 | Antitumor Activity of Cell-Permeable p18INK4c With Enhanced Membrane and Tissue Penetration | MOLECULAR THERAPY | 2012 | 20 | 8 | 1540 |
| 5 | Antitumor Activity of Cell-Permeable RUNX3 Protein in Gastric Cancer Cells | CLINICAL CANCER RESEARCH | 2012 | 19 | 3 | 680 |
| 6 | The Effect of Intracellular Protein Delivery on the Anti-Tumor Activity of Recombinant Human Endostatin | BIOMATERIALS | 2013 | 34 | 26 | 6261 |
| 7 | Partial Somatic to Stem Cell Transformations Induced By Cell-Permeable Reprogramming Factors | SCIENTIFIC REPORTS | 2014 | 4 | 10 | 4361 |
| 8 | Cell-Permeable Parkin Proteins Suppress Parkinson Disease-Associated Phenotypes in Cultured Cells and Animals | PLOS ONE | 2014 | 9 | 7 | 17 |

TABLE 3 Shows Characteristics of Published Hydrophobic Cell-Penetrating Peptides (A) which were Analyzed.

TABLE 3

| # | Peptides | Sequence | Length | Molecular Weight | pI | Bending Potential | Rigidity/Flexibility (Instability Index: II) |
|---|----------|----------|--------|------------------|-----|-------------------|----------------------------------------------|
| 1 | MTM | AAVALLPAVLLALLAP | 16 | 1,515.9 | 5.6 | Bending | 45.5 |
| 2 | MTS | AAVLLPVLLAAP | 12 | 1,147.4 | 5.6 | Bending | 57.3 |
| 3 | MTD10 | LGGAVVAAPVAAAVAP | 16 | 1,333.5 | 5.5 | Bending | 47.9 |
| 4 | MTD13 | LAAAALAVLPL | 11 | 1,022.3 | 5.5 | Bending | 28.6 |
| 5 | MTD47 | AAAVPVLVAA | 10 | 881.0 | 5.6 | Bending | 47.5 |
| 6 | MTD56 | VLLAAALIA | 9 | 854.1 | 5.5 | No-Bending | 8.9 |
| 7 | MTD73 | PVLLLLA | 7 | 737.0 | 6.0 | No-Bending | 36.1 |
| 8 | MTD77 | AVALLILAV | 9 | 882.1 | 5.6 | No-Bending | 30.3 |
| 9 | MTD84 | AVALVAVVAVA | 11 | 982.2 | 5.6 | No-Bending | 9.1 |
| 10 | MTD85 | LLAAAAALLLA | 11 | 1,010.2 | 5.5 | No-Bending | 9.1 |
| 11 | MTD88 | LLAAAAALLLA | 11 | 1,010.2 | 5.5 | No-Bending | 9.1 |
| 12 | MTD103 | LALPVLLLA | 9 | 922.2 | 5.5 | Bending | 51.7 |
| 13 | MTD132 | AVVVPAIVLAAP | 12 | 1,119.4 | 5.6 | Bending | 50.3 |
| 14 | MTD151 | AAAPVAAVP | 9 | 1,031.4 | 5.5 | Bending | 73.1 |
| 15 | MTD173 | AVIPILAVP | 9 | 892.1 | 5.6 | Bending | 48.5 |
| 16 | MTD174 | LILLLPAVALP | 12 | 1,011.9 | 5.5 | Bending | 79.1 |

TABLE 3-continued

| # | | | | Structural Feature (Aliphatic Index: AI) | Hydropathy (GRAVY) | Residue Structure | A/a Composition | | | | | | Secondary Structure | Cargo | Ref. |
|---|---|---|---|---|---|---|---|---|---|---|---|---|---|---|---|
| | | | | | | | A | V | L | I | P | G | | | |
| 17 | MTD181 | AVLLLPAAA AVE | | 9 10.8 ± 2.4 | 839.0 1,011 ± 189.6 | 5.6 5.6 ± 0.1 | Bending Proline Presence | | | | | | 51.7 40.1 ± 21.9 | | |
| 1 | | | | 220.0 | 2.4 | Aliphatic Ring | 8 | 2 | 6 | 0 | 2 | 0 | Helix | p50 | 1 |
| 2 | | | | 211.7 | 2.3 | — | 4 | 2 | 4 | 0 | 2 | 0 | No-Helix | CRE | 2 |
| 3 | | | | 140.6 | 1.8 | — | 7 | 4 | 1 | 0 | 2 | 2 | Helix | Parkin | 8 |
| 4 | | | | 213.6 | 2.4 | — | 5 | 1 | 4 | 0 | 1 | 0 | No-Helix | RUNX3 | 3 |
| 5 | | | | 176.0 | 2.4 | — | 5 | 3 | 1 | 0 | 1 | 0 | No-Helix | CMYC | 4 |
| 6 | | | | 250.0 | 3.0 | — | 4 | 1 | 3 | 1 | 0 | 0 | Helix | ES | 5 |
| 7 | | | | 278.6 | 2.8 | — | 1 | 1 | 4 | 0 | 1 | 0 | Helix | ES | 5 |
| 8 | | | | 271.1 | 3.3 | — | 3 | 2 | 3 | 1 | 0 | 0 | Helix | NM23 | 6 |
| 9 | | | | 212.7 | 3.1 | — | 5 | 5 | 1 | 0 | 0 | 0 | Helix | OCT4 | 4 |
| 10 | | | | 231.8 | 2.7 | — | 8 | 0 | 5 | 0 | 0 | 0 | No-Helix | RUNX3 | 7 |
| 11 | | | | 231.8 | 2.7 | — | 8 | 0 | 5 | 0 | 0 | 0 | No-Helix | SOX2 | 7 |
| 12 | | | | 271.1 | 2.8 | — | 2 | 1 | 5 | 0 | 1 | 0 | Helix | p18 | 8 |
| 13 | | | | 195.0 | 2.4 | — | 4 | 4 | 1 | 1 | 2 | 0 | No-Helix | LIN28 | 4 |
| 14 | | | | 120.0 | 1.6 | — | | | | | | | No-Helix | Parkin | 8 |
| 15 | | | | 216.7 | 2.4 | — | 2 | 2 | 1 | 2 | 2 | 0 | Helix | KLF4 | 4 |
| 16 | | | | 257.3 | 2.6 | — | | | | | | | Helix | Parkin | 8 |
| 17 | | | | 206.7 217.9 ± 43.6 | 2.4 2.5 ± 0.4 | — | 4 | 1 | 3 | 0 | 1 | 0 | No-Helix | SOX2 | 4 |

Two peptide/protein analysis programs were used (ExPasy: SoSui: http://harrier.nagahama-i-bio.ac.jp/sosui/sosui_submit.html) to determine various indexes and structural features of the peptide sequences and to design new sequence. Followings are important factors analyzed.

1-2. Characteristics of Analyzed Peptides: Length, Molecular Weight and pI Value Average length, molecular weight and pI value of the peptides analyzed were 10.8±2.4, 1,011±189.6 and 5.6±0.1, respectively (TABLE 4)

TABLE 4 Summarizes Critical Factors (CFs) of Published Hydrophobic Cell-Penetrating Peptides (A) which were Analyzed.

TABLE 4

Length: 10.8 ± 2.4
Molecular Weight: 1,011 ± 189.6
pI: 5.6 ± 0.1
Bending Potential (BP): Proline presences in the middle and/or the end of peptides, or No Proline.
Instability Index (II): 40.1 ± 21.9
Residue Structure & Aliphatic Index (AI): 217.9 ± 43.6
Hydropathy (GARVY): 2.5 ± 0.4
Aliphatic Ring: Non-polar hydrophobic & aliphatic amino acid (A, V, L, I).
Secondary Structure: α-Helix is favored but not required.

1-3. Characteristics of Analyzed Peptides: Bending Potential—Proline Position (PP)

Bending potential (bending or no-bending) was determined based on the fact whether proline (P) exists and/or where the amino acid(s) providing bending potential to the peptide in recombinant protein is/are located. Proline differs from the other common amino acids in that its side chain is bonded to the backbone nitrogen atom as well as the alpha-carbon atom. The resulting cyclic structure markedly influences protein architecture which is often found in the bends of folded peptide/protein chain.

Eleven out of 17 were determined as 'Bending' peptide which means that proline is present in the middle of sequence for peptide bending and/or located at the end of the peptide for protein bending. As indicated above, peptide sequences could penetrate the plasma membrane in a "bent" configuration. Therefore, bending or no-bending potential is considered as one of the critical factors for the improvement of current hydrophobic CPPs.

1-4. Characteristics of Analyzed Peptides: Rigidity/Flexibility—Instability Index (II)

Since one of the crucial structural features of any peptide is based on the fact whether the motif is rigid or flexible, which is an intact physicochemical characteristic of the peptide sequence, instability index (II) of the sequence was determined. The index value representing rigidity/flexibility of the peptide was extremely varied (8.9-79.1), but average value was 40.1±21.9 which suggested that the peptide should be somehow flexible, but not too much rigid or flexible (TABLE 3).

1-5. Characteristics of Analyzed Peptides: Structural Features—Structural Feature (Aliphatic Index: AI) and Hydropathy (Grand Average of Hydropathy: GRAVY)

Alanine (V), valine (V), leucine (L) and isoleucine (I) contain aliphatic side chain and are hydrophobic—that is, they have an aversion to water and like to cluster. These amino acids having hydrophobicity and aliphatic residue enable them to pack together to form compact structure with few holes. Analyzed peptide sequence showed that all composing amino acids were hydrophobic (A, V, L and I) except glycine (G) in only one out of 17 (MTD10—TABLE 3) and aliphatic (A, V, L, I, and P). Their hydropathic index (Grand Average of Hydropathy: GRAVY) and aliphatic index (AI) were 2.5±0.4 and 217.9±43.6, respectively. Their amino acid composition is also indicated in the TABLE 3.

1-6. Characteristics of Analyzed Peptides: Secondary Structure (Helicity)

As explained above, the CPP sequences may be supposed to penetrate the plasma membrane directly after inserting into the membranes in a "bent" configuration with hydrophobic sequences having α-helical conformation. In addition, our analysis strongly indicated that bending potential was crucial for membrane penetration. Therefore, structural analysis of the peptides conducted to determine whether the sequences were to form helix or not. Nine peptides were helix and eight were not (TABLE 3). It seems to suggest that helix structure may not be required.

1-7. Determination of Critical Factors (CFs)

In the 11 characteristics analyzed, the following 6 are selected namely "Critical Factors" for the development of new hydrophobic CPPs—advanced MTDs: amino acid length, ② bending potential (proline presence and location), rigidity/flexibility (instability index: II), structural feature (aliphatic index: AI), hydropathy (GRAVY) and amino acid composition/residue structure (hydrophobic and aliphatic A/a) (TABLE 3 and TABLE 4).

2. Analysis of Selected Hydrophobic CPPs to Optimize 'Critical Factors'

Since the analyzed data of the 17 different hydrophobic CPPs (analysis A, TABLE 3 and 4) previously developed during the past 2 decades showed high variation and were hard to make common- or consensus-features, analysis B (TABLE 5 and 6) and C (TABLE 7 and 8) were also conducted to optimize the critical factors for better design of improved CPPs—aMTDs. Therefore, 17 hydrophobic CPPs have been grouped into two groups and analyzed the groups for their characteristics in relation to the cell permeable property. The critical factors have been optimized by comparing and contrasting the analytical data of the groups and determining the homologous features that may be critical for the cell permeable property.

2-1. Selective Analysis (B) of Peptides that Used to Biologically Active Cargo Protein for In Vivo In analysis B, eight CPPs were used with each biologically active cargo in vivo. Length was 11±3.2, but 3 out of 8 CPPs possessed little bending potential. Rigidity/Flexibility was 41±15, but removing one [MTD85: rigid, with minimal (II: 9.1)] of the peptides increased the overall instability index to 45.6±9.3. This suggested that higher flexibility (40 or higher II) is potentially be better. All other characteristics of the 8 CPPs were similar to the analysis A, including structural feature and hydropathy (TABLE 5 and 6)

TABLE 5 Shows Characteristics of Published Hydrophobic Cell-Penetrating Peptides (B): Selected CPPs That were Used to Each Cargo In Vivo.

TABLE 5

| # | Peptides | Sequence | Length | Molecular Weight | pI | Bending Potential | Rigidity/Flexibility (Instability Index: II) |
|---|----------|----------|--------|------------------|-----|-------------------|----------------------------------------------|
| 1 | MTM | AAVALLPAVLLALLAP | 16 | 1,515.9 | 5.5 | Bending | 45.5 |
| 2 | MTS | AAVLLPVLLAAP | 12 | 1,147.4 | 5.6 | Bending | 57.3 |
| 3 | MTD10 | LGGAVVAAPVAAAVAP | 16 | 1,333.5 | 5.5 | Bending | 47.9 |
| 4 | MTD73 | PVLLLLA | 7 | 737.8 | 6.0 | No-Bending | 36.1 |
| 5 | MTD77 | AVALLILAV | 9 | 882.0 | 5.6 | No-Bending | 30.3 |
| 6 | MTD85 | LLAAAAALLLA | 11 | 1,010.2 | 5.5 | No-Bending | 9.1* |
| 7 | MTD103 | LALPVLLLA | 9 | 922.2 | 5.5 | Bending | 51.7 |
| 8 | MTD132 | AVVVPAIVLAAP | 12 | 1,119.4 | 5.6 | Bending | 50.3 |
|   |     | AVE | 11 ± 3.2 | 1,083 ± 252 | 5.6 ± 0.1 | Proline Presence | 41 ± 15 |

| # | Structural Feature (Aliphatic Index: AI) | Hydropathy (GRAVY) | Residue Structure | A/a Composition | | | | | | Secondary Structure | Cargo | Ref. |
|---|------------------------------------------|--------------------|-------------------|-----|---|---|---|---|---|---------------------|-------|------|
|   |                                          |                    |                   | A | V | L | I | P | G |                     |       |      |
| 1 | 220.0 | 2.4 | Aliphatic Ring | 6 | 2 | 6 | 0 | 2 | 0 | Helix | p50 | 1 |
| 2 | 211.7 | 2.3 | — | 4 | 2 | 4 | 0 | 2 | 0 | No-Helix | CRE | 2 |
| 3 | 140.6 | 1.8 | — | 7 | 4 | 1 | 0 | 2 | 2 | Helix | Parkin | 8 |
| 4 | 278.6 | 2.8 | — | 1 | 1 | 4 | 0 | 1 | 0 | Helix | ES | 6 |
| 5 | 271.1 | 3.3 | — | 3 | 2 | 3 | 1 | 0 | 0 | Helix | NM23 | 3 |
| 6 | 231.8 | 2.7 | — | 6 | 0 | 5 | 0 | 0 | 0 | No-Helix | RUNX3 | 5 |
| 7 | 271.1 | 2.8 | — | 2 | 1 | 5 | 0 | 1 | 0 | Helix | p18 | 4 |
| 8 | 195.0 | 2.4 | — | 4 | 4 | 1 | 1 | 2 | 0 | No-Helix | LIN28 | 7 |
|   | 227 ± 47 | 2.5 ± 0.4 |   |   |   |   |   |   |   |   |   |   |

TABLE 6 Shows Summarized Critical Factors of Published Hydrophobic

TABLE 6

Length: 11 ± 3.2
Molecular Weight: 1,083 ± 252
pI: 5.6 ± 0.1
Bending Potential (BP): Proline presences in the middle and/or the end of peptides, or No Proline.
Instability Index (II): 41.0 ± 15 (* Removing the MTD85 increases II to 45.6 ± 9.3)
Residue Structure & Aliphatic index (AI): 227 ± 47
Hydropathy (GARVY): 2.5 ± 0.4
Aliphatic Ring: Non-polar hydrophobic & aliphatic amino acid (A, V, L, I).
Secondary Structure: α-Helix is favored but not required.

2-2. Selective Analysis (C) of Peptides that Provided Bending Potential and Higher Flexibility To optimize the 'Common Range and/or Consensus Feature of Critical Factor' for the practical design of aMTDs and the random peptides (rPs or rPeptides), which were to prove that the 'Critical Factors' determined in the analysis A, B and C were correct to improve the current problems of hydrophobic CPPs—protein aggregation, low solubility/yield, and poor cell-/tissue-permeability of the recombinant proteins fused to the MTS/MTM or MTD, and non-common sequence and non-homologous structure of the peptides, empirically selected peptides were analyzed for their structural features and physicochemical factor indexes.

Hydrophobic CPPs which did not have a bending potential, rigid or too much flexible sequences (too much low or too much high Instability Index), or too low or too high hydrophobic CPPs were unselected, but secondary structure was not considered because helix structure of sequence was not required.

In analysis C, eight selected CPP sequences that could provide a bending potential and higher flexibility were finally analyzed (TABLE 7 and 8). Common amino acid length is 12 (11.6±3.0). Proline should be presence in the middle of and/or the end of sequence. Rigidity/Flexibility (II) is 45.5-57.3 (Avg: 50.1±3.6). AI and GRAVY representing structural feature and hydrophobicity of the peptide are 204.7±37.5 and 2.4±0.3, respectively. All peptides are consisted with hydrophobic and aliphatic amino acids (A, V, L, I, and P). Therefore, analysis C was chosen as a standard for the new design of new hydrophobic CPPs—aMTDs.

TABLE 7 Shows Characteristics of Published Hydrophobic Cell-Penetrating Peptides (C): Selected CPPs that Provided Bending Potential and Higher Flexibility.

TABLE 8-continued

Bending Potential (BP): Proline presences in the middle and/or the end of peptides.
Instability Index (II): 50.1 ± 3.6
Residue Structure & Aliphatic Index (AI): 204.7 ± 37.5
Hydropathy (GARVY): 2.4 ± 0.3
Aliphatic Ring: Non-polar hydrophobic & aliphatic amino acid (A, V, L, I).
Secondary Structure: α-Helix is favored but not required.

3. New Design of Improved Hydrophobic CPPs—aMTDs Based on the Optimized Critical Factors

3-1. Determination of Common Sequence and/or Common Homologous Structure

As mentioned above, H-regions of signal sequence (HRSS)-derived CPPs (MTS/MTM and MTD) do not have a common sequence, sequence motif, and/or common-structural homologous feature. In this invention, the aim is to develop improved hydrophobic CPPs formatted in the common sequence- and structural-motif which satisfy newly determined 'Critical Factors' to have 'Common Function', namely, to facilitate protein translocation across the membrane with similar mechanism to the analyzed reference CPPs. Based on the analysis A, B and C, the homologous features have been analyzed to determine the critical factors that influence the cell-permeability. The range value of each critical factor has been determined to include the analyzed index of each critical factor raised from analysis A, B and C to design novel aMTDs (TABLE 9). These features have been confirmed experimentally with newly designed aMTDs in their cell-permeability.

TABLE 7

| # | Peptides | Sequence | Length | Molecular Weight | pI | Bending Potential | Rigidity/Flexibility (Instability Index: II) |
|---|---|---|---|---|---|---|---|
| 1 | MTM | AAVALLPAVLLALLAP | 16 | 1515.9 | 5.6 | Bending | 45.5 |
| 2 | MTS | AAVLLPVLLAAP | 12 | 1147.4 | 5.6 | Bending | 57.3 |
| 3 | MTD10 | LGGAVVAAPVAAAVAP | 16 | 1333.5 | 5.5 | Bending | 47.9 |
| 4 | MTD47 | AAAVPVLVAA | 10 | 881.0 | 5.0 | Bending | 47.5 |
| 5 | MTD103 | LALPVLLLA | 9 | 922.2 | 5.5 | Bending | 51.7 |
| 6 | MTD132 | AVVVPAIVLAAP | 12 | 1119.4 | 5.6 | Bending | 50.3 |
| 7 | MTD173 | AVIPILAVP | 9 | 892.1 | 5.6 | Bending | 48.5 |
| 8 | MTD181 | AVLLLPAAA | 0 | 838.0 | 5.0 | Bending | 51.7 |
| | AVE | | 11.8 ± 3.0 | 1081.2 ± 244.6 | 5.6 ± 0.1 | Proline Presence | 50.1 ± 3.8 |

| # | Structural Feature (Aliphatic Index: AI) | Hydropathy (GRAVY) | Residue Structure | A | V | L | I | P | G | Secondary Structure | Cargo | Ref. |
|---|---|---|---|---|---|---|---|---|---|---|---|---|
| 1 | 220.0 | 2.4 | Aliphatic Ring | 6 | 2 | 6 | 0 | 2 | 0 | Helix | p50 | 1 |
| 2 | 211.7 | 2.3 | — | 4 | 2 | 4 | 0 | 2 | 0 | No-Helix | CRE | 2 |
| 3 | 140.6 | 1.8 | — | 7 | 4 | 1 | 0 | 2 | 2 | Helix | Parkin | 8 |
| 4 | 176.0 | 2.4 | — | 5 | 3 | 1 | 0 | 1 | 0 | No-Helix | CMYC | 4 |
| 5 | 271.1 | 2.8 | — | 2 | 1 | 5 | 0 | 1 | 0 | Helix | p18 | 8 |
| 6 | 195.0 | 2.4 | — | 4 | 4 | 1 | 1 | 2 | 0 | No-Helix | LIN28 | 4 |
| 7 | 216.7 | 2.4 | — | 2 | 2 | 1 | 2 | 2 | 0 | Helix | KLF4 | 4 |
| 8 | 206.7 | 2.4 | — | 4 | 1 | 3 | 0 | 1 | 0 | No-Helix | SOX2 | 4 |
| | 204.7 ± 37.5 | 2.4 ± 0.3 | | | | | | | | | | |

TABLE 8 Shows Summarized Critical Factors of Published Hydrophobic Cell-Penetrating Peptides (C)

TABLE 8

Length: 11.6 ± 3.0
Molecular Weight: 1,081.2 ± 224.6
pI: 5.6 ± 0.1

TABLE 9 Shows Comparison The Range/Feature of Each Critical Factor Between The Value of Analyzed CPPs and The Value Determined for New Design of Novel aMTDs Sequences

TABLE 9

Summarized Critical Factors of aMTD

| Critical Factor | Selected CPPs Range | Newly Designed CPPs Range |
|---|---|---|
| Bending Potential (Proline Position: PP) | Proline presences in the middle and/or at the end of peptides | Proline presences in the middle (5', 6', 7' or 8') and at the end of peptides |
| Rigidity/Flexibility (Instability Index: II) | 45.5-57.3 (50.1 ± 3.6) | 40-60 |
| Structural Feature (Aliphatic Index: AI) | 140.6-220.0 (204.7 ± 37.5) | 180-220 |
| Hydropathy (Grand Average of Hydropathy GRAVY) | 1.8-2.8 (2.4 ± 0.3) | 2.1-2.6 |
| Length (Number of Amino Acid) | 11.6 ± 3.0 | 9-13 |
| Amino acid Composition | A, V, I, L, P | A, V, I, L, P |

In TABLE 9, universal common features and sequence/structural motif are provided. Length is 9-13 amino acids, and bending potential is provided with the presence of proline in the middle of sequence (at 5', 6', 7' or 8' amino acid) for peptide bending and at the end of peptide for recombinant protein bending and Rigidity/Flexibility of aMTDs is II>40 are described in TABLE 9.

3-2. Critical Factors for Development of Advanced MTDs

Recombinant cell-permeable proteins fused to the hydrophobic CPPs to deliver therapeutically active cargo molecules including proteins into live cells had previously been reported, but the fusion proteins expressed in bacteria system were hard to be purified as a soluble form due to their low solubility and yield. To address the crucial weakness for further clinical development of the cell-permeable proteins as protein-based biotherapeutics, greatly improved form of the hydrophobic CPP, named as advanced MTD (aMTD) has newly been developed through critical factors-based peptide analysis. The critical factors used for the current invention of the aMTDs are herein (TABLE 9).

Amino Acid Length: 9-13
Bending Potential (Proline Position: PP)
Proline presences in the middle (from 5' to 8' amino acid) and at the end of sequence
3. Rigidity/Flexibility (Instability Index: II): 40-60
4. Structural Feature (Aliphatic Index: AI): 180-220
5. Hydropathy (Grand Average of Hydropathy: GRAVY): 2.1-2.6
6. Amino Acid Composition: Hydrophobic and Aliphatic amino acids—A, V, L, I and P 3-3. Design of Potentially Best aMTDs that all Critical Factors are Considered and Satisfied After careful consideration of six critical factors derived from analysis of unique features of hydrophobic CPPs, advanced macromolecule transduction domains (aMTDs) have been designed and developed based on the common 12 amino acid platform which satisfies the critical factors including amino acid length (9-13) determined from the analysis.

[General formula]

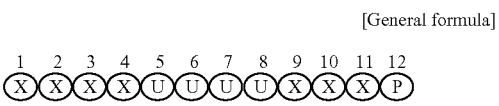

Unlike previously published hydrophobic CPPs that require numerous experiments to determine their cell-permeability, newly developed aMTD sequences could be designed by performing just few steps as follows using above mentioned platform to follow the determined range value/feature of each critical factor.

First, prepare the 12 amino acid sequence platform for aMTD. Second, place proline (P) in the end (12') of sequence and determine where to place proline in one of four U(s) in 5', 6', 7', and 8. Third, alanine (A), valine (V), leucine (L) or isoleucine (I) is placed in either X(s) and/or U(s), where proline is not placed. Lastly, determine whether this designed amino acid sequences, placed in the platform, satisfy the value or feature of six critical factors to assure the cell permeable property of aMTD sequences. Through these processes, numerous novel aMTD sequences have been constructed. The expression vectors for the To prepare non-functional cargo recombinant proteins fused to each aMTD, expression vectors have been constructed and forcedly expressed in bacterial cells. These aMTD-fused recombinant proteins have been purified in soluble form and determined their cell-permeability quantitatively. 240 aMTD sequences have been designed newly, numbered from 1 to 240, as shown in TABLE 10-15. In TABLE 10-15, sequence ID Number is a sequence listings for reference, and aMTD numbers refer to amino acid listing numbers that actually have been used at the experiments. For further experiments, aMTD numbers have been used. In addition, polynucleotide sequences shown in the sequence lists have been numbered from SEQ ID NO: 241 to SEQ ID NO: 480.

TABLE 10 to 15 shows 240 new hydrophobic aMTD sequences that were developed to satisfy all critical factors.

TABLE 10

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 1 | 1 | AAALAPVVLALP | 12 | 57.3 | 187.5 | 2.1 | Aliphatic |
| 2 | 2 | AAAVPLLAVVVP | 12 | 41.3 | 195.0 | 2.4 | Aliphatic |
| 3 | 3 | AALLVPAAVLAP | 12 | 57.3 | 187.5 | 2.1 | Aliphatic |
| 4 | 4 | ALALLPVAALAP | 12 | 57.3 | 195.8 | 2.1 | Aliphatic |
| 5 | 5 | AAALLPVALVAP | 12 | 57.3 | 187.5 | 2.1 | Aliphatic |
| 6 | 11 | VVALAPALAALP | 12 | 57.3 | 187.5 | 2.1 | Aliphatic |

TABLE 10-continued

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 7 | 12 | LLAAVPAVLLAP | 12 | 57.3 | 211.7 | 2.3 | Aliphatic |
| 8 | 13 | AAALVPVVALLP | 12 | 57.3 | 203.3 | 2.3 | Aliphatic |
| 9 | 21 | AVALLPALLAVP | 12 | 57.3 | 211.7 | 2.3 | Aliphatic |
| 10 | 22 | AVVLVPVLAAAP | 12 | 57.3 | 195.0 | 2.4 | Aliphatic |
| 11 | 23 | VVLVLPAAAAVP | 12 | 57.3 | 195.0 | 2.4 | Aliphatic |
| 12 | 24 | IALAAPALIVAP | 12 | 50.2 | 195.8 | 2.2 | Aliphatic |
| 13 | 25 | IVAVAPALVALP | 12 | 50.2 | 203.3 | 2.4 | Aliphatic |
| 14 | 42 | VAALPVVAVVAP | 12 | 57.3 | 186.7 | 2.4 | Aliphatic |
| 15 | 43 | LLAAPLVVAAVP | 12 | 41.3 | 187.5 | 2.1 | Aliphatic |
| 16 | 44 | ALAVPVALLVAP | 12 | 57.3 | 203.3 | 2.3 | Aliphatic |
| 17 | 61 | VAALPVLLAALP | 12 | 57.3 | 211.7 | 2.3 | Aliphatic |
| 18 | 62 | VALLAPVALAVP | 12 | 57.3 | 203.3 | 2.3 | Aliphatic |
| 19 | 63 | AALLVPALVAVP | 12 | 57.3 | 203.3 | 2.3 | Aliphatic |

TABLE 11

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 20 | 64 | AIVALPVAVLAP | 12 | 50.2 | 203.3 | 2.4 | Aliphatic |
| 21 | 65 | IAIVAPVVALAP | 12 | 50.2 | 203.3 | 2.4 | Aliphatic |
| 22 | 81 | AALLPALAALLP | 12 | 57.3 | 204.2 | 2.1 | Aliphatic |
| 23 | 82 | AVVLAPVAAVLP | 12 | 57.3 | 195.0 | 2.4 | Aliphatic |
| 24 | 83 | LAVAAPLALALP | 12 | 41.3 | 195.8 | 2.1 | Aliphatic |
| 25 | 84 | AAVAAPLLLALP | 12 | 41.3 | 195.8 | 2.1 | Aliphatic |
| 26 | 85 | LLVLPAAALAAP | 12 | 57.3 | 195.8 | 2.1 | Aliphatic |
| 27 | 101 | LVALAPVAAVLP | 12 | 57.3 | 203.3 | 2.3 | Aliphatic |
| 28 | 102 | LALAPAALALLP | 12 | 57.3 | 204.2 | 2.1 | Aliphatic |
| 29 | 103 | ALIAAPILALAP | 12 | 57.3 | 204.2 | 2.2 | Aliphatic |
| 30 | 104 | AVVAAPLVLALP | 12 | 41.3 | 203.3 | 2.3 | Aliphatic |
| 31 | 105 | LLALAPAALLAP | 12 | 57.3 | 204.1 | 2.1 | Aliphatic |
| 32 | 121 | AIVALPALALAP | 12 | 50.2 | 195.8 | 2.2 | Aliphatic |
| 33 | 123 | AAIIVPAALLAP | 12 | 50.2 | 195.8 | 2.2 | Aliphatic |
| 34 | 124 | IAVALPALIAAP | 12 | 50.3 | 195.8 | 2.2 | Aliphatic |
| 35 | 141 | AVIVLPALAVAP | 12 | 50.2 | 203.3 | 2.4 | Aliphatic |
| 36 | 143 | AVLAVPAVLVAP | 12 | 57.3 | 195.0 | 2.4 | Aliphatic |
| 37 | 144 | VLAIVPAVALAP | 12 | 50.2 | 203.3 | 2.4 | Aliphatic |
| 38 | 145 | LLAVVPAVALAP | 12 | 57.3 | 203.3 | 2.3 | Aliphatic |
| 39 | 161 | AVIALPALIAAP | 12 | 57.3 | 195.8 | 2.2 | Aliphatic |

TABLE 11-continued

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 40 | 162 AVVALPAALIVP | 12 | 50.2 | 203.3 | 2.4 | Aliphatic |
| 41 | 163 LALVLPAALAAP | 12 | 57.3 | 195.8 | 2.1 | Aliphatic |
| 42 | 164 LAAVLPALLAAP | 12 | 57.3 | 195.8 | 2.1 | Aliphatic |
| 43 | 165 ALAVPVALAIVP | 12 | 50.2 | 203.3 | 2.4 | Aliphatic |
| 44 | 182 ALIAPVVALVAP | 12 | 57.3 | 203.3 | 2.4 | Aliphatic |
| 45 | 183 LLAAPVVIALAP | 12 | 57.3 | 211.6 | 2.4 | Aliphatic |
| 46 | 184 LAAIVPAIIAVP | 12 | 50.2 | 211.6 | 2.4 | Aliphatic |
| 47 | 185 AALVLPLIIAAP | 12 | 41.3 | 220.0 | 2.4 | Aliphatic |
| 48 | 201 LALAVPALAALP | 12 | 57.3 | 195.8 | 2.1 | Aliphatic |
| 49 | 204 LIAALPAVAALP | 12 | 57.3 | 195.8 | 2.2 | Aliphatic |
| 50 | 205 ALALVPAIAALP | 12 | 57.3 | 195.8 | 2.2 | Aliphatic |
| 51 | 221 AAILAPIVALAP | 12 | 50.2 | 195.8 | 2.2 | Aliphatic |
| 52 | 222 ALLIAPAAVIAP | 12 | 57.3 | 195.8 | 2.2 | Aliphatic |
| 53 | 223 AILAVPIAVVAP | 12 | 57.3 | 203.3 | 2.4 | Aliphatic |
| 54 | 224 ILAAVPIALAAP | 12 | 57.3 | 195.8 | 2.2 | Aliphatic |
| 55 | 225 VAALLPAAAVLP | 12 | 57.3 | 187.5 | 2.1 | Aliphatic |
| 56 | 241 AAAVVPVLLVAP | 12 | 57.3 | 195.0 | 2.4 | Aliphatic |
| 57 | 242 AALLVPALVAAP | 12 | 57.3 | 187.5 | 2.1 | Aliphatic |
| 58 | 243 AAVLLPVALAAP | 12 | 57.3 | 187.5 | 2.1 | Aliphatic |
| 59 | 245 AAALAPVLALVP | 12 | 57.3 | 187.5 | 2.1 | Aliphatic |
| 60 | 261 LVLVPLLAAAAP | 12 | 41.3 | 211.6 | 2.3 | Aliphatic |
| 61 | 262 ALIAVPAIIVAP | 12 | 50.2 | 211.6 | 2.4 | Aliphatic |
| 62 | 263 ALAVIPAAAILP | 12 | 54.9 | 195.8 | 2.2 | Aliphatic |
| 63 | 264 LAAAPVVIVIAP | 12 | 50.2 | 203.3 | 2.4 | Aliphatic |
| 64 | 265 VLAIAPLLAAVP | 12 | 41.3 | 211.6 | 2.3 | Aliphatic |
| 65 | 281 ALIVLPAAVAVP | 12 | 50.2 | 203.3 | 2.4 | Aliphatic |
| 66 | 282 VLAVAPALIVAP | 12 | 50.2 | 203.3 | 2.4 | Aliphatic |
| 67 | 283 AALLAPALIVAP | 12 | 50.2 | 195.8 | 2.2 | Aliphatic |
| 68 | 284 ALIAPAVALIVP | 12 | 50.2 | 211.7 | 2.4 | Aliphatic |
| 69 | 285 AIVLLPAAVVAP | 12 | 50.2 | 203.3 | 2.4 | Aliphatic |

TABLE 12

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 70 | 301 VIAAPVLAVLAP | 12 | 57.3 | 203.3 | 2.4 | Aliphatic |
| 71 | 302 LALAPALALLAP | 12 | 57.3 | 204.2 | 2.1 | Aliphatic |
| 72 | 304 AIILAPIAAIAP | 12 | 57.3 | 204.2 | 2.3 | Aliphatic |
| 73 | 305 IALAAPILLAAP | 12 | 57.3 | 204.2 | 2.2 | Aliphatic |

TABLE 12-continued

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 74 | 321 IVAVALPALAVP | 12 | 50.2 | 203.3 | 2.3 | Aliphatic |
| 75 | 322 VVAIVLPALAAP | 12 | 50.2 | 203.3 | 2.3 | Aliphatic |
| 76 | 323 IVAVALPVALAP | 12 | 50.2 | 203.3 | 2.3 | Aliphatic |
| 77 | 324 IVAVALPAALVP | 12 | 50.2 | 203.3 | 2.3 | Aliphatic |
| 78 | 325 IVAVALPAVALP | 12 | 50.2 | 203.3 | 2.3 | Aliphatic |
| 79 | 341 IVAVALPAVLAP | 12 | 50.2 | 203.3 | 2.3 | Aliphatic |
| 80 | 342 VIVALAPAVLAP | 12 | 50.2 | 203.3 | 2.3 | Aliphatic |
| 81 | 343 IVAVALPALVAP | 12 | 50.2 | 203.3 | 2.3 | Aliphatic |
| 82 | 345 ALLIVAPVAVAP | 12 | 50.2 | 203.3 | 2.3 | Aliphatic |
| 83 | 361 AVVIVAPAVIAP | 12 | 50.2 | 195.0 | 2.4 | Aliphatic |
| 84 | 363 AVLAVAPALIVP | 12 | 50.2 | 203.3 | 2.3 | Aliphatic |
| 85 | 364 LVAAVAPALIVP | 12 | 50.2 | 203.3 | 2.3 | Aliphatic |
| 86 | 365 AVIVVAPALLAP | 12 | 50.2 | 203.3 | 2.3 | Aliphatic |
| 87 | 381 VVAIVLPAVAAP | 12 | 50.2 | 195.0 | 2.4 | Aliphatic |
| 88 | 382 AAALVIPAILAP | 12 | 54.9 | 195.8 | 2.2 | Aliphatic |
| 89 | 383 VIVALAPALLAP | 12 | 50.2 | 211.6 | 2.3 | Aliphatic |
| 90 | 384 VIVAIAPALLAP | 12 | 50.2 | 211.6 | 2.4 | Aliphatic |
| 91 | 385 IVAIAVPALVAP | 12 | 50.2 | 203.3 | 2.4 | Aliphatic |
| 92 | 401 AALAVIPAAILP | 12 | 54.9 | 195.8 | 2.2 | Aliphatic |
| 93 | 402 ALAAVIPAAILP | 12 | 54.9 | 195.8 | 2.2 | Aliphatic |
| 94 | 403 AAALVIPAAILP | 12 | 54.9 | 195.8 | 2.2 | Aliphatic |
| 95 | 404 LAAAVIPAAILP | 12 | 54.9 | 195.8 | 2.2 | Aliphatic |
| 96 | 405 LAAAVIPVAILP | 12 | 54.9 | 211.7 | 2.4 | Aliphatic |
| 97 | 421 AAILAAPLIAVP | 12 | 57.3 | 195.8 | 2.2 | Aliphatic |
| 98 | 422 VVAILAPLLAAP | 12 | 57.3 | 211.7 | 2.4 | Aliphatic |
| 99 | 424 AVVVAAPVLALP | 12 | 57.3 | 195.0 | 2.4 | Aliphatic |
| 100 | 425 AVVAIAPVLALP | 12 | 57.3 | 203.3 | 2.4 | Aliphatic |
| 101 | 442 ALAALVPAVLVP | 12 | 57.3 | 203.3 | 2.3 | Aliphatic |
| 102 | 443 ALAALVPVALVP | 12 | 57.3 | 203.3 | 2.3 | Aliphatic |
| 103 | 444 LAAALVPVALVP | 12 | 57.3 | 203.3 | 2.3 | Aliphatic |
| 104 | 445 ALAALVPALVVP | 12 | 57.3 | 203.3 | 2.3 | Aliphatic |
| 105 | 461 IAAVIVPAVALP | 12 | 50.2 | 203.3 | 2.4 | Aliphatic |
| 106 | 462 IAAVLVPAVALP | 12 | 57.3 | 203.3 | 2.4 | Aliphatic |
| 107 | 463 AVAILVPLLAAP | 12 | 57.3 | 211.7 | 2.4 | Aliphatic |
| 108 | 464 AVVILVPLAAAP | 12 | 57.3 | 203.3 | 2.4 | Aliphatic |
| 109 | 465 IAAVIVPVAALP | 12 | 50.2 | 203.3 | 2.4 | Aliphatic |
| 110 | 481 AIAIAIVPVALP | 12 | 50.2 | 211.6 | 2.4 | Aliphatic |
| 111 | 482 ILAVAAIPVAVP | 12 | 54.9 | 203.3 | 2.4 | Aliphatic |

TABLE 12-continued

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 112 | 483 | ILAAAIIPAALP | 12 | 54.9 | 204.1 | 2.2 | Aliphatic |
| 113 | 484 | LAVVLAAPAIVP | 12 | 50.2 | 203.3 | 2.4 | Aliphatic |
| 114 | 485 | AILAAIVPLAVP | 12 | 50.2 | 211.6 | 2.4 | Aliphatic |
| 115 | 501 | VIVALAVPALAP | 12 | 50.2 | 203.3 | 2.4 | Aliphatic |
| 116 | 502 | AIVALAVPVLAP | 12 | 50.2 | 203.3 | 2.4 | Aliphatic |
| 117 | 503 | AAIIIVLPAALP | 12 | 50.2 | 220.0 | 2.4 | Aliphatic |
| 118 | 504 | LIVALAVPALAP | 12 | 50.2 | 211.7 | 2.4 | Aliphatic |
| 119 | 505 | AIIIVIAPAAAP | 12 | 50.2 | 195.8 | 2.3 | Aliphatic |

TABLE 13

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 120 | 521 | LAALIVVPAVAP | 12 | 50.2 | 203.3 | 2.4 | Aliphatic |
| 121 | 522 | ALLVIAVPAVAP | 12 | 57.3 | 203.3 | 2.4 | Aliphatic |
| 122 | 524 | AVALIVVPALAP | 12 | 50.2 | 203.3 | 2.4 | Aliphatic |
| 123 | 525 | ALAIVVAPVAVP | 12 | 50.2 | 195.0 | 2.4 | Aliphatic |
| 124 | 541 | LLALIIAPAAAP | 12 | 57.3 | 204.1 | 2.1 | Aliphatic |
| 125 | 542 | ALALIIVPAVAP | 12 | 50.2 | 211.6 | 2.4 | Aliphatic |
| 126 | 543 | LLAALIA$^P$AAL$^P$ | 12 | 57.3 | 204.1 | 2.1 | Aliphatic |
| 127 | 544 | IVALIVAPAAVP | 12 | 43.1 | 203.3 | 2.4 | Aliphatic |
| 128 | 545 | VVLVLAAPAAVP | 12 | 57.3 | 195.0 | 2.3 | Aliphatic |
| 129 | 561 | AAVAIVLPAVVP | 12 | 50.2 | 195.0 | 2.4 | Aliphatic |
| 130 | 562 | ALIAAIVPALVP | 12 | 50.2 | 211.7 | 2.4 | Aliphatic |
| 131 | 563 | ALAVIVVPALAP | 12 | 50.2 | 203.3 | 2.4 | Aliphatic |
| 132 | 564 | VAIALIVPALAP | 12 | 50.2 | 211.7 | 2.4 | Aliphatic |
| 133 | 565 | VAIVLVAPAVAP | 12 | 50.2 | 195.0 | 2.4 | Aliphatic |
| 134 | 582 | VAVALIVPALAP | 12 | 50.2 | 203.3 | 2.4 | Aliphatic |
| 135 | 583 | AVILALAPIVAP | 12 | 50.2 | 211.6 | 2.4 | Aliphatic |
| 136 | 585 | ALIVAIAPALVP | 12 | 50.2 | 211.6 | 2.4 | Aliphatic |
| 137 | 601 | AAILIAVPIAAP | 12 | 57.3 | 195.8 | 2.3 | Aliphatic |
| 138 | 602 | VIVALAAPVLAP | 12 | 50.2 | 203.3 | 2.4 | Aliphatic |
| 139 | 603 | VLVALAAPVIAP | 12 | 57.3 | 203.3 | 2.4 | Aliphatic |
| 140 | 604 | VALIAVAPAVVP | 12 | 57.3 | 195.0 | 2.4 | Aliphatic |
| 141 | 605 | VIAAVLAPAVAP | 12 | 57.3 | 195.0 | 2.4 | Aliphatic |
| 142 | 622 | ALIVLAAPVAVP | 12 | 50.2 | 203.3 | 2.4 | Aliphatic |
| 143 | 623 | VAAAIALPAIVP | 12 | 50.2 | 187.5 | 2.3 | Aliphatic |
| 144 | 625 | ILAAAAAPLIVP | 12 | 50.2 | 195.8 | 2.2 | Aliphatic |

TABLE 13-continued

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 145 | 643 LALVLAAPAIVP | 12 | 50.2 | 211.6 | 2.4 | Aliphatic |
| 146 | 645 ALAVVALPAIVP | 12 | 50.2 | 203.3 | 2.4 | Aliphatic |
| 147 | 661 AAILAPIVAALP | 12 | 50.2 | 195.8 | 2.2 | Aliphatic |
| 148 | 664 ILIAIAIPAAAP | 12 | 54.9 | 204.1 | 2.3 | Aliphatic |
| 149 | 665 LAIVLAAPVAVP | 12 | 50.2 | 203.3 | 2.3 | Aliphatic |
| 150 | 666 AAIAIIAPAIVP | 12 | 50.2 | 195.8 | 2.3 | Aliphatic |
| 151 | 667 LAVAIVAPALVP | 12 | 50.2 | 203.3 | 2.3 | Aliphatic |
| 152 | 683 LAIVLAAPAVLP | 12 | 50.2 | 211.7 | 2.4 | Aliphatic |
| 153 | 684 AAIVLALPAVLP | 12 | 50.2 | 211.7 | 2.4 | Aliphatic |
| 154 | 685 ALLVAVLPAALP | 12 | 57.3 | 211.7 | 2.3 | Aliphatic |
| 155 | 686 AALVAVLPVALP | 12 | 57.3 | 203.3 | 2.3 | Aliphatic |
| 156 | 687 AILAVALPLLAP | 12 | 57.3 | 220.0 | 2.3 | Aliphatic |
| 157 | 703 IVAVALVPALAP | 12 | 50.2 | 203.3 | 2.4 | Aliphatic |
| 158 | 705 IVAVALLPALAP | 12 | 50.2 | 211.7 | 2.4 | Aliphatic |
| 159 | 706 IVAVALLPAVAP | 12 | 50.2 | 203.3 | 2.4 | Aliphatic |
| 160 | 707 IVALAVLPAVAP | 12 | 50.2 | 203.3 | 2.4 | Aliphatic |
| 161 | 724 VAVLAVLPALAP | 12 | 57.3 | 203.3 | 2.3 | Aliphatic |
| 162 | 725 IAVLAVAPAVLP | 12 | 57.3 | 203.3 | 2.3 | Aliphatic |
| 163 | 726 LAVAIIAPAVAP | 12 | 57.3 | 187.5 | 2.2 | Aliphatic |
| 164 | 727 VALAIALPAVLP | 12 | 57.3 | 211.6 | 2.3 | Aliphatic |
| 165 | 743 AIAIALVPVALP | 12 | 57.3 | 211.6 | 2.4 | Aliphatic |
| 166 | 744 AAVVIVAPVALP | 12 | 50.2 | 195.0 | 2.4 | Aliphatic |
| 167 | 746 VAIIVVAPALAP | 12 | 50.2 | 203.3 | 2.4 | Aliphatic |
| 168 | 747 VALLAIAPALAP | 12 | 57.3 | 195.8 | 2.2 | Aliphatic |
| 169 | 763 VAVLIAVPALAP | 12 | 57.3 | 203.3 | 2.3 | Aliphatic |

TABLE 14

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 170 | 764 AVALAVLPAVVP | 12 | 57.3 | 195.0 | 2.3 | Aliphatic |
| 171 | 765 AVALAVVPAVLP | 12 | 57.3 | 195.0 | 2.3 | Aliphatic |
| 172 | 766 IVVIAVAPAVAP | 12 | 50.2 | 195.0 | 2.4 | Aliphatic |
| 173 | 767 IVVAAVVPALAP | 12 | 50.2 | 195.0 | 2.4 | Aliphatic |
| 174 | 783 IVALVPAVAIAP | 12 | 50.2 | 203.3 | 2.5 | Aliphatic |
| 175 | 784 VAALPAVALVVP | 12 | 57.3 | 195.0 | 2.4 | Aliphatic |
| 176 | 786 LVAIAPLAVLAP | 12 | 41.3 | 211.7 | 2.4 | Aliphatic |
| 177 | 787 AVALVPVIVAAP | 12 | 50.2 | 195.0 | 2.4 | Aliphatic |
| 178 | 788 AIAVAIAPVALP | 12 | 57.3 | 187.5 | 2.3 | Aliphatic |

TABLE 14-continued

| Sequence ID Number | aMTD Sequences | Length | Rigidity/ Flexibility (II) | Sturctural Feature (AI) | Hydropathy (GRAVY) | Residue Structure |
|---|---|---|---|---|---|---|
| 179 | 803 AIALAVPVLALP | 12 | 57.3 | 211.7 | 2.4 | Aliphatic |
| 180 | 805 LVLIAAAPIALP | 12 | 41.3 | 220.0 | 2.4 | Aliphatic |
| 181 | 806 LVALAVPAAVLP | 12 | 57.3 | 203.3 | 2.3 | Aliphatic |
| 182 | 807 AVALAVPALVLP | 12 | 57.3 | 203.3 | 2.3 | Aliphatic |
| 183 | 808 LVVLAAAPLAVP | 12 | 41.3 | 203.3 | 2.3 | Aliphatic |
| 184 | 809 LIVLAAPALAAP | 12 | 50.2 | 195.8 | 2.2 | Aliphatic |
| 185 | 810 VIVLAAPALAAP | 12 | 50.2 | 187.5 | 2.2 | Aliphatic |
| 186 | 811 AVVLAVPALAVP | 12 | 57.3 | 195.0 | 2.3 | Aliphatic |
| 187 | 824 LIIVAAAPAVAP | 12 | 50.2 | 187.5 | 2.3 | Aliphatic |
| 188 | 825 IVAVIVAPAVAP | 12 | 43.2 | 195.0 | 2.5 | Aliphatic |
| 189 | 826 LVALAAPIIAVP | 12 | 41.3 | 211.7 | 2.4 | Aliphatic |
| 190 | 827 IAAVLAAPALVP | 12 | 57.3 | 187.5 | 2.2 | Aliphatic |
| 191 | 828 IALLAAPIIAVP | 12 | 41.3 | 220.0 | 2.4 | Aliphatic |
| 192 | 829 AALALVAPVIVP | 12 | 50.2 | 203.3 | 2.4 | Aliphatic |
| 193 | 830 IALVAAPVALVP | 12 | 57.3 | 203.3 | 2.4 | Aliphatic |
| 194 | 831 IIVAVAPAAIVP | 12 | 43.2 | 203.3 | 2.5 | Aliphatic |
| 195 | 832 AVAAIVPVIVAP | 12 | 43.2 | 195.0 | 2.5 | Aliphatic |
| 196 | 843 AVLVLVAPAAAP | 12 | 41.3 | 219.2 | 2.5 | Aliphatic |
| 197 | 844 VVALLAPLIAAP | 12 | 41.3 | 211.8 | 2.4 | Aliphatic |
| 198 | 845 AAVVIAPLLAVP | 12 | 41.3 | 203.3 | 2.4 | Aliphatic |
| 199 | 846 IAVAVAAPLLVP | 12 | 41.3 | 203.3 | 2.4 | Aliphatic |
| 200 | 847 LVAIVVLPAVAP | 12 | 50.2 | 219.2 | 2.6 | Aliphatic |
| 201 | 848 AVAIVVLPAVAP | 12 | 50.2 | 195.0 | 2.4 | Aliphatic |
| 202 | 849 AVILLAPLIAAP | 12 | 57.3 | 220.0 | 2.4 | Aliphatic |
| 203 | 850 LVIALAAPVALP | 12 | 57.3 | 211.7 | 2.4 | Aliphatic |
| 204 | 851 VLAVVLPAVALP | 12 | 57.3 | 219.2 | 2.5 | Aliphatic |
| 205 | 852 VLAVAAPAVLLP | 12 | 57.3 | 203.3 | 2.3 | Aliphatic |
| 206 | 863 AAVVLLPIIAAP | 12 | 41.3 | 211.7 | 2.4 | Aliphatic |
| 207 | 864 ALLVIAPAIAVP | 12 | 57.3 | 211.7 | 2.4 | Aliphatic |
| 208 | 865 AVLVIAVPAIAP | 12 | 57.3 | 203.3 | 2.5 | Aliphatic |
| 209 | 867 ALLVVIAPLAAP | 12 | 41.3 | 211.7 | 2.4 | Aliphatic |
| 210 | 868 VLVAAILPAAIP | 12 | 54.9 | 211.7 | 2.4 | Aliphatic |
| 211 | 870 VLVAAVLPIAAP | 12 | 41.3 | 203.3 | 2.4 | Aliphatic |
| 212 | 872 VLAAAVLPLVVP | 12 | 41.3 | 219.2 | 2.5 | Aliphatic |
| 213 | 875 AIAIVVPAVAVP | 12 | 50.2 | 195.0 | 2.4 | Aliphatic |
| 214 | 877 VAIIAVPAVVAP | 12 | 57.3 | 195.0 | 2.4 | Aliphatic |
| 215 | 878 IVALVAPAAVVP | 12 | 50.2 | 195.0 | 2.4 | Aliphatic |
| 216 | 879 AAIVLLPAVVVP | 12 | 50.2 | 219.1 | 2.5 | Aliphatic |

TABLE 14-continued

| Sequence ID Number | aMTD Sequences | Length | Rigidity/ Flexibility (II) | Sturctural Feature (AI) | Hydropathy (GRAVY) | Residue Structure |
|---|---|---|---|---|---|---|
| 217 | 881 AALIVVPAVAVP | 12 | 50.2 | 195.0 | 2.4 | Aliphatic |
| 218 | 882 AIALVVPAVAVP | 12 | 57.3 | 195.0 | 2.4 | Aliphatic |
| 219 | 883 LAIVPAAIAALP | 12 | 50.2 | 195.8 | 2.2 | Aliphatic |

TABLE 15

| Sequence ID Number | aMTD Sequences | Length | Rigidity/ Flexibility (II) | Sturctural Feature (AI) | Hydropathy (GRAVY) | Residue Structure |
|---|---|---|---|---|---|---|
| 220 | 885 LVAIAPAVAVLP | 12 | 57.3 | 203.3 | 2.4 | Aliphatic |
| 221 | 887 VLAVAPAVAVLP | 12 | 57.3 | 195.0 | 2.4 | Aliphatic |
| 222 | 888 ILAVVAIPAAAP | 12 | 54.9 | 187.5 | 2.3 | Aliphatic |
| 223 | 889 ILVAAAPIAALP | 12 | 57.3 | 195.8 | 2.2 | Aliphatic |
| 224 | 891 ILAVAAIPAALP | 12 | 54.9 | 195.8 | 2.2 | Aliphatic |
| 225 | 893 VIAIPAILAAAP | 12 | 54.9 | 195.8 | 2.3 | Aliphatic |
| 226 | 895 AIIIVVPAIAAP | 12 | 50.2 | 211.7 | 2.5 | Aliphatic |
| 227 | 896 AILIVVAPIAAP | 12 | 50.2 | 211.7 | 2.5 | Aliphatic |
| 228 | 897 AVIVPVAIIAAP | 12 | 50.2 | 203.3 | 2.5 | Aliphatic |
| 229 | 899 AVVIALPAVVAP | 12 | 57.3 | 195.0 | 2.4 | Aliphatic |
| 230 | 900 ALVAVIAPVVAP | 12 | 57.3 | 195.0 | 2.4 | Aliphatic |
| 231 | 901 ALVAVLPAVAVP | 12 | 57.3 | 195.0 | 2.4 | Aliphatic |
| 232 | 902 ALVAPLLAVAVP | 12 | 41.3 | 203.3 | 2.3 | Aliphatic |
| 233 | 904 AVLAVVAPVVAP | 12 | 57.3 | 186.7 | 2.4 | Aliphatic |
| 234 | 905 AVIAVAPLVVAP | 12 | 41.3 | 195.0 | 2.4 | Aliphatic |
| 235 | 906 AVIALAPVVVAP | 12 | 57.3 | 195.0 | 2.4 | Aliphatic |
| 236 | 907 VAIALAPVVVAP | 12 | 57.3 | 195.0 | 2.4 | Aliphatic |
| 237 | 908 VALALAPVVVAP | 12 | 57.3 | 195.0 | 2.3 | Aliphatic |
| 238 | 910 VAALLPAVVVAP | 12 | 57.3 | 195.0 | 2.3 | Aliphatic |
| 239 | 911 VALALPAVVVAP | 12 | 57.3 | 195.0 | 2.3 | Aliphatic |
| 240 | 912 VALLAPAVVVAP | 12 | 57.3 | 195.0 | 2.3 | Aliphatic |
| | | | 52.6 ± 5.1 | 201.7 ± 7.8 | 2.3 ± 0.1 | |

3-4. Design of the Peptides which Did not Satisfy at Least One Critical Factor

To demonstrate that this invention of new hydrophobic CPPs—aMTDs, which satisfy all critical factors described above, are correct and rationally designed, the peptides which do not satisfy at least one critical factor have also been designed. Total of 31 rPeptides (rPs) are designed, developed and categorized as follows: no bending peptides, either no proline in the middle as well at the end and/or no central proline; ② rigid peptides (II<40); too much flexible peptides; ④ aromatic peptides (aromatic ring presences); hydrophobic, But non-aromatic peptides; hydrophilic, but non-aliphatic peptides.

3-4-1. Peptides that do not Satisfy the Bending Potential

TABLE 16 shows the peptides that do not have any proline in the middle (at 5', 6', 7' or 8') and at the end of the sequences. In addition, TABLE 16 describes the peptides which do not have proline in the middle of the sequences. All these peptides are supposed to have no-bending potential.

TABLE 16

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| No-Bending Peptides (No Proline at 5, 6, 7 or 8 and/or 12) | 931 | AVLIAPAILAAA | 12 | 6 | 57.3 | 204.2 | 2.5 |
| | 936 | ALLILAAAVAAP | 12 | 12 | 41.3 | 204.2 | 2.4 |
| | 152 | LAAAVAAVAALL | 12 | None | 9.2 | 204.2 | 2.7 |
| | 27 | LAIVAAAAALVA | 12 | None | 2.1 | 204.2 | 2.8 |
| | 935 | ALLILPAAAVAA | 12 | 6 | 57.3 | 204.2 | 2.4 |
| | 670 | ALLILAAAVAAL | 12 | None | 25.2 | 236.6 | 2.8 |
| | 934 | LILAPAAVVAAA | 12 | 5 | 57.3 | 195.8 | 2.5 |
| | 37 | TTCSQQQYCTNG | 12 | None | 53.1 | 0.0 | -1.1 |
| | 16 | NNSCTTVTNGSQ | 12 | None | 47.4 | 0.0 | -1.4 |
| | 113 | PVAVALLIAVPP | 12 | 1, 11, 12 | 57.3 | 195.0 | 2.1 |

3-4-2. Peptides that do not Satisfy the Rigidity/Flexibility

To prove that rigidity/flexibility of the sequence is a crucial critical factor, rigid (Avg. II: 21.8±6.6) and too high flexible sequences (Avg. II: 82.3±21.0) were also designed. Rigid peptides that instability index is much lower than that of new aMTDs (II: 41.3-57.3, Avg. II: 53.3±5.7) are shown in TABLE 17. Bending, but too high flexible peptides that II is much higher than that of new aMTDs are also provided in TABLE 18.

TABLE 17

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| Rigid Peptides (II < 50) | 226 | ALVAAIPALAIP | 12 | 6 | 20.4 | 195.8 | 2.2 |
| | 6 | VIAMIPAAFWVA | 12 | 6 | 15.7 | 146.7 | 2.2 |
| | 750 | LAIAAIAPLAIP | 12 | 8, 12 | 22.8 | 204.2 | 2.2 |
| | 26 | AAIALAAPLAIV | 12 | 8 | 18.1 | 204.2 | 2.5 |
| | 527 | LVLAAVAPIAIP | 12 | 8, 12 | 22.8 | 211.7 | 2.4 |
| | 466 | IIAAAAPLAIIP | 12 | 7, 12 | 22.8 | 204.2 | 2.3 |
| | 167 | VAIAIPAALAIP | 12 | 6, 12 | 20.4 | 195.8 | 2.3 |
| | 246 | VVAVPLLVAFAA | 12 | 5 | 25.2 | 195.0 | 2.7 |
| | 426 | AAALAIPLAIIP | 12 | 7, 12 | 4.37 | 204.2 | 2.2 |
| | 606 | AAAIAAIPIIIP | 12 | 8, 12 | 4.4 | 204.2 | 2.4 |
| | 66 | AGVLGGPIMGVP | 12 | 7, 12 | 35.5 | 121.7 | 1.3 |
| | 248 | VAAIVPIAALVP | 12 | 6, 12 | 34.2 | 203.3 | 2.5 |
| | 227 | LAAIVPIAAAVP | 12 | 6, 12 | 34.2 | 187.5 | 2.2 |
| | 17 | GGCSAPQTTCSN | 12 | 6 | 51.6 | 8.3 | -0.5 |
| | 67 | LDAEVPLADDVP | 12 | 6, 12 | 34.2 | 130.0 | 0.3 |

TABLE 18

| Group | rPeptide ID | Sequences | Length | Proline Position (PP) | Rigidity/ Flexibility (II) | Sturctural Feature (AI) | Hydropathy (GARVY) |
|---|---|---|---|---|---|---|---|
| Bending Peptides but Too High Flexibility | 692 | PAPLPPVVILAV | 12 | 1, 3, 5, 6 | 105.5 | 186.7 | 1.8 |
| | 69 | PVAVLPPAALVP | 12 | 1, 6, 7, 12 | 89.4 | 162.5 | 1.6 |
| | 390 | VPLLVPVVPVVP | 12 | 2, 6, 9, 12 | 105.4 | 210.0 | 2.2 |
| | 350 | VPILVPVVPVVP | 12 | 2, 6, 9, 12 | 121.5 | 210.0 | 2.2 |
| | 331 | VPVLVPLVPVVP | 12 | 2, 6, 9, 12 | 105.4 | 210.0 | 2.2 |
| | 9 | VALVPAALILPP | 12 | 5, 11, 12 | 89.4 | 203.3 | 2.1 |
| | 68 | VAPVLPAAPLVP | 12 | 3, 6, 9, 12 | 105.5 | 162.5 | 1.6 |
| | 349 | VPVLVPVVPVVP | 12 | 2, 6, 9, 12 | 121.5 | 201.6 | 2.2 |
| | 937 | VPVLVPLPVPVV | 12 | 2, 6, 8, 10 | 121.5 | 210.0 | 2.2 |
| | 938 | VPVLLPVVVPVP | 12 | 2, 6, 10, 12 | 121.5 | 210.0 | 2.2 |
| | 329 | LPVLVPVVPVVP | 12 | 2, 6, 9, 12 | 121.5 | 210.0 | 2.2 |
| | 49 | VVPAAPAVPVVP | 12 | 3, 6, 9, 12 | 121.5 | 145.8 | 1.7 |
| | 772 | LPVAPVIPIIVP | 12 | 2, 5, 8, 12 | 79.9 | 210.8 | 2.1 |
| | 210 | ALIALPALPALP | 12 | 6, 9, 12 | 89.4 | 195.8 | 1.8 |
| | 28 | AVPLLPLVPAVP | 12 | 3, 6, 9, 12 | 89.4 | 186.8 | 1.8 |
| | 693 | AAPVLPVAVPIV | 12 | 3, 6, 10 | 82.3 | 186.7 | 2.1 |
| | 169 | VALVAPALILAP | 12 | 6, 12 | 73.4 | 211.7 | 2.4 |

TABLE 18-continued

| Group | rPeptide ID | Sequences | Length | Proline Position (PP) | Rigidity/ Flexibility (II) | Sturctural Feature (AI) | Hydropathy (GARVY) |
|---|---|---|---|---|---|---|---|
| | 29 | VLPPLPVLPVLP | 12 | 3, 4, 6, 9, 12 | 121.5 | 202.5 | 1.7 |
| | 190 | AAILAPAVIAPP | 12 | 6, 11, 12 | 89.4 | 163.3 | 1.8 |

3-4-3. Peptides that do not Satisfy the Structural Features

New hydrophobic CPPs-aMTDs are consisted with only hydrophobic and aliphatic amino acids (A, V, L, I and P) with average ranges of the indexes—AI: 180-220 and GRAVY: 2.1-2.6 (TABLE 9). Based on the structural indexes, the peptides which contain an aromatic residue (W, F or Y) are shown in TABLE 19 and the peptides which are hydrophobic but non-aromatic sequences that do not have an aromatic residue are designed (TABLE 20). Finally, hydrophilic and/or bending peptides which are consisted with non-aliphatic amino acids are shown in TABLE 21.

3-5. Summary of Newly Designed Peptides

Total of 457 sequences have been designed based on the critical factors. Designed potentially best aMTDs (hydrophobic, flexible, bending, aliphatic and 12-A/a length peptides) that do satisfy all range/feature of critical factors are 316. Designed rPeptides that do not satisfy at least one of the critical factors are 141 that no bending peptide sequences are 26; rigid peptide (11<40) sequences are 23; too much flexible peptides are 24; aromatic peptides (aromatic ring presences) are 27; hydrophobic, but non-aromatic peptides are 23; and hydrophilic, but non-aliphatic peptides are 18.

TABLE 19

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| Aromatic Peptides (Aromatic Ring Presences) | 30 | WFFAGPIMLIWP | 12 | 6, 12 | 9.2 | 105.8 | 1.4 |
| | 33 | AAAILAPAFLAV | 12 | 7 | 57.3 | 171.7 | 2.4 |
| | 131 | WIIAPVWLAWIA | 12 | 5 | 51.6 | 179.2 | 1.9 |
| | 922 | WYVIPVLPLVVP | 12 | 8, 12 | 41.3 | 194.2 | 2.2 |
| | 71 | FMWMWFPFMWYP | 12 | 7, 12 | 71.3 | 0.0 | 0.6 |
| | 921 | IWWFVVLPLVVP | 12 | 8, 12 | 41.3 | 194.2 | 2.2 |

TABLE 20

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| Hydrophobic but Non Aromatic Peptides | 436 | VVMLVVPAVMLP | 12 | 7, 12 | 57.3 | 194.2 | 2.6 |
| | 138 | PPAALLAILAVA | 12 | 1, 2 | 57.3 | 195.8 | 2.2 |
| | 77 | PVALVLVALVAP | 12 | 1, 12 | 41.3 | 219.2 | 2.5 |
| | 577 | MLMIALVPMIAV | 12 | 8 | 18.9 | 195.0 | 2.7 |
| | 97 | ALLAAPPALLAL | 12 | 6, 7 | 57.3 | 204.2 | 2.1 |
| | 214 | ALIVAPALMALP | 12 | 6, 12 | 60.5 | 187.5 | 2.2 |
| | 59 | AVLAAPVVAALA | 12 | 6 | 41.3 | 187.5 | 2.5 |
| | 54 | LAVAAPPVVALL | 12 | 6, 7 | 57.3 | 203.3 | 2.3 |

TABLE 21

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| Hydrophilic Peptides but Non Aliphatic | 949 | SGNSCQQCGNSS | 12 | None | 41.7 | 0.0 | -1.1 |
| | 39 | CYNTSPCTGCCY | 12 | 6 | 52.5 | 0.0 | 0.0 |
| | 19 | YVSCCTYTNGSQ | 12 | None | 47.7 | 0.0 | -1.0 |
| | 947 | CYYNQQSNNNNQ | 12 | None | 59.6 | 0.0 | -2.4 |
| | 139 | TGSTNSPTCTST | 12 | 7 | 53.4 | 0.0 | -0.7 |
| | 18 | NYCCTPTTNGQS | 12 | 6 | 47.9 | 0.0 | -0.9 |
| | 20 | NYCNTCPTYGQS | 12 | 7 | 47.4 | 0.0 | -0.9 |
| | 635 | GSTGGSQQNNQY | 12 | None | 31.9 | 0.0 | -1.9 |
| | 40 | TYNTSCTPGTCY | 12 | 8 | 49.4 | 0.0 | -0.6 |
| | 57 | QNNCNTSSQGGG | 12 | None | 52.4 | 0.0 | -1.6 |
| | 159 | CYSGSTSQNQPP | 12 | 11.12 | 51.0 | 0.0 | -1.3 |
| | 700 | GTSNTCQSNQNS | 12 | None | 19.1 | 0.0 | -1.6 |
| | 38 | YYNQSTCGGQCY | 12 | None | 53.8 | 0.0 | -1.0 |

4. Preparation of Recombinant Report Proteins Fused to aMTDs and rPeptides

Recombinant proteins fused to aMTDs and others [rPeptides, reference hydrophobic CPP sequences (MTM and MTD)] were expressed in bacteria system, purified with single-step affinity chromatography and prepared as soluble proteins in physiological condition. These recombinant proteins have been tested for the ability of their cell-permeability by utilizing flow cytometry and laser scanning confocal microscopy.

4-1. Selection of Cargo Protein for Recombinant Proteins Fused to Peptide Sequences For clinical/non-clinical application, aMTD-fused cargo materials would be biologically active molecules that could be one of the following: enzymes, transcription factors, toxic, antigenic peptides, antibodies and antibody fragments. Furthermore, biologically active molecules could be one of these following macromolecules: enzymes, hormones, carriers, immunoglobulin, membrane-bound proteins, transmembrane proteins, internal proteins, external proteins, secreted proteins, virus proteins, native proteins, glycoproteins, fragmented proteins, disulphide bonded proteins, recombinant proteins, chemically modified proteins and prions. In addition, these biologically active molecules could be one of the following: nucleic acid, coding nucleic acid sequence, mRNAs, antisense RNA molecule, carbohydrate, lipid and glycolipid.

According to these pre-required conditions, a non-functional cargo to evaluate aMTD-mediated protein uptake has been selected and called as Cargo A (CRA) that should be soluble and non-functional. The domain (A/a 289-840; 184 A/a length) is derived from protein S (Genbank ID: CP000113.1).

4-2. Construction of Expression Vector and Preparation of Recombinant Proteins Coding sequences for recombinant proteins fused to each aMTD are cloned Nde1 (5') and SalI (3') in pET-28a(+) (Novagen, Darmstadt, Germany) from PCR-amplified DNA segments. PCR primers and amino acid sequences for the recombinant proteins fused to aMTD and rPeptides are summarized in TABLE 23 to 38, respectively. Structure of the recombinant proteins is displayed in FIG. 1.

The recombinant proteins were forcedly expressed in *E. coli* BL21 (DE3) cells grown to an $OD_{600}$ of 0.6 and induced for 2 hours with 0.7 mM isopropyl-β-D-thiogalactopyranoside (IPTG). The proteins were purified by $Ni^{2+}$ affinity chromatography as directed by the supplier (Qiagen, Hilden, Germany) in natural condition. After the purification, purified proteins were dissolved in a physiological buffer such as DMEM medium.

TABLE 22

| | |
|---|---|
| Potentially Best aMTDs (Hydrophobic, Flexible, Bending, Aliphatic & Helical) | 240 |
| Random Peptides | 31 |
| No Bending Peptides (No Proline at 5 or 6 and/or 12) | 02 |
| No Bending Peptides (No Central Proline) | 01 |
| Rigid Peptides (II<50) | 09 |
| Too Much Flexible Peptides | 09 |
| Aromatic Peptides (Aromatic Ring Presences) | 01 |
| Hydrophobic, But Non-Aromatic Peptides | 02 |
| Hydrophilic, But Non-Aliphatic Peptides | 07 |

TABLE 23

| | aMTD Sequence | 5'-Primer |
|---|---|---|
| 1 | AAALAPVVLALP | GGGTTTCATATGGCGGCGGCGCTGGCGCCGGTGGTGCTGGCGCTGCCGGCAAATATTACCGTTTTCTAT |
| 2 | AAAVPLLAVVVP | GGGTTTCATATGGCGGCGGCGGTGCCGCTGCTGGCGGTGGTGGTGCCGGCAAATATTACCGTTTTCTAT |
| 3 | AALLVPAAVLAP | GGGTTTCATATGGCGGCGCTGCTGGTGCCGGCGGCGGTGCTGGCGCCGGCAAATATTACCGTTTTCTAT |
| 4 | ALALLPVAALAP | GGGTTTCATATGGCGCTGGCGCTGCTGCCGGTGGCGGCGCTGGCGCCGGCAAATATTACCGTTTTCTAT |
| 5 | AAALLPVALVAP | GGGTTTCATATGGCGGCGGCGCTGCTGCCGGTGGCGCTGGTGGCGCCGGCAAATATTACCGTTTTCTAT |
| 6 | VIAMIPAAFWVA | GGGTTTCATATGGTGATTGCCATGATTCCGGCCCCGTTTTGGGTGGCGGCAAATATTACCGTTTTCTAT |
| 9 | VALVPAALILPP | GGGTTTCATATGGTGGCGCTGGTGCCGCGGCGGCTGATTCTGGCCCCGGCAAATATTACCGTTTTCTAT |
| 11 | VVALAPALAALP | GGGTTTCATATGGTGGCGCTGCTGGTGCCGGCGGCGGTGCTGGCGCCGGCAAATATTACCGTTTTCTAT |
| 12 | LLAAVPAVLLAP | GGGTTTCATATGCTGGTGGCGGCGGTGCCGGCGGTGCTGCTGGCGGCGGCAAATATTACCGTTTTCTAT |
| 13 | AAALVPVVALLP | GGGTTTCATATGGCGGCGGCGCTGGTGCCGGTGGTGGCGCTGCTGCCGGCAAATATTACCGTTTTCTAT |
| 16 | NNSCTTYTNGSQ | GGGTTTCATATGAACAACAGCTGCACCACCTATACCAACGGCAGCCAGGCAAATATTACCGTTTTCTAT |
| 17 | GGCSAPQTTCSN | GGGTTTCATATGGGCGGCTGCAGCGCGCCGCAGACCACCTGCAGCAACGCAAATATTACCGTTTTCTAT |
| 18 | NYCCTPTTNGQS | GGGTTTCATATGAACTATTGCTGCACCCCGACCACCAACGGCCAGAGCGCAAATATTACCGTTTTCTAT |
| 19 | YVSCCTYTNGSQ | GGGTTTCATATGTATGTGAGCTGCTGCACCTATACCAACGGCAGCCAGGCAAATATTACCGTTTTCTAT |
| 20 | NYCNTCPTYGQS | GGGTTTCATATGAACTATTGCAACACCTGCCCGACCTATGGCCAGAGCGCAAATATTACCGTTTTCTAT |
| 21 | AVALLPALLAVP | GGGTTTCATATGGCGGTGGCGCTGCTGCCGGCGCTGCTGGCGGTGCCGGCAAATATTACCGTTTTCTAT |
| 22 | AVVLVPVLAAAP | GGGTTTCATATGGCGGTGGTGCTGGTGCCGGTGCTGGCGGCGGCGCCGGCAAATATTACCGTTTTCTAT |
| 23 | VVLVLPAAAAVP | GGGTTTCATATGGTGGTGCTGGTGCTGCCGGCGGCGGCGGTGCCGGCAAATATTACCGTTTTCTAT |
| 24 | IALAAPALIVAP | GGGTTTCATATGATTGCGCTGGCGGCGCCGGCGCTGATTGTGGCGCCGGCAAATATTACCGTTTTCTAT |

TABLE 23-continued

| aMTD | Sequence | 5'-Primer |
|---|---|---|
| 25 | IVAVAPALVALP | GGGTTTCATATGATTGTGGCGGTGGCGCCGGCGCTGGTGGCGCTCCCGGCAAATATTACCGTTTTCTAT |
| 26 | AAIALAAPLAIV | GGGTTTCATATGGCGGCGATTGCGCTGGCGGCGCCGCTGGCGATTGTGGCAAATATTACCGTTTTCTAT |
| 27 | LAIVAAAALVA | GGGTTTCATATGCTGGCGATTGTGGCGGCGGCGGCGGCGCTGGTGGCGGCAAATATTACCGTTTTCTAT |
| 28 | AVPLLPLVPAVP | GGGTTTCATATGGCGGTGCCGCTGCTGCCGCTGGTGCCGGCGGTGCCGGCAAATATTACCGTTTTCTAT |
| 29 | VLPPLPVLPVLP | GGGTTTCATATGGTGCTGCCGCCGCTGCCGGTGCTGCCGGTGCTGCCGGCAAATATTACCGTTTTCTAT |
| 30 | AMALLPAAVAVA | GGGTTTCATATGGCGATGGCGCTGCTGCCGGCGGCGGTGGCGGTGGCGGCAAATATTACCGTTTTCTAT |
| 33 | AAAILAPAFLAV | GGGTTTCATATGGCGGCGGCGATTCTGGCGCCGGCGTTTCTGGCGGTGGCAAATATTACCGTTTTCTAT |
| 37 | TTCSQQQYCTNG | GGGTTTCATATGTATTATAACCAGAGCACCTGCGGCGGCCAGTGCTATGCAAATATTACCGTTTTCTAT |
| 38 | YYNQSTCGGQCY | GGGTTTCATATGACCACCTGCAGCCAGCAGCAGTATTGCACCAACGGCGCAAATATTACCGTTTTCTAT |
| 39 | CYNTSPCTGCCY | GGGTTTCATATGTGCTATAACACCAGCCCGTGCACCGGCTGCTGCTATGCAAATATTACCGTTTTCTAT |
| 40 | TYNTSCTPGTCY | GGGTTTCATATGACCTATAACACCAGCTGCACCCCGGGCACCTGCTATGCAAATATTACCGTTTTCTAT |

TABLE 24

| aMTD | Sequence | 5'-Primer |
|---|---|---|
| 42 | VAALPVVAVVAP | GGGTTTCATATGGTGGCGGCGCTGCCGGTGGTGGCGGTGGTGGCGCCGGCAAATATTACCGTTTTCTAT |
| 43 | LLAAPLVVAAVP | GGGTTTCATATGCTGCTGGCGGCGCCGCTGGTGGTGGCGGCGGTGCCGGCAAATATTACCGTTTTCTAT |
| 44 | ALAVPVALLVAP | GGGTTTCATATGGCGCTGGCGGTGCCGGTGGCGCTGCTGGTGGCGCCGGCAAATATTACCGTTTTCTAT |
| 49 | VVPAAPAVPVVP | GGGTTTCATATGGTGGTGCCGGCGGCGCCGGCGGTGCCGTGGTGCCGGCAAATATTACCGTTTTCTAT |
| 54 | LAVAAPPVVALL | GGGTTTCATATGCTGGCGGTGGCGGCGCCGCCGGTGGTGGCGCTGCTGGCAAATATTACCGTTTTCTAT |
| 57 | QNNCNTSSQGGG | GGGTTTCATATGCAGAACAACTGCAACACCAGCAGCCAGGGCGGCGGCGCAAATATTACCGTTTTCTAT |
| 59 | AVLAAPVVAALA | GGGTTTCATATGGCGGTGCTGGCGGCGCCGGTGGTGGCGGCGCTGGCGGCAAATATTACCGTTTTCTAT |
| 61 | VAALPVLLAALP | GGGTTTCATATGGTGGCGGCGCTGCCGGTGGTGCTGGCGGCGCTGCCGGCAAATATTACCGTTTTCTAT |
| 62 | VALLAPVALAVP | GGGTTTCATATGGTGGCGCTGCTGGCGCCGGTGGCGCTGGCGGTGCCGGCAAATATTACCGTTTTCTAT |
| 63 | AALLVPALVAVP | GGGTTTCATATGGCGGCGCTGCTGGTGCCGGCGCTGGTGGCGGTGCCGGCAAATATTACCGTTTTCTAT |
| 64 | AIVALPVAVLAF | GGGTTTCATATGGCGATTGTGGCGCTGCCGGTGGCGGTGCTGGCGCCGGCAAATATTACCGTTTTCTAT |
| 65 | IAIVAPVVALAP | GGGTTTCATATGATTGCGATTGTGGCGCCGGTGGTGGCGCTGGCGCCGGCAAATATTACCGTTTTCTAT |
| 66 | AGVLGGPIMGVP | GGGTTTCATATGGCGGGCGTGCTGGGCGGCCCGATTATGGGCGTGCCGGCAAATATTACCGTTTTCTAT |
| 67 | LDAEVPLADDVP | GGGTTTCATATGCTGGATGCGGAAGTGCCGCTGGCGGATGATGTGCCGGCAAATATTACCGTTTTCTAT |
| 68 | VAPVLPAAPLVP | GGGTTTCATATGGTGGCGCCGGTGCTGCCGGCGGCGCCGCTGGTGCCGGCAAATATTACCGTTTTCTAT |
| 69 | PVAVLPPAALVP | GGGTTTCATATGCCGGTGGCGGTGCTGCCGCCGGCGGCGCTGGTGCCGGCAAATATTACCGTTTTCTAT |
| 71 | PMWMWFPFMWYP | GGGTTTCATATGTTTATGTGGATGTGGTTTCCGTTTATGTGGTATCCGGCAAATATTACCGTTTTCTAT |
| 77 | AMLLMPIVLIAP | GGGTTTCATATGGCGATGCTGCTGATGCCGATTGTGCTGATTGCGCCGGCAAATATTACCGTTTTCTAT |
| 81 | AALLPALAALLP | GGGTTTCATATGGCGGCGCTGCTGCCGGCGCTGGCGGCGCTGCTGCCGGCAAATATTACCGTTTTCTAT |
| 82 | AVVLAPVAAVLP | GGGTTTCATATGGCGGTGGTGCTGGCGCCGGTGGCGGCGGTGGCGCCGGCAAATATTACCGTTTTCTAT |
| 83 | LAVAAPLALALP | GGGTTTCATATGCTGGCGGTGGCGGCGCCGCTGGCGCTGGCGCTGCCGGCAAATATTACCGTTTTCTAT |
| 84 | AAVAAPLLLALP | GGGTTTCATATGGCGGCGGTGGCGGCGCCGCTGCTGCTGGCGCTGCCGGCAAATATTACCGTTTTCTAT |
| 85 | LLVLPAAALAAP | GGGTTTCATATGCTGCTGGTGCTGCCGGCGGCGGCGCTGGCGGCGCCGGCAAATATTACCGTTTTCTAT |
| 97 | ALLAAPPALLAL | GGGTTTCATATGGCGCTGCTGCCGGCGCCGCCGGCGCTGCTGGCGCTGGCAAATATTACCGTTTTCTAT |

TABLE 24-continued

| aMTD Sequence | 5'-Primer |
|---|---|
| 101 LVALAPVAAVLP | GGGTTTCATATGCTGGTGGCGGTGGCGCCGGTGGCGGCGGTGCTGCCGGCAAATATTACCGTTTTCTAT |
| 102 LALAPAALALLP | GGGTTTCATATGCTGGCGCTGGCGCCGGCGGCGCTGGCGCTGCTGCCGGCAAATATTACCGTTTTCTAT |
| 103 ALIAAPILALAP | GGGTTTCATATGGCGCTGATTGCGGCGCCGATTCTGGCGCTGGCGCCGGCAAATATTACCGTTTTCTAT |
| 104 AVVAAPLVLALP | GGGTTTCATATGGCGGTGGTGGCGGCGCCGCTGGTGCTGGCGCTGCCGGCAAATATTACCGTTTTCTAT |
| 105 LLALAPAALLAP | GGGTTTCATATGCTGCTGGCGCTGGCGCCGGCGGCGCTGCTGGCGCCGGCAAATATTACCGTTTTCTAT |
| 113 PVAVALLIAVPP | GGGTTTCATATGCCGGTGGCGGTGGCGCTGCTGATTGCGGTGCCGCCGGCAAATATTACCGTTTTCTAT |
| 121 AIVALPALALAP | GGGTTTCATATGGCGATTGTGGCGCTGCCGGCGCTGGCGCTGGCGCCGGCAAATATTACCGTTTTCTAT |
| 123 AAIIVPAALLAP | GGGTTTCATATGGCGGCGATTATTGTGCCGGCGGCGCTGCTGGCGCCGGCAAATATTACCGTTTTCTAT |
| 124 IAVALPALIAAP | GGGTTTCATATGATTGCGGTGGCGCTGCCGGCGCTGATTGCGGCGCCGGCAAATATTACCGTTTTCTAT |
| 131 WIIAPVWLAWIA | GGGTTTCATATGTGGATTATTGCGCCGGTGTGGCTGGCGTGGATTGCGGCAAATATTACCGTTTTCTAT |
| 138 PPAALLAILAVA | GGGTTTCATATGCCGCCGGCGGCGCTGCTGGCGATTCTGGCGGTGGCGGCAAATATTACCGTTTTCTAT |
| 139 TGSTNSPTCTST | GGGTTTCATATGACCGGCAGCACCAACAGCCCGACCTGCACCAGCACCGCAAATATTACCGTTTTCTAT |
| 141 AVIVLPALAVAP | GGGTTTCATATGGCGGTGATTGTGCTGCCGGCGCTGGCGGTGGCGCCGGCAAATATTACCGTTTTCTAT |
| 142 LLAAVPVALVAP | GGGTTTCATATGCTGCTGGCGGCGGTGCCGGTGGCGCTGGTGGCGCCGGCAAATATTACCGTTTTCTAT |
| 143 AVLAVPAVLVAP | GGGTTTCATATGGCGGTGCTGGCGGTGCCGGCGGTGCTGGTGGCGCCGGCAAATATTACCGTTTTCTAT |
| 144 VLAIVPAVALAP | GGGTTTCATATGGTGCTGGCGATTGTGCCGGCGGTGGCGCTGGCGCCGGCAAATATTACCGTTTTCTAT |
| 145 LLAVVPAVALAP | GGGTTTCATATGCTGCTGGCGGTGGTGCCGGCGGTGGCGCTGGCGCCGGCAAATATTACCGTTTTCTAT |
| 152 LAAAVAAVAALL | GGGTTTCATATGCTGGCGGCGGCGGTGGCGGCGGTGGCGGCGCTGCTGGCAAATATTACCGTTTTCTAT |
| 159 CYSGSTSQNQPP | GGGTTTCATATGTGCTATAGCGGCAGCACCAGCCAGAACCAGCCGCCGGCAAATATTACCGTTTTCTAT |
| 161 AVIALPALIAAP | GGGTTTCATATGGCGGTGATTGCGCTGCCGGCGCTGATTGCGGCGCCGGCAAATATTACCGTTTTCTAT |
| 162 AVVALPAALIVP | GGGTTTCATATGGCGGTGGTGGCGCTGCCGGCGGCGCTGATTGTGCCGGCAAATATTACCGTTTTCTAT |
| 163 LALVLPAALAAP | GGGTTTCATATGCTGGCGCTGGTGCTGCCGGCGGCGCTGGCGGCGCCGGCAAATATTACCGTTTTCTAT |

TABLE 25

| aMTD Sequence | 5'-Primer |
|---|---|
| 164 LAAVLPALLAAP | GGGTTTCATATGCTGGCGGCGGTGCTGCCGGCGCTGCTGGCGGCGCCGGCAAATATTACCGTTTTCTAT |
| 165 ALAVPVALAIVP | GGGTTTCATATGGCGCTGGCGGTGCCGGTGGCGCTGGCGATTGTGCCGGCAAATATTACCGTTTTCTAT |
| 167 VAIAIPAALAIP | GGGTTTCATATGGTGGCGATTGCGATTCCGGCGGCGCTGGCGATTCCGGCAAATATTACCGTTTTCTAT |
| 169 VALVAPALILAP | GGGTTTCATATGGTGGCGCTGGTGGCGCCGGCGCTGATTCTGGCGCCGGCAAATATTACCGTTTTCTAT |
| 182 ALIAPVVALVAP | GGGTTTCATATGGCGCTGATTGCGCCGGTGGTGGCGCTGGTGGCGCCGGCAAATATTACCGTTTTCTAT |
| 183 LLAAPVVIALAP | GGGTTTCATATGCTGCTGGCGGCGCCGGTGGTGATTGCGCTGGCGCCGGCAAATATTACCGTTTTCTAT |
| 184 LAAIVPAIIAVP | GGGTTTCATATGCTGGCGGCGATTGTGCCGGCGATTATTGCGGTGCCGGCAAATATTACCGTTTTCTAT |
| 185 AALVLPLIIAAP | GGGTTTCATATGGCGGCGCTGGTGCTGCCGCTGATTATTGCGGCGCCGGCAAATATTACCGTTTTCTAT |
| 189 VILVAPAVIAPP | GGGTTTCATATGGTGATTCTGGTGGCGCCGGCGGTGATTGCCGCCGCCGGCAAATATTACCGTTTTCTAT |
| 190 AAILAPAVIAPP | GGGTTTCATATGGCGGCGATTCTGGCGCCGGCGGTGATTGCGCCGCCGGCAAATATTACCGTTTTCTAT |
| 201 LALAVPALAALP | GGGTTTCATATGCTGGCGCTGGCGGTGCCGGCGCTGGCGGCGCTGCCGGCAAATATTACCGTTTTCTAT |
| 204 LIAALPAVAALP | GGGTTTCATATGCTGATTGCGGCGCTGCCGGCGGTGGCGGCGCTGCCGGCAAATATTACCGTTTTCTAT |
| 205 ALALVPAIAALP | GGGTTTCATATGGCGCTGGCGCTGGTGCCGGCGATTGCGGCGCTGCCGGCAAATATTACCGTTTTCTAT |
| 210 ALIALPALPALP | GGGTTTCATATGGCGCTGATTGCGCTGCCGGCGCTGCCGGCGCTGCCGGCAAATATTACCGTTTTCTAT |

TABLE 25-continued

| aMTD Sequence | 5'-Primer |
|---|---|
| 214 ALIVAPALMALF | GGGTTTCATATGGCGCTGATTGTGGCGCCGGCGCTGATGGCGCTGCCGGCAAATATTACCGTTTTCTAT |
| 221 AAILAPIVALAP | GGGTTTCATATGGCGGCGATTCTGGCGCCGATTGTGGCGCTGGCGCCGGCAAATATTACCGTTTTCTAT |
| 222 ALLIAPAAVIAP | GGGTTTCATATGGCGCTGCTGATTGCGCCGGCGGCGGTGATTGCGCCGGCAAATATTACCGTTTTCTAT |
| 223 AILAVPIAVVAP | GGGTTTCATATGGCGATTCTGGCGGTGCCGATTGCGGTGGTGGCGCCGGCAAATATTACCGTTTTCTAT |
| 224 ILAAVPIALAAP | GGGTTTCATATGATTCTGGCGGCGGTGCCGATTGCGCTGGCGGCGCCGGCAAATATTACCGTTTTCTAT |
| 225 VAALLPAAAVLP | GGGTTTCATATGGTGGCGGCGCTGCTGCCCGCGGCGGCGGTGCTGCCGGCAAATATTACCGTTTTCTAT |
| 226 ALVAAIPALAIP | GGGTTTCATATGGCGCTGGTGGCGGCGATTCCGGCGCTGGCGATTCCGGCAAATATTACCGTTTTCTAT |
| 227 LAAIVPIAAAVP | GGGTTTCATATGCTGGCGGCGATTGTGCCGATTGCGGCGGCGGTGCCGGCAAATATTACCGTTTTCTAT |
| 241 AAAVVPVLLVAP | GGGTTTCATATGGCGGCGGCGGTGGTGCCGGTGCTGCTGGTGGCGCCGGCAAATATTACCGTTTTCTAT |
| 242 AALLVPALVAAP | GGGTTTCATATGGCGGCGCTGCTGGTGCCGGCGCTGGTGGCGGCGCCGGCAAATATTACCGTTTTCTAT |
| 243 AAVLLPVALAAP | GGGTTTCATATGGCGGCGGTGCTGCTGCCGGTGGCGCTGGCGGCGCCGGCAAATATTACCGTTTTCTAT |
| 245 AAALAPVLALVP | GGGTTTCATATGGCGGCGGCGCTGGCGCCGGTGCTGGCGCTGGTGCCGGCAAATATTACCGTTTTCTAT |
| 246 VVAVPLLVAFAA | GGGTTTCATATGGTGGTGGCGGTGCCGCTGCTGGTGGCGTTTGCGGCGGCAAATATTACCGTTTTCTAT |
| 248 VAAIVPIAALVP | GGGTTTCATATGGTGGCGGCGATTGTGCCGATTGCGGCGCTGGTGCCGGCAAATATTACCGTTTTCTAT |
| 261 LVLVPLLAAAAP | GGGTTTCATATGCTGGTGCTGGTGCCGCTGCTGGCGGCGGCGGCGCCGGCAAATATTACCGTTTTCTAT |
| 262 ALIAVPAIIVAP | GGGTTTCATATGGCGCTGATTGCGGTGCCGGCGATTATTGTGGCGCCGGCAAATATTACCGTTTTCTAT |
| 263 ALAVIPAAAILP | GGGTTTCATATGGCGCTGGCGGTGATTCCGGCGGCGGCGATTCTGCCGGCAAATATTACCGTTTTCTAT |
| 264 LAAAPVVIVIAP | GGGTTTCATATGCTGGCGGCGGCGCCGGTGGTGATTGTGATTGCGCCGGCAAATATTACCGTTTTCTAT |
| 265 VLAIAPLLAAVP | GGGTTTCATATGGTGCTGGCGATTGCGCCGCTGCTGGCGGCGGTGCCGGCAAATATTACCGTTTTCTAT |
| 281 ALIVLPAAVAVP | GGGTTTCATATGGCGCTGATTGTGCTGCCGGCGGCGGTGGCGGTGCCGGCAAATATTACCGTTTTCTAT |
| 282 VLAVAPALIVAP | GGGTTTCATATGGTGCTGGCGGTGGCGCCGGCGCTGATTGTGGCGCCGGCAAATATTACCGTTTTCTAT |
| 283 AALLAPALIVAP | GGGTTTCATATGGCGGCGCTGCTGGCGCCGGCGCTGATTGTGGCGCCGGCAAATATTACCGTTTTCTAT |
| 284 ALIAPAVALIVP | GGGTTTCATATGGCGCTGATTGCGCCGGCGGTGGCGCTGATTGTGCCGGCAAATATTACCGTTTTCTAT |
| 285 AIVLLPAAVVAP | GGGTTTCATATGGCGATTGTGCTGCTGCCGGCGGCGGTGGTGGCGCCGGCAAATATTACCGTTTTCTAT |
| 301 VIAAPVLAVLAP | GGGTTTCATATGGTGATTGCGGCGCCGGTGCTGGCGGTGCTGGCGCCGGCAAATATTACCGTTTTCTAT |
| 302 LALAPALALLAP | GGGTTTCATATGCTGGCGCTGGCGCCGGCGCTGGCGCTGCTGGCGCCGGCAAATATTACCGTTTTCTAT |
| 304 AIILAPIAAIAP | GGGTTTCATATGGCGATTATTCTGGCGCCGATTGCGGCGATTGCGCCGGCAAATATTACCGTTTTCTAT |
| 305 IALAAPILLAAP | GGGTTTCATATGATTGCGCTGGCGGCGCCGATTCTGCTGGCGGCGCCGGCAAATATTACCGTTTTCTAT |
| 321 IVAVALPALAVP | GGGTTTCATATGATTGTGGCGGTGGCGCTGCCGGCGCTGGCGGTGCCGGCAAATATTACCGTTTTCTAT |
| 322 VVAIVLPALAAP | GGGTTTCATATGGTGGTGGCGATTGTGCTGCCGGCGCTGGCGGCGCCGGCAAATATTACCGTTTTCTAT |
| 323 IVAVALPVALAP | GGGTTTCATATGATTGTGGCGGTGGCGCTGCCGGTGGCGCTGGCGCCGGCAAATATTACCGTTTTCTAT |
| 324 IVAVALPAALVP | GGGTTTCATATGATTGTGGCGGTGGCGCTGCCGGCGGCGCTGGTGCCGGCAAATATTACCGTTTTCTAT |

TABLE 26

| aMTD Sequence | 5'-Primer |
|---|---|
| 325 IVAVALPAVALP | GGGTTTCATATGATTGTGGCGGTGGCGCTGCCGCCGGTGGCGCTGCCGGCAAATATTACCGTTTTCTAT |
| 329 LPVLVPVVPVVP | GGGTTTCATATGCTGCCGCTCCTCGTGCCGCTGGTGCCGGTGGTGCCGGCAAATATTACCGTTTTCTAT |
| 331 VPVLVPLVPVVP | GGGTTTCATATGCTGCCGCTCCTCGTGCCGCTGGTGCCGGTGGTGCCGGCAAATATTACCGTTTTCTAT |

TABLE 26-continued

| aMTD Sequence | 5'-Primer |
| --- | --- |
| 341 IVAVALPAVLAP | GGGTTTCATATGATTGTGGCGGTGCCGCTGCCGGCGGTGGCTGGCGCGGCAAATATTACCGTTTTCTAT |
| 342 VIVALAPAVLAP | GGGTTTCATATGGTGATTGTGGCGCTCGCGCCCCGGTCCTGGCGCCGGCAAATATTACCGTTTTCTAT |
| 343 IVAVALPALVAP | GGGTTTCATATGATTGTCCCCGTCCCCCTGCCCCCCCTGGTCCCCCCGGCAAATATTACCGTTTTCTAT |
| 345 ALLIVAPVAVAP | GGGTTTCATATGGCCCCTGCTCATTGTGGCGCCGGTGGCGGTGGCGCGGCAAATATTACCGTTTTCTAT |
| 349 VPVLVPVVPVVP | GGGTTTCATATGCTGCCGCTGCTGGTGCCGGTGGTGCCGGTGGTCCCGGCAAATATTACCGTTTTCTAT |
| 350 VPILVPVVPVVP | GGGTTTCATATGGTGCCGGTGCTGGTGCCGGTGGTGCCGGTGGTGCCGGCAAATATTACCGTTTTCTAT |
| 361 AVVIVAPAVIAP | GGGTTTCATATGGCGGTGGTGATTGTGCCGGTGGTGCCGGTGGTGCCGGCAAATATTACCGTTTTCTAT |
| 363 AVLAVAPALIVP | GGGTTTCATATGGCGGTGCTGGCGGTGGCGCCGGCGCTGATTGTGCCGGCAAATATTACCGTTTTCTAT |
| 364 LVAAVAPALIVP | GGGTTTCATATGCTGGTGGTGGCGGTGGCGCCGGGCCTGATTGTGCCGGCAAATATTACCGTTTTCTAT |
| 365 AVIVVAPALLAP | GGGTTTCATATGGCGGTGGTGGCGGTGGCGCCGGGCCTGATTGTGCCGGCAAATATTACCGTTTTCTAT |
| 381 VVAIVLPAVAAP | GGGTTTCATATGGTGGTGGTGGCCATGGTGCTGCCGCGGATGGCCGGGGCAAATATTACCGTTTTCTAT |
| 382 AAALVIPAILAP | GGGTTTCATATGGCGGCGGCCTGGTGATTCCGGCGATTCTGGCGCCGGGCAAATATTACCGTTTTCTAT |
| 383 VIVALAPALLAP | GGGTTTCATATGGTGATTGTGGCGCTGGCGCCGGCGCTGCTGGCGCCGGCAAATATTACCGTTTTCTAT |
| 384 VIVAIAPALLAP | GGGTTTCATATGGTGATTGTGGCGATTGCGCCGGCGCTGCTGGCGCCGGCAAATATTACCGTTTTCTAT |
| 385 IVAIAVPALVAP | GGGTTTCATATGATTGTGGCTATTGCTCTGCCGGCGCTGGTCCCGCCGGCAAATATTACCGTTTTCTAT |
| 390 VPLLVPVVPVVP | GGGTTTCATATGGTGCCGCTCCTGGTGCCGGTGGTGCCGGTGGTGCCGGCAAATATTACCGTTTTCTAT |
| 401 AALAVIPAAILP | GGGTTTCATATGGCGGCGCTGGCGGTGATTCCGGCGGCGATTCTGCCGGCAAATATTACCGTTTTCTAT |
| 402 ALAAVIPAAILP | GGGTTTCATATGGCGCTGCCGGCGGTGATTCCGGCGGCGATTCTGCCGGCAAATATTACCGTTTTCTAT |
| 403 AAALVIPAAILP | GGGTTTCATATGGCGGCGCGGCTGGTGATTCCGGCGGCGATTCTGCCGGCAAATATTACCGTTTTCTAT |
| 404 LAAAVIPAAILP | GGGTTTCATATGCTGGCGGCGGCGGTGATTCCGGCGGCGATTCTGCCGGCAAATATTACCGTTTTCTAT |
| 405 LAAAVIPVAILP | GGGTTTCATATGCTGGCGGCGGCGGTGATTCCGGCGGCGATTCTGCCGGCAAATATTACCGTTTTCTAT |
| 421 AAILAAPLIAVP | GGGTTTCATATGGCGGCGATTCTGGCGGCGCCGCTGATTGCGGTGCCGGCAAATATTACCGTTTTCTAT |
| 422 VVAILAPLLAAP | GGGTTTCATATGGTGGTGGCGATTCTGGCGCCGCTGCTGGCGGCGCCGGCAAATATTACCGTTTTCTAT |
| 424 AVVVAAPVLALP | GGGTTTCATATGGCGGTGGTGGTGGCGGCGCCGGTGCTGGCGCTGCCGGCAAATATTACCGTTTTCTAT |
| 425 AVVAIAPVLALP | GGGTTTCATATGGCGGTGGTGGCGATTGCGCCGGTGCTGGCGCTGCCGGCAAATATTACCGTTTTCTAT |
| 426 AAALAIPLAIIP | GGGTTTCATATGGCGGCGGCGCTGGCGATTCCGCTGGCGATTATTCCGGCAAATATTACCGTTTTCTAT |
| 436 AVVLVIMPAAIP | GGGTTTCATATGGCGGGTGGTGCTGGTGATTATGCCGGCGGCGATCCGGCAAATATTACCGTTTTCTAT |
| 442 ALAALVPAVLVP | GGGTTTCATATGGCGCTGGCGGCGCTGGTGCCGGCGGTGCTGGTGCCGGCAAATATTACCGTTTTCTAT |
| 443 ALAALVPVALVP | GGGTTTCATATGGCGCTGGCGGCGCTGGTGCCGGTGGCGCTGGTGCCGGCAAATATTACCGTTTTCTAT |
| 444 LAAALVPVALVP | GGGTTTCATATGGCGCTGGCGGCGCTGGTGCCGGTGGCGCTGGTGCCGGCAAATATTACCGTTTTCTAT |
| 445 ALAALVPALVVP | GGGTTTCATATGGCGCTGGTGGCGCTGGTGCCGGTGGTGGTGGTGCCGGCAAATATTACCGTTTTCTAT |
| 461 IAAVIVPAVALP | GGGTTTCATATGATTGCGGCGGTGATTGTGCCGGCGGTGGCGCTGCCGGCAAATATTACCGTTTTCTAT |
| 462 IAAVLVPAVALP | GGGTTTCATATGATTGCGGCGGTGATGGTGCCGGCGGTGGCGCTGCCGGCAAATATTACCGTTTTCTAT |
| 463 AVAILVPLLAAP | GGGTTTCATATGGCGCTGGCGATTCTGGTGCCGCTGCTGGCGGCGCCGGCAAATATTACCGTTTTCTAT |
| 464 AVVILVPLAAAP | GGGTTTCATATGGCGCTGGCGATTCTGGTGCCGCTGGCCCCGGCGCCGGCAAATATTACCGTTTTCTAT |
| 465 IAAVIVPVAALP | GGGTTTCATATGATTGCGGCGGTGATTGTGCCGGTGGCGGCGCTGCCGGCAAATATTACCGTTTTCTAT |
| 466 IIAAAAPLAIIP | GGGTTTCATATGATTATTGCGGCGGCCGCGCCGCTGCCGATTATTCCGGCAAATATTACCGTTTTCTAT |
| 481 AIAIAIVPVALP | GGGTTTCATATGGCGATTGCGATTGCGATTGTGCCGGTGGCGCTGCCGGCAAATATTACCGTTTTCTAT |
| 482 ILAVAAIPVAVP | GGGTTTCATATGATTCTGGCGGTGGCGGCGATTCCGGTGGCGGTGCCGGCAAATATTACCGTTTTCTAT |

TABLE 26-continued

| aMTD Sequence | 5'-Primer |
| --- | --- |
| 483 ILAAAIIPAALP | GGGTTTCATATGATTCTGGCGACGGCCATTATTCCGGCGGCGCTGCCGGCAAATATTACCGTTTTCTAT |
| 484 LAVVLAAPAIVP | GGGTTTCATATGCTGGCGGTGGTGCTGGCGGCGCCGGCGATTGTGCCGGCAAATATTACCGTTTTCTAT |
| 485 AILAAIVPLAVP | GGGTTTCATATGGCGATTCTGGCGGCGATTGTGCCGCTGGCGGTGCCGGCAAATATTACCGTTTTCTAT |
| 501 VIvALAVPALAP | GGGTTTCATATGGTGATTGTGGCGCTGGCGGTGCCGGCGCTGGCGCCGGCAAATATTACCGTTTTCTAT |

TABLE 27

| aMTD Sequence | 5'-Primer |
| --- | --- |
| 502 AIVALAVPVLAP | GGGTTTCATATGCCGATTGTGGCCCTGGCGTCCCGGTCCTGGCGCCGGGCAAATATTACCGTTTTCTAT |
| 503 AAIIIVLPAALP | GGGTTTCATATGGCGGCGATTATTATTGTGCTGCCGGCGGCGCTGCCGGCAAATATTACCGTTTTCTAT |
| 504 LIVALAVPALAP | GGGTTTCATATGCTGATTCTGGCGCTGGCGGTGCCGCTGGGGCCGCCGGCAAATATTACCGTTTTCTAT |
| 505 AIIIVIAPAAAP | GGGTTTCATATGGCGATTATTATTGTGATTGCGCCGGCGGCGGCGCCGGCAAATATTACCGTTTTCTAT |
| 521 LAALIVVPAVAP | GGGTTTCATATGCTGGCGGCGCTGATTGTGGTGCCGGCGGTGGCGCCGGCAAATATTACCGTTTTCTAT |
| 522 ALLVIAVPAVAP | GGGTTTCATATGGCGCTGCTGGTGATTGCGGTGCGGCGGTGGCGCCGGCAAATATTACCGTTTTCTAT |
| 524 AVALIVVPALAP | GGGTTTCATATGGCGGTGGCGCTGATTGTGGTGCCGGCGCTGGCGCCGGCAAATATTACCGTTTTCTAT |
| 525 ALAIVVAPVAVP | GGGTTTCATATGGCGCTGGCGATTGTGGTGGCGCCGGTGGCGGTGCCGGCAAATATTACCGTTTTCTAT |
| 527 LVLAAVAPIAIP | GGGTTTCATATGCTGGTGCTGGCGGCGGTGGCGCCGATTGCGATTCCGGCAAATATTACCGTTTTCTAT |
| 541 LLALIIAPAAAP | GGGTTTCATATGCTGCTGGCGCTGATTATTGCGCCGGCGGCGGCGCCGGCAAATATTACCGTTTTCTAT |
| 542 ALALIIVPAVAP | GGGTTTCATATGCTGCTGGCGCTGATTATTGTGCCGGCGGCGGCGCCGGCAAATATTACCGTTTTCTAT |
| 543 LLAALIAPAALP | GGGTTTCATATGCTGCTGGCGGCGCTGATTGCGCCGCCGGCGCTGCCGGCAAATATTACCGTTTTCTAT |
| 544 IVALIVAPAAVP | GGGTTTCATATGATTGTGGCGCTGATTGTGCGCGCCGGCGCCGGTGCGGCAAATATTACCGTTTTCTAT |
| 545 VVLVLAAPAAVP | GGGTTTCATATGGTGGTGCTGGTGCTGGCGGGCCGGCCACGGTGCCGGGCAAATATTACCGTTTTCTAT |
| 561 AAVAIVLPAVVP | GGGTTTCATATGGCGCCGGTGGCCATTGTGCTGCGCCCGGTGGTGCCGGCAAATATTACCGTTTTCTAT |
| 562 ALIAAIVPALVP | GGGTTTCATATGGCGCTGATTGCGGCGATTGTGCCGGCGCTGGTGCCGGCAAATATTACCGTTTTCTAT |
| 563 ALAVIVVPALAP | GGGTTTCATATGGCGCTGGCGGTGATTGTGGTGCCGGCGCTGGCGCCGGCAAATATTACCGTTTTCTAT |
| 564 VAIALIVPALAP | GGGTTTCATATGGTGGCCATTCCGCTGATTGTGCCGGCGCTCGCGCCGGCAAATATTACCGTTTTCTAT |
| 565 VAIVLVAPAVAP | GGGTTTCATATGGTGGCGATTGTGCTGGTGGCGCCGGCGGTGGCGCCGGCAAATATTACCGTTTTCTAT |
| 577 AAVLIVPIMVMP | GGGTTTCATATGCCGGCCGTGCTGATTGTGCCGATTATGGTGATGCCGGCAAATATTACCGTTTTCTAT |
| 582 VAVALIVPALAP | CGGTTTCATATGGTGGCGGTGGCGCTGATTGTGCCGGCGCTGGCGCCGGCAAATATTACCGTTTTCTAT |
| 583 AVILALAPIVAP | GGGTTTCATATGGCGGTGATTCTGCCGCTGGCGCCGATTGTGGCGCCGGCAAATATTACCGTTTTCTAT |
| 585 ALIVAIAPALVP | GGGTTTCATATGGCGCTGATTGTGGCGATTGCGCCGGCGCTGGTGCCGGCAAATATTACCGTTTTCTAT |
| 601 AAILIAVPIAAP | GGGTTTCATATGGCGGCCATTCTGATTGCCGTGCCGATTGCGGCGCCGGCAAATATTACCGTTTTCTAT |
| 602 VIVALAAPVLAP | GGGTTTCATATGGTGATTGTGGCGCTGGCGGCGCCGGTGCTGGCGCCGGCAAATATTACCGTTTTCTAT |
| 603 VLVALAAPVIAP | GGGTTTCATATGGTGCTGGTGGCGCTGGCGGCGCCGGTGATTGCGCCGGCAAATATTACCGTTTTCTAT |
| 604 VALIAVAPVVP | GGGTTTCATATGGTGGCGCTGATTGCGGTGGCGCCGGCGGTGGTGCCGGCAAATATTACCGTTTTCTAT |
| 605 VIAAVLAPVAVP | GGGTTTCATATGGTGATTGCGGCGGTGCTGGCGCCGGTGGCGGTGCCGGCAAATATTACCGTTTTCTAT |
| 606 AAAIAAIPIIIP | GGGTTTCATATGGCGGCGGCGATTGCGGCGATTCCCATTATTATTCCGGCAAATATTACCGTTTTCTAT |
| 622 ALIVLAAPVAVP | GGGTTTCATATGGCGCTGATTGTGCTGGCGGCGCCGGTGGCGGTGCCGGCAAATATTACCGTTTTCTAT |
| 623 VAAAIALPAIVP | GGGTTTCATATGGTGGCGGCGGCGATTGCGCTGCCGGCGATTGTGCCGGCAAATATTACCGTTTTCTAT |
| 625 ILAAAAAPLIVP | GGGTTTCATATGATTCTGGCGGCGGCGGCGGCGCCGCTGATTGTGCCGGCAAATATTACCGTTTTCTAT |

TABLE 27-continued

| aMTD Sequence | 5'-Primer |
|---|---|
| 635 GSTGGSQQNNQY | GGGTTTCATATGGCCAGCACCGGCGGCAGCCAGCAGAACAACCAGTATGCAAATATTACCGTTTTCTAT |
| 643 LALVLAAPAIVP | GGGTTTCATATGCTGGCGCTGGTGCTGGCGGCGCCGGCGATTGTGCCGGCAAATATTACCGTTTTCTAT |
| 645 ALAVVALPAIVP | GGGTTTCATATGCCGCTGGCCGTGCTGGCGCTGCCGCCGATTGTGCCGGCAAATATTACCGTTTTCTAT |
| 661 AAILAPIVAALP | GGGTTTCATATGGCGGCGATTCTGCCGCCGATTGTGGCGGCGCTGCCGGCAAATATTACCGTTTTCTAT |
| 664 ILIAIAIPAAAP | GGGTTTCATATGATTCTGATTGCGATTGCGATTCCGGCGGCGGCGCCGGCAAATATTACCGTTTTCTAT |
| 665 LAIVLAAPVAVP | GGGTTTCATATGCTGGCGATTGTGCTGGCGGCGCCGGTGGCGGTGCCGGCAAATATTACCGTTTTCTAT |
| 666 AAIAIIAPAIVP | GGGTTTCATATGGCGGCGATTGCGATTATTGCGCCGGCGATTGTGCCGGCAAATATTACCGTTTTCTAT |
| 667 LAVAIVAPALVP | GGGTTTCATATGCTGGCGGTGGCGATTGTGGCGCCGGCGCTGGTGCCGGCAAATATTACCGTTTTCTAT |
| 676 VPLLVPVPVVVP | GGGTTTCATATGGTGCCGCTGCTGGTGCCGGTGCCGGTGGTGGTGCCGGCAAATATTACCGTTTTCTAT |
| 683 LAIVLAAPAVLP | GGGTTTCATATGCTGGCGATTGTGCTGGCGGCGCCGGCGGTGCTGCCGGCAAATATTACCGTTTTCTAT |
| 684 AAIVLALPAVLP | GGGTTTCATATGGCGGCGATTGTGCTGGCGCTGCCGGCGGTGCTGCCGGCAAATATTACCGTTTTCTAT |
| 685 ALLVAVLPAALP | GGGTTTCATATGGCGCTGCTGGTGGCGGTGCTGCCGGCGGCGCTGCCGGCAAATATTACCGTTTTCTAT |
| 686 AALVAVLPVALP | GGGTTTCATATGGCGGCGCTGGTGGCGGTGCTGCCGGTGGCGCTGCCGGCAAATATTACCGTTTTCTAT |
| 687 AILAVALPLLAP | GGGTTTCATATGGCGATTCTGGCGGTGGCGCTGCCGCTGCTGGCGCCGGCAAATATTACCGTTTTCTAT |

TABLE 28

| aMTD Sequence | 5'-Primer |
|---|---|
| 692 PAPLPPVVILAV | GGGTTTCATATGCCGGCGCCGCTGCCGCCGGTGGTGATTCTGGCGGTGGCAAATATTACCGTTTTCTAT |
| 693 AAPVLPVAVPIV | GGGTTTCATATGGCGGCGCCGGTGCTGCCGGTGGCGGTGCCGATTGTGCAAATATTACCGTTTTCTAT |
| 700 CTSNTCQSNQNS | GGGTTTCATATGGGCACCAGCAACACCTGCCAGAGCAACCAGAACAGC GCAAATATTACCGTTTTCTAT |
| 703 IVAVALVPALAP | GGGTTTCATATGATTGTGGCGGTGGCGCTGGTGCCGGCGCTGGCGCCGGCAAATATTACCGTTTTCTAT |
| 705 IVAVALLPALAP | GGGTTTCATATATTGTGGCGGTGGCGCTGCTGCCGGCGCTGGCGCCGGCAAATATTACCGTTTTCTAT |
| 706 IVAVALLPVAP | GGGTTTCATATGATTGTGGCGGTGGCGCTGCTGCCGGCGGTGGCGCCGGCAAATATTACCGTTTTCTAT |
| 707 IVALAVLPAVAP | GGGTTTCATATGATTGTGGCGCTGGCGGTGCTGCCGGCGGTGGCGCCGGCAAATATTACCGTTTTCTAT |
| 724 VAVLAVLPALAP | GGGTTTCATATGGTGGCGGTGCTGGCGGTGCTGCCGGCGCTGGCGCCGGCAAATATTACCGTTTTCTAT |
| 725 IAVLAVAPAVLF | GGGTTTCATATGATTGCGGTGCTGGCGGTGGCGCCGGCGGTGCTGCCGGCAAATATTACCGTTTTCTAT |
| 726 LAVAIIAPAVAP | GGGTTTCATATGCTGGCGGTGGCGATTATTGCGCCGGCGGTGGCGCCGGCAAATATTACCGTTTTCTAT |
| 727 VALAIALPAVLP | GGGTTTCATATGGTGGCGCTGGCGATTGCGCTGCCGGCGGTGCTGCCGGCAAATATTACCGTTTTCTAT |
| 743 AIAIALVPVALP | GGGTTTCATATGGCGATTGCGATTGCGCTGGTGCCGGTGGCGCTGCCGGCAAATATTACCGTTTTCTAT |
| 744 AAVVIVAPVALP | GGGTTTCATATGGCGGCGGTGGTGATTGTGGCGCCGGTGGCGCTGCCGGCAAATATTACCGTTTTCTAT |
| 745 AAILAIVAPLAP | GGGTTTCATATGGCGGCGATTCTGGCGATTGTGGCGCCGCTGGCGCCGGCCAATATTACCGTTTTCTAT |
| 746 VAIIVAPALAP | GGGTTTCATATGGTGGCGATTATTGTGGCGGCGCCGGCGCTGGCGCCGGCAAATATTACCGTTTTCTAT |
| 747 VALLAIAPALAP | GGGTTTCATATGGTGGCGCTGCTGGCGATTGCGCCGGCGCTGGCGCCGGCAAATATTACCGTTTTCTAT |
| 750 LAIAAIAPLAIP | GGGTTTCATATGCTGGCGATTGCGGCGATTGCGCCGCTGGCGATTCCGGCAAATATTACCGTTTTCTAT |
| 763 VAVLIAVPALAF | GGGTTTCATATGGTGGCGGTGCTGCTTGCGGTGCCGGCGCTGGCGCCGGCAAATATTACCGTTTTCTAT |
| 764 AVALAVLPAVVP | GGGTTTCATATGGCGGTGGCGCTGGCGGTGCTGCCGGCGGTGGTGCCGGCAAATATTACCGTTTTCTAT |
| 765 AVALAVVPAVLP | GGGTTTCATATGGCGGTGGCGCTGGCGGTGGTGCCGGCGGTGCTGCCGGCAAATATTACCGTTTTCTAT |
| 766 IVVIAVAPAVAP | GGGTTTCATATGATTGTGGTGATTGCGGTGGCGCCGGCGGTGGCGCCGGCAAATATTACCGTTTTCTAT |

TABLE 28-continued

| aMTD Sequence | 5'-Primer |
|---|---|
| 767 IVVAAVVPALAP | GGGTTTCATATGATTGTGGTGGCGGCGGTGGTGCCGGCGCTGGCGCCGGCAAATATTACCGTTTTCTAT |
| 772 LPVAPVIPIIVP | GGGTTTCATATGCTGCCGGTGGCGCCGGTGATTCCGATTATTGTGCCGGCAAATATTACCGTTTTCTAT |
| 783 IVALVPAVAIAP | GGGTTTCATATGATTGTGGCGCTGGTGCCGGCGGTGGCGATTGCGCCGGCAAATATTACCGTTTTCTAT |
| 784 VAALPAVALVVP | GGGTTTCATATGGTGGCGGCGCTGCCGGCGGTGGCGCTGGTGGTGCCGGCAAATATTACCGTTTTCTAT |
| 786 LVAIAPLAVLAP | GGGTTTCATATGCTGGTGGCGATTGCGCCGCTGGCGGTGCTGGCGCCGGCAAATATTACCGTTTTCTAT |
| 787 AVALVPVIVAAP | GGGTTTCATATGGCGGTGGCGCTGGTGCCGGTGATTGTGGCGGCGCCGGCAAATATTACCGTTTTCTAT |
| 788 AIAVAIAPVALP | GGGTTTCATATGGCGATTGCGGTGGCGATTGCGCCGGTGGCGCTGCCGGCAAATATTACCGTTTTCTAT |
| 803 AIALAVPVLALP | GGGTTTCATATGGCGATTGCGCTGGCGGTGCCGGTGCTGGCGCTGCCGGCAAATATTACCGTTTTCTAT |
| 805 LVLIAAAPIALP | GGGTTTCATATGCTGGTGCTGATTGCGGCGGCGCCGATTGCGCTGCCGGCAAATATTACCGTTTTCTAT |
| 806 LVALAVPAAVLP | GGGTTTCATATGCTGGTGGCGCTGGCGGTGCCGGCGGCGGTGCTGCCGGCAAATATTACCGTTTTCTAT |
| 807 AVALAVPALVLP | GGGTTTCATATGGCGGTGGCGCTGGCGGTGCCGGCGCTGGTGCTGCCGGCAAATATTACCGTTTTCTAT |
| 808 LVVLAAAPLAVP | GGGTTTCATATGCTGGTGGTGCTGGCGGCGGCGCCGCTGGCGGTGCCGGCAAATATTACCGTTTTCTAT |
| 809 LIVLAAPALAAP | GGGTTTCATATGCTGATTGTGCTGGCGGCGCCGGCGCTGGCGGCGCCGGCAAATATTACCGTTTTCTAT |
| 810 VIVLAAPALAAP | GGGTTTCATATCGTGATTGTGCTGGCGGCGCCGGCGCTGGCGGCGCCGGCAAATATTACCGTTTTCTAT |
| 811 AVVLAVPALAVP | GGGTTTCATATCGCGGTGGTGCTGGCGGTGCCGGCGCTGGCGGTGCCGGCAAATATTACCGTTTTCTAT |
| 824 LIIVAAAPAVAP | GGGTTTCATATGCTGATTATTGTGGCGGCGGCGCCGGCGGTGGCGCCGGCAAATATTACCGTTTTCTAT |
| 825 IVAVIVAPAVAP | GGGTTTCATATGATTGTGGCGGTGATTGTGGCGCCGGCGGTGGCGCCGGCAAATATTACCGTTTTCTAT |
| 826 LVALAAPIIAVP | GGGTTTCATATGCTGGTGGCGCTGGCGGCGCCGATTATTGCGGTGCCGGCAAATATTACCGTTTTCTAT |
| 827 IAAVLAAPALVP | GGGTTTCATATCATTGCGGCGGTGCTGGCGGCGCCGGCGCTGGTGCCGGCAAATATTACCGTTTTCTAT |
| 828 IALLAAPIIAVP | GGGTTTCATATGATTGCGCTGCTGGCGGCGCCGATTATTGCGGTGCCGGCAAATATTACCGTTTTCTAT |
| 829 AALALVAPVIVP | GGGTTTCATATGGCGGCGCTGGCGCTGGTGGCGCCGGTGATTGTGCCGGCAAATATTACCGTTTTCTAT |
| 830 IALVAAPVALVP | GGGTTTCATATGATTGCGCTGGTGGCGGCGCCGGTGGCGCTGGTGCCGGCAAATATTACCGTTTTCTAT |
| 831 IIVAVAPAAIVP | GGGTTTCATATGATTATTGTGGCGGTGGCGCCGGCGGCGATTGTGCCGGCAAATATTACCGTTTTCTAT |
| 832 AVAAIVPVIVAP | GGGTTTCATATGGCGGTGGCGGCGATTGTGCCGGTGATTGTGGCGCCGGCAAATATTACCGTTTTCTAT |
| 843 AVLVLVAPAAAP | GGGTTTCATATGGCGGTGCTGGTGCTGGTGGCGCCGGCGGCGGCGCCGGCAAATATTACCGTTTTCTAT |

TABLE 29

| aMTD Sequence | 5'-Primer |
|---|---|
| 844 VVALLAPLIAAP | GGGTTTCATATGGTGGTGGCGCTGCTGGCGCCGCTGATTGCGGCGCCGGCAAATATTACCGTTTTCTAT |
| 845 AAVVIAPLLAVP | GGGTTTCATATGGCGGCGGTGGTGATTGCGCCGCTGCTGGCGGTGCCGGCAAATATTACCGTTTTCTAT |
| 846 IAVAVAAPLLVP | GGGTTTCATATGATTGCGGTGGCGGTGGCGGCGCCGCTGCTGGTGCCGGCAAATATTACCGTTTTCTAT |
| 847 LVAIVVLPAVAP | GGGTTTCATATGCTGGTGGCGATTGTGGTGCTGCCGGCGGTGGCGCCGGCAAATATTACCGTTTTCTAT |
| 848 AVAIVVLPAVAP | GGGTTTCATATGGCGGTGGCGATTGTGGTGCTGCCGGCGGTGGCGCCGGCAAATATTACCGTTTTCTAT |
| 849 AVILLAPLIAAP | GGGTTTCATATGGCGGTGATTCTGCTGGCGCCGCTGATTGCGGCGCCGGCAAATATTACCGTTTTCTAT |
| 850 LVIALAAPVALP | GGGTTTCATATGCTGGTGATTGCGCTGGCGGCGCCGGTGGCGCTGCCGGCAAATATTACCGTTTTCTAT |
| 851 VLAVVLPAVALP | GGGTTTCATATGGTGCTGGCGGTGGTGCTGCCGGCGGTGGCGCTGCCGGCAAATATTACCGTTTTCTAT |
| 852 VLAVAAPAVLLP | GGGTTTCATATGGTGCTGGCGGTGGCGGCGCCGGCGGTGCTGCTGCCGGCAAATATTACCGTTTTCTAT |
| 863 AAVVLLPIIAAP | GGGTTTCATATGGCGGCGGTGGTGCTGCTGCCGATTATTGCGGCGCCGGCAAATATTACCGTTTTCTAT |
| 864 ALLVIAPAIAVP | GGGTTTCATATGGCGCTGCTGGTGATTGCGCCGGCGATTGCGGTGCCGGCAAATATTACCGTTTTCTAT |

TABLE 29-continued

| aMTD Sequence | 5'-Primer |
|---|---|
| 865 AVIVIAVPAIAP | GGGTTTCATATGGCGGTGCTGGTGATTGCGGTGCCGGCGATTGCGCCGGCAAATATTACCGTTTTCTAT |
| 867 ALLVVIAPLAAP | GGGTTTCATATGGCGCTGCTGGTGGTGATTGCGCCGCTGGCGGCGCCGGCAAATATTACCGTTTTCTAT |
| 868 VLVAAILPAAIP | GGGTTTCATATGGTGCTGGTGGCGGCGATTCTGCCGGCGGCGATTCCGGCAAATATTACCGTTTTCTAT |
| 870 VLVAAVLPIAAP | GGGTTTCATATGGTGCTGGTGGCGGCGGTGCTGCCGATTGCGGCGCCGGCAAATATTACCGTTTTCTAT |
| 872 VLAAAVLPLVVP | GGGTTTCATATGGTGCTGGCGGCGGCGGTGCTGCCGCTGGTGGTGCCGGCAAATATTACCGTTTTCTAT |
| 875 AIAIVVPAVAVP | GGGTTTCATATGGCGATTGCGATTGTGGTGCCGGCGGTGGCGGTGCCGGCAAATATTACCGTTTTCTAT |
| 877 VAIIAVPAVVAP | GGGTTTCATATGGTGGCGATTATTGCGGTGCCGGCGGTGGTGGCGCCGGCAAATATTACCGTTTTCTAT |
| 878 IVALVAPAAVVP | GGGTTTCATATGATTGTGGCGCTGGTGGCGCCGGCGGCGGTGGTGCCGGCAAATATTACCGTTTTCTAT |
| 879 AAIVLLPAVVVP | GGGTTTCATATGGCGGCGATTGTGCTGCTGCCGGCGGTGGTGGTGCCGGCAAATATTACCGTTTTCTAT |
| 881 AALIVVPAVAVP | GGGTTTCATATGGCGGCGCTGATTGTGGTGCCGGCGGTGGCGGTGCCGGCAAATATTACCGTTTTCTAT |
| 882 AIALVVPAVAVP | GGGTTTCATATGGCGATTGCGCTGGTGGTGCCGGCGGTGGCGGTGCCGGCAAATATTACCGTTTTCTAT |
| 883 LAIVPAAIAALP | GGGTTTCATATGCTGGCGATTGTGCCGGCGGCGATTGCGGCGCTGCCGGCAAATATTACCGTTTTCTAT |
| 884 VLIVPAAIAALP | GGGTTTCATATGGTGCTGATTGTGCCGGCGGCGATTGCGGCGCTGCCGGCAAATATTACCGTTTTCTAT |
| 885 LVAIAPAVAVLP | GGGTTTCATATGCTGGTGGCGATTGCGCCGGCGGTGGCGGTGCTGCCGGCAAATATTACCGTTTTCTAT |
| 886 VLAVPAAIAALP | GGGTTTCATATGGTGCTGGCGGTGCCGGCGGCGATTGCGGCGCTGCCGGCAAATATTACCGTTTTCTAT |
| 887 VLAVAPAVAVLP | GGGTTTCATATGGTGCTGGCGGTGGCGCCGGCGGTGGCGGTGCTGCCGGCAAATATTACCGTTTTCTAT |
| 888 ILAVVAIPAAAP | GGGTTTCATATGATTCTGGCGGTGGTGGCGATTCCGGCGGCGGCGCCGGCAAATATTACCGTTTTCTAT |
| 889 ILVAAAPIAALP | GGGTTTCATATGATTCTGGTGGCGGCGGCGCCGATTGCGGCGCTGCCGGCAAATATTACCGTTTTCTAT |
| 891 ILAVAAIPAALP | GGGTTTCATATGATTCTGGCGGTGGCGGCGATTCCGGCGGCGCTGCCGGCAAATATTACCGTTTTCTAT |
| 893 VIAIPAILAAAP | GGGTTTCATATGGTGATTGCGATTCCGGCGATTCTGGCGGCGGCGCCGGCAAATATTACCGTTTTCTAT |
| 895 AIIIVVPAIAAP | GGGTTTCATATGGCGATTATTATTGTGGTGCCGGCGATTGCGGCGCCGGCAAATATTACCGTTTTCTAT |
| 896 AILIVVAPIAAP | GGGTTTCATATGGCGATTCTGATTGTGGTGGCGCCGATTGCGGCGCCGGCAAATATTACCGTTTTCTAT |
| 897 AVIVPVAIIAAP | GGGTTTCATATGGCGGTGATTGTGCCGGTGGCGATTATTGCGGCGCCGGCAAATATTACCGTTTTCTAT |
| 899 AVVIALPAVVAP | GGGTTTCATATGGCGGTGGTGATTGCGCTGCCGGCGGTGGTGGCGCCGGCAAATATTACCGTTTTCTAT |
| 900 ALVAVIAPVVAP | GGGTTTCATATGGCGCTGGTGGCGGTGATTGCGCCGGTGGTGGCGCCGGCAAATATTACCGTTTTCTAT |
| 901 ALVAVLPAVAVP | GGGTTTCATATGGGGCTGGTGGCGGTGCTGCCGGCGGTGGCGGTGCCGGCAAATATTACCGTTTTCTAT |
| 902 ALVAPLLAVAVP | GGGTTTCATATGGCGCTGGTGGCGCCGCTGCTGGCGGTGGCGGTGCCGGCAAATATTACCGTTTTCTAT |
| 904 AVLAVVAPVVAP | GGGTTTCATATGGCGGTGCTGGCGGTGGTGGCGCCGGTGGTGGCGCCGGCAAATATTACCGTTTTCTAT |
| 905 AVIAVAPLVVAP | GGGTTTCATATGGCGGTGATTGCGGTGGCGCCGCTGGTGGTGGCGCCGGCAAATATTACCGTTTTCTAT |
| 906 AVIALAPVVVAP | GGGTTTCATATGGCGGTGATTGCGCTGGCGCCGGTGGTGGTGGCGCCGGCAAATATTACCGTTTTCTAT |
| 907 VAIALAPVVVAP | GGGTTTCATATGGTGGCGATTGCGCTGGCGCCGGTGGTGGTGGCGCCGGCAAATATTACCGTTTTCTAT |
| 908 VALALAPVVVAP | GGGTTTCATATGGTGGCGCTGGCGCTGGCGCCGGTGGTGGTGGCGCCGGCAAATATTACCGTTTTCTAT |
| 910 VAALLPAVVVAP | GGGTTTCATATGGTGGCGGCGCTGCTGCCGGCGGTGGTGGTGGCGCCGGCAAATATTACCGTTTTCTAT |
| 911 VALALPAVVVAP | GGGTTTCATATGGTGGCGCTGGCGCTGCCGGCGGTGGTGGTGGCGCCGGCAAATATTACCGTTTTCTAT |
| 912 VALLAPAVVVAP | GGGTTTCATATGGTGGCGCTGCTGGCGCCGGCGGTGGTGGTGGCGCCGGCAAATATTACCGTTTTCTAT |

TABLE 30 aMTD Sequences

| | | 5'-Primer |
|---|---|---|
| 921 | IWAFVVLPLVVP | GGGTTTCATATGATTTGGTGGTTTGTGGTGCTGCCGCTGGTGGTGCCGGCAAATATTACCGTTTTCTAT |
| 922 | WYVIFVLPLVVP | GGGTTTCATATGTGGTATGTGATTTTTGTGCTGCCGCTGGTGGTGCCGGCAAATATTACCGTTTTCTAT |
| 931 | AVLIAPAILAAA | GGGTTTCATATGGCGGTGCTGATTGCGCCGGCGATTCTGGCGGCGGCGGCAAATATTACCGTTTTCTAT |
| 934 | LILAPAAVVAAA | GGGTTTCATATGGCGCTGCTGATTCTGCCGGCGGCGGCGGTGGCGGCGGCAAATATTACCGTTTTCTAT |
| 935 | ALLILPAAAVAA | GGGTTTCATATGGCGCTGCTGATTCTGCCGGCGGCGGCGGTGGCGGCGCAAATATTACCGTTTTCTAT |
| 936 | ALLILAAAVAAP | GGGTTTCATATGGCGCTGCTGATTCTGGCGGCGGCGGTGGCGGCGCCGGCAAATATTACCGTTTTCTAT |
| 937 | VPVLVPLPVPVV | GGGTTTCATATGGTGCGGCTGCTGGTGCCGCTGCCGGTGCCGGTCGTGGCAAATATTACCGTTTTCTAT |
| 938 | VPVLLPVVVPVP | GGGTTTCATATGGTGCCGGTGCTGCTGCCGGTGGTGGTGCCGGTGCCGGCAAATATTACCGTTTTCTAT |
| 947 | GYYNQQSNNNNQ | GGGTTTCATATGTGCTATTATAATGAGCAGTCGAATAATAATAATCAGGCAAATATTACCGTTTTCTAT |
| 949 | SGNSGQQGGNSS | GGGTTTCATATGTCCGGGAATTGGTGCGAGCAGTGCGGGAATTCGTGGGCAAATATTACGGTTTTGTAT |

| | 3'-Primer |
|---|---|
| | CGCGTCGACTTACCTCGGCTGCACCGGCACGCAGATGAC |

TABLE 31

| aMTQ | Sequence | 5'-Primer Design |
|---|---|---|
| 1 | AAALAPVVLALP | Gly Phe His Met Ala Ala Ala Leu Ala Pro Val Val Leu Ala Leu Pro Ala Asn Ile Thr Val Phe Tyr |
| 2 | AAAVPLLAVVVP | Gly Phe His Met Ala Ala Ala Val Pro Leu Leu Ala Val Val Val Pro Ala Asn Ile The Val Phe |
| 3 | AALLVPAAVLAP | Gly Phe His Met Ala Ala Leu Leu Val Pro Ala Ala Val Leu Ala Pro Ala Asn Ile The Val Phe |
| 4 | ALALLPVAALAP | Gly Phe His Met Ala Leu Ala Leu Leu Pro Val Ala Ala Leu Ala Pro Ala Asn Ile The Val Phe |
| 5 | AAALLPVALVAP | Gly Phe His Met Ala Ala Ala Leu Leu Pro Val Ala Leu Val Ala Pro Ala Asn Ile The Val Phe |
| 6 | VIANNPAAPWVA | Gly Phe His Met Val Ile Ala Met Ile Pro Ala Ala Phe Trp Val Ala Ala Asn Ile The Val Phe |
| 9 | VALVPAALILPP | Gly Phe His Met Val Ala Leu Val Pro Ala Ala Leu Ile Leu Pro Pro Ala Asn Ile The Val Phe |
| 11 | VVALAPALAALP | Gly Phe His Met Val Val Ala Leu Ala Pro Ala Leu Ala Ala Leu Pro Ala Asn Ile The Val Phe |
| 12 | LLAAVPAVLLAP | Gly Phe His Met Leu Leu Ala Ala Val Pro Ala Val Leu Leu Ala Pro Ala Asn Ile The Val Phe |
| 13 | AAALVPVVALLP | Gly Phe His Met Ala Ala Ala Leu Val Pro Val Val Ala Leu Leu Pro Ala Asn Ile The Val Phe |
| 16 | NNSCTTYTNGSQ | Gly Phe His Met Asn Asn Ser Cys Thr Thr Tyr Thr Asn Gly Ser Gln Ala Asn Ile The Val Phe |
| 17 | GGCSAPQTTCSN | Gly Phe His Met Gly Gly Cys Ser Ala Pro Gln Thr Thr Cys Ser Asn Ala Asn Ile The Val Phe |
| 18 | NYCCTPTTNGQS | Gly Phe His Met Asn Tyr Cys Cys Thr Pro Thr Thr Asn Gly Gln Ser Ala Asn Ile The Val Phe |
| 19 | YVSCCTYTNGSQ | Gly Phe His Met Tyr Val Ser Cys Cys Thr Tyr Thr Asn Gly Ser Gln Ala Asn Ile The Val Phe |
| 20 | NYCNTCPTYGQS | Gly Phe His Met Asn Tyr Cys Asn Thr Cys Pro Thr Tyr Gly Gln Ser Ala Asn Ile The Val Phe |

TABLE 31-continued

| aMTD | Sequence | 5'-Primer Design |
|---|---|---|
| 21 | AVALLPALLAVP | Gly Phe His Met Ala Val Ala Leu Leu Pro Ala Leu Leu Ala Val Pro Ala Asn Ile The Val Phe |
| 22 | AVVLVPVLAAAP | Gly Phe His Met Ala Val Val Leu Val Pro Val Leu Ala Ala Ala Pro Ala Asn Ile The Val Phe |
| 23 | VVLVLPAAAAVP | Gly Phe His Met Val Val Leu Val Leu Pro Ala Ala Ala Ala Val Pro Ala Asn Ile The Val Phe |
| 24 | IALAAPALIVAP | Gly Phe His Met Ile Ala Leu Ala Ala Pro Ala Leu Ile Val Ala Pro Ala Asn Ile The Val Phe |
| 25 | IVAVAPALVALP | Gly Phe His Met Ile Val Ala Val Ala Pro Ala Leu Val Ala Leu Pro Ala Asn Ile The Val Phe |
| 26 | AAIALAAPLAIV | Gly Phe His Met Ala Ala Ile Ala Leu Ala Ala Pro Leu Ala Ile Val Ala Asn Ile The Val Phe |
| 27 | LAIVAAAALVA | Gly Phe His Met Leu Ala Ile Val Ala Ala Ala Ala Leu Val Ala Ala Asn Ile The Val Phe |
| 28 | AVPLLPLVPAVP | Gly Phe His Met Ala Val Pro Leu Leu Pro Leu Val Pro Ala Val Pro Ala Asn Ile The Val Phe |

TABLE 32

| aMTD | Sequence | 5'-Primer Design |
|---|---|---|
| 29 | VLPPLPVLPVLP | Gly Phe His Met Val Leu Pro Pro Leu Pro Val Leu Pro Val Leu Pro Ala Asn Ile Thr Val Phe |
| 30 | AMALLPAAVAVA | Gly Phe His Met Ala Met Ala Leu Leu Pro Ala Ala Val Ala Val Ala Ala Asn Ile The Val Phe |
| 33 | AAAILAPAFLAV | Gly Phe His Met Ala Ala Ala Ile Leu Ala Pro Ala Phe Leu Ala Val Ala Asn Ile The Val Phe |
| 37 | TTCSQQQYCTNG | Gly Phe His Met Thr Thr Cys Ser Gln Gln Gln Tyr Cys Thr Asn Gly Ala Asn Ile The Val Phe |
| 38 | YYNQSTCGGCCY | Gly Phe His Met Tyr Tyr Asn Gln Ser Thr Cys Gly Gly Gln Cys Tyr Ala Asn Ile The Val Phe |
| 39 | CYNTSPCTGCCY | Gly Phe His Met Cys Tyr Asn Thr Ser Pro Cys Thr Gly Cys Cys Tyr Ala Asn Ile The Val Phe |
| 40 | TYNTSCTPGTCY | Gly Phe His Met Thr Tyr Asn Thr Ser Cys Thr Pro Gly Thr Cys Tyr Ala Asn Ile The Val Phe |
| 42 | VAALPVVAVVAP | Gly Phe His Met Val Ala Ala Leu Pro Val Val Ala Val Val Ala Pro Ala Asn Ile The Val Phe |
| 43 | LLAAPLVVAAVP | Gly Phe His Met Leu Leu Ala Ala Pro Leu Val Val Ala Ala Val Pro Ala Asn Ile The Val Phe |
| 44 | ALAVPVALLVAP | Gly Phe His Met Ala Leu Ala Val Pro Val Ala Leu Leu Val Ala Pro Ala Asn Ile The Val Phe |
| 49 | VVPAAPAVPVVP | Gly Phe His Met Val Val Pro Ala Ala Pro Ala Val Pro Val Val Pro Ala Asn Ile The Val Phe |
| 54 | LAVAAPPVVALL | Gly Phe His Met Leu Ala Val Ala Ala Pro Pro Val Val Ala Leu Leu Ala Asn Ile The Val Phe |
| 57 | QNNCNTSSQGGG | Gly Phe His Met Gln Asn Asn Cys Asn Thr Ser Ser Gln Gly Gly Gly Ala Asn Ile The Val Phe |
| 59 | AVLAAPVVAALA | Gly Phe His Met Ala Val Leu Ala Ala Pro Val Val Ala Ala Leu Ala Ala Asn Ile The Val Phe |
| 61 | VAALPVLLAALP | Gly Phe His Met Val Ala Ala Leu Pro Val Leu Leu Ala Ala Leu Pro Ala Asn Ile The Val Phe |
| 62 | VALLAPVALAVP | Gly Phe His Met Val Ala Leu Leu Ala Pro Val Ala Leu Ala Val Pro Ala Asn Ile The Val Phe |

TABLE 32-continued

| aMTD | Sequence | 5'-Primer Design | | | | | | | | | | | | | | | | | |
|---|---|---|---|---|---|---|---|---|---|---|---|---|---|---|---|---|---|---|---|
| 63 | AALLVPALVAVP | Gly | Phe | His | Met | Ala | Ala | Leu | Leu | Val | Pro | Ala | Leu | Val | Ala | Val | Pro | Ala | Asn Ile The Val Phe |
| 64 | AIVALPVAVLAP | Gly | Phe | His | Met | Ala | Ile | Val | Ala | Leu | Pro | Val | Ala | Val | Leu | Ala | Pro | Ala | Asn Ile The Val Phe |
| 65 | IAIVAPVVALAP | Gly | Phe | His | Met | Ile | Ala | Ile | Val | Ala | Pro | Val | Val | Ala | Leu | Ala | Pro | Ala | Asn Ile The Val Phe |
| 66 | AGVLGGPIMGVP | Gly | Phe | His | Met | Ala | Gly | Val | Leu | Gly | Gly | Pro | Ile | Met | Gly | Val | Pro | Ala | Asn Ile The Val Phe |
| 67 | LDAEVPLADDVP | Gly | Phe | His | Met | Leu | Asp | Ala | Glu | Val | Pro | Leu | Ala | Asp | Asp | Val | Pro | Ala | Asn Ile The Val Phe |
| 68 | VAPVLPAAPLVP | Gly | Phe | His | Met | Val | Ala | Pro | Val | Leu | Pro | Ala | Ala | Pro | Leu | Val | Pro | Ala | Asn Ile The Val Phe |
| 69 | PVAVLPPAALVP | Gly | Phe | His | Met | Pro | Val | Ala | Val | Leu | Pro | Pro | Ala | Ala | Leu | Val | Pro | Ala | Asn Ile The Val Phe |
| 71 | FMWMWFPFWWYP | Gly | Phe | His | Met | Phe | Met | Trp | Met | Trp | Phe | Pro | Phe | Met | Trp | Tyr | Pro | Ala | Asn Ile The Val Phe |
| 77 | AMLLMPIVLIAP | Gly | Phe | His | Met | Ala | Met | Leu | Leu | Met | Pro | Ile | Val | Leu | Ile | Ala | Pro | Ala | Asn Ile The Val Phe |
| 81 | AALLPALAALLP | Gly | Phe | His | Met | Ala | Ala | Leu | Leu | Pro | Ala | Leu | Ala | Ala | Leu | Leu | Pro | Ala | Asn Ile The Val Phe |
| 82 | AVVLAPVAAVLP | Gly | Phe | His | Met | Ala | Val | Val | Leu | Ala | Pro | Val | Ala | Ala | Val | Leu | Pro | Ala | Asn Ile The Val Phe |
| 83 | LAVAAPLALALP | Gly | Phe | His | Met | Leu | Ala | Val | Ala | Ala | Pro | Leu | Ala | Leu | Ala | Leu | Pro | Ala | Asn Ile The Val Phe |
| 84 | AAVAAPLLLALP | Gly | Phe | His | Met | Ala | Ala | Val | Ala | Ala | Pro | Leu | Leu | Leu | Ala | Leu | Pro | Ala | Asn Ile The Val Phe |
| 85 | LLVLPAAALAAP | Gly | Phe | His | Met | Leu | Leu | Val | Leu | Pro | Ala | Ala | Ala | Leu | Ala | Ala | Pro | Ala | Asn Ile The Val Phe |
| 97 | ALLAAPPALLAL | Gly | Phe | His | Met | Ala | Leu | Leu | Ala | Ala | Pro | Pro | Ala | Leu | Leu | Ala | Leu | Ala | Asn Ile The Val Phe |
| 101 | LVALAPVAAVLP | Gly | Phe | His | Met | Leu | Val | Ala | Leu | Ala | Pro | Val | Ala | Ala | Val | Leu | Pro | Ala | Asn Ile The Val Phe |
| 102 | LALAPAALALLP | Gly | Phe | His | Met | Leu | Ala | Leu | Ala | Pro | Ala | Ala | Leu | Ala | Leu | Leu | Pro | Ala | Asn Ile The Val Phe |
| 103 | ALIAAPLALAP | Gly | Phe | His | Met | Ala | Leu | Ile | Ala | Ala | Pro | Ile | Leu | Ala | Leu | Ala | Pro | Ala | Asn Ile The Val Phe |
| 104 | AVVAAPLVLALP | Gly | Phe | His | Met | Ala | Val | Val | Ala | Ala | Pro | Leu | Val | Leu | Ala | Leu | Pro | Ala | Asn Ile The Val Phe |
| 105 | LLALAPAALLAP | Gly | Phe | His | Met | Leu | Leu | Ala | Leu | Ala | Pro | Ala | Ala | Leu | Leu | Ala | Pro | Ala | Asn Ile The Val Phe |
| 113 | PVAVALLIAVPP | Gly | Phe | His | Met | Pro | Val | Ala | Val | Ala | Leu | Leu | Ile | Ala | Val | Pro | Pro | Ala | Asn Ile The Val Phe |
| 121 | AIVALPALALAP | Gly | Phe | His | Met | Ala | Ile | Val | Ala | Leu | Pro | Ala | Leu | Ala | Leu | Ala | Pro | Ala | Asn Ile The Val Phe |
| 123 | AAIIVPAALLAP | Gly | Phe | His | Met | Ala | Ala | Ile | Ile | Val | Pro | Ala | Ala | Leu | Leu | Ala | Pro | Ala | Asn Ile The Val Phe |
| 124 | IAVALPALIAAP | Gly | Phe | His | Met | Ile | Ala | Val | Ala | Leu | Pro | Ala | Leu | Ile | Ala | Ala | Pro | Ala | Asn Ile The Val Phe |
| 131 | WIIAPVWLAWIA | Gly | Phe | His | Met | Trp | Ile | Ile | Ala | Pro | Val | Trp | Leu | Ala | Trp | Ile | Ala | Ala | Asn Ile The Val Phe |
| 138 | PPAALLAILAVA | Gly | Phe | His | Met | Pro | Pro | Ala | Ala | Leu | Leu | Ala | Ile | Leu | Ala | Val | Ala | Ala | Asn Ile The Val Phe |

TABLE 32-continued

| aMTD | Sequence | 5'-Primer Design |
|---|---|---|
| 139 | TGSTNSPTCTST | Gly Phe His Met Thr Gly Ser Thr Asn Ser Pro Thr Cys Thr Ser Thr Ala Asn Ile The Val Phe |
| 141 | AVIVLFALAVAP | Gly Phe His Met Ala Val Ile Val Leu Pro Ala Leu Ala Val Ala Pro Ala Asn Ile The Val Phe |
| 142 | LLAAVPVALVAP | Gly Phe His Met Leu Leu Ala Ala Val Pro Val Ala Leu Val Ala Pro Ala Asn Ile The Val Phe |
| 143 | AVLAVPAVLVAP | Gly Phe His Met Ala Val Leu Ala Val Pro Ala Val Leu Val Ala Pro Ala Asn Ile The Val Phe |
| 144 | VLAIVPAVALAP | Gly Phe His Met Val Leu Ala Ile Val Pro Ala Val Ala Leu Ala Pro Ala Asn Ile The Val Phe |

TABLE 33

| aMTD | Sequence | 5'-Primer Design |
|---|---|---|
| 145 | LLAVVPAVALAP | Gly Phe His Met Leu Leu Ala Val Val Pro Ala Val Ala Leu Ala Pro Ala Asn Ile The Val Phe |
| 152 | LAAAVAAVAALL | Gly Phe His Met Leu Ala Ala Ala Val Ala Ala Val Ala Ala Leu Leu Ala Asn Ile The Val Phe |
| 159 | CYSGSTSQNQPP | Gly Phe His Met Cys Tyr Ser Gly Ser Thr Ser Gln Asn Gln Pro Pro Ala Asn Ile The Val Phe |
| 161 | AVIALPALIAAP | Gly Phe His Met Ala Val Ile Ala Leu Pro Ala Leu Ile Ala Ala Pro Ala Asn Ile The Val Phe |
| 162 | AVVALPAALIVP | Gly Phe His Met Ala Val Val Ala Leu Pro Ala Ala Leu Ile Val Pro Ala Asn Ile The Val Phe |
| 163 | LALVLPAALAAP | Gly Phe His Met Leu Ala Leu Val Leu Pro Ala Ala Leu Ala Ala Pro Ala Asn Ile The Val Phe |
| 164 | LAAVLPALLAAP | Gly Phe His Met Leu Ala Ala Val Leu Pro Ala Leu Leu Ala Ala Pro Ala Asn Ile The Val Phe |
| 165 | ALAVPVALAIVP | Gly Phe His Met Ala Leu Ala Val Pro Val Ala Leu Ala Ile Val Pro Ala Asn Ile The Val Phe |
| 167 | VAIAIPAALAIP | Gly Phe His Met Val Ala Ile Ala Ile Pro Ala Ala Leu Ala Ile Pro Ala Asn Ile The Val Phe |
| 169 | VALVAPALILAP | Gly Phe His Met Val Ala Leu Val Ala Pro Ala Leu Ile Leu Ala Pro Ala Asn Ile The Val Phe |
| 182 | ALIAPVVALVAP | Gly Phe His Met Ala Leu Ile Ala Pro Val Val Ala Leu Val Ala Pro Ala Asn Ile The Val Phe |
| 183 | LLAAPVVIALAP | Gly Phe His Met Leu Leu Ala Ala Pro Val Val Ile Ala Leu Ala Pro Ala Asn Ile The Val Phe |
| 184 | LAAIVPAIIAVP | Gly Phe His Met Leu Ala Ala Ile Val Pro Ala Ile Ile Ala Val Pro Ala Asn Ile The Val Phe |
| 185 | AALVLPLIIAAP | Gly Phe His Met Ala Ala Leu Val Leu Pro Leu Ile Ile Ala Ala Pro Ala Asn Ile The Val Phe |
| 189 | VILVAPAVIAPP | Gly Phe His Met Val Ile Leu Val Ala Pro Ala Val Ile Ala Pro Pro Ala Asn Ile The Val Phe |
| 190 | AAILAPAVIAPP | Gly Phe His Met Ala Ala Ile Leu Ala Pro Ala Val Ile Ala Pro Pro Ala Asn Ile The Val Phe |
| 201 | LALAVPALAALP | Gly Phe His Met Leu Ala Leu Ala Val Pro Ala Leu Ala Ala Leu Pro Ala Asn Ile The Val Phe |
| 204 | LIAALPAVAALP | Gly Phe His Met Leu Ile Ala Ala Leu Pro Ala Val Ala Ala Leu Pro Ala Asn Ile The Val Phe |

TABLE 33-continued

| aMTD | Sequence | 5'-Primer Design |
|---|---|---|
| 205 | ALALVPAIAALP | Gly Phe His Met Ala Leu Ala Leu Val Pro Ala Ile Ala Ala Leu Pro Ala Asn Ile The Val Phe |
| 210 | ALIALPALPALP | Gly Phe His Met Ala Leu Ile Ala Leu Pro Ala Leu Pro Ala Leu Pro Ala Asn Ile The Val Phe |
| 214 | ALIVAPALMALP | Gly Phe His Met Ala Leu Ile Val Ala Pro Ala Leu Met Ala Leu Pro Ala Asn Ile The Val Phe |
| 221 | AAILAPIVALAP | Gly Phe His Met Ala Ala Ile Leu Ala Pro Ile Val Ala Leu Ala Pro Ala Asn Ile The Val Phe |
| 222 | ALLIAPAAVIAP | Gly Phe His Met Ala Leu Leu Ile Ala Pro Ala Ala Val Ile Ala Pro Ala Asn Ile The Val Phe |
| 223 | AILAVPIAVVAP | Gly Phe His Met Ala Ile Leu Ala Val Pro Ile Ala Val Val Ala Pro Ala Asn Ile The Val Phe |
| 224 | ILAAVPIALAAP | Gly Phe His Met Ile Leu Ala Ala Val Pro Ile Ala Leu Ala Ala Pro Ala Asn Ile The Val Phe |
| 225 | VAALLPAAAVLP | Gly Phe His Met Val Ala Ala Leu Leu Pro Ala Ala Ala Val Leu Pro Ala Asn Ile The Val Phe |
| 226 | ALVAAIPALAIP | Gly Phe His Met Ala Leu Val Ala Ala Ile Pro Ala Leu Ala Ile Pro Ala Asn Ile The Val Phe |
| 227 | LAAIVPIAAAVP | Gly Phe His Met Leu Ala Ala Ile Val Pro Ile Ala Ala Ala Val Pro Ala Asn Ile The Val Phe |
| 241 | AAAVVPVLLVAP | Gly Phe His Met Ala Ala Ala Val Val Pro Val Leu Leu Val Ala Pro Ala Asn Ile The Val Phe |
| 242 | AALLVPALVAAP | Gly Phe His Met Ala Ala Leu Leu Val Pro Ala Leu Val Ala Ala Pro Ala Asn Ile The Val Phe |
| 243 | AAVLLPVALAAP | Gly Phe His Met Ala Ala Val Leu Leu Pro Val Ala Leu Ala Ala Pro Ala Asn Ile The Val Phe |
| 245 | AAALAPVLALVP | Gly Phe His Met Ala Ala Ala Leu Ala Pro Val Leu Ala Leu Val Pro Ala Asn Ile The Val Phe |
| 246 | VVAVPLLVAFAA | Gly Phe His Met Val Val Ala Val Pro Leu Leu Val Ala Phe Ala Ala Ala Asn Ile The Val Phe |
| 248 | VAAIVPIAALVF | Gly Phe His Met Val Ala Ala Ile Val Pro Ile Ala Ala Leu Val Pro Ala Asn Ile The Val Phe |
| 261 | LVLVPLLAAAAP | Gly Phe His Met Leu Val Leu Val Pro Leu Leu Ala Ala Ala Ala Pro Ala Asn Ile The Val Phe |
| 262 | ALIAVPAIIVAP | Gly Phe His Met Ala Leu Ile Ala Val Pro Ala Ile Ile Val Ala Pro Ala Asn Ile The Val Phe |
| 263 | ALAVIPAAAILP | Gly Phe His Met Ala Leu Ala Val Ile Pro Ala Ala Ala Ile Leu Pro Ala Asn Ile The Val Phe |
| 264 | LAAAPVVIVIAP | Gly Phe His Met Leu Ala Ala Ala Pro Val Val Ile Val Ile Ala Pro Ala Asn Ile The Val Phe |
| 265 | VLAIAPLLAAVP | Gly Phe His Met Val Leu Ala Ile Ala Pro Leu Leu Ala Ala Val Pro Ala Asn Ile The Val Phe |
| 281 | ALIVLPAAVAVP | Gly Phe His Met Ala Leu Ile Val Leu Pro Ala Ala Val Ala Val Pro Ala Asn Ile The Val Phe |
| 282 | VLAVAPALIVAP | Gly Phe His Met Val Leu Ala Val Ala Pro Ala Leu Ile Val Ala Pro Ala Asn Ile The Val Phe |
| 283 | AALLAPALIVAP | Gly Phe His Met Ala Ala Leu Leu Ala Pro Ala Leu Ile Val Ala Pro Ala Asn Ile The Val Phe |
| 284 | ALIAPAVALIVP | Gly Phe His Met Ala Leu Ile Ala Pro Ala Val Ala Leu Ile Val Pro Ala Asn Ile The Val Phe |
| 285 | AIVLLPAAVVAP | Gly Phe His Met Ala Ile Val Leu Leu Pro Ala Ala Val Val Ala Pro Ala Asn Ile The Val Phe |

TABLE 33-continued

| aMTD | Sequence | 5'-Primer Design |
|---|---|---|
| 301 | VIAAPVLAVLAP | Gly Phe His Met Val Ile Ala Ala Pro Val Leu Ala Val Leu Ala Pro Ala Asn Ile The Val Phe |
| 302 | LALAPALALLAP | Gly Phe His Met Leu Ala Leu Ala Pro Ala Leu Ala Leu Leu Ala Pro Ala Asn Ile The Val Phe |
| 304 | AIILAPIAAIAP | Gly Phe His Met Ala Ile Ile Leu Ala Pro Ile Ala Ala Ile Ala Pro Ala Asn Ile The Val Phe |

TABLE 34

| aMTD | Sequence | 5'-Primer Design |
|---|---|---|
| 305 | IALAAPILLAAP | Gly Phe His Met Ile Ala Leu Ala Ala Pro Ile Leu Leu Ala Ala Pro Ala Asn Ile The Val Phe |
| 321 | IVAVALPALAVP | Gly Phe His Met Ile Val Ala Val Ala Leu Pro Ala Leu Ala Val Pro Ala Asn Ile The Val Phe |
| 322 | VVAIVLPALAAP | Gly Phe His Met Val Val Ala Ile Val Leu Pro Ala Leu Ala Ala Pro Ala Asn Ile The Val Phe |
| 323 | IVAVALPVALAP | Gly Phe His Met Ile Val Ala Val Ala Leu Pro Val Ala Leu Ala Pro Ala Asn Ile The Val Phe |
| 324 | IVAVALPAALVP | Gly Phe His Met Ile Val Ala Val Ala Leu Pro Ala Ala Leu Val Pro Ala Asn Ile The Val Phe |
| 325 | IVAVALPAVALP | Gly Phe His Met Ile Val Ala Val Ala Leu Pro Ala Val Ala Leu Pro Ala Asn Ile The Val Phe |
| 329 | LPVLPVVPVVVP | Gly Phe His Met Leu Pro Val Leu Val Pro Val Val Pro Val Val Pro Ala Asn Ile The Val Phe |
| 331 | VPVLVPLVPVVP | Gly Phe His Met Val Pro Val Leu Val Pro Leu Val Pro Val Val Pro Ala Asn Ile The Val Phe |
| 341 | IVAVALPAVLAP | Gly Phe His Met Ile Val Ala Val Ala Leu Pro Ala Val Leu Ala Pro Ala Asn Ile The Val Phe |
| 342 | VIVALAPAVLAP | Gly Phe His Met Val Ile Val Ala Leu Ala Pro Ala Val Leu Ala Pro Ala Asn Ile The Val Phe |
| 343 | IVAVALPALVAP | Gly Phe His Met Ile Val Ala Val Ala Leu Pro Ala Leu Val Ala Pro Ala Asn Ile The Val Phe |
| 345 | ALLIVAPVAVAP | Gly Phe His Met Ala Leu Leu Ile Val Ala Pro Val Ala Val Ala Pro Ala Asn Ile The Val Phe |
| 349 | VPVLVPVVPVVP | Gly Phe His Met Val Pro Val Leu Val Pro Val Val Pro Val Val Pro Ala Asn Ile The Val Phe |
| 350 | VPILVPVVPVVP | Gly Phe His Met Val Pro Ile Leu Val Pro Val Val Pro Val Val Pro Ala Asn Ile The Val Phe |
| 361 | AVVIVAPAVIAP | Gly Phe His Met Ala Val Val Ile Val Ala Pro Ala Val Ile Ala Pro Ala Asn Ile The Val Phe |
| 363 | AVLAVAPALIVP | Gly Phe His Met Ala Val Leu Ala Val Ala Pro Ala Leu Ile Val Pro Ala Asn Ile The Val Phe |
| 364 | LVAAVAPALIVP | Gly Phe His Met Leu Val Ala Ala Val Ala Pro Ala Leu Ile Val Pro Ala Asn Ile The Val Phe |
| 365 | AVIVVAFPLLAP | Gly Phe His Met Ala Val Ile Val Val Ala Pro Ala Leu Leu Ala Pro Ala Asn Ile The Val Phe |
| 381 | VVAIVLPAVAAP | Gly Phe His Met Val Val Ala Ile Val Leu Pro Ala Val Ala Ala Pro Ala Asn Ile The Val Phe |
| 382 | AAALVIPAILAP | Gly Phe His Met Ala Ala Ala Leu Val Ile Pro Ala Ile Leu Ala Pro Ala Asn Ile The Val Phe |

TABLE 34-continued

| aMTD | Sequence | 5'-Primer Design |
|------|----------|------------------|
| 383 | VIVALAPALLAP | Gly Phe His Met Val Ile Val Ala Leu Ala Pro Ala Leu Leu Ala Pro Ala Asn Ile The Val Phe |
| 384 | VIVAIAPALLAP | Gly Phe His Met Val Ile Val Ala Ile Ala Pro Ala Leu Leu Ala Pro Ala Asn Ile The Val Phe |
| 385 | IVAIAVPALVAP | Gly Phe His Met Ile Val Ala Ile Ala Val Pro Ala Leu Val Ala Pro Ala Asn Ile The Val Phe |
| 390 | VPLLVPVVPVVP | Gly Phe His Met Val Pro Leu Leu Val Pro Val Val Pro Val Val Pro Ala Asn Ile The Val Phe |
| 401 | AALAVIPAAILP | Gly Phe His Met Ala Ala Leu Ala Val Ile Pro Ala Ala Ile Leu Pro Ala Asn Ile The Val Phe |
| 402 | ALAAVIPAAILP | Gly Phe His Met Ala Leu Ala Ala Val Ile Pro Ala Ala Ile Leu Pro Ala Asn Ile The Val Phe |
| 403 | AAALVIPAAILP | Gly Phe His Met Ala Ala Ala Leu Val Ile Pro Ala Ala Ile Leu Pro Ala Asn Ile The Val Phe |
| 404 | LAAAVIPAAILP | Gly Phe His Met Leu Ala Ala Ala Val Ile Pro Ala Ala Ile Leu Pro Ala Asn Ile The Val Phe |
| 405 | LAAAVIPVAILP | Gly Phe His Met Leu Ala Ala Ala Val Ile Pro Val Ala Ile Leu Pro Ala Asn Ile The Val Phe |
| 421 | AAILAAPLIAVP | Gly Phe His Met Ala Ala Ile Leu Ala Ala Pro Leu Ile Ala Val Pro Ala Asn Ile The Val Phe |
| 422 | VVAILAPLLAAP | Gly Phe His Met Val Val Ala Ile Leu Ala Pro Leu Leu Ala Ala Pro Ala Asn Ile The Val Phe |
| 424 | AVVVAAPVLALP | Gly Phe His Met Ala Val Val Val Ala Ala Pro Val Leu Ala Leu Pro Ala Asn Ile The Val Phe |
| 425 | AVVAIAPVLALP | Gly Phe His Met Ala Val Val Ala Ile Ala Pro Val Leu Ala Leu Pro Ala Asn Ile The Val Phe |
| 426 | AAALAIPLAIIP | Gly Phe His Met Ala Ala Ala Leu Ala Ile Pro Leu Ala Ile Ile Pro Ala Asn Ile The Val Phe |
| 436 | AVVLVIMPAAIP | Gly Phe His Met Ala Val Val Leu Val Ile Met Pro Ala Ala Ile Pro Ala Asn Ile The Val Phe |
| 442 | ALAALVPAVLVP | Gly Phe His Met Ala Leu Ala Ala Leu Val Pro Ala Val Leu Val Pro Ala Asn Ile The Val Phe |
| 443 | ALAALVPVALVP | Gly Phe His Met Ala Leu Ala Ala Leu Val Pro Val Ala Leu Val Pro Ala Asn Ile The Val Phe |
| 444 | LAAALVPVALVP | Gly Phe His Met Leu Ala Ala Ala Leu Val Pro Val Ala Leu Val Pro Ala Asn Ile The Val Phe |
| 445 | ALAALVPALVVP | Gly Phe His Met Ala Leu Ala Ala Leu Val Pro Ala Leu Val Val Pro Ala Asn Ile The Val Phe |
| 461 | IAAVIVPAVALP | Gly Phe His Met Ile Ala Ala Val Ile Val Pro Ala Val Ala Leu Pro Ala Asn Ile The Val Phe |
| 462 | IAAVLVPAVALP | Gly Phe His Met Ile Ala Ala Val Leu Val Pro Ala Val Ala Leu Pro Ala Asn Ile The Val Phe |
| 463 | AVAILVPLLAAP | Gly Phe His Met Ala Val Ala Ile Leu Val Pro Leu Leu Ala Ala Pro Ala Asn Ile The Val Phe |
| 464 | AVVILVPLAAAP | Gly Phe His Met Ala Val Val Ile Leu Val Pro Leu Ala Ala Ala Pro Ala Asn Ile The Val Phe |
| 465 | IAAVIVPVAALP | Gly Phe His Met Ile Ala Ala Val Ile Val Pro Val Ala Ala Leu Pro Ala Asn Ile The Val Phe |
| 466 | IIAAAAPLAIIP | Gly Phe His Met Ile Ile Ala Ala Ala Ala Pro Leu Ala Ile Ile Pro Ala Asn Ile The Val Phe |
| 481 | AIAIAIVPVALP | Gly Phe His Met Ala Ile Ala Ile Ala Ile Val Pro Val Ala Leu Pro Ala Asn Ile The Val Phe |

TABLE 34-continued

| aMTD | Sequence | 5'-Primer Design |
| --- | --- | --- |
| 482 | ILAVAAIPVAVP | Gly Phe His Met Ile Leu Ala Val Ala Ala Ile Pro Val Ala Val Pro Ala Asn Ile The Val Phe |

TABLE 35

| aMTD | Sequence | 5'-Primer Design |
| --- | --- | --- |
| 483 | ILAAAIIPAALP | Gly Phe His Met Ile Leu Ala Ala Ala Ile Ile Pro Ala Ala Leu Pro Ala Asn Ile The Val Phe |
| 484 | LAVVLAAPAIVP | Gly Phe His Met Leu Ala Val Val Leu Ala Ala Pro Ala Ile Val Pro Ala Asn Ile The Val Phe |
| 485 | AILAAIVPLAVP | Gly Phe His Met Ala Ile Leu Ala Ala Ile Val Pro Leu Ala Val Pro Ala Asn Ile The Val Phe |
| 501 | VIVALAVPALAP | Gly Phe His Met Val Ile Val Ala Leu Ala Val Pro Ala Leu Ala Pro Ala Asn Ile The Val Phe |
| 502 | AIVALAVPVLAP | Gly Phe His Met Ala Ile Val Ala Leu Ala Val Pro Val Leu Ala Pro Ala Asn Ile The Val Phe |
| 503 | AAIIIVLPAALP | Gly Phe His Met Ala Ala Ile Ile Ile Val Leu Pro Ala Ala Leu Pro Ala Asn Ile The Val Phe |
| 504 | LIVALAVPALAP | Gly Phe His Met Leu Ile Val Ala Leu Ala Val Pro Ala Leu Ala Pro Ala Asn Ile The Val Phe |
| 505 | AIIIVIAPAAAP | Gly Phe His Met Ala Ile Ile Ile Val Ile Ala Pro Ala Ala Ala Pro Ala Asn Ile The Val Phe |
| 521 | LAALIVVPAVAP | Gly Phe His Met Leu Ala Ala Leu Ile Val Val Pro Ala Val Ala Pro Ala Asn Ile The Val Phe |
| 522 | ALLVIAVPAVAP | Gly Phe His Met Ala Leu Leu Val Ile Ala Val Pro Ala Val Ala Pro Ala Asn Ile The Val Phe |
| 524 | AVALIVVPALAP | Gly Phe His Met Ala Val Ala Leu Ile Val Val Pro Ala Leu Ala Pro Ala Asn Ile The Val Phe |
| 525 | ALAIVVAPVAVP | Gly Phe His Met Ala Leu Ala Ile Val Val Ala Pro Val Ala Val Pro Ala Asn Ile The Val Phe |
| 527 | LVLAAVAPIAIP | Gly Phe His Met Leu Val Leu Ala Ala Val Ala Pro Ile Ala Ile Pro Ala Asn Ile The Val Phe |
| 541 | LLALIIAPAAAP | Gly Phe His Met Leu Leu Ala Leu Ile Ile Ala Pro Ala Ala Ala Pro Ala Asn Ile The Val Phe |
| 542 | ALALIIVPAVAP | Gly Phe His Met Ala Leu Ala Leu Ile Ile Val Pro Ala Val Ala Pro Ala Asn Ile The Val Phe |
| 543 | LLAALIAPAALP | Gly Phe His Met Leu Leu Ala Ala Leu Ile Ala Pro Ala Ala Leu Pro Ala Asn Ile The Val Phe |
| 544 | IVALIVAPAAVP | Gly Phe His Met Ile Val Ala Leu Ile Val Ala Pro Ala Ala Val Pro Ala Asn Ile The Val Phe |
| 545 | VVLVLAAPAAVP | Gly Phe His Met Val Val Leu Val Leu Ala Ala Pro Ala Ala Val Pro Ala Asn Ile The Val Phe |
| 561 | AAVAIVLPAVVP | Gly Phe His Met Ala Ala Val Ala Ile Val Leu Pro Ala Val Val Pro Ala Asn Ile The Val Phe |
| 562 | ALIAAIVPALVP | Gly Phe His Met Ala Leu Ile Ala Ala Ile Val Pro Ala Leu Val Pro Ala Asn Ile The Val Phe |
| 563 | ALAVIVPALAP | Gly Phe His Met Ala Leu Ala Val Ile Val Val Pro Ala Leu Ala Pro Ala Asn Ile The Val Phe |
| 564 | VAIALIVPALAP | Gly Phe His Met Val Ala Ile Ala Leu Ile Val Pro Ala Leu Ala Pro Ala Asn Ile The Val Phe |

TABLE 35-continued

| aMTD | Sequence | 5'-Primer Design | | | | | | | | | | | | | | | | |
|---|---|---|---|---|---|---|---|---|---|---|---|---|---|---|---|---|---|---|
| 565 | VAIVLVAPAVAP | Gly | Phe | His | Met | Val | Ala | Ile | Val | Leu | Val | Ala | Pro | Ala | Val | Ala | Pro | Ala Asn Ile The Val Phe |
| 577 | AAVLIVPIMVMP | Gly | Phe | His | Met | Ala | Ala | Val | Leu | Ile | Val | Pro | Ile | Met | Val | Met | Pro | Ala Asn Ile The Val Phe |
| 582 | VAVALIVPALAP | Gly | Phe | His | Met | Val | Ala | Val | Ala | Leu | Ile | Val | Pro | Ala | Leu | Ala | Pro | Ala Asn Ile The Val Phe |
| 583 | AVILALAPIVAP | Gly | Phe | His | Met | Ala | Val | Ile | Leu | Ala | Leu | Ala | Pro | Ile | Val | Ala | Pro | Ala Asn Ile The Val Phe |
| 585 | ALIVAIAPALVP | Gly | Phe | His | Met | Ala | Leu | Ile | Val | Ala | Ile | Ala | Pro | Ala | Leu | Val | Pro | Ala Asn Ile The Val Phe |
| 601 | AAILIAVPIAAP | Gly | Phe | His | Met | Ala | Ala | Ile | Leu | Ile | Ala | Val | Pro | Ile | Ala | Ala | Pro | Ala Asn Ile The Val Phe |
| 602 | VIVALAAPVLAP | Gly | Phe | His | Met | Val | Ile | Val | Ala | Leu | Ala | Ala | Pro | Val | Leu | Ala | Pro | Ala Asn Ile The Val Phe |
| 603 | VLVALAAPVIAP | Gly | Phe | His | Met | Val | Leu | Val | Ala | Leu | Ala | Ala | Pro | Val | Ile | Ala | Pro | Ala Asn Ile The Val Phe |
| 604 | VALIAVAPAVVP | Gly | Phe | His | Met | Val | Ala | Leu | Ile | Ala | Val | Ala | Pro | Ala | Val | Val | Pro | Ala Asn Ile The Val Phe |
| 605 | VIAAVLAPVAVP | Gly | Phe | His | Met | Val | Ile | Ala | Ala | Val | Leu | Ala | Pro | Val | Ala | Val | Pro | Ala Asn Ile The Val Phe |
| 606 | AAAIAAIPIIIP | Gly | Phe | His | Met | Ala | Ala | Ala | Ile | Ala | Ala | Ile | Pro | Ile | Ile | Ile | Pro | Ala Asn Ile The Val Phe |
| 622 | ALIVLAAPVAVP | Gly | Phe | His | Met | Ala | Leu | Ile | Val | Leu | Ala | Ala | Pro | Val | Ala | Val | Pro | Ala Asn Ile The Val Phe |
| 623 | VAAAIALPAIVP | Gly | Phe | His | Met | Val | Ala | Ala | Ala | Ile | Ala | Leu | Pro | Ala | Ile | Val | Pro | Ala Asn Ile The Val Phe |
| 625 | ILAAAAPLIVP | Gly | Phe | His | Met | Ile | Leu | Ala | Ala | Ala | Ala | Ala | Pro | Leu | Ile | Val | Pro | Ala Asn Ile The Val Phe |
| 635 | GSTGGSQQNNQY | Gly | Phe | His | Met | Gly | Ser | Thr | Gly | Gly | Ser | Gln | Gln | Asn | Asn | Gln | Tyr | Ala Asn Ile The Val Phe |
| 643 | LALVLAAPAIVP | Gly | Phe | His | Met | Leu | Ala | Leu | Val | Leu | Ala | Ala | Pro | Ala | Ile | Val | Pro | Ala Asn Ile The Val Phe |
| 645 | ALAVVALPAIVP | Gly | Phe | His | Met | Ala | Leu | Ala | Val | Val | Ala | Leu | Pro | Ala | Ile | Val | Pro | Ala Asn Ile The Val Phe |
| 661 | AAILAPIVAALP | Gly | Phe | His | Met | Ala | Ala | Ile | Leu | Ala | Pro | Ile | Val | Ala | Ala | Leu | Pro | Ala Asn Ile The Val Phe |
| 664 | ILIAIAIPAAAP | Gly | Phe | His | Met | Ile | Leu | Ile | Ala | Ile | Ala | Ile | Pro | Ala | Ala | Ala | Pro | Ala Asn Ile The Val Phe |
| 665 | LAIVLAAPVAVP | Gly | Phe | His | Met | Leu | Ala | Ile | Val | Leu | Ala | Ala | Pro | Val | Ala | Val | Pro | Ala Asn Ile The Val Phe |
| 666 | AAIAIIAPAIVP | Gly | Phe | His | Met | Ala | Ala | Ile | Ala | Ile | Ile | Ala | Pro | Ala | Ile | Val | Pro | Ala Asn Ile The Val Phe |
| 667 | LAVAIVAPALVP | Gly | Phe | His | Met | Leu | Ala | Val | Ala | Ile | Val | Ala | Pro | Ala | Leu | Val | Pro | Ala Asn Ile The Val Phe |
| 676 | VPLLVPVPVVVP | Gly | Phe | His | Met | Val | Pro | Leu | Leu | Val | Pro | Val | Pro | Val | Val | Val | Pro | Ala Asn Ile The Val Phe |
| 683 | LAIVLAAPAVLP | Gly | Phe | His | Met | Leu | Ala | Ile | Val | Leu | Ala | Ala | Pro | Ala | Val | Leu | Pro | Ala Asn Ile The Val Phe |
| 684 | AAIVLALPAVLP | Gly | Phe | His | Met | Ala | Ala | Ile | Val | Leu | Ala | Leu | Pro | Ala | Val | Leu | Pro | Ala Asn Ile The Val Phe |

TABLE 36

| aMTD | Sequence | 5'-Primer Design |
|---|---|---|
| 685 | ALLVAVLPAALP | Gly Phe His Met Ala Leu Leu Val Ala Val Leu Pro Ala Ala Leu Pro Ala Asn Ile The Val Phe |
| 686 | AALVAVLPVALP | Gly Phe His Met Ala Ala Leu Val Ala Val Leu Pro Val Ala Leu Pro Ala Asn Ile The Val Phe |
| 687 | AILAVALPLLAP | Gly Phe His Met Ala Ile Leu Ala Val Ala Leu Pro Leu Leu Ala Pro Ala Asn Ile The Val Phe |
| 692 | PAPLPPVVILAV | Gly Phe His Met Pro Ala Pro Leu Pro Pro Val Val Ile Leu Ala Val Ala Asn Ile The Val Phe |
| 693 | AAPVLPVAVPIV | Gly Phe His Met Ala Ala Pro Val Leu Pro Val Ala Val Pro Ile Val Ala Asn Ile The Val Phe |
| 700 | GTSNTCQSNQNS | Gly Phe His Met Gly Thr Ser Asn Thr Cys Gln Ser Asn Gln Asn Ser Ala Asn Ile The Val Phe |
| 703 | IVAVALVPALAP | Gly Phe His Met Ile Val Ala Val Ala Leu Val Pro Ala Leu Ala Pro Ala Asn Ile The Val Phe |
| 705 | IVAVALLPALAP | Gly Phe His Met Ile Val Ala Val Ala Leu Leu Pro Ala Leu Ala Pro Ala Asn Ile The Val Phe |
| 706 | IVAVALLPAVAP | Gly Phe His Met Ile Val Ala Val Ala Leu Leu Pro Ala Val Ala Pro Ala Asn Ile The Val Phe |
| 707 | IVALAVLPAVAP | Gly Phe His Met Ile Val Ala Leu Ala Val Leu Pro Ala Val Ala Pro Ala Asn Ile The Val Phe |
| 724 | VAVLAVLPALAP | Gly Phe His Met Val Ala Val Leu Ala Val Leu Pro Ala Leu Ala Pro Ala Asn Ile The Val Phe |
| 725 | IAVLAVAPAVLP | Gly Phe His Met Ile Ala Val Leu Ala Val Ala Pro Ala Val Leu Pro Ala Asn Ile The Val Phe |
| 726 | LAVAIIAPAVAP | Gly Phe His Met Leu Ala Val Ala Ile Ile Ala Pro Ala Val Ala Pro Ala Asn Ile The Val Phe |
| 727 | VALAIALPAVLP | Gly Phe His Met Val Ala Leu Ala Ile Ala Leu Pro Ala Val Leu Pro Ala Asn Ile The Val Phe |
| 743 | AIAIALVPVALP | Gly Phe His Met Ala Ile Ala Ile Ala Leu Val Pro Val Ala Leu Pro Ala Asn Ile The Val Phe |
| 744 | AAVVIVAPVALP | Gly Phe His Met Ala Ala Val Val Ile Val Ala Pro Val Ala Leu Pro Ala Asn Ile The Val Phe |
| 745 | AAILAIVAPLAP | Gly Phe His Met Ala Ala Ile Leu Ala Ile Val Ala Pro Leu Ala Pro Ala Asn Ile The Val Phe |
| 746 | VAIIVVAPALAP | Gly Phe His Met Val Ala Ile Ile Val Val Ala Pro Ala Leu Ala Pro Ala Asn Ile The Val Phe |
| 747 | VALLAIAPALAP | Gly Phe His Met Val Ala Leu Leu Ala Ile Ala Pro Ala Leu Ala Pro Ala Asn Ile The Val Phe |
| 750 | LAIAAIAPLAIP | Gly Phe His Met Leu Ala Ile Ala Ala Ile Ala Pro Leu Ala Ile Pro Ala Asn Ile The Val Phe |
| 763 | VAVLIAVPALAP | Gly Phe His Met Val Ala Val Leu Ile Ala Val Pro Ala Leu Ala Pro Ala Asn Ile The Val Phe |
| 764 | AVALAVLPAVVP | Gly Phe His Met Ala Val Ala Leu Ala Val Leu Pro Ala Val Val Pro Ala Asn Ile The Val Phe |
| 765 | AVALAVVPAVLP | Gly Phe His Met Ala Val Ala Leu Ala Val Val Pro Ala Val Leu Pro Ala Asn Ile The Val Phe |
| 766 | IVVIAVAPAVAP | Gly Phe His Met Ile Val Val Ile Ala Val Ala Pro Ala Val Ala Pro Ala Asn Ile The Val Phe |
| 767 | IVVAAVVPALAP | Gly Phe His Met Ile Val Val Ala Ala Val Val Pro Ala Leu Ala Pro Ala Asn Ile The Val Phe |
| 772 | LPVAPVIPIIVP | Gly Phe His Met Leu Pro Val Ala Pro Val Ile Pro Ile Ile Val Pro Ala Asn Ile The Val Phe |

TABLE 36-continued

| aMTD | Sequence | 5'-Primer Design |
|---|---|---|
| 783 | IVALVPAVAIAP | Gly Phe His Met Ile Val Ala Leu Val Pro Ala Val Ala Ile Ala Pro Ala Asn Ile The Val Phe |
| 784 | VAALPAVALVVP | Gly Phe His Met Val Ala Ala Leu Pro Ala Val Ala Leu Val Val Pro Ala Asn Ile The Val Phe |
| 786 | LVAIAPLAVLAP | Gly Phe His Met Leu Val Ala Ile Ala Pro Leu Ala Val Leu Ala Pro Ala Asn Ile The Val Phe |
| 787 | AVALVPVIVAAP | Gly Phe His Met Ala Val Ala Leu Val Pro Val Ile Val Ala Ala Pro Ala Asn Ile The Val Phe |
| 788 | AIAVAIAPVALP | Gly Phe His Met Ala Ile Ala Val Ala Ile Ala Pro Val Ala Leu Pro Ala Asn Ile The Val Phe |
| 803 | AIALAVPVLALP | Gly Phe His Met Ala Ile Ala Leu Ala Val Pro Val Leu Ala Leu Pro Ala Asn Ile The Val Phe |
| 805 | LVLIAAAPIALP | Gly Phe His Met Leu Val Leu Ile Ala Ala Ala Pro Ile Ala Leu Pro Ala Asn Ile The Val Phe |
| 806 | LVALAVPAAVLP | Gly Phe His Met Leu Val Ala Leu Ala Val Pro Ala Ala Val Leu Pro Ala Asn Ile The Val Phe |
| 807 | AVALAVPALVLP | Gly Phe His Met Ala Val Ala Leu Ala Val Pro Ala Leu Val Leu Pro Ala Asn Ile The Val Phe |
| 808 | LVVLAAAPLAVP | Gly Phe His Met Leu Val Val Leu Ala Ala Ala Pro Leu Ala Val Pro Ala Asn Ile The Val Phe |
| 809 | LIVLAAPALAAP | Gly Phe His Met Leu Ile Val Leu Ala Ala Pro Ala Leu Ala Ala Pro Ala Asn Ile The Val Phe |
| 810 | VIVLAAPALAAP | Gly Phe His Met Val Ile Val Leu Ala Ala Pro Ala Leu Ala Ala Pro Ala Asn Ile The Val Phe |
| 811 | AVVLAVPALAVP | Gly Phe His Met Ala Val Val Leu Ala Val Pro Ala Leu Ala Val Pro Ala Asn Ile The Val Phe |
| 824 | LIIVAAAPAVAP | Gly Phe His Met Leu Ile Ile Val Ala Ala Ala Pro Ala Val Ala Pro Ala Asn Ile The Val Phe |
| 825 | IVAVIVAPAVAP | Gly Phe His Met Ile Val Ala Val Ile Val Ala Pro Ala Val Ala Pro Ala Asn Ile The Val Phe |
| 826 | LVALAAPIIAVP | Gly Phe His Met Leu Val Ala Leu Ala Ala Pro Ile Ile Ala Val Pro Ala Asn Ile The Val Phe |
| 827 | IAAVLAAPALVP | Gly Phe His Met Ile Ala Ala Val Leu Ala Ala Pro Ala Leu Val Pro Ala Asn Ile The Val Phe |
| 828 | IALLAAPIIAVP | Gly Phe His Met Ile Ala Leu Leu Ala Ala Pro Ile Ile Ala Val Pro Ala Asn Ile The Val Phe |
| 829 | AALALVAPVIVP | Gly Phe His Met Ala Ala Leu Ala Leu Val Ala Pro Val Ile Val Pro Ala Asn Ile The Val Phe |
| 830 | IALVAAPVALVP | Gly Phe His Met Ile Ala Leu Val Ala Ala Pro Val Ala Leu Val Pro Ala Asn Ile The Val Phe |
| 831 | IIVAVAPAAIVP | Gly Phe His Met Ile Ile Val Ala Val Ala Pro Ala Ala Ile Val Pro Ale Asn Ile The Val Phe |

TABLE 37

| aMTD | Sequence | 5'-Primer Design |
|---|---|---|
| 832 | AVAAIVPVIVAP | Gly Phe His Met Ala Val Ala Ala Ile Val Pro Val Ile Val Ala Pro Ala Asn Ile The Val Phe |
| 843 | AVLVLVAPAAAP | Gly Phe His Met Ala Val Leu Val Leu Val Ala Pro Ala Ala Ala Pro Ala Asn Ile The Val Phe |
| 844 | VVALLAPLIAAP | Gly Phe His Met Val Val Ala Leu Leu Ala Pro Leu Ile Ala Ala Pro Ala Asn Ile The Val Phe |

TABLE 37-continued

| aMTD | Sequence | 5'-Primer Design | | | | | | | | | | | | | | | | | |
|---|---|---|---|---|---|---|---|---|---|---|---|---|---|---|---|---|---|---|---|
| 845 | AAVVIAPLLAVP | Gly | Phe | His | Met | Ala | Ala | Val | Val | Ile | Ala | Pro | Leu | Leu | Ala | Val | Pro | Ala | Asn Ile The Val Phe |
| 846 | IAVAVAAPLLVP | Gly | Phe | His | Met | Ile | Ala | Val | Ala | Val | Ala | Ala | Pro | Leu | Leu | Val | Pro | Ala | Asn Ile The Val Phe |
| 847 | LVAIVVLPAVAP | Gly | Phe | His | Met | Leu | Val | Ala | Ile | Val | Val | Leu | Pro | Ala | Val | Ala | Pro | Ala | Asn Ile The Val Phe |
| 848 | AVAIVVLPAVAP | Gly | Phe | His | Met | Ala | Val | Ala | Ile | Val | Val | Leu | Pro | Ala | Val | Ala | Pro | Ala | Asn Ile The Val Phe |
| 849 | AVILLAPLIAAP | Gly | Phe | His | Met | Ala | Val | Ile | Leu | Leu | Ala | Pro | Leu | Ile | Ala | Ala | Pro | Ala | Asn Ile The Val Phe |
| 850 | LVIALAAPVALP | Gly | Phe | His | Met | Leu | Val | Ile | Ala | Leu | Ala | Ala | Pro | Val | Ala | Leu | Pro | Ala | Asn Ile The Val Phe |
| 851 | VLAVVLPAVALP | Gly | Phe | His | Met | Val | Leu | Ala | Val | Val | Leu | Pro | Ala | Val | Ala | Leu | Pro | Ala | Asn Ile The Val Phe |
| 852 | VLAVAAPAVLLP | Gly | Phe | His | Met | Val | Leu | Ala | Val | Ala | Ala | Pro | Ala | Val | Leu | Leu | Pro | Ala | Asn Ile The Val Phe |
| 863 | AAVVLLPIIAAP | Gly | Phe | His | Met | Ala | Ala | Val | Val | Leu | Leu | Pro | Ile | Ile | Ala | Ala | Pro | Ala | Asn Ile The Val Phe |
| 864 | ALLVIAPAIAVP | Gly | Phe | His | Met | Ala | Leu | Leu | Val | Ile | Ala | Pro | Ala | Ile | Ala | Val | Pro | Ala | Asn Ile The Val Phe |
| 865 | AVLVIAVPAIAP | Gly | Phe | His | Met | Ala | Val | Leu | Val | Ile | Ala | Val | Pro | Ala | Ile | Ala | Pro | Ala | Asn Ile The Val Phe |
| 867 | ALLVVIAPLAAP | Gly | Phe | His | Met | Ala | Leu | Leu | Val | Val | Ile | Ala | Pro | Leu | Ala | Ala | Pro | Ala | Asn Ile The Val Phe |
| 868 | VLVAAILPAAIP | Gly | Phe | His | Met | Val | Leu | Val | Ala | Ala | Ile | Leu | Pro | Ala | Ala | Ile | Pro | Ala | Asn Ile The Val Phe |
| 870 | VLVAAVLPIAAP | Gly | Phe | His | Met | Val | Leu | Val | Ala | Ala | Val | Leu | Pro | Ile | Ala | Ala | Pro | Ala | Asn Ile The Val Phe |
| 872 | VLAAAVLPLVVP | Gly | Phe | His | Met | Val | Leu | Ala | Ala | Ala | Val | Leu | Pro | Leu | Val | Val | Pro | Ala | Asn Ile The Val Phe |
| 875 | AIAIVVPAVAVP | Gly | Phe | His | Met | Ala | Ile | Ala | Ile | Val | Val | Pro | Ala | Val | Ala | Val | Pro | Ala | Asn Ile The Val Phe |
| 877 | VAIIAVPAVVAP | Gly | Phe | His | Met | Val | Ala | Ile | Ile | Ala | Val | Pro | Ala | Val | Val | Ala | Pro | Ala | Asn Ile The Val Phe |
| 878 | IVALVAPAAVVP | Gly | Phe | His | Met | Ile | Val | Ala | Leu | Val | Ala | Pro | Ala | Ala | Val | Val | Pro | Ala | Asn Ile The Val Phe |
| 879 | AAIVLLPAVVVP | Gly | Phe | His | Met | Ala | Ala | Ile | Val | Leu | Leu | Pro | Ala | Val | Val | Val | Pro | Ala | Asn Ile The Val Phe |
| 881 | AALIVVPAVAVP | Gly | Phe | His | Met | Ala | Ala | Leu | Ile | Val | Val | Pro | Ala | Val | Ala | Val | Pro | Ala | Asn Ile The Val Phe |
| 882 | AIALVVPAVAVP | Gly | Phe | His | Met | Ala | Ile | Ala | Leu | Val | Val | Pro | Ala | Val | Ala | Val | Pro | Ala | Asn Ile The Val Phe |
| 883 | LAIVPAAIAALP | Gly | Phe | His | Met | Leu | Ala | Ile | Val | Pro | Ala | Ala | Ile | Ala | Ala | Leu | Pro | Ala | Asn Ile The Val Phe |
| 884 | VLIVPAAIAALP | Gly | Phe | His | Met | Val | Leu | Ile | Val | Pro | Ala | Ala | Ile | Ala | Ala | Leu | Pro | Ala | Asn Ile The Val Phe |
| 885 | LVAIAPAVAVLP | Gly | Phe | His | Met | Leu | Val | Ala | Ile | Ala | Pro | Ala | Val | Ala | Val | Leu | Pro | Ala | Asn Ile The Val Phe |
| 886 | VLAVPAAIAALP | Gly | Phe | His | Met | Val | Leu | Ala | Val | Pro | Ala | Ala | Ile | Ala | Ala | Leu | Pro | Ala | Asn Ile The Val Phe |
| 887 | VLAVAPAVAVLP | Gly | Phe | His | Met | Val | Leu | Ala | Val | Ala | Pro | Ala | Val | Ala | Val | Leu | Pro | Ala | Asn Ile The Val Phe |

TABLE 37-continued

| aMTD | Sequence | 5'-Primer Design |
|---|---|---|
| 888 | ILAVVAIPAAAP | Gly Phe His Met Ile Leu Ala Val Val Ala Ile Pro Ala Ala Ala Pro Ala Asn Ile The Val Phe |
| 889 | ILVAAAPIAALP | Gly Phe His Met Ile Leu Val Ala Ala Ala Pro Ile Ala Ala Leu Pro Ala Asn Ile The Val Phe |
| 891 | ILAVAAIPAALP | Gly Phe His Met Ile Leu Ala Val Ala Ala Ile Pro Ala Ala Leu Pro Ala Asn Ile The Val Phe |
| 893 | VIAIPAILAAAP | Gly Phe His Met Val Ile Ala Ile Pro Ala Ile Leu Ala Ala Ala Pro Ala Asn Ile The Val Phe |
| 895 | AIIIVVPAIAAP | Gly Phe His Met Ala Ile Ile Ile Val Val Pro Ala Ile Ala Ala Pro Ala Asn Ile The Val Phe |
| 896 | AILIVVAPIAAP | Gly Phe His Met Ala Ile Leu Ile Val Val Ala Pro Ile Ala Ala Pro Ala Asn Ile The Val Phe |
| 897 | AVIVPVAIIAAP | Gly Phe His Met Ala Val Ile Val Pro Val Ala Ile Ile Ala Ala Pro Ala Asn Ile The Val Phe |
| 899 | AVVIALPAVVAP | Gly Phe His Met Ala Val Val Ile Ala Leu Pro Ala Val Val Ala Pro Ala Asn Ile The Val Phe |
| 900 | ALVAVIAPVVAP | Gly Phe His Met Ala Leu Val Ala Val Ile Ala Pro Val Val Ala Pro Ala Asn Ile The Val Phe |
| 901 | ALVAVLPAVAVP | Gly Phe His Met Ala Leu Val Ala Val Leu Pro Ala Val Ala Val Pro Ala Asn Ile The Val Phe |
| 902 | ALVAPLLAVAVP | Gly Phe His Met Ala Leu Val Ala Pro Leu Leu Ala Val Ala Val Pro Ala Asn Ile The Val Phe |
| 904 | AVLAVVAPVVAP | Gly Phe His Met Ala Val Leu Ala Val Val Ala Pro Val Val Ala Pro Ala Asn Ile The Val Phe |
| 905 | AVIAVAPLVVAP | Gly Phe His Met Ala Val Ile Ala Val Ala Pro Leu Val Val Ala Pro Ala Asn Ile The Val Phe |
| 906 | AVIALAPVVVAP | Gly Phe His Met Ala Val Ile Ala Leu Ala Pro Val Val Val Ala Pro Ala Asn Ile The Val Phe |
| 907 | VAIALAPVVVAP | Gly Phe His Met Val Ala Ile Ala Leu Ala Pro Val Val Val Ala Pro Ala Asn Ile The Val Phe |
| 908 | VALALAPVVVAP | Gly Phe His Met Val Ala Leu Ala Leu Ala Pro Val Val Val Ala Pro Ala Asn Ile The Val Phe |
| 910 | VAALLPAVVVAP | Gly Phe His Met Val Ala Ala Leu Leu Pro Ala Val Val Val Ala Pro Ala Asn Ile The Val Phe |
| 911 | VALALPAVVVAP | Gly Phe His Met Val Ala Leu Ala Leu Pro Ala Val Val Val Ala Pro Ala Asn Ile The Val Phe |

TABLE 38

| aMTD Sequences | | |
|---|---|---|
| | | 5'-Primer Design |
| 912 | VALLAPAVVVAP | Gly Phe His Met Val Ala Leu Leu Ala Pro Ala Val Val Val Ala Pro Ala Asn Ile The Val Phe |
| 921 | IWWFVVLPLVVP | Gly Phe His Met Ile Trp Trp Phe Val Val Leu Pro Leu Val Val Pro Ala Asn Ile The Val Phe |
| 922 | WYVIFVLPLVVP | Gly Phe His Met Trp Tyr Val Ile Phe Val Leu Pro Leu Val Val Pro Ala Asn Ile The Val Phe |
| 931 | AVLIAPAILAAA | Gly Phe His Met Ala Val Leu Ile Ala Pro Ala Ile Leu Ala Ala Ala Ala Asn Ile The Val Phe |

TABLE 38-continued aMTD Sequences

| 934 | LILAPAAVVAAA | Gly Phe His Met Leu Ile Leu Ala Pro Ala Ala Val Val Ala Ala Ala Ala Asn Ile The Val Phe |
| 935 | ALLILPAAAVAA | Gly Phe His Met Ala Leu Leu Ile Leu Pro Ala Ala Ala Val Ala Ala Ala Asn Ile The Val Phe |
| 936 | ALLILAAAVAAP | Gly Phe His Met Ala Leu Leu Ile Leu Ala Ala Ala Val Ala Ala Pro Ala Asn Ile The Val Phe |
| 937 | VPVLVPLPVPVV | Gly Phe His Met Val Pro Val Leu Val Pro Leu Pro Val Pro Val Val Ala Asn Ile The Val Phe |
| 938 | VPVLLPVVVPVP | Gly Phe His Met Val Pro Val Leu Leu Pro Val Val Val Pro Val Pro Ala Asn Ile The Val Phe |
| 947 | CYYNQQSNNNNQ | Gly Phe His Met Cys Tyr Tyr Asn Gln Gln Ser Asn Asn Asn Asn Gln Ala Asn Ile The Val Phe |
| 949 | SGNSCQQCGNSS | Gly Phe His Met Ser Gly Asn Ser Cys Gln Gln Cys Gly Asn Ser Ser Ala Asn Ile The Val Phe |

3'-Primer Design

Arg Val Asp Leu Pro Arg Leu His Arg His Gly Asp Asp

4-3. Expression of aMTD- or Random Peptide (rP)-Fused Recombinant Proteins

The present invention also relates to the development method of aMTD sequences having cell-permeability. Using the standardized six critical factors, 316 aMTD sequences have been designed. In addition, 141 rPeptides are also developed that lack one of these critical factors: no bending peptides: i) absence of proline both in the middle and at the end of sequence or ii) absence of proline either in the middle or at the end of sequence, rigid peptides, ③ too much flexible peptides, aromatic peptides (aromatic ring presence), hydrophobic but non-aromatic peptides, and hydrophilic but non-aliphatic peptides (TABLE 22).

These rPeptides are devised to be compared and contrasted with aMTDs in order to analyze structure/sequence activity relationship (SAR) of each critical factor with regard to the peptides' intracellular delivery potential. All peptide (aMTD or rPeptide)-containing recombinant proteins have been fused to the CRA to enhance the solubility of the recombinant proteins to be expressed, purified, prepared and analyzed.

These designed 316 aMTDs and 141 rPeptides fused to CRA were all cloned (FIG. 2) and tested for inducible expression in *E. coli* (FIG. 3). Out of these peptides, 240 aMTDs were Inducibly expressed, purified and prepared in soluble form (FIG. 4). In addition, 31 rPeptides were also prepared as soluble form (FIG. 4).

To prepare the proteins fused to rPeptides, 60 proteins were expressed that were 10 out of 26 rPeptides in the category of no bending peptides (TABLE 16); 15 out of 23 in the category of rigid peptides [instability index (II)<40] (TABLE 17); 19 out of 24 in the category of too much flexible peptides (TABLE 18); 6 out of 27 in the category of aromatic peptides (TABLE 19); 8 out of 23 in the category of hydrophobic but non-aromatic peptides (TABLE 20); and 12 out of 18 in the category of hydrophilic but non-aliphatic peptides (TABLE 21).

4-4. Quantitative Cell-Permeability of aMTD-Fused Recombinant Proteins

The aMTDs and rPeptides were fluorescently labeled and compared based on the critical factors for cell-permeability by using flow cytometry and confocal laser scanning microscopy (FIG. 5 to 8). The cellular uptake of the peptide-fused non-functional cargo recombinant proteins could quantitatively be evaluated in flow cytometry, while confocal laser scanning microscopy allows intracellular uptake to be assessed visually. The analysis included recombinant proteins fused to a negative control [rP38] that has opposite characteristics (hydrophilic and aromatic sequence: YYNQSTCGGQCY) to the aMTDs (hydrophobic and aliphatic sequences). Relative cell-permeability (relative fold) of aMTDs to the negative control was also analyzed (TABLE 39 and FIG. 9).

TABLE 39 shows Comparison Analysis of Cell-Permeability of aMTDs with a Negative Control (A: rP38).

TABLE 39

|  | Negative Control rP38 |
|---|---|
| aMTD The Average of 240 aMTDs | 19.6 ± 1.6* (Best: 164.2) |

*Relative Fold (aMTD in Geo Mean in its comparison to rP38)

Relative cell-permeability (relative fold) of aMTDs to the reference CPPs [B: MTM12 (AAVLLPVLLAAP), C: MTD85 (AVALLILAV)] was also analyzed (TABLE 40 and 41)

TABLE 40 shows Comparison Analysis of Cell-Permeability of aMTDs with a Reference CPP (B: MTM12).

TABLE 40

|  | MTM12 |
|---|---|
| aMTD The Average of 240 aMTDs | 13.1 ± 1.1* (Best: 109.9) |

*Relative Fold (aMTD in Geo Mean in its comparison to MTM12)

TABLE 41 shows Comparison Analysis of Cell-Permeability of aMTDs with a Reference CPP (C: MTD85).

TABLE 41

|  | MTD85 |
| --- | --- |
| aMTD The Average of 240 aMTDs | 6.6 ± 0.5* (Best: 55.5) |

*Relative Fold (aMTD in Geo Mean in its comparison to MTD85)

Geometric means of negative control (histidine-tagged rP38-fused CRA recombinant protein) subtracted by that of naked protein (histidine-tagged CRA protein) lacking any peptide (rP38 or aMTD) was standardized as relative fold of 1. Relative cell-permeability of 240 aMTDs to the negative control (A type) was significantly increased by up to 164 fold, with average increase of 19.6±1.6 (TABLE 42-47).

TABLE 42

| aMTD | Sequences | Length | Proline Position (PP) | Rigidity/ Flexibility (II) | Structural Feature (AI) | Hydropathy (GRAVY) | Relative Ratio (Fold) | | |
| --- | --- | --- | --- | --- | --- | --- | --- | --- | --- |
| | | | | | | | A | B | C |
| 899 | AVVIALPAVVAP | 12 | 7 | 57.3 | 195.0 | 2.4 | 164.2 | 109.9 | 55.5 |
| 908 | VALALAPVVVAP | 12 | 7 | 57.3 | 195.0 | 2.3 | 150.6 | 100.8 | 50.9 |
| 910 | VAALLPAVVVAP | 12 | 6 | 57.3 | 195.0 | 2.3 | 148.5 | 99.4 | 50.2 |
| 810 | VIVLAAPALAAP | 12 | 7 | 50.2 | 187.5 | 2.2 | 120.0 | 80.3 | 40.6 |
| 904 | AVLAVVAPVVAP | 12 | 8 | 57.3 | 186.7 | 2.4 | 105.7 | 70.8 | 35.8 |
| 321 | IVAVALPALAVP | 12 | 7 | 50.2 | 203.3 | 2.3 | 97.8 | 65.2 | 32.9 |
| 851 | VLAVVLPAVALP | 12 | 7 | 57.3 | 219.2 | 2.5 | 96.6 | 64.7 | 32.7 |
| 911 | VALALPAVVVAP | 12 | 6 | 57.3 | 195.0 | 2.3 | 84.8 | 56.8 | 28.7 |
| 852 | VLAVAAPAVLLP | 12 | 7 | 57.3 | 203.3 | 2.3 | 84.6 | 56.6 | 28.6 |
| 803 | AIALAVPVLALP | 12 | 7 | 57.3 | 211.7 | 2.4 | 74.7 | 50.0 | 25.3 |
| 888 | ILAVVAIPAAAP | 12 | 8 | 54.9 | 187.5 | 2.3 | 71.0 | 47.5 | 24.0 |
| 825 | IVAVIVAPAVAP | 12 | 8 | 43.2 | 195.0 | 2.5 | 69.7 | 46.6 | 23.6 |
| 895 | AIIIVVPAIAAP | 12 | 7 | 50.2 | 211.7 | 2.5 | 60.8 | 40.7 | 20.6 |
| 896 | AILIVVAPIAAP | 12 | 8 | 50.2 | 211.7 | 2.5 | 57.5 | 38.5 | 19.4 |
| 727 | VALAIALPAVLP | 12 | 8 | 57.3 | 211.6 | 2.3 | 54.7 | 36.7 | 18.5 |
| 603 | VLVALAAPVIAP | 12 | 8 | 57.3 | 203.3 | 2.4 | 54.1 | 36.1 | 18.2 |
| 847 | LVAIVVLPAVAP | 12 | 8 | 50.2 | 219.2 | 2.6 | 50.2 | 33.4 | 16.9 |
| 826 | LVALAAPIIAVP | 12 | 7 | 41.3 | 211.7 | 2.4 | 49.2 | 32.9 | 16.6 |
| 724 | VAVLAVLPALAP | 12 | 8 | 57.3 | 203.3 | 2.3 | 47.5 | 31.8 | 16.1 |
| 563 | ALAVIVVPALAP | 12 | 8 | 50.2 | 203.3 | 2.4 | 47.1 | 31.4 | 15.9 |
| 811 | AVVLAVPALAVP | 12 | 7 | 57.3 | 195.0 | 2.3 | 46.5 | 31.1 | 15.7 |
| 831 | IIVAVAPAAIVP | 12 | 7 | 43.2 | 203.3 | 2.5 | 46.3 | 31.0 | 15.7 |
| 829 | AALALVAPVIVP | 12 | 8 | 50.2 | 203.3 | 2.4 | 44.8 | 30.0 | 15.2 |
| 891 | ILAVAAIPAALP | 12 | 8 | 54.9 | 195.8 | 2.2 | 44.7 | 29.9 | 15.1 |
| 905 | AVIAVAPLVVAP | 12 | 7 | 41.3 | 195.0 | 2.4 | 44.0 | 29.5 | 14.9 |
| 564 | VAIALIVPALAP | 12 | 8 | 50.2 | 211.7 | 2.4 | 43.6 | 29.1 | 14.7 |
| 124 | IAVALPALIAAP | 12 | 6 | 50.3 | 195.8 | 2.2 | 43.6 | 29.0 | 14.7 |
| 827 | IAAVLAAPALVP | 12 | 8 | 57.3 | 187.5 | 2.2 | 43.0 | 28.8 | 14.6 |
| 2 | AAAVPLLAVVVP | 12 | 5 | 41.3 | 195.0 | 2.4 | 40.9 | 27.2 | 13.8 |
| 385 | IVAIAVPALVAP | 12 | 7 | 50.2 | 203.3 | 2.4 | 38.8 | 25.9 | 13.1 |
| 828 | IALLAAPIIAVP | 12 | 7 | 41.3 | 220.0 | 2.4 | 36.8 | 24.6 | 12.4 |

TABLE 42-continued

| aMTD Sequences | Length | Proline Position (PP) | Rigidity/ Flexibility (II) | Sturctural Feature (AI) | Hydropathy (GRAVY) | Relative Ratio (Fold) | | |
|---|---|---|---|---|---|---|---|---|
| | | | | | | A | B | C |
| 806 LVALAVPAAVLP | 12 | 7 | 57.3 | 203.3 | 2.3 | 36.7 | 24.6 | 12.4 |
| 845 AAVVIAPLLAVP | 12 | 7 | 41.3 | 203.3 | 2.4 | 35.8 | 24.0 | 12.1 |
| 882 AIALVVPAVAVP | 12 | 7 | 57.3 | 195.0 | 2.4 | 35.0 | 23.4 | 11.8 |
| 545 VVLVLAAPAAVP | 12 | 8 | 57.3 | 195.0 | 2.3 | 34.6 | 23.1 | 11.7 |
| 161 AVIALPALIAAP | 12 | 6 | 57.3 | 195.8 | 2.2 | 34.5 | 23.0 | 11.6 |
| 481 AIAIAIVPVALP | 12 | 8 | 50.2 | 211.6 | 2.4 | 34.3 | 23.0 | 11.6 |
| 900 ALVAVIAPVVAP | 12 | 8 | 57.3 | 195.0 | 2.4 | 34.3 | 22.9 | 11.6 |
| 223 AILAVPIAVVAP | 12 | 6 | 57.3 | 203.3 | 2.4 | 33.0 | 22.1 | 11.2 |
| 824 LIIVAAAPAVAP | 12 | 8 | 50.2 | 187.5 | 2.3 | 32.8 | 21.9 | 11.1 |
| 562 ALIAAIVPALVP | 12 | 8 | 50.2 | 211.7 | 2.4 | 32.7 | 21.8 | 11.0 |
| 222 ALLIAPAAVIAP | 12 | 6 | 57.3 | 195.8 | 2.2 | 32.6 | 21.7 | 11.0 |
| 61 VAALPVLLAALP | 12 | 5 | 57.3 | 211.7 | 2.3 | 31.2 | 20.8 | 10.5 |
| 582 VAVALIVPALAP | 12 | 8 | 50.2 | 203.3 | 2.4 | 30.6 | 20.4 | 10.3 |
| 889 ILVAAAPIAALP | 12 | 7 | 57.3 | 195.8 | 2.2 | 30.3 | 20.3 | 10.3 |
| 787 AVALVPVIVAAP | 12 | 6 | 50.2 | 195.0 | 2.4 | 29.3 | 19.6 | 9.9 |
| 703 IVAVALVPALAP | 12 | 8 | 50.2 | 203.3 | 2.4 | 29.2 | 19.5 | 9.9 |
| 705 IVAVALLPALAP | 12 | 8 | 50.2 | 211.7 | 2.4 | 28.6 | 19.1 | 9.7 |
| 885 LVAIAPAVAVLP | 12 | 6 | 57.3 | 203.3 | 2.4 | 28.3 | 19.0 | 9.6 |
| 3 AALLVPAAVLAP | 12 | 6 | 57.3 | 187.5 | 2.1 | 27.0 | 18.0 | 9.1 |
| 601 AAILIAVPIAAP | 12 | 8 | 57.3 | 195.8 | 2.3 | 26.8 | 17.9 | 9.0 |
| 843 AVLVLAPAAAP | 12 | 8 | 41.3 | 219.2 | 2.5 | 26.4 | 17.7 | 8.9 |
| 403 AAALVIPAAILP | 12 | 7 | 54.9 | 195.8 | 2.2 | 25.2 | 16.8 | 8.5 |
| 544 IVALIVAPAAVP | 12 | 8 | 43.1 | 203.3 | 2.4 | 23.4 | 15.6 | 7.9 |
| 522 ALLVIAVPAVAP | 12 | 8 | 57.3 | 203.3 | 2.4 | 22.7 | 15.2 | 7.7 |

TABLE 43

| aMTD Sequences | Length | Proline Position (PP) | Rigidity/ Flexibility (II) | Sturctural Feature (AI) | Hydropathy (GRAVY) | Relative Ratio (Fold) | | |
|---|---|---|---|---|---|---|---|---|
| | | | | | | A | B | C |
| 805 LVLIAAAPIALP | 12 | 8 | 41.3 | 220.0 | 2.4 | 22.3 | 14.9 | 7.6 |
| 464 AVVILVPLAAAP | 12 | 7 | 57.3 | 203.3 | 2.4 | 22.3 | 14.9 | 7.5 |
| 405 LAAAVIPVAILP | 12 | 7 | 54.9 | 211.7 | 2.4 | 22.2 | 14.8 | 7.5 |
| 747 VALLAIAPALAP | 12 | 8 | 57.3 | 195.8 | 2.2 | 22.0 | 14.8 | 7.5 |
| 501 VIVALAVPALAP | 12 | 8 | 50.2 | 203.3 | 2.4 | 21.5 | 14.4 | 7.3 |
| 661 AAILAPIVAALP | 12 | 6 | 50.2 | 195.8 | 2.2 | 21.4 | 14.3 | 7.2 |
| 786 LVAIAPLAVLAP | 12 | 6 | 41.3 | 211.7 | 2.4 | 21.2 | 14.2 | 7.2 |
| 625 ILAAAAAPLIVP | 12 | 8 | 50.2 | 195.8 | 2.2 | 20.9 | 13.9 | 7.0 |

TABLE 43-continued

| aMTD Sequences | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|
| | | | | | | A | B | C |
| 442 ALAALVPAVLVP | 12 | 7 | 57.3 | 203.3 | 2.3 | 20.4 | 13.6 | 6.9 |
| 912 VALLAPAVVVAP | 12 | 6 | 57.3 | 195.0 | 2.3 | 19.9 | 13.3 | 6.7 |
| 165 ALAVPVALAIVP | 12 | 5 | 50.2 | 203.3 | 2.4 | 19.8 | 13.2 | 6.7 |
| 422 VVAILAPLLAAP | 12 | 7 | 57.3 | 211.7 | 2.4 | 19.6 | 13.1 | 6.6 |
| 686 AALVAVLPVALP | 12 | 8 | 57.3 | 203.3 | 2.3 | 19.5 | 13.1 | 6.6 |
| 343 IVAVALPALVAP | 12 | 7 | 50.2 | 203.3 | 2.3 | 19.4 | 12.9 | 6.5 |
| 323 IVAVALPVALAP | 12 | 7 | 50.2 | 203.3 | 2.3 | 19.1 | 12.8 | 6.4 |
| 461 IAAVIVPAVALP | 12 | 7 | 50.2 | 203.3 | 2.4 | 19.0 | 12.7 | 6.4 |
| 21 AVALLPALLAVP | 12 | 6 | 57.3 | 211.7 | 2.3 | 18.9 | 12.6 | 6.4 |
| 404 LAAAVIPAAILP | 12 | 7 | 54.9 | 195.8 | 2.2 | 18.9 | 12.6 | 6.4 |
| 261 LVLVPLLAAAAP | 12 | 5 | 41.3 | 211.6 | 2.3 | 18.5 | 12.3 | 6.2 |
| 524 AVALIVVPALAP | 12 | 8 | 50.2 | 203.3 | 2.4 | 18.3 | 12.2 | 6.2 |
| 225 VAALLPAAAVLP | 12 | 6 | 57.3 | 187.5 | 2.1 | 18.3 | 12.2 | 6.2 |
| 264 LAAAPVVIVIAP | 12 | 5 | 50.2 | 203.3 | 2.4 | 18.2 | 12.1 | 6.1 |
| 1 AAALAPVVLALP | 12 | 6 | 57.3 | 187.5 | 2.1 | 17.7 | 11.8 | 6.0 |
| 382 AAALVIPAILAP | 12 | 7 | 54.3 | 195.8 | 2.2 | 17.7 | 11.8 | 6.0 |
| 463 AVAILVPLLAAP | 12 | 7 | 57.3 | 211.7 | 2.4 | 17.6 | 11.7 | 5.9 |
| 322 VVAIVLPALAAP | 12 | 7 | 50.2 | 203.3 | 2.3 | 17.6 | 11.7 | 5.9 |
| 503 AAIIIVLPAALP | 12 | 8 | 50.2 | 220.0 | 2.4 | 17.6 | 11.8 | 5.9 |
| 870 VLVAAVLPIAAP | 12 | 8 | 41.3 | 203.3 | 2.4 | 16.6 | 11.1 | 5.6 |
| 241 AAAVVPVLLVAP | 12 | 6 | 57.3 | 195.0 | 2.4 | 16.6 | 11.0 | 5.6 |
| 726 LAVAIIAPAVAP | 12 | 8 | 57.3 | 187.5 | 2.2 | 16.5 | 11.0 | 5.6 |
| 341 IVAVALPAVLAP | 12 | 7 | 50.2 | 203.3 | 2.3 | 16.4 | 10.9 | 5.5 |
| 542 ALALIVPAVAP | 12 | 8 | 50.2 | 211.6 | 2.4 | 16.2 | 10.8 | 5.5 |
| 361 AVVIVAPAVIAP | 12 | 7 | 50.2 | 195.0 | 2.4 | 16.0 | 10.7 | 5.4 |
| 224 ILAAVPIALAAP | 12 | 6 | 57.3 | 195.8 | 2.2 | 15.8 | 10.6 | 5.3 |
| 482 ILAVAAIPVAVP | 12 | 8 | 54.9 | 203.3 | 2.4 | 15.8 | 10.6 | 5.3 |
| 64 AIVALPVAVLAP | 12 | 6 | 50.2 | 203.3 | 2.4 | 15.8 | 10.6 | 5.3 |
| 484 LAVVLAAPAIVP | 12 | 8 | 50.2 | 203.3 | 2.4 | 15.6 | 10.4 | 5.3 |
| 868 VLVAAILPAAIP | 12 | 8 | 54.9 | 211.7 | 2.4 | 14.9 | 10.0 | 5.0 |
| 541 LLALIIAPAAAP | 12 | 8 | 57.3 | 204.1 | 2.1 | 14.8 | 9.9 | 5.0 |
| 666 AAIAIIAPAIVP | 12 | 8 | 50.2 | 195.8 | 2.3 | 14.7 | 9.9 | 5.0 |
| 665 LAIVLAAPVAVP | 12 | 8 | 50.2 | 203.3 | 2.3 | 14.7 | 9.9 | 5.0 |
| 363 AVLAVAPALIVP | 12 | 7 | 50.2 | 203.3 | 2.3 | 14.7 | 9.8 | 4.9 |
| 242 AALLVPALVAAP | 12 | 6 | 57.3 | 187.5 | 2.1 | 14.6 | 9.7 | 4.9 |
| 384 VIVAIAPALLAP | 12 | 7 | 50.2 | 211.6 | 2.4 | 14.0 | 9.4 | 4.7 |
| 877 VAIIAVPAVVAP | 12 | 7 | 57.3 | 195.0 | 2.4 | 14.0 | 9.4 | 4.7 |

TABLE 43-continued

| aMTD Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|
| 863 AAVVLLPIIAAP | 12 | 7 | 41.3 | 211.7 | 2.4 | 13.8 | 9.3 | 4.7 |
| 525 ALAIVVAPVAVP | 12 | 8 | 50.2 | 195.0 | 2.4 | 13.8 | 9.2 | 4.7 |
| 875 AIAIVVPAVAVP | 12 | 7 | 50.2 | 195.0 | 2.4 | 13.8 | 9.2 | 4.7 |
| 285 AIVLLPAAVVAP | 12 | 6 | 50.2 | 203.3 | 2.4 | 13.3 | 8.9 | 4.5 |
| 281 ALIVLPAAVAVP | 12 | 6 | 50.2 | 203.3 | 2.4 | 13.3 | 8.9 | 4.5 |
| 867 ALLVVIAPLAAP | 12 | 8 | 41.3 | 211.7 | 2.4 | 13.2 | 8.8 | 4.4 |
| 766 IVVIAVAPAVAP | 12 | 8 | 50.2 | 195.0 | 2.4 | 12.9 | 8.6 | 4.4 |
| 342 VIVALAPAVLAP | 12 | 7 | 50.2 | 203.3 | 2.3 | 12.7 | 8.5 | 4.3 |
| 881 AALIVVPAVAVP | 12 | 7 | 50.2 | 195.0 | 2.4 | 12.7 | 8.5 | 4.3 |
| 505 AIIIVIAPAAAP | 12 | 8 | 50.2 | 195.8 | 2.3 | 12.4 | 8.3 | 4.2 |

TABLE 44

| aMTD Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|
| 763 VAVLIAVPALAP | 12 | 8 | 57.3 | 203.3 | 2.3 | 12.3 | 7.2 | 4.2 |
| 706 IVAVALLPAVAP | 12 | 8 | 50.2 | 203.3 | 2.4 | 12.0 | 7.0 | 4.1 |
| 687 AILAVALPLLAP | 12 | 8 | 57.3 | 220.0 | 2.3 | 12.0 | 7.0 | 4.1 |
| 643 LALVLAAPAIVP | 12 | 8 | 50.2 | 211.6 | 2.4 | 11.8 | 7.9 | 4.0 |
| 282 VLAVAPALIVAP | 12 | 6 | 50.2 | 203.3 | 2.4 | 11.8 | 7.9 | 4.0 |
| 543 LLAALIAPAALP | 12 | 8 | 57.3 | 204.1 | 2.1 | 11.7 | 7.8 | 4.0 |
| 325 IVAVALPAVALP | 12 | 7 | 50.2 | 203.3 | 2.3 | 11.7 | 7.8 | 4.0 |
| 846 IAVAVAAPLLVP | 12 | 8 | 41.3 | 203.3 | 2.4 | 11.7 | 6.8 | 4.0 |
| 383 VIVALAPALLAP | 12 | 7 | 50.2 | 211.6 | 2.3 | 11.6 | 7.7 | 3.9 |
| 381 VVAIVLPAVAAP | 12 | 7 | 50.2 | 195.0 | 2.4 | 11.5 | 7.7 | 3.9 |
| 808 LVVLAAAPLAVP | 12 | 8 | 41.3 | 203.3 | 2.3 | 11.5 | 7.6 | 3.9 |
| 865 AVLVIAVPAIAP | 12 | 8 | 57.3 | 203.3 | 2.5 | 11.3 | 7.5 | 3.8 |
| 725 IAVLAVAPAVLP | 12 | 8 | 57.3 | 203.3 | 2.3 | 11.2 | 7.5 | 3.8 |
| 844 VVALLAPLIAAP | 12 | 7 | 41.3 | 211.8 | 2.4 | 11.2 | 7.5 | 3.8 |
| 897 AVIVPVAIIAAP | 12 | 5 | 50.2 | 203.3 | 2.5 | 11.2 | 7.5 | 3.8 |
| 605 VIAAVLAPVAVP | 12 | 8 | 57.3 | 195.0 | 2.4 | 11.0 | 7.4 | 3.7 |
| 744 AAVVIVAPVALP | 12 | 8 | 50.2 | 195.0 | 2.4 | 11.0 | 7.3 | 3.7 |
| 221 AAILAPIVALAP | 12 | 6 | 50.2 | 195.8 | 2.2 | 10.9 | 7.3 | 3.7 |
| 622 ALIVLAAPVAVP | 12 | 8 | 50.2 | 203.3 | 2.4 | 10.6 | 7.1 | 3.6 |
| 401 AALAVIPAAILP | 12 | 7 | 54.9 | 195.8 | 2.2 | 10.6 | 7.1 | 3.6 |
| 324 IVAVALPAALVP | 12 | 7 | 50.2 | 203.3 | 2.3 | 10.3 | 6.9 | 3.5 |
| 878 IVALVAPAAVVP | 12 | 7 | 50.2 | 195.0 | 2.4 | 10.3 | 6.9 | 3.5 |

TABLE 44-continued

| aMTD Sequences | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|
| | | | | | | A | B | C |
| 302 LALAPALALLAP | 12 | 5 | 57.3 | 204.2 | 2.1 | 10.2 | 6.8 | 3.4 |
| 635 ALLVAVLPAALP | 12 | 8 | 57.3 | 211.7 | 2.3 | 10.2 | 5.9 | 3.4 |
| 848 AVAIVVLPAVAP | 12 | 8 | 50.2 | 195.0 | 2.4 | 10.0 | 6.7 | 3.4 |
| 602 VIVALAAPVLAP | 12 | 8 | 50.2 | 203.3 | 2.4 | 9.9 | 5.8 | 3.4 |
| 788 AIAVAIAPVALP | 12 | 8 | 57.3 | 187.5 | 2.3 | 9.8 | 6.6 | 3.3 |
| 145 LLAVVPAVALAP | 12 | 6 | 57.3 | 203.3 | 2.3 | 9.5 | 6.3 | 3.2 |
| 11 VVALAPALAALP | 12 | 6 | 57.3 | 187.5 | 2.1 | 9.5 | 6.3 | 3.2 |
| 141 AVIVLPALAVAP | 12 | 6 | 50.2 | 203.3 | 2.4 | 9.4 | 6.3 | 3.2 |
| 521 LAALIVVPAVAP | 12 | 8 | 50.2 | 203.3 | 2.4 | 9.4 | 6.3 | 3.2 |
| 425 AVVAIAPVLALP | 12 | 7 | 57.3 | 203.3 | 2.4 | 9.4 | 6.3 | 3.2 |
| 365 AVIVVAPALLAP | 12 | 7 | 50.2 | 203.3 | 2.3 | 9.3 | 6.2 | 3.1 |
| 263 ALAVIPAAAILP | 12 | 6 | 54.9 | 195.8 | 2.2 | 9.0 | 6.0 | 3.0 |
| 345 ALLIVAPVAVAP | 12 | 7 | 50.2 | 203.3 | 2.3 | 8.9 | 5.9 | 3.0 |
| 850 LVIALAAPVALP | 12 | 8 | 57.3 | 211.7 | 2.4 | 8.8 | 5.9 | 3.0 |
| 144 VLAIVPAVALAP | 12 | 6 | 50.2 | 203.3 | 2.4 | 8.8 | 5.9 | 3.0 |
| 767 IVVAAVVPALAP | 12 | 8 | 50.2 | 195.0 | 2.4 | 8.5 | 5.0 | 2.9 |
| 185 AALVLPLIIAAP | 12 | 6 | 41.3 | 220.0 | 2.4 | 8.5 | 5.7 | 2.9 |
| 849 AVILLAPLIAAP | 12 | 7 | 57.3 | 220.0 | 2.4 | 8.3 | 4.8 | 2.8 |
| 864 ALLVIAPAIAVP | 12 | 7 | 57.3 | 211.7 | 2.4 | 8.2 | 4.8 | 2.8 |
| 162 AVVALPAALIVP | 12 | 6 | 50.2 | 203.3 | 2.4 | 8.2 | 5.5 | 2.8 |
| 164 LAAVLPALLAAP | 12 | 6 | 57.3 | 195.8 | 2.1 | 8.2 | 5.5 | 2.8 |
| 907 VAIALAPVVVAP | 12 | 7 | 57.3 | 195.0 | 2.4 | 8.1 | 5.4 | 2.8 |
| 444 LAAALVPVALVP | 12 | 7 | 57.3 | 203.3 | 2.3 | 8.1 | 5.4 | 2.7 |
| 443 ALAALVPVALVP | 12 | 7 | 57.3 | 203.3 | 2.3 | 8.0 | 5.3 | 2.7 |
| 901 ALAVLPAVAVP | 12 | 7 | 57.3 | 195.0 | 2.4 | 7.7 | 5.1 | 2.6 |
| 887 VLAVAPAVAVLP | 12 | 6 | 57.3 | 195.0 | 2.4 | 7.7 | 5.1 | 2.6 |
| 746 VAIIVVAPALAP | 12 | 8 | 50.2 | 203.3 | 2.4 | 7.6 | 4.4 | 2.6 |
| 902 ALVAPLLAVAVP | 12 | 5 | 41.3 | 203.3 | 2.3 | 7.6 | 5.1 | 2.6 |
| 565 VAIVLVAPAVAP | 12 | 8 | 50.2 | 195.0 | 2.4 | 7.5 | 5.0 | 2.5 |
| 245 AAALAPVLALVP | 12 | 6 | 57.3 | 187.5 | 2.1 | 7.5 | 5.0 | 2.5 |
| 743 AIAIALVPVALP | 12 | 8 | 57.3 | 211.6 | 2.4 | 7.4 | 4.9 | 2.5 |
| 465 AVVILVPLAAAP | 12 | 7 | 57.3 | 203.3 | 2.4 | 7.4 | 4.9 | 2.5 |
| 104 AVVAAPLVLALP | 12 | 6 | 41.3 | 203.3 | 2.3 | 7.3 | 4.9 | 2.5 |

TABLE 45

| aMTD Sequences | | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|---|
| | | | | | | | A | B | C |
| 707 | IVALAVLPAVAP | 12 | 8 | 50.2 | 203.3 | 2.4 | 7.3 | 4.9 | 2.5 |
| 872 | VLAAAVLPLVVP | 12 | 8 | 41.3 | 219.2 | 2.5 | 7.3 | 4.9 | 2.5 |
| 583 | AVILALAPIVAP | 12 | 8 | 50.2 | 211.6 | 2.4 | 7.3 | 4.8 | 2.4 |
| 879 | AAIVLLPAVVVP | 12 | 7 | 50.2 | 219.1 | 2.5 | 7.2 | 4.8 | 2.4 |
| 784 | VAALPAVALVVP | 12 | 5 | 57.3 | 195.0 | 2.4 | 7.1 | 4.7 | 2.4 |
| 893 | VIAIPAILAAAP | 12 | 5 | 54.9 | 195.8 | 2.3 | 7.0 | 4.7 | 2.4 |
| 13 | AAALVPVVALLP | 12 | 6 | 57.3 | 203.3 | 2.3 | 7.0 | 4.7 | 2.4 |
| 809 | LIVLAAPALAAP | 12 | 7 | 50.2 | 195.8 | 2.2 | 7.0 | 4.7 | 2.4 |
| 445 | ALAALVPALVVP | 12 | 7 | 57.3 | 203.3 | 2.3 | 6.9 | 4.6 | 2.3 |
| 81 | AALLPALAALLP | 12 | 5 | 57.3 | 204.2 | 2.1 | 6.9 | 4.6 | 2.3 |
| 667 | LAVAIVAPALVP | 12 | 8 | 50.2 | 203.3 | 2.3 | 6.9 | 4.6 | 2.3 |
| 906 | AVIALAPVVVAP | 12 | 7 | 57.3 | 195.0 | 2.4 | 6.8 | 4.6 | 2.3 |
| 483 | ILAAAIIPAALP | 12 | 8 | 54.9 | 204.1 | 2.2 | 6.8 | 4.5 | 2.3 |
| 485 | AILAAIVPLAVP | 12 | 8 | 50.2 | 211.6 | 2.4 | 6.8 | 4.5 | 2.3 |
| 421 | AAILAAPLIAVP | 12 | 7 | 57.3 | 195.8 | 2.2 | 6.7 | 4.5 | 2.3 |
| 585 | ALIVAIAPALVP | 12 | 8 | 50.2 | 211.6 | 2.4 | 6.6 | 4.4 | 2.2 |
| 424 | AVVVAAPVLALP | 12 | 7 | 57.3 | 195.0 | 2.4 | 6.6 | 4.4 | 2.2 |
| 364 | LVAAVAPALIVP | 12 | 7 | 50.2 | 203.3 | 2.3 | 6.5 | 4.3 | 2.2 |
| 402 | ALAAVIPAAILP | 12 | 7 | 54.9 | 195.8 | 2.2 | 6.4 | 4.3 | 2.2 |
| 462 | IAAVLVPAVALP | 12 | 7 | 57.3 | 203.3 | 2.4 | 6.3 | 4.2 | 2.1 |
| 265 | VLAIAPLLAAVP | 12 | 6 | 41.3 | 211.6 | 2.3 | 6.0 | 4.0 | 2.0 |
| 301 | VIAAPVLAVLAP | 12 | 6 | 57.3 | 203.3 | 2.4 | 6.0 | 4.0 | 2.0 |
| 183 | LLAAPVVIALAP | 12 | 6 | 57.3 | 211.6 | 2.4 | 6.0 | 4.0 | 2.0 |
| 243 | AAVLLPVALAAP | 12 | 6 | 57.3 | 187.5 | 2.1 | 5.9 | 3.9 | 2.0 |
| 664 | ILIAIAIPAAAP | 12 | 8 | 54.9 | 204.1 | 2.3 | 5.7 | 3.8 | 1.9 |
| 783 | IVALVPAVAIAP | 12 | 6 | 50.2 | 203.3 | 2.5 | 5.7 | 3.8 | 1.9 |
| 502 | AIVALAVPVLAP | 12 | 8 | 50.2 | 203.3 | 2.4 | 5.6 | 3.7 | 1.9 |
| 262 | ALIAVPAIIVAP | 12 | 6 | 50.2 | 211.6 | 2.4 | 5.5 | 3.7 | 1.9 |
| 683 | LAIVLAAPAVLP | 12 | 8 | 50.2 | 211.7 | 2.4 | 5.5 | 3.2 | 1.9 |
| 830 | IALVAAPVALVP | 12 | 7 | 57.3 | 203.3 | 2.4 | 5.3 | 3.5 | 1.8 |
| 764 | AVALAVLPAVVP | 12 | 8 | 57.3 | 195.0 | 2.3 | 5.0 | 3.4 | 1.7 |
| 807 | AVALAVPALVLP | 12 | 7 | 57.3 | 203.3 | 2.3 | 5.0 | 3.3 | 1.7 |
| 184 | LAAIVPAIIAVP | 12 | 6 | 50.2 | 211.6 | 2.4 | 4.8 | 3.2 | 1.6 |
| 305 | IALAAPILLAAP | 12 | 6 | 57.3 | 204.2 | 2.2 | 4.8 | 3.2 | 1.6 |
| 101 | LVALAPVAAVLP | 12 | 6 | 57.3 | 203.3 | 2.3 | 4.5 | 3.0 | 1.5 |
| 304 | AIILAPIAAIAP | 12 | 6 | 57.3 | 204.2 | 2.3 | 4.4 | 3.0 | 1.5 |
| 604 | VALIAVAPAVVP | 12 | 3 | 57.3 | 195.0 | 2.4 | 4.3 | 2.5 | 1.5 |

TABLE 45-continued

| aMTD | Sequences | Length | Proline Position (PP) | Rigidity/ Flexibility (II) | Sturctural Feature (AI) | Hydropathy (GRAVY) | Relative Ratio (Fold) A | B | C |
|---|---|---|---|---|---|---|---|---|---|
| 645 | ALAVVALPAIVP | 12 | 8 | 50.2 | 203.3 | 2.4 | 4.3 | 2.9 | 1.5 |
| 201 | LALAVPALAALP | 12 | 6 | 57.3 | 195.8 | 2.1 | 4.2 | 2.8 | 1.4 |
| 163 | LALVLPAALAAP | 12 | 6 | 57.3 | 195.8 | 2.1 | 4.1 | 2.4 | 1.4 |
| 832 | AVAAIVPVIVAP | 12 | 7 | 43.2 | 195.0 | 2.5 | 4.1 | 2.7 | 1.4 |
| 182 | ALIAPVVALVAP | 12 | 6 | 57.3 | 203.3 | 2.4 | 4.0 | 2.7 | 1.4 |
| 23 | VVLVLPAAAAVP | 12 | 6 | 57.3 | 195.0 | 2.4 | 4.0 | 2.6 | 1.3 |
| 105 | LLALAPAALLAP | 12 | 6 | 57.3 | 204.1 | 2.1 | 4.0 | 2.6 | 1.3 |
| 561 | AAVAIVLPAVVP | 12 | 8 | 50.2 | 195.0 | 2.4 | 3.9 | 2.6 | 1.3 |
| 765 | AVALAVVPAVLP | 12 | 8 | 57.3 | 195.0 | 2.3 | 3.8 | 2.2 | 1.3 |
| 684 | AAIVLALPAVLP | 12 | 8 | 50.2 | 211.7 | 2.4 | 3.5 | 2.1 | 1.2 |
| 143 | AVLAVPAVLVAP | 12 | 6 | 57.3 | 195.0 | 2.4 | 3.3 | 2.2 | 1.1 |
| 504 | LIVALAVPALAP | 12 | 8 | 50.2 | 211.7 | 2.4 | 3.3 | 2.2 | 1.1 |
| 22 | AVVLVPVLAAAP | 12 | 6 | 57.3 | 195.0 | 2.4 | 3.1 | 2.1 | 1.1 |
| 5 | AAALLPVALVAP | 12 | 6 | 57.3 | 187.5 | 21 | 3.1 | 2.1 | 1.0 |
| 283 | AALLAPALIVAP | 12 | 6 | 50.2 | 195.8 | 2.2 | 3.1 | 2.0 | 1.0 |
| 65 | IAIVAPVVALAP | 12 | 6 | 50.2 | 203.3 | 2.4 | 3.0 | 2.0 | 1.0 |
| 883 | LAIVPAAIAALP | 12 | 6 | 50.2 | 195.8 | 2.2 | 3.0 | 2.0 | 1.0 |
| 123 | AAIIVPAALLAP | 12 | 6 | 50.2 | 195.8 | 2.2 | 2.9 | 2.0 | 1.0 |

TABLE 46

| aMTD | Sequences | Length | Proline Position (PP) | Rigidity/ Flexibility (II) | Sturctural Feature (AI) | Hydropathy (GRAVY) | Relative Ratio (Fold) A | B | C |
|---|---|---|---|---|---|---|---|---|---|
| 284 | ALIAPAVALIVP | 12 | 5 | 50.2 | 211.7 | 2.4 | 2.8 | 1.8 | 0.9 |
| 205 | ALALVPAIAALP | 12 | 6 | 57.3 | 195.8 | 2.2 | 2.6 | 1.7 | 0.9 |
| 42 | VAALPVVAVVAP | 12 | 5 | 57.3 | 186.7 | 2.4 | 2.5 | 1.7 | 0.8 |
| 121 | AIVALPALALAP | 12 | 6 | 50.2 | 195.8 | 2.2 | 2.5 | 1.7 | 0.8 |
| 25 | IVAVAPALVALP | 12 | 6 | 50.2 | 203.3 | 2.4 | 2.4 | 1.6 | 0.8 |
| 24 | IALAAPALIVAP | 12 | 6 | 50.2 | 195.8 | 2.2 | 2.3 | 1.6 | 0.8 |
| 204 | LIAALPAVAALP | 12 | 6 | 57.3 | 195.8 | 2.2 | 2.2 | 1.5 | 0.8 |
| 12 | LLAAVPAVLLAP | 12 | 6 | 57.3 | 211.7 | 2.3 | 2.2 | 1.5 | 0.7 |
| 43 | LLAAPLVVAAVP | 12 | 5 | 41.3 | 187.5 | 2.1 | 2.1 | 1.4 | 0.7 |
| 103 | ALIAAPILALAP | 12 | 6 | 57.3 | 204.2 | 2.2 | 2.1 | 1.4 | 0.7 |
| 82 | AVVLAPVAAVLP | 12 | 6 | 57.3 | 195.0 | 2.4 | 2.1 | 1.4 | 0.7 |
| 4 | ALALLPVAALAP | 12 | 6 | 57.3 | 195.8 | 2.1 | 2.0 | 1.3 | 0.7 |
| 85 | LLVLPAAALAAP | 12 | 5 | 57.3 | 195.8 | 2.1 | 1.9 | 1.3 | 0.7 |
| 63 | AALLVPALVAVP | 12 | 6 | 57.3 | 203.3 | 2.3 | 1.9 | 1.3 | 0.7 |

TABLE 46-continued

| aMTD | Sequences | Length | Proline Position (PP) | Rigidity/ Flexibility (II) | Sturctural Feature (AI) | Hydropathy (GRAVY) | Relative Ratio (Fold) A | B | C |
|---|---|---|---|---|---|---|---|---|---|
| 44 | ALAVPVALLVAP | 12 | 5 | 57.3 | 203.3 | 2.3 | 1.6 | 1.1 | 0.5 |
| 84 | AAVAAPLLLALP | 12 | 6 | 41.3 | 195.8 | 2.1 | 1.5 | 1.0 | 0.5 |
| 62 | VALLAPVALAVP | 12 | 6 | 57.3 | 203.3 | 2.3 | 1.4 | 0.9 | 0.5 |
| 83 | LAVAAPLALALP | 12 | 6 | 41.3 | 195.8 | 2.1 | 1.4 | 0.9 | 0.5 |
| 102 | LALAPAALALLP | 12 | 5 | 57.3 | 204.2 | 2.1 | 1.4 | 0.9 | 0.5 |
| 623 | VAAAIALPAIVP | 12 | 8 | 50.2 | 187.5 | 2.3 | 0.8 | 0.6 | 0.3 |
| | | | | | | | 19.6 ± 1.6 | 13.1 ± 1.1 | 6.6 ± 0.5 |

Moreover, compared to reference CPPs (B type: MTM12 and C type: MTD85), novel 240 aMTDs averaged of 13±1.1 (maximum 109.9) and 6.6±0.5 (maximum 55.5) fold higher cell-permeability, respectively (TABLE 42-47).

TABLE 47

| | Negative Control rP38 | MTM12 | MTD85 |
|---|---|---|---|
| aMTD The Average of 240 aMTDs | 19.6 ± 1.6* (Best: 164.2) | 13.1 ± 1.1* (Best: 109.9) | 6.6 ± 0.5* (Best: 55.5) |

*Relative Fold (aMTD in Geo Mean in its comparison to rP38, MTM12 or MTD85)

In addition, cell-permeability of 31 rPeptides has been compared with that of 240 aMTDs (0.3±0.04; TABLE 48 and 49).

TABLE 48

| Number | ID | Sequence | Length | Proline Position (PP) | Rigidity/ Flexibility (II) | Sturctural Feature (AI) | Hydropathy (GRAVY) | Relative Ratio to aMTD AVE |
|---|---|---|---|---|---|---|---|---|
| 1 | 692 | PAPLPPVVILAV | 12 | 1, 3, 5, 6 | 105.5 | 186.7 | 1.8 | 0.74 |
| 2 | 26 | AAIALAAPLAIV | 12 | 8 | 18.1 | 204.2 | 2.5 | 0.65 |
| 3 | 113 | PVAVALLIAVPP | 12 | 1, 11, 12 | 57.3 | 195.0 | 2.1 | 0.61 |
| 4 | 466 | IIAAAAPLAIIP | 12 | 7, 12 | 22.8 | 204.2 | 2.3 | 0.52 |
| 5 | 167 | VAIAIPAALAIP | 12 | 6, 12 | 20.4 | 195.8 | 2.3 | 0.50 |
| 6 | 97 | ALLAAPPALLAL | 12 | 6, 7 | 57.3 | 204.2 | 2.1 | 0.41 |
| 7 | 390 | VPLLVPVVPVVP | 12 | 2, 6, 9, 12 | 105.4 | 210.0 | 2.2 | 0.41 |
| 8 | 426 | AAALAIPLAIIP | 12 | 7, 12 | 4, 37 | 204.2 | 2.2 | 0.40 |
| 9 | 214 | ALIVAPALMALP | 12 | 6, 12 | 60.5 | 187.5 | 2.2 | 0.33 |
| 10 | 68 | VAPVLPAAPLVP | 12 | 3, 6, 9, 12 | 105.5 | 162.5 | 1.6 | 0.32 |
| 11 | 39 | CYNTSPCTGCCY | 12 | 6 | 52.5 | 0.0 | 0.0 | 0.29 |
| 12 | 934 | LILAPAAVVAAA | 12 | 5 | 57.3 | 195.8 | 2.5 | 0.28 |
| 13 | 938 | VPVLLPVVVPVP | 12 | 2, 6, 10, 12 | 121.5 | 210.0 | 2.2 | 0.28 |
| 14 | 329 | LPVLVPVVPVVP | 12 | 2, 6, 9, 12 | 121.5 | 210.0 | 2.2 | 0.23 |
| 15 | 606 | AAAIAAIPIIIP | 12 | 8, 12 | 4.4 | 204.2 | 2.4 | 0.20 |
| 16 | 49 | VVPAAPAVPVVP | 12 | 3, 6, 9, 12 | 121.5 | 145.8 | 1.7 | 0.18 |

TABLE 48-continued

| Number | ID | Sequence | Length | Proline Position (PP) | Rigidity/ Flexibility (II) | Structural Feature (AI) | Hydropathy (GRAVY) | Relative Ratio to aMTD AVE |
|---|---|---|---|---|---|---|---|---|
| 17 | 139 | TGSTNSPTCTST | 12 | 7 | 53.4 | 0.0 | -0.7 | 0.17 |
| 18 | 772 | LPVAPVIPIIVP | 12 | 2, 5, 8, 12 | 79.9 | 210.8 | 2.1 | 0.16 |
| 19 | 921 | IWWFVVLPLVVP | 12 | 8, 12 | 41.3 | 194.2 | 2.2 | 0.14 |
| 20 | 66 | AGVLGGPIMGVP | 12 | 7, 12 | 35.5 | 121.7 | 1.3 | 0.13 |
| 21 | 693 | AAPVLPVAVPIV | 12 | 3, 6, 10 | 82.3 | 186.7 | 2.1 | 0.13 |
| 22 | 18 | NYCCTPTTNGQS | 12 | 6 | 47.9 | 0.0 | -0.9 | 0.10 |
| 23 | 16 | NNSCTTYTNGSQ | 12 | None | 47.4 | 0.0 | -1.4 | 0.08 |
| 24 | 227 | LAAIVPIAAAVP | 12 | 6, 12 | 34.2 | 187.5 | 2.2 | 0.08 |
| 25 | 17 | GGCSAPQTTCSN | 12 | 6 | 51.6 | 8.3 | -0.5 | 0.08 |
| 26 | 67 | LDAEVPLADDVP | 12 | 6, 12 | 34.2 | 130.0 | 0.3 | 0.08 |
| 27 | 635 | GSTGGSQQNNQY | 12 | None | 31.9 | 0.0 | -1.9 | 0.07 |
| 28 | 29 | VLPPLPVLPVLP | 12 | 3, 4, 6, 9, 12 | 121.5 | 202.5 | 1.7 | 0.07 |
| 29 | 57 | QNNCNTSSQGGG | 12 | None | 52.4 | 0.0 | -1.6 | 0.06 |
| 30 | 700 | GTSNTCQSNQNS | 12 | None | 19.1 | 0.0 | -1.6 | 0.05 |
| 31 | 38 | YYNQSTCGGQCY | 12 | ND | 53.8 | 0.0 | -1.0 | 0.05 |
|  |  |  |  |  |  |  | AVE | 0.3 ± 0.04 |

TABLE 49

|  | Relative Ratio to aMTD AVE* |
|---|---|
| rPeptide The Average of 31 aMTDs | 0.3 ± 0.04 |

*Out of 240 aMTDs, average relative fold of aMTD had been 19.6 fold compared to type A (rP38).

In summary, relatively cell-permeability of aMTDs has shown maximum of 164.0, 109.9 and 55.5 fold higher to rP38, MTM12 and MTD85, respectively. In average of total 240 aMTD sequences, 19.6±1.6, 13.1±1.1 and 6.6±0.5 fold higher cell-permeability are shown to the rP38, MTM12 and MTD85, respectively (TABLE 42-47). Relative cell-permeability of negative control (rP38) to the 240 aMTDs is only 0.3±0.04 fold.

4-5. Intracellular Delivery and Localization of aMTD-Fused Recombinant Proteins

Recombinant proteins fused to the aMTDs were tested to determine their intracellular delivery and localization by laser scanning confocal microscopy with a negative control (rP38) and previous published CPPs (MTM12 and MTD85) as the positive control references. NIH3T3 cells were exposed to 10 μM of FITC-labeled protein for 1 hour at 37° C., and nuclei were counterstained with DAPI. Then, cells were examined by confocal laser scanning microscopy (FIG. 7). Recombinant proteins fused to aMTDs clearly display intracellular delivery and cytoplasmic localization (FIG. 7) that are typically higher than the reference CPPs (MTM12 and MTD85). The rP38-fused recombinant protein did not show internalized fluorescence signal (FIG. 7a). In addition, as seen in FIG. 8, rPeptides (his-tagged CRA recombinant proteins fused to each rPeptide) display lower- or non-cell-permeability.

4-6. Summary of Quantitative and Visual Cell-Permeability of Newly Developed aMTDs Histidine-tagged aMTD-fused cargo recombinant proteins have been greatly enhanced in their solubility and yield. Thus, FITC-conjugated recombinant proteins have also been tested to quantitate and visualize intracellular localization of the proteins and demonstrated higher cell-permeability compared to the reference CPPs.

In the previous studies using the hydrophobic signal-sequence-derived CPPs—MTS/MTM or MTDs, 17 published sequences have been identified and analyzed in various characteristics such as length, molecular weight, pI value, bending potential, rigidity, flexibility, structural feature, hydropathy, amino acid residue and composition, and secondary structure of the peptides. Based on these analytical data of the sequences, novel artificial and non-natural peptide sequences designated as advanced MTDs (aMTDs) have been invented and determined their functional activity in intracellular delivery potential with aMTD-fused recombinant proteins.

aMTD-fused recombinant proteins have promoted the ability of protein transduction into the cells compared to the recombinant proteins containing rPeptides and/or reference hydrophobic CPPs (MTM12 and MTD85). According to the results, it has been demonstrated that critical factors of cell-penetrating peptide sequences play a major role to determine peptide-mediated intracellular delivery by penetrating plasma membrane. In addition, cell-permeability can considerably be improved by following the rational that all satisfy the critical factors.

5. Structure/Sequence Activity Relationship (SAR) of aMTDs on Delivery Potential After determining the cell-permeability of novel aMTDs, structure/sequence activity relationship (SAR) has been analyzed for each critical factor in selected some of and all of novel aMTDs (FIG. 13 to 16 and TABLE 50).

TABLE 50

| Rank of Delivery Potential | Rigidity/ Flexibility (II) | Structural Feature (AI) | Hydropathy (GRAVY) | Relative Ratio (Fold) | | | Amino Acid Composition | | | |
|---|---|---|---|---|---|---|---|---|---|---|
| | | | | A | B | C | A | V | I | L |
| 1~10 | 55.9 | 199.2 | 2.3 | 112.7 | 75.5 | 38.1 | 4.0 | 3.5 | 0.4 | 2.1 |
| 11~20 | 51.2 | 205.8 | 2.4 | 56.2 | 37.6 | 19.0 | 4.0 | 2.7 | 1.7 | 1.6 |
| 21~30 | 49.1 | 199.2 | 2.3 | 43.6 | 28.9 | 14.6 | 4.3 | 2.7 | 1.4 | 1.6 |
| 31~40 | 52.7 | 201.0 | 2.4 | 34.8 | 23.3 | 11.8 | 4.2 | 2.7 | 1.5 | 1.6 |
| 41~50 | 53.8 | 201.9 | 2.3 | 30.0 | 20.0 | 10.1 | 4.3 | 2.3 | 1.1 | 2.3 |
| 51~60 | 51.5 | 205.2 | 2.4 | 23.5 | 15.7 | 7.9 | 4.4 | 2.1 | 1.5 | 2.0 |
| 222~231 | 52.2 | 197.2 | 2.3 | 2.2 | 1.5 | 0.8 | 4.5 | 2.1 | 1.0 | 2.4 |
| 232~241 | 54.1 | 199.7 | 2.2 | 1.7 | 1.2 | 0.6 | 4.6 | 1.7 | 0.2 | 3.5 |

5-1.

Proline Position: In regards to the bending potential (proline position: PP), aMTDs with its proline at 7' or 8' amino acid in their sequences have much higher cell-permeability compared to the sequences in which their proline position is at 5' or 6' (FIGS. 14a and 15a).

5-2.

Hydropathy: In addition, when the aMTDs have GRAVY (Grand Average of Hydropathy) ranging in 2.1-2.2, these sequences display relatively lower cell-permeability, while the aMTDs with 2.3-2.6 GRAVY are shown significantly higher one (FIGS. 14b and 15b).

5-3.

rPeptide SAR: To the SAR of aMTDs, rPeptides have shown similar SAR correlations in the cell-permeability, pertaining to their proline position (PP) and hydropathy (GRAVY). These results confirms that rPeptides with high GRAVY (2.4-2.6) have better cell-permeability (FIG. 16).

5-4. Analysis of Amino Acid Composition:

In addition to proline position and hydropathy, the difference of amino acid composition is also analyzed. Since aMTDs are designed based on critical factors, each aMTD-fused recombinant protein has equally two proline sequences in the composition. Other hydrophobic and aliphatic amino acids—alanine, isoleucine, leucine and valine—are combined to form the rest of aMTD peptide sequences.

Alanine:

In the composition of amino acids, the result does not show a significant difference by the number of alanine in terms of the aMTD's delivery potential because all of the aMTDs have three to five alanines. In the sequences, however, four alanine compositions show the most effective delivery potential (geometric mean) (FIG. 13a).

Leucine and Isoleucine:

Meanwhile, the compositions of isoleucine and leucine in the aMTD sequences show inverse relationship between the number of amino acid (I and L) and delivery potential of aMTDs. Lower number of isoleucine and leucine in the sequences tends to have higher delivery potential (geometric mean) (FIGS. 13a and 13b).

Valine:

Conversely, the composition of valine of aMTD sequences shows positive correlation with their cell-permeability. When the number of valine in the sequence is low, the delivery potential of aMTD is also relatively low (FIG. 13b).

Ten aMTDs having the highest cell-permeability are selected (average geometric mean: 2584±126). Their average number of valine in the sequences is 3.5; 10 aMTDs having relatively low cell-permeability (average geometric mean: 80±4) had average of 1.9 valine amino acids. The average number of valine in the sequences is lowered as their cell-permeability is also lowered as shown in FIG. 13b. Compared to higher cell-permeable aMTDs group, lower sequences had average of 1.9 in their valine composition. Therefore, to obtain high cell-permeable sequence, an average of 2-4 valines should be composed in the sequence.

5-5. Conclusion of SAR Analysis: As seen in FIG. 15, all 240 aMTDs have been examined for these association of the cell-permeability and the critical factors: bending potential (PP), rigidity/flexibility (II), structure feature (AI), and hydropathy (GRAVY), amino acid length and composition. Through this analysis, cell-permeability of aMTDs tends to be lower when their central proline position is at 5' or 6' and GRAVY is 2.1 or lower (FIG. 15). Moreover, after investigating 10 higher and 10 lower cell-permeable aMTDs, these trends are clearly shown to confirm the association of cell-permeability with the central proline position and hydropathy.

6. Experimental Confirmation of Index Range/Feature of Critical Factors

The range and feature of five out of six critical factors have been empirically and experimentally determined that are also included in the index range and feature of the critical factors initially proposed before conducting the experiments and SAR analysis. In terms of index range and feature of critical factors of newly developed 240 aMTDs, the bending potential (proline position: PP), rigidity/flexibility (Instability Index: II), structural feature (Aliphatic Index: AI), hydropathy (GRAVY), amino acid length and composition are all within the characteristics of the critical factors derived from analysis of reference hydrophobic CPPs.

Therefore, our hypothesis to design and develop new hydrophobic CPP sequences as advanced MTDs is empirically and experimentally proved and demonstrated that critical factor-based new aMTD rational design is correct.

TABLE 51

Summarized Critical Factors of aMTD

| Critical Factor | Newly Designed CPPs Range | Analysis of Experimental Results Range |
|---|---|---|
| Bending Potential (Praline Position: PP) | Proline presences in the middle (5', 6', 7' or 8') and at the end of peptides | Proline presences in the middle (5', 6', 7' or 8') and at the end of peptides |

TABLE 51-continued

Summarized Critical Factors of aMTD

| Critical Factor | Newly Designed CPPs Range | Analysis of Experimental Results Range |
|---|---|---|
| Rigidity/Flexibility (Instability Index: II) | 40-60 | 41.3-57.3 |
| Structural Feature (Aliphatic Index: AI) | 180-220 | 187.5-220.0 |
| Hydropathy (Grand Average of Hydropathy GRAVY) | 2.1-2.6 | 2.2-2.6 |
| Length (Number of Amino Acid) | 9-13 | 12 |
| Amino acid Composition | A, V, I, L, P | A, V, I, L, P |

7. Summary of this Invention

For this invention, 240 aMTD sequences have been designed and developed based on the critical factors. Quantitative and visual cell-permeability of 240 aMTDs (hydrophobic, flexible, bending, aliphatic and 12 a/a-length peptides) are all practically determined.

To measure the cell-permeability of aMTDs, rPeptides have also been designed and tested. As seen in FIG. 13 to 15, there are vivid association of cell-permeability and the critical factors of the peptides. Out of these critical factors, we are able to configure that the most effective cell-permeable aMTDs have the amino acid length of 12; composition of A, V, L, I and P; multiple proline located at either 7' or 8' and at the end (12'); instability index ranged of 41.3-57.3; aliphatic index ranged of 187.5-220.0; and hydropathy (GRAVY) ranged of 2.2-2.6.

These examined critical factors are within the range that we have set for our critical factors; therefore, we are able to confirm that the aMTDs that satisfy these critical factors have relatively high cell-permeability and much higher intracellular delivery potential compared to reference hydrophobic CPPs reported during the past two decades.

8. Discovery and Development of Protein-Based New Biotherapeutics with MITT Enabled by aMTDs for Protein Therapy It has been widely evident that many human diseases are caused by proteins with deficiency or over-expression that causes mutations such as gain-of-function or loss-of-function. If biologically active proteins could be delivered for replacing abnormal proteins within a short time frame, possibly within an hour or two, in a quantitative manner, the dosage may be regulated depending on when and how proteins may be needed. By significantly improving the solubility and yield of novel aMTD in this invention (TABLE 47), one could expect its practical potential as an agent to effectively deliver therapeutic macromolecules such as proteins, peptides, nucleic acids, and other chemical compounds into live cells as well as live mammals including human. Therefore, newly developed MITT utilizing the pool (240) of novel aMTDs can be used as a platform technology for discovery and development of protein-based biotherapeutics to apprehend intracellular protein therapy after determining the optimal cargo-aMTD relationship.

EXAMPLE

The following examples are presented to aid practitioners of the invention, to provide experimental support for the invention, and to provide model protocols. In no way are these examples to be understood to limit the invention.

Example 1. Development of Novel Advanced Macromolecule Transduction Domain (aMTD)

H-regions of signal sequences (HRSP)-derived CPPs (MTS/MTM and MTD) do not have a common sequence, a sequence motif, and/or a common structural homologous feature. In this invention, the aim is to develop improved hydrophobic CPPs formatted in the common sequence and structural motif that satisfy newly determined 'critical factors' to have a 'common function', to facilitate protein translocation across the plasma membrane with similar mechanism to the analyzed CPPs.

The structural motif as follows:

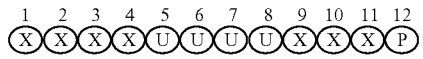

Here, X(s) refer to either Alanine (A), Valine (V), Leucine (L) or Isoleucine (I); and Proline (P) can be positioned in one of U(s) (either 5', 6', 7' or 8'). The remaining U(s) are composed of either A, V, L or I, P at the 12' is Proline.

In TABLE 9, universal common sequence/structural motif is provided as follows. The amino acid length of the peptides in this invention ranges from 9 to 13 amino acids, mostly 12 amino acids, and their bending potentials are dependent with the presence and location of proline in the middle of sequence (at 5', 6', 7' or 8' amino acid) and at the end of peptide (at 12') for recombinant protein bending. Instability index (II) for rigidity/flexibility of aMTDs is 11<40, grand average of hydropathy (GRAVY) for hydropathy is around 2.2, and aliphatic index (AI) for structural features is around 200 (TABLE 9). Based on these standardized critical factors, new hydrophobic peptide sequences, namely advanced macromolecule transduction domain peptides (aMTDs), in this invention have been developed and summarized in TABLE 10 to 15.

Example 2. Construction of Expression Vectors for Recombinant Proteins Fused to aMTDs Our newly developed technology has enabled us to expand the method for making cell-permeable recombinant proteins. The expression vectors were designed for histidine-tagged CRA proteins fused with aMTDs or rPeptides. To construct expression vectors for recombinant proteins, polymerase chain reaction (PCR) had been devised to amplify each designed aMTD or rPeptide fused to CRA.

The PCR reactions (100 ng genomic DNA, 10 pmol each primer, each 0.2 mM dNTP mixture, 1× reaction buffer and 2.5 U Pfu(+) DNA polymerase (Doctor protein, Korea)) was digested on the restriction enzyme site between Nde I (5') and Sal I (3') involving 35 cycles of denaturation (95° C.), annealing (62° C.), and extension (72° C.) for 30 seconds each. For the last extension cycle, the PCR reactions remained for 5 minutes at 72° C. Then, they were cloned into the site of pET-28a(+) vectors (Novagen, Madison, Wis., USA). DNA ligation was performed using T4 DNA ligase at 4° C. overnight. These plasmids were mixed with competent cells of E. coli DH5-alpha strain on the ice for 10 minutes. This mixture was placed on the ice for 2 minutes after it was heat shocked in the water bath at 42° C. for 90 seconds. Then, the mixture added with LB broth media was recovered in 37° C. shaking incubator for 1 hour. Transformant was plated on LB broth agar plate with kanamycin (50 µg/mL) (Biopure, Johnson, Tenn.) before incubating at 37° C. overnight. From a single colony, plasmid DNA was extracted, and after the digestion of Nde I and Sal I restriction enzymes, digested DNA was confirmed at 645 bp by using 1.2% agarose gels electrophoresis (FIG. 2). PCR primers for the CRA recombinant proteins fused to aMTD and random peptides (rPeptide) are summarized in TABLE 23 to 30. Amino acid sequences of aMTD and rPeptide primers are shown in TABLE 31 to 38.

Example 3. Inducible Expression, Purification and Preparation of Recombinant Proteins Fused to aMTDs and rPeptides To express recombinant proteins, pET-28a(+) vectors for the expression of CRA proteins fused to a negative control [rPeptide 38 (rP38)], reference hydrophobic CPPs (MTM12 and MTD85) and aMTDs were transformed in *E. coli* BL21 (DE3) strains. Cells were grown at 37° C. in LB medium containing kanamycin (50 µg/ml) with a vigorous shaking and induced at $OD_{600}$=0.6 by adding 0.7 mM IPTG (Biopure) for 2 hours at 37° C. Induced recombinant proteins were loaded on 15% SDS-PAGE gel and stained with Coomassie Brilliant Blue (InstantBlue, Expedeon, Novexin, UK) (FIG. 3).

The *E. coli* cultures were harvested by centrifugation at 5,000×rpm for 10 minutes, and the supernatant was discarded. The pellet was resuspended in the lysis buffer (50 mM $NaH_2PO_4$, 10 mM Imidazol, 300 mM NaCl, pH 8.0). The cell lysates were sonicated on ice using a sonicator (Sonics and Materials, Inc., Newtowen, Conn.) equipped with a probe. After centrifuging the cell lysates at 5,000× rpm for 10 minutes to pellet the cellular debris, the supernatant was incubated with lysis buffer-equilibrated Ni-NTA resin (Qiagen, Hilden, Germany) gently by open-column system (Bio-rad, Hercules, Calif.). After washing protein-bound resin with 200 ml wash buffer (50 mM $NaH_2PO_4$, 20 mM Imidazol, 300 mM NaCl, pH 8.0), the bounded proteins were eluted with elution buffer (50 mM $NaH_2PO_4$, 250 mM Imidazol, 300 mM NaCl, pH 8.0).

Recombinant proteins purified under natural condition were analyzed on 15% SDS-PAGE gel and stained with Coomassie Brilliant Blue (FIG. 4). All of the recombinant proteins were dialyzed for 8 hours and overnight against physiological buffer, a 1:1 mixture of cell culture medium (Dulbecco's Modified Eagle's Medium: DMEM, Hyclone, Logan, Utah) and Dulbecco's phosphate buffered saline (DPBS, Gibco, Grand Island, N.Y.). From 316 aMTDs and 141 rPeptides cloned, 240 aMTD- and 31 rPeptide-fused recombinant proteins were induced, purified, prepared and analyzed for their cell-permeability.

Example 4. Determination of Quantitative Cell-Permeability of Recombinant Proteins For quantitative cell-permeability, the aMTD- or rPeptide-fused recombinant proteins were conjugated to fluorescein isothiocyanate (FITC) according to the manufacturer's instructions (Sigma-Aldrich, St. Louis, Mo.). RAW 264.7 cells were treated with 10 µM FITC-labeled recombinant proteins for 1 hour at 37° C., washed three times with cold PBS, treated with 0.25% tripsin/EDTA (Sigma-Aldrich, St. Louis, Mo.) for 20 minutes at 37° C. to remove cell-surface bound proteins. Cell-permeability of these recombinant proteins were analyzed by flow cytometry (Guava, Millipore, Darmstadt, Germany) using the FlowJo cytometric analysis software (FIG. 5 to 6). The relative cell-permeability of aMTDs were measured and compared with the negative control (rP38) and reference hydrophobic CPPs (MTM12 and MTD85) (TABLE 47).

Example 5. Determination of Cell-Permeability and Intracellular Localization of Recombinant Proteins For a visual reference of cell-permeability, NIH3T3 cells were cultured for 24 hours on coverslip in 24-wells chamber slides, treated with 10 µM FITC-conjugated recombinant proteins for 1 hour at 37° C., and washed three times with cold PBS. Treated cells were fixed in 4% paraformaldehyde (PFA, Junsei, Tokyo, Japan) for 10 minutes at room temperature, washed three times with PBS, and mounted with VECTASHIELD Mounting Medium (Vector laboratories, Burlingame, Calif.), and counter stained with DAPI (4',6-diamidino-2-phenylindole). The intracellular localization of the fluorescent signal was determined by confocal laser scanning microscopy (LSM700, Zeiss, Germany; FIGS. 7 and 8)

---

The invention claimed is:

1. Advanced macromolecule transduction domain (aMTD) sequences that transduce biologically active macromolecules into the plasma membrane of cells and consist of amino acid sequences having the following characteristics:
   a. Amino Acid Length: 12;
   b. Bending Potential: Proline (P) positioned in the middle at 7' or 8' and at the end of the sequence;
   c. Rigidity/Flexibility: Instability Index (II): 40-60;
   d. Structural Feature: Aliphatic Index (AI): 180-220;
   e. Hydropathy: Grand Average of Hydropathy (GRAVY): 2.3-2.6; and
   f. Amino Acid Composition: the aMTD sequences consist of hydrophobic and/or aliphatic amino acids selected from the group consisting of alanine (A), valine (V), leucine (L), isoleucine (I) and proline (P).

2. The aMTD sequences according to claim 1, wherein the amino acid sequences have the below general formula composed of 12 amino acid sequences:

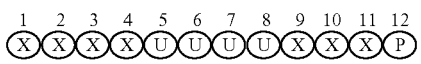

wherein, X(s) refer to either Alanine (A), Valine (V), Leucine (L) or Isoleucine (I); Proline (P) is positioned in one of U(s) at 7' or 8'; the remaining U(s) consist of either A, V, L or I; and P at the 12' is Proline.

3. The aMTD sequences according to claim 2, wherein the amino acid sequences having the general formula are selected from the group consisting of SEQ ID NOs: 74 to 87, 89 to 91, 96, 98 to 111, 113 to 123, 125, 127 to 143, 145, 146, 148 to 162, 164 to 167, 169 to 173, 178 to 183, 186 to 189, 191 to 218, 222, 226, 227, 229 to 231 and 233 to 237.

4. Isolated polynucleotides that encode aMTD sequences according to claim 2.

5. The isolated polynucleotides according to claim 4, wherein the isolated polynucleotides are selected from the group consisting of SEQ ID NOs: 314 to 327, 329 to 331, 336, 338 to 351, 353 to 363, 365, 367 to 383, 385, 386, 388 to 402, 404 to 407, 409 to 413, 418 to 423, 426 to 429, 431 to 458, 462, 466, 467, 469 to 471 and 473 to 477.

* * * * *